(12) United States Patent
Vrudhula et al.

(10) Patent No.: US 8,901,305 B2
(45) Date of Patent: Dec. 2, 2014

(54) ARYL LACTAM KINASE INHIBITORS

(71) Applicant: Bristol-Myers Squibb Company, Princeton, NJ (US)

(72) Inventors: Vivekananda M. Vrudhula, Killingworth, CT (US); Senliang Pan, Woodbridge, CT (US); Ramkumar Rajamani, Woodbridge, CT (US); Susheel Jethanand Nara, Bangalore (IN); Maheswaran Sivasamban Karatholuvhu, Chennai (IN); Tarun Kumar Maishal, Bangalore (IN); Jonathan L. Ditta, Meriden, CT (US); Carolyn Diane Dzierba, Middletown, CT (US); Joanne J. Bronson, Durham, CT (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/946,344

(22) Filed: Jul. 19, 2013

(65) Prior Publication Data
US 2014/0038999 A1 Feb. 6, 2014

Related U.S. Application Data

(60) Provisional application No. 61/677,856, filed on Jul. 31, 2012.

(51) Int. Cl.
*A61K 31/44* (2006.01)
*C07D 471/00* (2006.01)
*C07D 471/04* (2006.01)

(52) U.S. Cl.
CPC .................................. *C07D 471/04* (2013.01)
USPC ........................................... 546/81; 514/292

(58) Field of Classification Search
CPC .................................................. C07D 471/04
See application file for complete search history.

(56) References Cited

U.S. PATENT DOCUMENTS

| 8,703,953 | B2 | 4/2014 | Vrudhula et al. |
| 2013/0245021 | A1 | 9/2013 | Bi et al. |
| 2013/0253194 | A1 | 9/2013 | Bi et al. |
| 2014/0080834 | A1 | 3/2014 | Lanthorn et al. |
| 2014/0179725 | A1 | 6/2014 | Vrudhula et al. |

FOREIGN PATENT DOCUMENTS

| CN | 1733708 A | 2/2006 |
| JP | 2007-217408 A | 8/2007 |
| WO | WO 94/12461 | 6/1994 |
| WO | WO 96/21464 | 7/1996 |
| WO | WO 03/086325 | 10/2003 |
| WO | WO 2004/056745 | 7/2004 |
| WO | WO 2004/072018 | 8/2004 |
| WO | WO 2005/000309 | 1/2005 |
| WO | WO 2006/012227 | 2/2006 |
| WO | WO 2007/117715 | 10/2007 |
| WO | WO 2008/022154 | 2/2008 |
| WO | WO 2013/134036 | 9/2013 |

OTHER PUBLICATIONS

Arnott, G. Organic Letters (2008), 10(14), 3089-3092.*
Buonanno, a., "The neuregulin signaling pathway and schizophrenia: From genes to synapses and neural circuits", Brain Research Bulletin, vol. 83, pp. 122-131 (2010).
Conner, S.D. et al., "AAK1-Mediated p2 Phosphorylation is Stimulated by Assembled Clathrin", Traffic, vol. 4, pp. 885-890 (2003).
Conner, S.D. et al., "Identification of an adaptor-associated kinase, AAK1, as a regulator of clathrin-mediated endocytosis", the Journal of Cell Biology, vol. 156, No. 5, pp. 921-929 (2002).
Greenwood, T.A. et al., "Analysis of 94 Candidate Genes and 12 Endophenotypes for Schizophrenia from the Consortium on the Genetics of Schizophrenia", Am. J. Psychiatry, vol. 168, No. 9, pp. 930-946 (2011).
Henderson, D.M. et al., "A Novel AAK1 Splice Variant Functions at Multiple Steps of the Endocytic Pathway", Molecular Biology of the Cell, vol. 18, pp. 2698-2706 (2007).
Jaaro-Peled, H. et al., "Review of Pathological Hallmarks of Schizophrenia: Comparison of Genetic Models with Patients and Nongenetic Models", Schizophrenia Bulletin, vol. 36, No. 2, pp. 301-313 (2010).
Jackson, a.P. et al., "Clathrin promotes incorporation of cargo into coated pits by activation of the AP2 adaptor p2 kinase", the Journal of Cell Biology, vol. 163, No. 2, pp. 231-236 (2003).
Kuai, L. et al., "AAK1 Identified as an Inhibitor of Neuregulin-1/ ErbB4Dependent Neurotrophic Factor Signaling Using Integrative Chemical Genomics and Proteomics", Chemistry & Biology, vol. 18, pp. 891-906 (2011).
Latourelle, J.C. et al., "Genomewide association study for onset age in Parkinson disease", Bmc Medical Genetics, vol. 10 (2009), doi:10. 1186/1471-2350-10-98.
Motley, a.M. et al., "Functional Analysis of Ap-2 a and p2 Subunits", Molecular Biology of the Cell, vol. 17, pp. 5298-5308 (2006).
Ricotta, D. et al., "Phosphorylation of the AP2 µ subunit by AAK1 mediates high affinity binding to membrane protein sorting signals", the Journal of Cell Biology, vol. 156, No. 5, pp. 791-795 (2002).
Wen, L. et al., "Neuregulin 1 regulates pyramidal neuron activity via ErbB4 in parvalbumin-positive interneurons", Proc. Natl. Acad. Sci., vol. 107, No. 3, pp. 1211-1216 (2010).

* cited by examiner

*Primary Examiner* — Heidi Reese
(74) *Attorney, Agent, or Firm* — Pamela A. Mingo

(57) ABSTRACT

The present disclosure is generally directed to compounds which can inhibit AAK1 (adaptor associated kinase 1), compositions comprising such compounds, and methods for inhibiting AAK1.

11 Claims, 1 Drawing Sheet

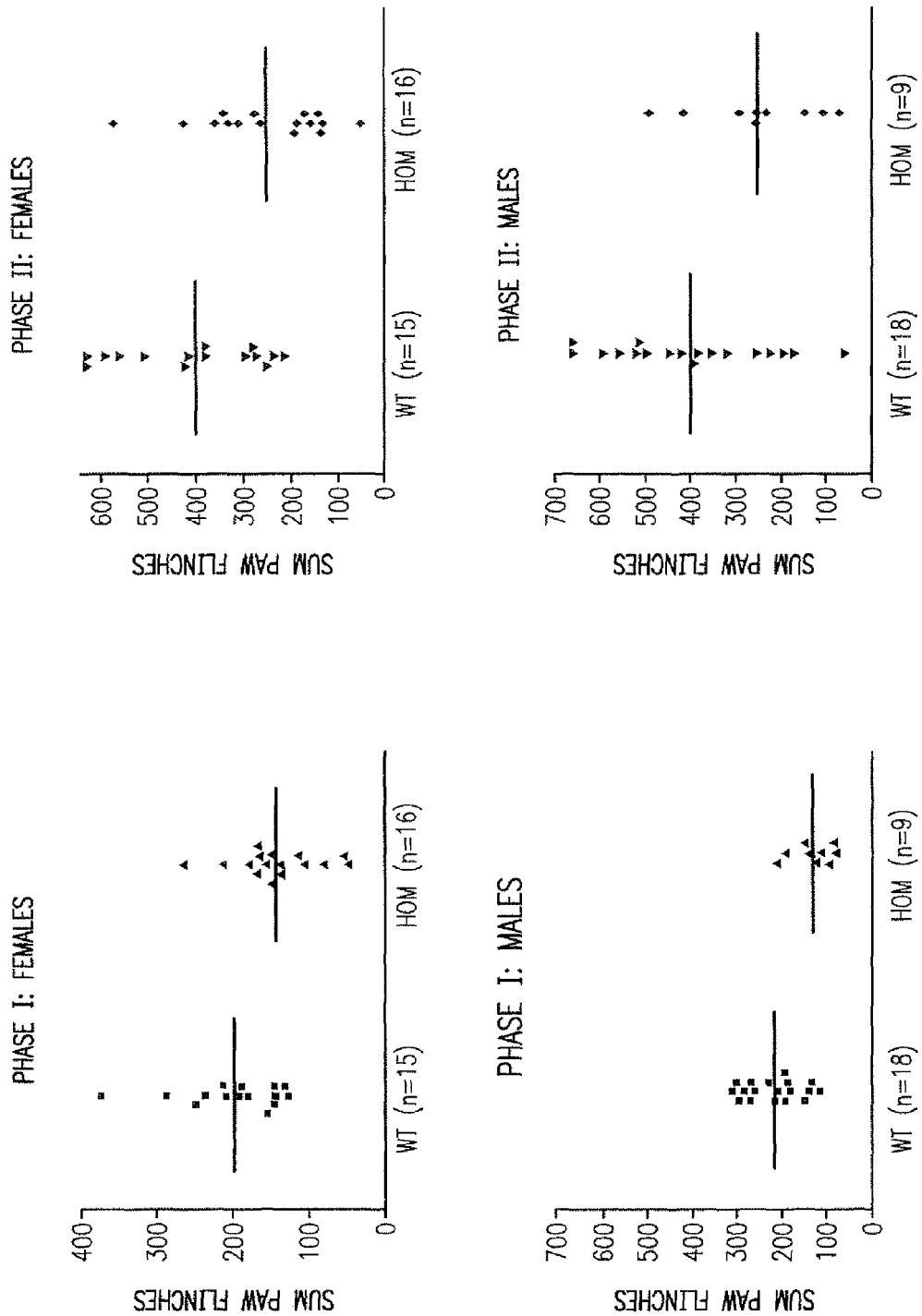

ARYL LACTAM KINASE INHIBITORS

CROSS-REFERENCE TO RELATED APPLICATIONS

This application claims the benefit of U.S. Provisional Application Ser. No. 61/677,856 filed Jul. 31, 2012.

The present disclosure is generally directed to compounds which can inhibit adaptor associated kinase 1 (AAK1), compositions comprising such compounds, and methods for inhibiting AAK1.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., Proc. Natl. Acad. Sci. USA. 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In a first aspect the present disclosure provides a compound of formula (I)

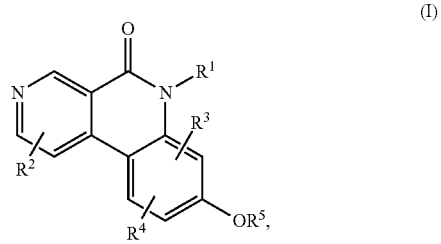

or a pharmaceutically acceptable salt thereof, wherein:
$R^1$ is selected from hydrogen, $C_2$-$C_4$alkenyl, $C_1$-$C_3$alkoxy, $C_1$-$C_3$alkoxy$C_1$-$C_3$alkyl, $C_1$-$C_3$alkyl, $C_1$-$C_3$alkylamino, aryl$C_1$-$C_3$alkyl, $C_3$-$C_6$cycloalkyl, $C_3$-$C_6$cycloalkyl$C_1$-$C_3$alkyl, $C_1$-$C_3$haloalkyl, and $C_1$-$C_3$hydroxyalkyl;

$R^2$ is selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, $C_1$-$C_3$haloalkyl, $C_2$-$C_3$haloalkylamino, $C_2$-$C_3$haloalkylcarbonylamino, hydroxy, and phenyl$C_1$-$C_3$alkylamino, wherein the phenyl is optionally substituted with a $C_1$-$C_3$alkoxy group;

$R^3$ and $R^4$ are independently selected from hydrogen, $C_1$-$C_4$alkoxy, $C_1$-$C_3$alkoxy$C_1$-$C_3$alkyl, $C_1$-$C_3$alkoxycarbonyl, $C_1$-$C_4$alkyl, $C_1$-$C_3$alkylsulfonyl, aminocarbonyl, cyano, $C_3$-$C_6$cycloalkyl, di($C_1$-$C_3$alkyl)aminocarbonyl, halo, $C_1$-$C_3$haloalkoxy, $C_1$-$C_3$haloalkyl, heteroaryl, hydroxy, $C_1$-$C_3$hydroxyalkyl, and phenyl optionally substituted with a halo group;

$R^5$ is $C_1$-$C_3$alkyl-Y or $C_2$-$C_8$alkyl, wherein the $C_2$-$C_8$alkyl is optionally substituted with one, two, three, or four groups independently selected from $C_1$-$C_3$alkoxy, $C_1$-$C_3$alkylamino, $C_1$-$C_3$alkoxy$C_2$-$C_3$alkylamino, amino, aryl, di($C_1$-$C_3$alkyl)amino, halo, $C_1$-$C_3$haloalkylamino, $C_1$-$C_3$haloalkylcarbonylamino, hydroxy, —NR$^x$R$^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;

$R^x$ and $R^y$, together with the nitrogen atom to which they are attached, form a three- to six-membered ring; and
Y is selected from

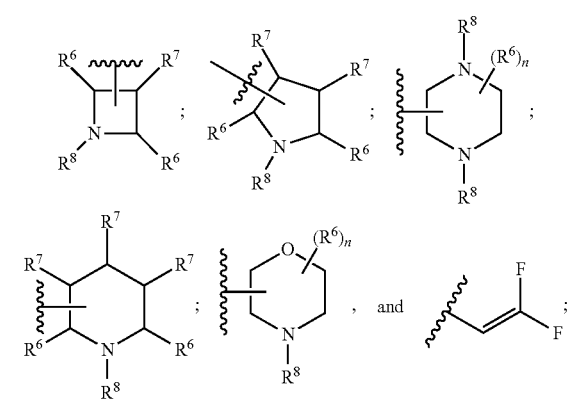

wherein n is 0, 1, 2, or 3;
each $R^6$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl;
each $R^7$ is independently selected from hydrogen, $C_1$-$C_3$alkoxy and hydroxy; and
$R^8$ is selected from hydrogen, $C_1$-$C_6$alkyl, $C_3$-$C_6$cycloalkyl, and $C_1$-$C_6$alkylcarbonyl.

In a first embodiment of the first aspect the present disclosure provides a compound of formula (I) wherein $R^5$ is $C_2$-$C_8$alkyl, wherein the $C_2$-$C_8$alkyl is optionally substituted with one, two, three, or four groups independently selected from $C_1$-$C_3$alkoxy, amino, $C_1$-$C_3$alkylamino, di($C_1$-$C_3$alkyl)amino, halo, and $C_3$-$C_8$cycloalkyl; or $R^5$ is $C_1$-$C_3$alkyl-Y wherein Y is

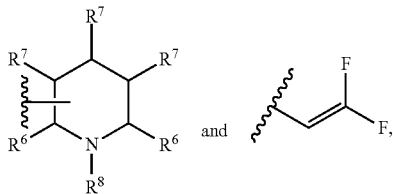

wherein $R^6$, $R^7$, and $R^8$ are hydrogen.

In a second embodiment of the first aspect the present disclosure provides a compound of formula (I) wherein $R^5$ is $C_2$-$C_8$alkyl optionally substituted with one, two, three, or four groups independently selected from amino and halo.

In a third embodiment of the first aspect the present disclosure provides a compound of formula (I) wherein $R^1$ is selected from hydrogen, $C_2$-$C_4$alkenyl, $C_1$-$C_3$alkoxy$C_1$-$C_3$alkyl, $C_1$-$C_3$alkyl, aryl$C_1$-$C_3$alkyl, $C_3$-$C_6$cycloalkyl$C_1$-$C_3$alkyl, $C_1$-$C_3$haloalkyl, and $C_1$-$C_3$hydroxyalkyl;
$R^2$ is selected from hydrogen, $C_1$-$C_3$alkoxy, $C_1$-$C_3$alkyl, $C_1$-$C_3$alkylcarbonylamino, amino, halo, $C_1$-$C_3$haloalkyl, and phenyl$C_1$-$C_3$alkylamino, wherein the phenyl is optionally substituted with a $C_1$-$C_3$alkoxy group;
$R^3$ and $R^4$ are independently selected from hydrogen, $C_1$-$C_4$alkoxy, $C_1$-$C_3$alkoxy$C_1$-$C_3$alkyl, $C_1$-$C_3$alkoxycarbonyl, $C_1$-$C_4$alkyl, $C_1$-$C_3$alkylsulfonyl, aminocarbonyl, cyano, $C_3$-$C_6$cycloalkyl, di($C_1$-$C_3$alkyl)aminocarbonyl, halo, $C_1$-$C_3$haloalkoxy, $C_1$-$C_3$haloalkyl, heteroaryl, hydroxy, $C_1$-$C_3$hydroxyalkyl, and phenyl optionally substituted with a halo group;
$R^5$ is $C_1$-$C_3$alkyl-Y or $C_2$-$C_8$alkyl, wherein the $C_2$-$C_8$alkyl is optionally substituted with one, two, three, or four groups independently selected from $C_1$-$C_3$alkoxy, $C_1$-$C_3$alkylamino, amino, di($C_1$-$C_3$alkyl)amino, halo, and $C_3$-$C_8$cycloalkyl; and wherein Y is selected from

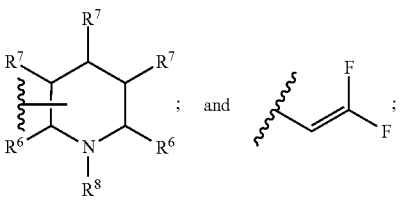

wherein $R^6$, $R^7$, and $R^8$ are hydrogen.

In a second aspect the present disclosure provides a compound of formula (II)

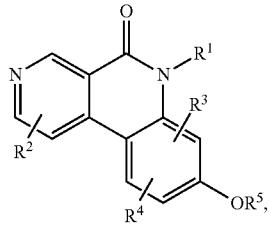

or a pharmaceutically acceptable salt thereof, wherein:
$R^1$ is selected from hydrogen, $C_2$-$C_4$alkenyl, $C_1$-$C_3$alkoxy, $C_1$-$C_3$alkoxy $C_1$-$C_3$alkyl, $C_1$-$C_3$alkyl, $C_1$-$C_3$alkylamino, aryl$C_1$-$C_3$alkyl, $C_3$-$C_6$cycloalkyl, $C_3$-$C_6$cycloalkyl$C_1$-$C_3$alkyl, and $C_1$-$C_3$haloalkyl;
$R^2$ is selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, $C_1$-$C_3$haloalkyl, $C_2$-$C_3$haloalkylamino, $C_2$-$C_3$haloalkylcarbonylamino, and hydroxy;
$R^3$ and $R^4$ are independently selected from hydrogen, $C_1$-$C_4$alkyl, cyano, $C_3$-$C_6$cycloalkyl, halo, $C_1$-$C_3$haloalkyl, and hydroxy;
$R^5$ is $C_1$-$C_3$alkyl-Y or $C_2$-$C_8$alkyl, wherein the $C_2$-$C_8$alkyl is optionally substituted with one, two, or three groups independently selected from $C_1$-$C_3$alkoxy, $C_1$-$C_3$alkylamino, $C_1$-$C_3$alkoxy$C_2$-$C_3$alkylamino, amino, aryl, halo, $C_1$-$C_3$haloalkylamino, $C_1$-$C_3$haloalkylcarbonylamino, hydroxy, —$NR^xR^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;
$R^x$ and $R^y$, together with the nitrogen atom to which they are attached, form a three- to six-membered ring; and
Y is selected from

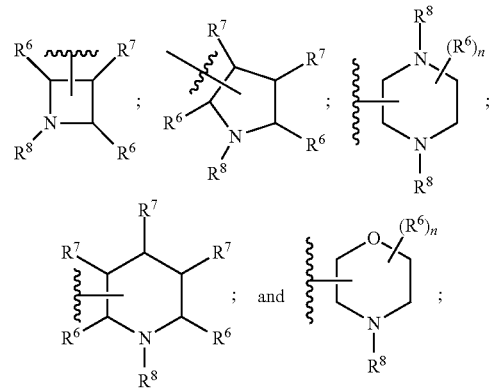

wherein n is 0, 1, 2, or 3;
each $R^6$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl;
each $R^7$ is independently selected from hydrogen, $C_1$-$C_3$alkoxy and hydroxy; and
$R^8$ is selected from hydrogen, $C_1$-$C_6$alkyl, $C_3$-$C_6$cycloalkyl, and $C_1$-$C_6$alkylcarbonyl.

In a first embodiment of the second aspect the present disclosure provides a compound of formula (I), or a pharmaceutically acceptable salt thereof, wherein $R^5$ is $C_2$-$C_8$alkyl optionally substituted with one, two, or three groups independently selected from $C_1$-$C_3$alkoxy, $C_1$-$C_3$alkylamino, $C_1$-$C_3$alkoxyC$_2$-$C_3$alkylamino, amino, aryl, halo, $C_1$-$C_3$haloalkylamino, $C_1$-$C_3$haloalkylcarbonylamino, hydroxy, —NR$^x$R$^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxyC$_2$-$C_3$alkylamino, amino, aryl, arylC$_1$-$C_3$alkyl, halo, $C_1$-$C_3$haloalkyl, $C_1$-$C_3$haloalkylamino and hydroxy. In a second embodiment of the second aspect $R^5$ is $C_2$-$C_8$alkyl optionally substituted with one, two, or three groups independently selected from amino and halo.

In a third embodiment of the second aspect the present disclosure provides a compound of formula (I), or a pharmaceutically acceptable salt thereof, wherein $R^1$ is selected from hydrogen, $C_2$-$C_4$alkenyl, $C_1$-$C_3$alkoxyC$_1$-$C_3$alkyl, $C_1$-$C_3$alkyl, arylC$_1$-$C_3$alkyl, and $C_3$-$C_6$cycloalkylC$_1$-$C_3$alkyl;

$R^2$ is selected from hydrogen, $C_1$-$C_3$alkyl, $C_1$-$C_3$alkylcarbonylamino, and amino;

$R^3$ and $R^4$ are independently selected from hydrogen, $C_1$-$C_4$alkyl, cyano, $C_3$-$C_6$cycloalkyl, halo, and hydroxy; and $R^5$ is $C_2$-$C_8$alkyl optionally substituted with one, two, or three groups independently selected from amino and halo.

In a third aspect the present disclosure provides composition comprising a pharmaceutically acceptable amount of a compound of formula (I), or a pharmaceutically acceptable salt thereof, and a pharmaceutically acceptable carrier.

In a fourth aspect the present disclosure provides a method of inhibiting adaptor associated kinase 1 (AAK1) activity, comprising contacting AAK1 with a compound of formula (I), or a pharmaceutically acceptable salt thereof.

In a fifth aspect the present disclosure provides a method for treating or managing a disease or a disorder mediated by AAK1 activity, the method comprising administering to a patient in need thereof a therapeutically effective amount of a compound of formula (I), or a pharmaceutically acceptable salt thereof. In a first embodiment of the fifth aspect the disease or disorder is selected from Alzheimer's disease, bipolar disorder, pain, Parkinson's disease, and schizophrenia. In a second embodiment of the fifth aspect the pain is neuropathic pain. In a third embodiment of the fifth aspect the neuropathic pain is fibromyalgia or peripheral neuropathy.

Other aspects of the present disclosure may include suitable combinations of embodiments disclosed herein.

Yet other aspects and embodiments may be found in the description provided herein.

BRIEF DESCRIPTION OF THE FIGURES

Aspects of the disclosure are illustrated in FIG. 1, which shows results obtained from a formalin pain model using AAK1 homozygous (−/−) knockout mice and their wild-type (+/+) littermates. The AAK1 homozygous (−/−) knockout mice show a clear reduction in both acute and tonic pain response as compared to their wild-type (+/+) littermates.

This disclosure is based, in part, on the discovery that AAK1 knockout mice exhibit a high resistance to pain. That discovery prompted research that ultimately led to the discovery of AAK1 inhibitors, compositions comprising them, and methods of their use.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^6$ groups may be the same or different.

As used in the present specification, the following terms have the meanings indicated:

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

In some instances, the number of carbon atoms in any particular group is denoted before the recitation of the group. For example, the term "$C_{1-6}$ alkyl" denotes an alkyl group containing one to six carbon atoms. Where these designations exist they supercede all other definitions contained herein.

The term "alkenyl," as used herein, refers to a straight or branched chain group containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylamino," as used herein, refers to —NHR wherein R is an alkoxyalkyl group.

The term "alkoxycarbonyl," as used herein, refers to an alkoxy group attached to the parent molecular moiety through a carbonyl group.

The term "alkoxycarbonylamino," as used herein, refers to an —NHR wherein R is an alkoxycarbonyl group.

The term "alkyl," as used herein, refers to a group derived from a straight or branched chain saturated hydrocarbon.

The term "alkylamino," as used herein refers to —NHR, wherein R is an alkyl group.

The term "alkylcarbonyl," as used herein, refers to an alkyl group attached to the parent molecular moiety through a carbonyl group.

The term "alkylcarbonylamino," as used herein, refers to —NHR wherein R is an alkylcarbonyl group.

The term "alkylsulfonyl," as used herein, refers to an alkyl group attached to the parent molecular moiety through a sulfonyl group.

The term "amino," as used herein, refers to —NH$_2$.

The term "aminocarbonyl," as used herein, refers to —C(O)NH$_2$.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present invention can be attached to the parent molecular moiety through any substitutable carbon atom in the group. Representative examples of aryl groups include, but are not limited to, indanyl, indenyl, naphthyl, phenyl, and tetrahydronaphthyl.

The term "arylalkyl," as used herein, refers to an alkyl group substituted with one, two, or three aryl groups.

The term "arylamino," as used herein, refers to —NHR wherein R is an aryl group.

The term "arylcarbonyl," as used herein, refers to an aryl group attached to the parent molecular moiety through a carbonyl group.

The term "arylcarbonylamino," as used herein refers to —NHR wherein R is an arylcarbonyl group.

The term "carbonyl," as used herein, refers to —C(O)—.

The term "cyano," as used herein, refers to —CN.

The term "cycloalkyl," as used herein, refers to a saturated monocyclic hydrocarbon ring system having zero heteroatoms. Representative examples of cycloalkyl groups include, but are not limited to, cyclopropyl, cyclopentyl, and cyclohexyl.

The term "(cycloalkyl)alkyl," as used herein, refers to an alkyl group substituted with one, two, or three cycloalkyl groups.

The term "cycloalkylamino," as used herein, refers to —NHR wherein R is a cycloalkyl group.

The term "cycloalkylcarbonyl," as used herein, refers to a cycloalkyl group attached to the parent molecular moiety through a carbonyl group.

The term "cycloalkylcarbonylamino," as used herein, refers to —NHR wherein R is a cycloalkylcarbonyl group.

The term "cycloalkyloxy," as used herein, refers to a cycloalkyl group attached to the parent molecular moiety through an oxygen atom.

The term "dialkylamino," as used herein, refers to —NR$_2$ wherein R is alkyl. The two R groups may be the same or different.

The term "dialkylaminocarbonyl," as used herein, refers to —C(O)NR$_2$, wherein R is alkyl. The two R groups may be the same or different.

The term "halo," as used herein, refers to Br, Cl, F, and/or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "haloalkylamino," as used herein, refers to —NHR wherein R is a haloalkyl group.

The term "haloalkylcarbonyl," as used herein, refers to a haloalkyl group attached to the parent molecular moiety through a carbonyl group.

The term "haloalkylcarbonylamino," as used herein, refers to —NHR wherein R is a haloalkylcarbonyl group.

The term "heteroaryl," as used herein, refers to a five- or six-membered aromatic ring containing one or two heteroatoms independently selected from nitrogen, oxygen, and sulfur.

The term "hydroxy," as used herein, refers to —OH.

The term "hydroxyalkyl," as used herein, refers to an alkyl group substituted with one, two, or three hydroxy groups.

The term "phenylalkylamino" as used herein, refers to —NHR, wherein R is a phenylalkyl group.

The term "sulfonyl," as used herein, refers to —SO$_2$.

Asymmetric centers may exist in the compounds of the present disclosure. It should be understood that the disclosure encompasses all stereochemical isomeric forms, or mixtures thereof, which possess the ability to inhibit AAK1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

One embodiment of this disclosure encompasses methods of inhibiting adaptor associated kinase 1 (AAK1), both in vitro and in vivo, which comprise contacting AAK1 with a compound of formula I or a pharmaceutically acceptable salt thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. Unless otherwise indicated, a "therapeutically effective amount" of a compound is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent.

The term "therapeutically effective amount," as used herein, refers to an amount of a compound or compounds sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Compounds of the disclosure may be administered in combination with one or more additional therapeutic or prophylactic agents. For example, when used for the treatment of pain, possible additional agents include immunosuppressive agents, anti-inflammatory agents, and/or other agents used in the treatment of pain.

Immunosuppressants suitable for use in the methods and compositions of this disclosure include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples of immunosuppressants include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Other immunosuppressants include inosine monophosphate dehydrogenase inhibitors, such as mycophenolate mofetil (CellCept®) and mycophenolic acid (Myfortic®).

Anti-inflammatory drugs suitable for use in the methods and compositions of this disclosure include those known in the art. Examples include glucocorticoids and NSAIDs. Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include, but are not limited to, agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the disclosure may be administered in combination with one or more additional therapeutic or prophylactic agents directed at the underlying disease or condition. For example, when used to treat diabetic neuropathy, compounds of the disclosure may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

Unless otherwise indicated, the terms "manage," "managing", and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: RT or rt or r.t. for room temperature or retention time (context will dictate); $t_R$ for retention time; h or hr or hrs for hours; min or mins for minutes; MeOH for methanol; EtOH for ethanol; EtOAc or EtOAC for ethyl acetate; OAc for acetate; DCM for dichloromethane; DMA for N,N-dimethylacetamide; DMF for N,N-dimethylformamide; NMP for N-methylpyrrolidinone; MeCN or ACN for acetonitrile; AcCl for acetyl chloride; THF for tetrahydrofuran; DMSO for dimethylsulfoxide; MeOD for $CD_3OD$; m-CPBA for meta-chloroperoxybenzoic acid; DCM for dichloromethane; Me for methyl; Et for ethyl; Ac for acetyl; Ph for phenyl; BOC or Boc for tert-butoxycarbonyl; EDC for 1-ethyl-3-(3-dimethylaminopropyl)carbodiimide; DBU for 1,8-diazabicycloundec-7-ene; HOBT or HOBt for hydroxybenzotriazole; NCS for N-chlorosuccinimide; TEA or $Et_3N$ for triethylamine; DIPEA, DIEA, or i-$Pr_2NEt$ for diisopropylethylamine; DEA for diethylamine; DAST for diethylaminosulfur trifluoride; NBS for N-bromosuccinimide; TOSMIC for tosylmethyl isocyanide; DIBAL for diisobutylaluminum hydride; LDA for lithium diisopropylamide; TFA for trifluoroacetic acid; dppf or DPPF for 1,1'-bis(diphenylphosphino)ferrocene; dba for dibenzylidiendiacetone; n-BuLi for n-butyllithium; LHMDS or LiHMDS for lithium hexamethyldisilazide; TMS for trimethylsilyl; and PMB-Cl for para-methoxybenzyl chloride.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Scheme 1

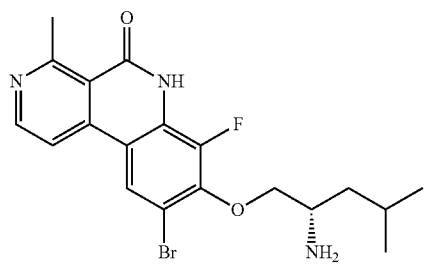

The compound of formula 9 is prepared by method outlined in Scheme 1. 4-Chloronicotinic acid can be subjected to esterification using standard conditions such as treatment with oxalyl chloride and methanol. The ester 2, so obtained can be subjected to Suzuki cross coupling reaction with an appropriate coupling partner such as fluoroboronic acid 3, under standard Suzuki conditions employing a base such as cesium carbonate and a catalyst such as Pd(PPh$_3$)$_4$ as described by Zhang, Lei et. al. (*Journal of Medicinal Chemistry*, 2011, 54, 1724-1739). The biaryl ester 4, can then be subjected to palladium catalyzed ether synthesis including reaction conditions familiar to those skilled in the art following procedures such as those described by Gowrisankar, et. al. (*J. Am. Chem. Soc.* 2010, 132, 11592-11598). The reactions can be performed using appropriately protected, racemic or optically amino alcohols to afford racemic or optically pure ethers. The biaryl ester represented by formula 5, can be subjected to hydrolysis to yield corresponding carboxylic acid 6 under standard saponification conditions using a base such as lithium hydroxide in a solvent such as water as described in *Protective Groups in Organic Synthesis* (Greene, Wuts; 3$^{rd}$ ed., 1999, John Wiley & Sons, Inc.). The acid 6 can be converted to amide 7 by using standard coupling conditions such as EDC, HOBt and ammonium chloride. The amide 7, upon treatment with a hydride source such as sodium hydride in a solvent such as THF under inert atmosphere can afford the constrained lactam, 8. The constrained lactam ether analog represented by 8 can be subjected to deprotection of the side chain amino group using appropriate conditions as described in *Protective Groups in Organic Synthesis* (Greene, Wuts; 3$^{rd}$ ed., 1999, John Wiley & Sons, Inc.) to yield compounds represented by formula 9.

Scheme 2

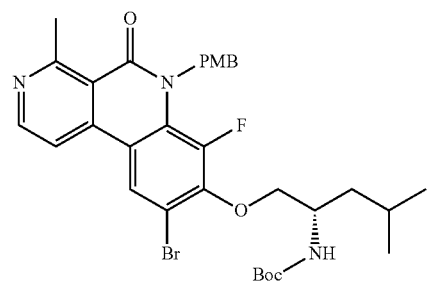

The compounds represented by formula 13 and 14 are prepared by methods outlined in Scheme 2. The biaryl ester 4, prepared as described in Scheme 1, can be subjected to hydrolysis under standard saponification conditions using a base such as lithium or sodium hydroxide in a solvent such as water as described in *Protective Groups in Organic Synthesis* (Greene, Wuts; 3$^{rd}$ ed., 1999, John Wiley & Sons, Inc.) to yield corresponding carboxylic acids, which upon treatment with standard amide coupling conditions such as EDC, HOBt and ammonium chloride or substituted amine can be converted to amides 10. Cyclization of amides 10 can be affected by treatment with a hydride source such as sodium hydride in a solvent such as THF under inert atmosphere to afford constrained lactam chloro cores 11. Chloro cores 11 can be subjected to palladium catalyzed ether synthesis using reaction conditions familiar to those skilled in the art following procedures such as those described by Gowrisankar, et. al. (*J. Am. Chem. Soc.* 2010, 132, 11592-11598) to afford compounds represented by formula 12. The reactions can be performed using appropriately protected, racemic or optically pure (S) or (R)-aminoalcohols to afford racemic or optically pure ethers 12. The ether analogs can be subjected to deprotection of the side chain amino group using appropriate conditions as described in Protective *Groups in Organic Synthesis* (Greene, Wuts; 3$^{rd}$ ed., 1999, John Wiley & Sons, Inc.) to yield compounds of formula 13. In cases where R$^2$ is serving as a protecting group, this group can be removed using appropriate conditions as described in Protective *Groups in Organic Synthesis* (Greene, Wuts; 3$^{rd}$ ed., 1999, John Wiley & Sons, Inc.)

Scheme 3

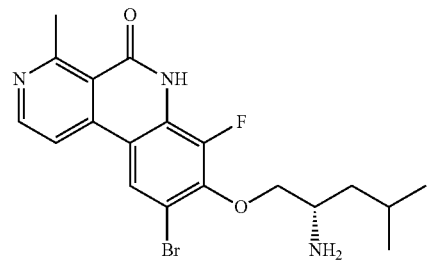

The compounds represented by formula 17 and 19 are prepared by methods outlined in Scheme 3. The constrained lactam ether, 15, synthesized as shown in Scheme 2, can be subjected to halogenation employing N-halosuccinimide in polar aprotic solvents such as acetonitrile in the dark to yield mono-halo (X=halo, $R^3$=H) or dihalo-substituted ($R^3$=X=halo) ethers 16. The side chain of ethers 16 can be subjected to deprotection using appropriate conditions as described in Protective *Groups in Organic Synthesis* (Greene, Wuts; $3^{rd}$ ed., 1999, John Wiley & Sons, Inc.) to yield compounds of formula 17. Alternatively, compound 16 can be subjected to a palladium coupling such as Suzuki cross coupling reaction with an appropriate coupling partner such as trimethylboroxine or cyclopropyl boronic acid under standard Suzuki conditions employing a base such as cesium carbonate and a catalyst such as $Pd(PPh_3)_4$ as described by Zhang, Lei et. al. (*Journal of Medicinal Chemistry*, 2011, 54, 1724-1739), or to a copper catalyzed cyanation reaction as described by Miroslav et. al. (*Collection of Czechoslovak Chemical Communications*, 1983, 48, 1765-1773) to install $R^4$ of the compounds represented by formula 18. Lactam 16 can be subjected to a copper catalyzed hydroxylation reaction using conditions such as those described by Punniyamurthy et. al. (*Synthesis*, 2010, 4268-4272) to provide 18 wherein $R^4$=OH. The ether analogs 18 can be subjected to deprotection of the side chain amino group using appropriate conditions as described in Protective *Groups in Organic Synthesis* (Greene, Wuts; $3^{rd}$ ed., 1999, John Wiley & Sons, Inc.) to yield compounds of formula 19.

Scheme 4

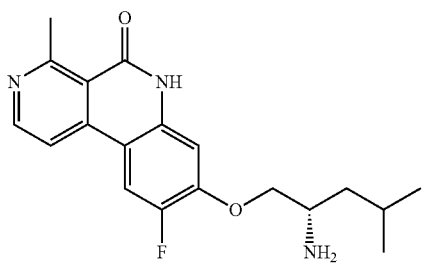

The compounds represented by formula 29 can be prepared as shown in Scheme 4. Boc-protection of 20 using base such as LiHMDS and Boc anhydride led to 21. Directed orthometallation followed by treatment with dimethylformamide can furnish the pyridine aldehyde derivative 22 using methods such as those described by Charles et. al. (*J. Med. Chem.*, 2010, 53, 3330-3348). The aldehyde can then be subjected to Suzuki cross coupling reaction with an appropriate coupling partner such as fluoroboronic acid 3, under standard Suzuki conditions employing a base such as cesium carbonate and a catalyst such as $Pd(PPh_3)_4$ as described by Zhang, Lei et. al. (*Journal of Medicinal Chemistry*, 2011, 54, 1724-1739) to give biaryl aldehyde 23. Treatment of biaryl aldehyde 23 with methyl amine can provide cyclic iminium fluoride 24, which upon oxidation with reagents such as $KMnO_4$ give lactam 25. Treatment of lactam 25 with trifluoroacetic acid can afford 26, which can be protected with a group such as p-methoxy benzyl using appropriate conditions as described in Protective *Groups in Organic Synthesis* (Greene, Wuts; $3^{rd}$ ed., 1999, John Wiley & Sons, Inc.) can afford lactam 27. Lactam core 27 can be subjected to palladium catalyzed ether synthesis using reaction conditions familiar to those skilled in the art following procedures such as those described by Gowrisankar, et. al. (*J. Am. Chem. Soc.* 2010, 132, 11592-11598) to afford compound represented by formula 28. The ether analog can be subjected to global deprotection of the side chain amino group using appropriate conditions as described in Protective *Groups in Organic Synthesis* (Greene, Wuts; $3^{rd}$ ed., 1999, John Wiley & Sons, Inc.) to yield compound 29.

Scheme 5

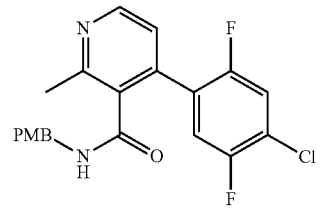

The compounds represented by the formula 39 can be prepared as shown in Scheme 5. Bromination of 30 with NBS followed by acylation with acetyl chloride and pyridine can furnish bromide 31. Suzuki cross coupling of the bromide 31 with vinyl boronic acid anhydride pyridine complex under standard Suzuki conditions employing base such as sodium carbonate and a catalyst such as $Pd(PPh_3)_4$ as described by Zhang, Lei et. al. (*Journal of Medicinal Chemistry*, 2011, 54, 1724-1739) can furnish vinyl pyridine 32. Vinyl pyridine 32 can be oxidized using osmium tetroxide and sodium metaperiodate to yield corresponding aldehyde 33, which can then be subjected to Suzuki cross coupling reaction with an appropriate coupling partner such as fluoroboronic acid 3, under standard Suzuki conditions employing a base such as cesium carbonate and a catalyst such as $Pd(PPh_3)_4$ as described by Zhang, Lei et. al. (*Journal of Medicinal Chemistry*, 2011, 54, 1724-1739) to give biaryl aldehyde 34. Treatment of biaryl aldehyde 34 with methyl amine can lead to the cyclic iminium fluoride 35 which can be reduced to the corresponding constrained piperidine 36 by using an agent such as sodium borohydride. Constrained piperidine 36 upon oxidation with $KMnO_4$ can give lactam 37. Lactam core 37 can be subjected to palladium catalyzed ether synthesis using reaction conditions familiar to those skilled in the art following procedures such as those described by Gowrisankar, et. al. (*J. Am. Chem. Soc.* 2010, 132, 11592-11598) to afford compound represented by formula 38. The ether analog can be subjected to deprotection of the side chain amino group using appropriate conditions as described in Protective *Groups in Organic Synthesis* (Greene, Wuts; $3^{rd}$ ed., 1999, John Wiley & Sons, Inc.) to yield compounds 39.

Scheme 6

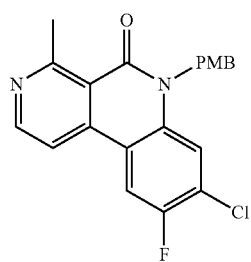

The compounds represented by formula 42-46 are prepared by methods outlined in Scheme 6. The constrained lactam ether, 40, synthesized as shown in Scheme 2, can be subjected to halogenation by employing N-halosuccinimide in polar aprotic solvents such as acetonitrile in the dark to yield mono-halo (X=halo, R³=H) or dihalo-substituted (R³=X=halo) ethers 41. Compound 41 can be subjected to a palladium coupling such as a Suzuki cross coupling reaction with an appropriate coupling partner such as trimethylboroxine, vinylboronic acid or cyclopropylboronic acid under standard Suzuki conditions employing a base such as cesium carbonate and a catalyst such as Pd(PPh₃)₄ as described by Zhang, Lei et. al. (*Journal of Medicinal Chemistry*, 2011, 54, 1724-1739), or to a copper catalyzed cyanation reaction as described by Miroslav et. al. (*Collection of Czechoslovak Chemical Communications*, 1983, 48, 1765-1773) to install R⁴ of the compounds represented by formula 42. Lactam 41 can alternatively be subjected to a copper catalyzed hydroxylation reaction using conditions such as those described by Punniyamurthy et. al. (*Synthesis*, 2010, 4268-4272) to provide 42 wherein R⁴=OH. In the cases of intermediates 42 where R⁴=vinyl, oxidative cleavage of the vinyl group with reagents such as osmium tetroxide and sodium periodate can provide aldehydes 44. The aldehyde can be converted to the difluoromethyl analog 45 by treatment with Deoxo-Fluor®. If R¹ contains an amine group or another functional group that is protected, the protecting group in analogs 42 and 45 is removed by treating the substrate with the appropriate reagents as described in Protective Groups in Organic Synthesis (Greene, Wuts; 3rd ed., 1999, John Wiley & Sons, Inc.) to yield compounds of formula 43 and 46, respectively.

Scheme 7

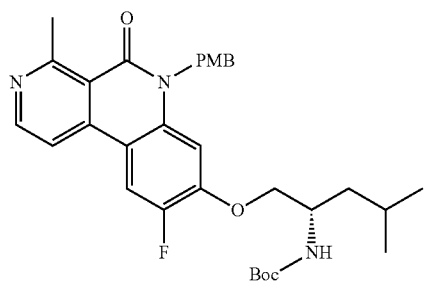

The compounds represented by formula 47 and 48 are prepared by methods outlined in Scheme 7. The aldehyde, 44, synthesized as shown in Scheme 6, can be subjected to TOSMIC and a base such as potassium carbonate to afford oxazoles 47. Alternatively, aldehydes 44 can be subjected to a reduction with reagents such as sodium borohydride or lithium borohydride in a solvent such as EtOH or MeOH to yield compounds represented by formula 48. If R¹ contains an amine group or another functional group that is protected, the protecting group is removed by treating the substrate with the appropriate reagents as described in Protective Groups in Organic Synthesis (Greene, Wuts; 3rd ed., 1999, John Wiley & Sons, Inc.) to provide deprotected compounds of the formula 47 and 48.

Scheme 8

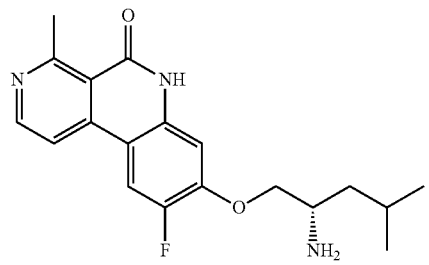

The compounds represented by formula 52-53 are prepared by methods outlined in Scheme 8. The constrained lactam ether, 49, synthesized as shown in the above schemes, can be subjected to halogenation employing N-halosuccinimide in polar aprotic solvents such as acetonitrile in the dark to yield halo ethers 50. Compound 50 can be subjected to a palladium coupling such as Suzuki cross coupling reaction with an appropriate coupling partner such as a vinylboronic acid under standard Suzuki conditions employing a base such as cesium carbonate and a catalyst such as Pd(PPh₃)₄ as described by Zhang, Lei et. al. (*Journal of Medicinal Chemistry*, 2011, 54, 1724-1739), or to a Stille coupling with an appropriate coupling partner such as a tributyl(1-ethoxyvinyl)stannane or under standard Stille conditions employing a catalyst such as tris(dibenzylidineacetone)dipalladium and a ligand such as DPPF at elevated temperatures to afford compounds represented by formula 51. The vinyl group of 51 can be subjected to a hydrogenation in the presence of palladium on carbon to provide compounds represented by formula 52. Alternatively, of R is an alkoxy group, 51 can be subjected to hydrolysis with an aqueous acid such as HCl to provide ketone compounds represented by formula 53. If R¹ contains an amine group or another functional group that is protected, the protecting group is removed by treating the substrate with the appropriate reagents as described in Protective Groups in Organic Synthesis (Greene, Wuts; 3rd ed., 1999, John Wiley & Sons, Inc.) to provide deprotected compounds of the formula 52 and 53.

Scheme 9

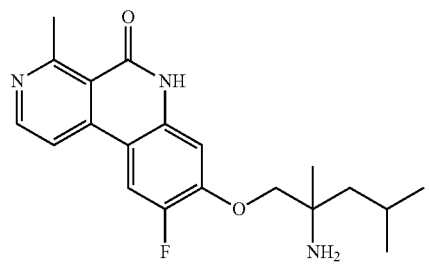

The compounds represented by formula 54 are prepared by methods outlined in Scheme 9. The constrained lactam ether, 53, synthesized as shown in Scheme 8, can be treated with a Grignard reagent in a solvent such as diethyl ether or THF to provide compounds represented by formula 54. If R¹ contains an amine group or another functional group that is protected, the protecting group is removed by treating the substrate with the appropriate reagents as described in Protective Groups in Organic Synthesis (Greene, Wuts; 3rd ed., 1999, John Wiley & Sons, Inc.) to provide deprotected compounds of the formula 54.

Scheme 10

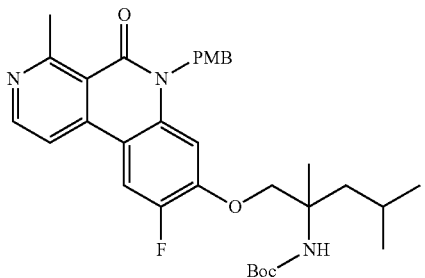

The compounds represented by formula 56-58 are prepared by methods outlined in Scheme 10. The constrained lactam ether, 50, synthesized as shown in Scheme 8, can be subjected to cyanation employing a standard Negishi coupling using $Zn(CN)_2$ and a catalyst such as $Pd(PPh_3)_4$ in solvent such as DMF, or using CuCN at temperatures ranging from 50 to 120° C. to yield compounds represented by formula 55. Nitrile compound 55 can be hydrolyzed with aqueous HCl at elevated temperatures followed by ester formation with thionyl or oxalyl chloride followed by quenching with an alcohol to afford compounds represented by formula 57. Alternatively, nitrile compound 55 can be hydrolyzed to the amide by employing a base such as cesium carbonate in a solvent such as DMF at temperatures ranging from 100-120° C. to provide compounds represented by formula 58. If $R^1$ contains an amine group or another functional group that is protected, the protecting group is removed by treating the substrate with the appropriate reagents as described in Protective Groups in Organic Synthesis (Greene, Wuts; 3rd ed., 1999, John Wiley & Sons, Inc.) to provide compounds of formula 56-58.

Scheme 11

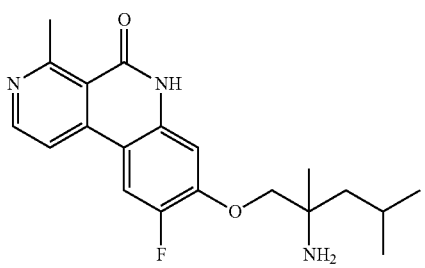

The compounds represented by formula 60-62 are prepared by methods outlined in Scheme 11. The constrained lactam ether, 50, synthesized as shown in Scheme 8, can be subjected to copper catalyzed trifluoromethylation by employing copper(I) iodide and trimethyl(trifluoromethyl)silane in a solvent such as NMP at high temperatures to afford compounds represented by formula 59. Alternatively, halo compound 50 can be subjected to copper-catalyzed coupling employing copper(I) iodide, 1H-pyrazole, N1, N2-dimethylethane-1,2-diamine, and a base such as potassium phosphate in a solvent such as DMF and 1,4-dioxane at high temperatures to afford compounds represented by formula 60. Alternatively, halo compound 50 can be subjected to copper catalyzed methoxylation employing copper(I) iodide, L-proline, sodium methoxide, and a base such as potassium carbonate in a solvent such as DMSO at elevated temperatures to afford compounds represented by formula 61. Alternatively, halo compound 50 can be subjected to copper catalyzed sulfoxylation employing copper(I) iodide, L-proline, methanesulfinic acid sodium salt, and a base such as sodium hydroxide in a solvent such as DMSO at elevated temperatures to afford compounds represented by formula 62. If $R^1$ contains an amine group or another functional group that is protected, the protecting group is removed by treating the substrate with the appropriate reagents as described in Protective Groups in Organic Synthesis (Greene, Wuts; 3rd ed., 1999, John Wiley & Sons, Inc.) to provide compounds of formula 60-62.

Scheme 12

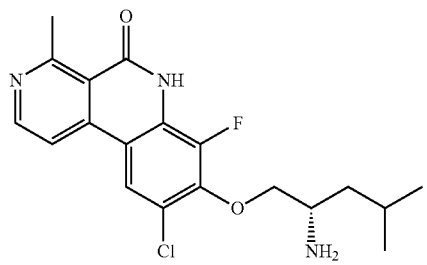

Intermediates represented by formula 65 are prepared by methods outlined in Scheme 12. The biaryl amide 11, prepared as described in Scheme 2, can be subjected to oxidation with m-CPBA in a solvent such as DCM to afford compounds represented by formula 63. Intermediates 63 can be treated with $POCl_3$ followed by sodium methoxide in methanol to afford intermediates represented by formula 65.

Scheme 13

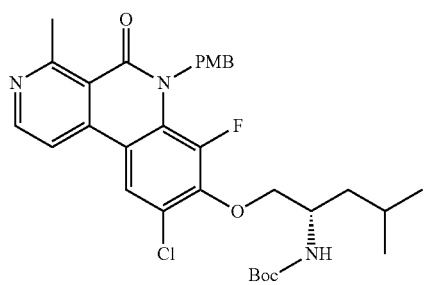

The intermediates represented by formula 67 are prepared by methods outlined in Scheme 13. The biaryl amides 11, prepared as described in Scheme 2, can be subjected to oxidation with selenium dioxide in a solvent such as AcOH to afford compounds represented by formula 66. Intermediates 66 can be treated with bis-(2-methoxyethyl)aminosulfur trifluoride in a solvent such as DCM to afford intermediates represented by formula 67.

Scheme 14

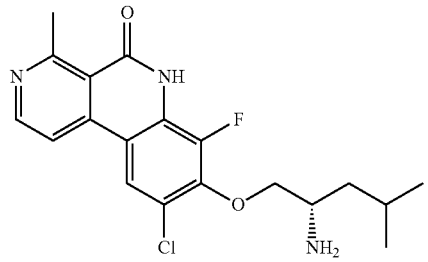

The intermediates represented by formula 68 are prepared by methods outlined in Scheme 14. Biaryl amides 8, prepared as described in Scheme 1, can be subjected to alkylation with an alkyl halide in the presence of a base such as NaH or potassium carbonate in a solvent such as DMF, or in the case of $R^1$=$CH_2CH_2OH$, the amide can be subjected to ethyl carbonate in the presence of 18-crown-6 and a base such as potassium carbonate to afford intermediates represented by formula 68.

Scheme 15

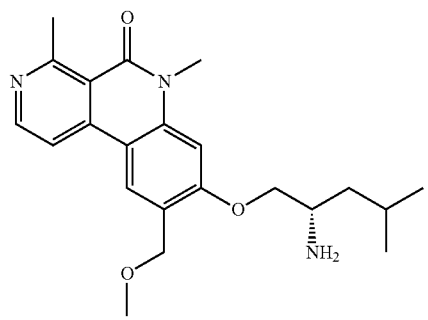

The intermediates represented by formula 71 and 72 are prepared by methods outlined in Scheme 15. The biaryl amide 11, prepared as described in Scheme 2, can be subjected to halogenation by employing N-halosuccinimide in polar aprotic solvents such as acetonitrile in the dark to yield halides 69. Compounds 69 can be treated with copper (I) iodide and potassium hydroxide in the presence of 1,10-phenanthroline to afforded intermediates represented by the formula 70. Intermediates 70 can be treated with sodium 2-chloro-2,2-difluoroacetate and a base such as potassium carbonate to afford intermediated represented by the formula 71. Alternatively, compounds 70 can be treated with a base such as sodium hydride and an alkylating agent such as methyl iodide in a solvent such as DMF to afforded intermediates represented by the formula 72.

Scheme 16

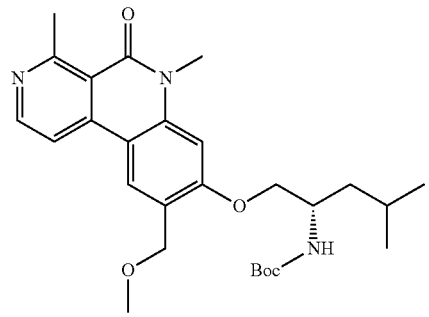

The compounds represented by formula 74 and 75 are prepared by methods outlined in Scheme 16. The intermediate 73, prepared as described in Scheme 2, can be subjected to alkylation with methyl iodide and a base such as sodium hydride in a solvent such as DMF, followed by deprotection with TFA or HCl to afford compounds of the formula 74. Alternatively, intermediate 73 can be deprotected with TFA or HCl, followed by treatment with formaldehyde in formic acid to afford compounds of the formula 75.

Scheme 17

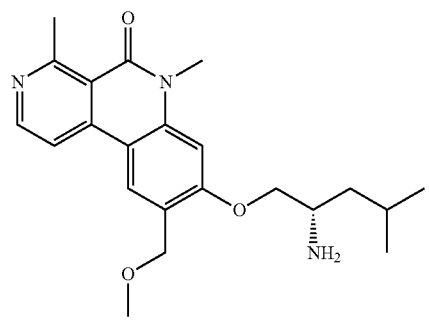

Intermediate 80 is prepared by methods outlined in Scheme 17. Intermediate 80 can be esterified by treatment with TMS-diazomethane in a solvent such as THF at low temperature, or by converting the acid to the acid chloride with thionyl chloride or oxalyl chloride and quenching with an alcohol such as MeOH or EtOH to provide ester 77.

Intermediate 77 can be subjected to osmium tetroxide and sodium periodate in the presence of 2,6-lutidine in a solvent such as 1,4-dioxane and water to afford intermediate 78. Intermediate 78 can be treated with DAST to provide intermediate 79. Intermediate 79 can be subjected to reduction with a reagent such as lithium aluminum hydride or lithium borohydride in a solvent such as THF to provide intermediate 80.

Scheme 18

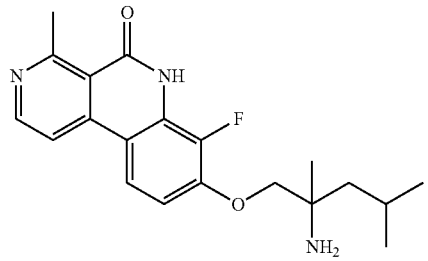

Intermediate 83 is prepared by methods outlined in Scheme 18. Intermediate 81 can be esterified by treatment with HCl in EtOH to provide ester 82. Intermediate 82 can be subjected to reduction with a reagent such as lithium aluminum hydride or sodium borohydride in a solvent such as THF to provide intermediate 83.

Scheme 19

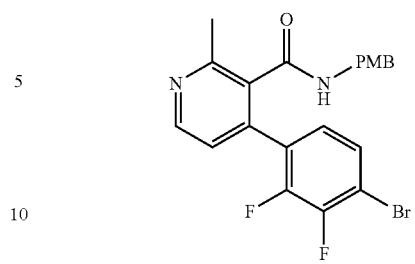

Intermediate 90 is prepared by methods outlined in Scheme 19. Intermediate 84 can be esterified by treatment with TMSCl in MeOH to provide ester 85. Intermediate 85 can be treated with Boc$_2$O and DMAP in a solvent such as acetonitrile to afford intermediate 86. Intermediate 86 can be subjected to reduction with a reagent such as DIBAL in a solvent such as THF or diethyl ether to provide intermediate 87. Intermediate 87 can be mono-deprotected by treatment with LiBr in acetonitrile to afford intermediate 88. Intermediate 88 can be subjected to sodium 2-chloro-2,2-difluoroacetate in DMF to afford intermediate 89. Intermediate 89 can be reduced with LiBH$_4$ in THF to afford intermediate 90.

Various analogues synthesized using Schemes 1-19 are listed in Table 1. AAK1 functional potency for select compounds are listed as IC$_{50}$ ranges where a=<1 nM; b=1-10 nM; c=10.01-100 nM; d=100.01-2000 nM.

TABLE 1

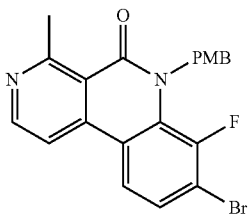

| Ex. | stereo-chem | R$^1$ | R$^2$ | R$^3$ | R$^4$ | R$^5$ | (M + H)$^+$ | AAK1 IC$_{50}$ (nM) | cell IC$_{50}$ (nM) |
|---|---|---|---|---|---|---|---|---|---|
| 1 | S | H | H | H | H | 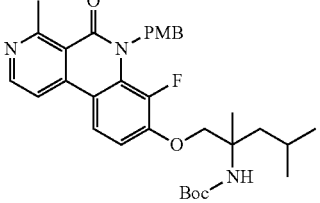 | 312.2 | 5.7 | 14 |
| 2 | S | Me | H | H | H | 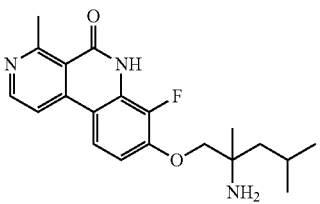 | 326.2 | b | 7.0 |

TABLE 1-continued
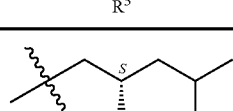
| Ex. | stereo-chem | R¹ | R² | R³ | R⁴ | R⁵ | (M + H)⁺ | AAK1 IC$_{50}$ (nM) | cell IC$_{50}$ (nM) |
|---|---|---|---|---|---|---|---|---|---|
| 3 | S | Me | H | H | Br | 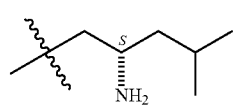 | 404.0 | 2.7 | 1.6 |
| 4 | S | Me | H | H | Me | 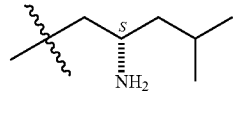 | 340.2 | b | 2.4 |
| 5 | S | Me | H | H | CN | 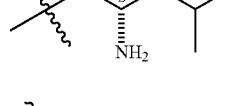 | 351.2 | b | 2.5 |
| 6 | S | Me | H | H | cycPr | 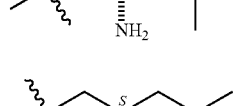 | 366.2 | b | 2.1 |
| 7 | S | Me | H | H | OH | 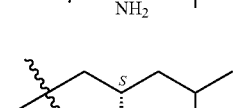 | 342.2 | 11 | — |
| 8 | S | i-Pr | H | H | H | 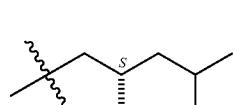 | 354.2 | c | — |
| 9 | S | allyl | H | H | H | 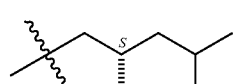 | 352.2 | 9.7 | 24 |
| 10 | S | Me | H | Cl | Cl | 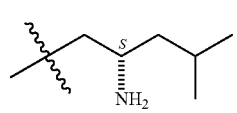 | 394.2 | c | 29 |
| 11 | S | Bn | H | H | H | 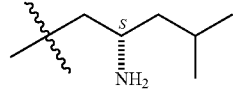 | 402.2 | 73 | — |
| 12 | S | CH₂CH₂OMe | H | H | H |  | 370.2 | 85 | — |
| 13 | S | CH₂-cyc-Pr | H | H | H |  | 366.2 | c | — |

TABLE 1-continued

| Ex. | stereo-chem | R¹ | R² | R³ | R⁴ | R⁵ | (M + H)⁺ | AAK1 IC$_{50}$ (nM) | cell IC$_{50}$ (nM) |
|---|---|---|---|---|---|---|---|---|---|
| 14 | S | Me | H | H | F | (S)-CH$_2$CH(NH$_2$)CH$_2$CH(CH$_3$)$_2$ | 344.2 | 7.0 | b |
| 15 | RS | Me | H | H | H | CH$_2$CH(NH$_2$)CH$_2$CH$_2$CF$_3$ | 366.1 | c | c |
| 16 | S | Me | 4-Me | H | H | (S)-CH$_2$CH(NH$_2$)CH$_2$CH(CH$_3$)$_2$ | 340.2 | c | c |
| 17 | S | Me | 4-NH$_2$ | H | H | (S)-CH$_2$CH(NH$_2$)CH$_2$CH(CH$_3$)$_2$ | 341.2 | 3.0 | b |
| 18 | S | Me | 2-NHAc | H | H | (S)-CH$_2$CH(NH$_2$)CH$_2$CH(CH$_3$)$_2$ | 383.2 | d | — |
| 19 | R | Me | 4-Me | H | H | (R)-CH$_2$CH(NH$_2$)CH$_2$CH(CH$_3$)$_2$ | 340.2 | c | c |
| 20 | R | Me | 4-Me | H | Cl | (R)-CH$_2$CH(NH$_2$)CH$_2$CH(CH$_3$)$_2$ | 374.2 | b | b |
| 21 | S | Me | 4-Me | H | H | (S)-CH$_2$CH(NH$_2$)CH$_2$-cyclopropyl | 338.2 | 23 | — |
| 22 | S | Me | 4-Me | H | H | (S)-CH$_2$CH(NH$_2$)CH$_2$-cyclobutyl | 352.3 | 12 | — |
| 23 | S | Me | 4-Me | H | Cl | (S)-CH$_2$CH(NH$_2$)CH$_2$-cyclopropyl | 372.2 | 0.12 | b |
| 24 | S | Me | 4-Me | H | Cl | (S)-CH$_2$CH(NH$_2$)CH$_2$-cyclobutyl | 386.2 | b | b |

TABLE 1-continued
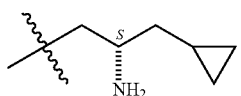
| Ex. | stereo-chem | R¹ | R² | R³ | R⁴ | R⁵ | (M + H)⁺ | AAK1 IC$_{50}$ (nM) | cell IC$_{50}$ (nM) |
|---|---|---|---|---|---|---|---|---|---|
| 25 | S | Me | 4-Me | H | Me | 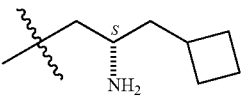 | 366.3 | 0.55 | b |
| 26 | S | Me | 4-Me | H | Me | 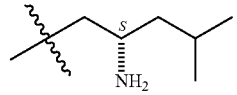 | 352.2 | 2.9 | b |
| 27 | S | Me | 4-Me | H | CHF$_2$ | 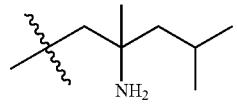 | 390.2 | a | 0.3 |
| 28 | RS | Me | H | H | H | 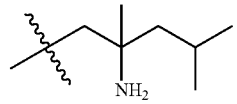 | 340.0 | 1.1 | — |
| 29 | RS | Me | 4-Me | F | H | 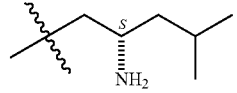 | 372.0 | d | — |
| 30 | Dia-1 | Me | 4-Me | H | CH(OH)Me | 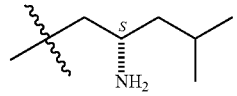 | 384.2 | 1.7 | — |
| 31 | Dia-2 | Me | 4-Me | H | CH(OH)Me | 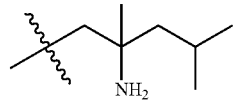 | 384.2 | c | — |
| 32 | RS | Me | 4-Me | H | H | 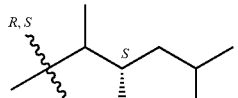 | 354.2 | 3.9 | c |
| 33 | Dia mix | Me | 4-Me | H | H | 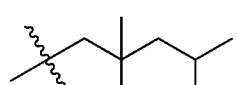 | 354.0 | c | 11 |
| 34 | RS | Me | 4-Me | H | OCH3 | 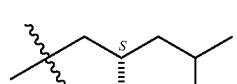 | 384.2 | 5.9 | — |
| 35 | S | Me | 4-Me | H | C(OH)Me$_2$ |  | 398.0 | 114 | — |

TABLE 1-continued

| Ex. | stereo-chem | R¹ | R² | R³ | R⁴ | R⁵ | (M + H)⁺ | AAK1 IC$_{50}$ (nM) | cell IC$_{50}$ (nM) |
|---|---|---|---|---|---|---|---|---|---|
| 36 | S | Me | 4-Me | H | Et | (S)-CH(Me)CH$_2$CH(Me)$_2$ with NH$_2$ | 368.4 | 0.35 | — |
| 37 | Ent-1 | Me | 4-Me | H | H | C(Me)$_2$CH$_2$CH(Me)$_2$ with NH$_2$ | 354.2 | 3.9 | c |
| 38 | Ent-2 | Me | 4-Me | H | H | C(Me)$_2$CH$_2$CH(Me)$_2$ with NH$_2$ | 354.2 | 13 | — |
| 39 | S | Me | H | H | H | (S)-CH(Me)CH$_2$CH(Me)$_2$ with NMe$_2$ | 354.0 | c | — |
| 40 | S | Me | 4-Me | H | H | (S)-CH(Me)CH$_2$CH(Me)$_2$ with NMe$_2$ | 368.0 | 123 | — |
| 41 | RS | Me | 4-Me | H | Cl | C(Me)$_2$CH$_2$CH(Me)$_2$ with NH$_2$ | 388.0 | 0.64 | 3.3 |
| 42 | S | Me | 4-OCH3 | H | H | (S)-CH(Me)CH$_2$CH(Me)$_2$ with NH$_2$ | 356.0 | d | — |
| 43 | S | Me | H | H | Cl | (S)-CH(Me)CH$_2$CH(Me)$_2$ with NH$_2$ | 360.2 | b | 5.0 |
| 44 | S | CH$_2$CH$_2$OH | H | H | H | (S)-CH(Me)CH$_2$CH(Me)$_2$ with NH$_2$ | 356.2 | 41 | — |
| 45 | S | CH$_2$CF$_3$ | H | H | H | (S)-CH(Me)CH$_2$CH(Me)$_2$ with NH$_2$ | 394.2 | 29 | — |
| 46 | S | Me | H | H | Et | (S)-CH(Me)CH$_2$CH(Me)$_2$ with NH$_2$ | 354.2 | b | 3.1 |

TABLE 1-continued

| Ex. | stereo-chem | R$^1$ | R$^2$ | R$^3$ | R$^4$ | R$^5$ | (M + H)$^+$ | AAK1 IC$_{50}$ (nM) | cell IC$_{50}$ (nM) |
|---|---|---|---|---|---|---|---|---|---|
| 47 | S | Me | H | H | iPr | (S)-CH$_2$CH(NH$_2$)CH$_2$CH(CH$_3$)$_2$ | 368.2 | 4.5 | c |
| 48 | S | Me | H | H | 5-oxazole | (S)-CH$_2$CH(NH$_2$)CH$_2$CH(CH$_3$)$_2$ | 393.2 | b | 1.8 |
| 49 | S | H | 4-Me | H | Br | (S)-CH$_2$CH(NH$_2$)CH$_2$CH(CH$_3$)$_2$ | 402.0 | b | 0.6 |
| 50 | S | Me | 4-NHPMB | H | H | (S)-CH$_2$CH(NH$_2$)CH$_2$CH(CH$_3$)$_2$ | 461.0 | 33 | — |
| 51 | S | Me | H | H | 4-F—Ph | (S)-CH$_2$CH(NH$_2$)CH$_2$CH(CH$_3$)$_2$ | 420.0 | d | — |
| 52 | S | Me | 4-NH2 | H | F | CH$_2$CH(NH$_2$)CH$_2$CH$_2$CF$_3$ | 359.2 | b | 2.4 |
| 53 | S | Me | H | H | H | (S)-CH$_2$CH(NH$_2$)CH$_2$OiPr | 342.2 | 119 | — |
| 54 | S | Me | H | H | H | (S)-CH$_2$CH(NHMe)CH$_2$CH(CH$_3$)$_2$ | 340.2 | c | — |
| 55 | S | Me | H | H | H | (S)-CH$_2$CH(NH$_2$)CH$_2$CF$_2$H | 348.2 | c | — |
| 56 | RS | Me | H | H | CN | CH$_2$CH(NH$_2$)CH$_2$CH$_2$CF$_3$ | 391.2 | b | b |
| 57 | RS | Me | H | H | H | CH$_2$-(2-piperidinyl) | 324.2 | 229 | — |

TABLE 1-continued

| Ex. | stereo-chem | R¹ | R² | R³ | R⁴ | R⁵ | (M + H)⁺ | AAK1 IC$_{50}$ (nM) | cell IC$_{50}$ (nM) |
|---|---|---|---|---|---|---|---|---|---|
| 58 | Ent-1 | Me | H | H | H | (isobutyl, quaternary C-Me, NH$_2$) | 340.0 | 11 | c |
| 59 | Ent-2 | Me | H | H | H | (isobutyl, quaternary C-Me, NH$_2$) | 340.0 | b | c |
| 60 | S | Me | 4-CHF2 | H | H | (S, isobutyl, NH$_2$) | 376.2 | d | — |
| 61 | S | Me | 4-Me | Cl | H | (S, isobutyl, NH$_2$) | 373.8 | 126 | — |
| 62 | S | Me | 4-Me | H | Cl | (S, isobutyl, NH$_2$) | 373.8 | b | b |
| 63 | S | Me | 4-Me | H | Me | (S, isobutyl, NH$_2$) | 353.9 | b | b |
| 64 | S | Me | 4-Me | H | CN | (S, isobutyl, NH$_2$) | 365.2 | a | 0.6 |
| 65 | S | Me | 4-Me | H | CN | (isobutyl, quaternary C-Me, NH$_2$) | 379.0 | a | b |
| 66 | S | Me | 2-Me | H | Br | (isobutyl, quaternary C-Me, NH$_2$) | 418.0 | d | — |
| 67 | S | Me | 2-Me | H | H | (S, isobutyl, NH$_2$) | 340.2 | 893 | — |
| 68 | S | Me | 2-Me | H | Cl | (S, isobutyl, NH$_2$) | 373.8 | c | — |

TABLE 1-continued
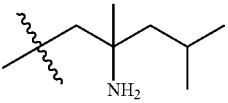
| Ex. | stereo-chem | $R^1$ | $R^2$ | $R^3$ | $R^4$ | $R^5$ | $(M + H)^+$ | AAK1 $IC_{50}$ (nM) | cell $IC_{50}$ (nM) |
|---|---|---|---|---|---|---|---|---|---|
| 69 | S | Me | H | H | H | 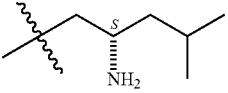 | 314.2 | c | — |
| 70 | S | Me | 4-Me | H | F | 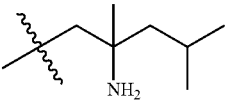 [SMILES: *CC(C)(N)CC(C)C] | 358.2 | b | b |
| 71 | S | Me | 4-Me | H | CH2OH | 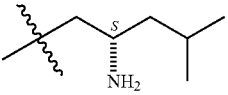 | 370.2 | b | — |
| 72 | S | Me | 4-Me | H | 5-oxazole | 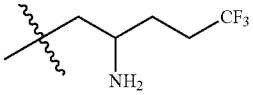 | 407.2 | a | a |
| 73 | RS | Me | 4-Me | H | CN | 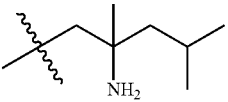 | 405.4 | b | b |
| 74 | S | Me | 4-Me | H | N-pyrazole | 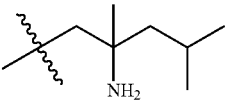 | 406.2 | b | — |
| 75 | S | Me | 4-Me | H | $CF_3$ | 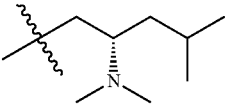 [SMILES: *C[C@H](CC(C)C)N(C)C] | 408.2 | b | b |
| 76 | S | Me | 4-Me | H | $SO_2Me$ | 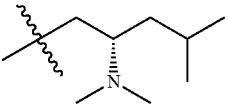 [SMILES: *C[C@H](CC(C)C)N(C)C] | 466.1 | d | — |
| 77 | S | H | 4-Me | H | H | 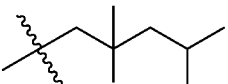 | 326.2 | b | — |
| 78 | R | Me | 4-Me | H | CN | 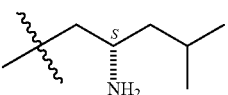 | 365.2 | 0.8 | b |
| 79 | S | $CH_2CH_2OMe$ | 4-Me | H | Cl |  | 384.2 | b | — |

TABLE 1-continued
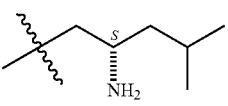
| Ex. | stereo-chem | R¹ | R² | R³ | R⁴ | R⁵ | (M + H)⁺ | AAK1 IC$_{50}$ (nM) | cell IC$_{50}$ (nM) |
|---|---|---|---|---|---|---|---|---|---|
| 80 | S | CH$_2$CH$_2$OMe | 4-Me | H | H | 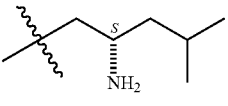 | 418.2 | 134 | — |
| 81 | S | Me | 4-Me | F | H | 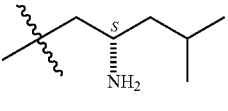 | 358.2 | d | — |
| 82 | S | H | 4-Me | F | H | 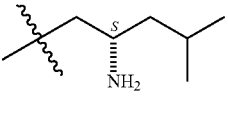 | 342.2 | 150 | — |
| 83 | S | Me | 4-Me | H | 5-thiazole | 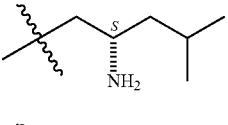 | 423.2 | b | b |
| 84 | S | Me | 4-Me | H | CO$_2$Me | 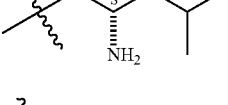 | 398.2 | b | — |
| 85 | S | Me | 1-F | H | H | 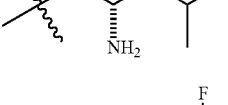 | 344.2 | c | — |
| 86 | S | Me | 4-Me | H | 2-pyridyl | 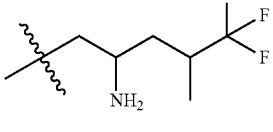 | 417.6 | c | c |
| 87 | Dia-1 | Me | 4-Me | H | H | 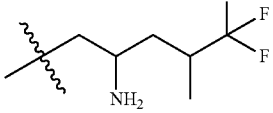 | 394.6 | b | — |
| 88 | Dia-2 | Me | 4-Me | H | H | 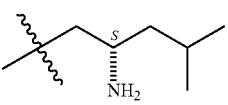 | 394.6 | b | c |
| 89 | S | Me | 4-Me | H | OMe | 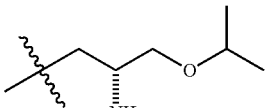 | 370.2 | b | — |
| 90 | S | Me | 4-Me | H | OCHF$_2$ |  | 406.2 | c | — |

TABLE 1-continued

| Ex. | stereo-chem | R¹ | R² | R³ | R⁴ | R⁵ | (M + H)⁺ | AAK1 IC$_{50}$ (nM) | cell IC$_{50}$ (nM) |
|---|---|---|---|---|---|---|---|---|---|
| 91 | Ent-1 | Me | 4-Me | H | H | (S)-isobutyl-CH(NHMe)-CH₂- | 366.1 | c | — |
| 92 | Ent-2 | Me | 4-Me | H | H | (S)-CF₂Me-CH₂-CH(NH₂)-CH₂- | 366.1 | b | — |
| 93 | RS | Me | H | H | H | CF₃-CH₂-CH(NH₂)-CH₂- | 352.0 | c | — |
| 94 | S | Me | 4-Me | H | CONH₂ | piperidin-2-yl-CH₂- | 383.2 | c | — |
| 95 | S | Me | 4-Me | H | H | Me₂C(NH₂)-CH₂-iPr | 354.0 | c | — |
| 96 | S | Me | 4-Me | H | CONMe₂ | (S)-isobutyl-CH(NH₂)-CH₂- | 411.2 | d | — |
| 97 | RS | Me | 1-F | H | H | Me-C(NH₂)-CH₂-iPr | 358.2 | b | c |
| 98 | S | Me | 1-OCH₃ | H | H | (S)-isobutyl-CH(NH₂)-CH₂- | 356.0 | d | — |
| 99 | S | H | 4-Me | OCH₃ | H | (S)-isobutyl-CH(NH₂)-CH₂- | 356.2 | d | — |
| 100 | S | H | 4-Me | F | Br | (S)-isobutyl-CH(NH₂)-CH₂- | 423.0 | b | — |
| 101 | S | H | 4-Me | H | F | (S)-isobutyl-CH(NHMe)-CH₂- | 344.0 | b | 5.2 |

TABLE 1-continued

| Ex. | stereo-chem | R¹ | R² | R³ | R⁴ | R⁵ | (M + H)⁺ | AAK1 IC$_{50}$ (nM) | cell IC$_{50}$ (nM) |
|---|---|---|---|---|---|---|---|---|---|
| 102 | RS | H | 4-Me | H | F | (4-methylpentan-2-yl with NH₂, quaternary C) | 358.0 | b | — |
| 103 | S | H | 4-Me | F | Cl | (S)-4-methylpentan-2-yl-NH₂ | 378.0 | b | c |
| 104 | S | Me | 4-Me | H | CH₂OMe | (S)-4-methylpentan-2-yl-NH₂ | 384.2 | c | — |
| 105 | RS | H | 4-Me | F | H | CH₂OMe with NH₂ | 358.0 | c | — |
| 106 | S | Me | 4-Me | H | CN | 5,5-difluoropent-4-en-2-yl-NH₂ | 385.3 | a | a |
| 107 | S | Me | 4-Me | F | Cl | (S)-4-methylpentan-2-yl-NH₂ | 392.2 | b | — |

DESCRIPTION OF THE SPECIFIC EMBODIMENTS

In the following examples, proton NMR spectra were recorded on either a Bruker 400 or 500 MHz NMR spectrometer. Chemical shifts are reported in δ values relative to tetramethylsilane. LC/MS were run on a Shimadzu LC coupled to a Waters Micromass ZQ. HPLC retention times were obtained using at least one of the following methods:

LC-MS methods:

LC/MS Method A: Column: PUROSPHER@star RP-18 (4×55 mm), 3 µm; Buffer: 20 mM NH₄OAC IN WATER; Mphase A: Buffer+ACN (90+10); Mphase B: Buffer+MeCN (10+90); Flow: 2.5 mL/min)

LC/MS Method B: Column: ZORBAX SB C18 (46×50 mm), 5 µm; Positive mode Mphase A: 10% MeOH-90% H₂O-0.1% TFA; Mphase B: 90% MeOH-10% H₂O-0.1% TFA; Flow: 5 mL/min)

LC/MS Method C: Column—Ascentis Express C8 (5×2.1 mm), 2.7 µm; Mphase A: 2% MeCN-98% H₂O-10 mM NH₄COOH; Mphase B: 98% ACN-2% H2O-10 mM NH₄COOH; Flow: 1 mL/min)

LC/MS Method D: Column—ACQUITY UPLC BEH C18 (2.1×50 mm), 1.7 µm; Mphase A: 0.1% TFA in water; Mphase B: 1% TFA in ACN; Flow: 1/min)

LC/MS Method E: Column—ACQUITY UPLC BEH C18 (2.1×50 mm), 1.7 µm; Mphase A: 5 mM NH₄OAc:ACN (95:5); Mphase B: 5 mM NH₄OAc:ACN (5:95); Flow: 1/min)

LC/MS Method F: Column: X-Bridge BEH C18 (50×2.1 mm), 2.5 µm; Mphase A: ACN+H₂O (2+98)+0.1% TFA; Mphase B: ACN+H₂O (98+2)+0.05% TFA; Flow: 1.2 mL/min.

LC-MS method G: Column: Kinetex C18 (50×2.1 mm), 2.6 um: Mphase A: 2% ACN-98% H₂O-10 mM; Mphase B: 98% ACN-2% H₂O-10 mM NH₄COOH; Flow: 1/min).

LC-MS method H: Column: BEH C18 (50×3.0 mm), 1.7 µm: Mphase A: 5% ACN-95% H₂O-10 mM; Mphase B: 95% ACN-5% H₂O-10 mM NH₄COOH; Flow: 1.2/min).

LC-MS method I: Column: Ace Excel 2 C18 (50×3.0 mm), 2.0 µm: Mphase A: 2% ACN-98% H₂O-10 mM; Mphase B: 98% ACN-2% H₂O-10 mM NH₄COOH; Flow: 1.2/min).

Chiral HPLC methods:

Method A: CHIRALCEL OJH (250×4.6) mm 5 micron Mob. phase: 0.2% DEA in n-hexane:ethanol (80:20)

Method B: CHIRALPAK AD-H (250×4.6) mm 5 micron Mob. Phase A: 0.2% DEA in n-hexane (70) B: ethanol (30)

Method C: CHIRALPAK-ASH (250×4.6) mm 5 micron Mob. Phase A: 0.2% DEA in n-hexane:ethanol (90:10)

Analytical HPLC methods:

Method A: Waters analytical C18 sunfire column (4.6×150 mm, 3.5 μm); mobile phase:
Buffer: 0.05% TFA in H$_2$O pH=2.5 adjusted with ammonia
A=buffer and acetonitrile (95:5), B=acetonitrile and buffer (95:5); 0-15 min, 0% B→50% B; 15-18 min, 50% B→100% B; 18-23 min, 100% B; flow rate=1 mL/min; λ=254 nm and 220 nm; run time=28 min.

Method B: Waters analytical phenyl xbridge column (4.6×150 mm, 3.5 μm), mobile phase: Buffer: 0.05% TFA in H$_2$O pH=2.5 adjusted with ammonia
A=buffer and acetonitrile (95:5), B=acetonitrile and buffer (95:5); 0-15 min, 0% B→50% B; 15-18 min, 50% B→100% B; 18-23 min, 100% B; flow rate=1 mL/min; λ=254 nm and 220 nm; run time=28 min.

Method C: Waters analytical C18 sunfire column (3.0×150 mm, 3.5 μm); mobile phase: A=10 mM amm. bicarbonate (pH=9.5)/95% H2O/5% methanol, B=10 mM amm. bicarbonate (pH=9.5)/5% H$_2$O/95% methanol; 0-15 min, 0% B→100% B; 15-18 min, 100% B; flow rate=1 mL/min; λ=254 nm; run time=18 min.

Method D: Waters analytical phenyl xbridge column (3.0×150 mm, 3.5 μm), mobile phase: A=10 mM amm. bicarbonate (pH=9.5)/95% H2O/5% methanol, B=10 mM amm. bicarbonate (pH=9.5)/5% H2O/95% methanol; 0-15 min, 0% B→100% B; 15-18 min, 100% B; flow rate=1 mL/min; λ=254 nm; run time=18 min.

Example 1

(S)-8-(2-amino-4-methylpentyloxy)benzo[c][2,7]naphthyridin-5(6H)-one

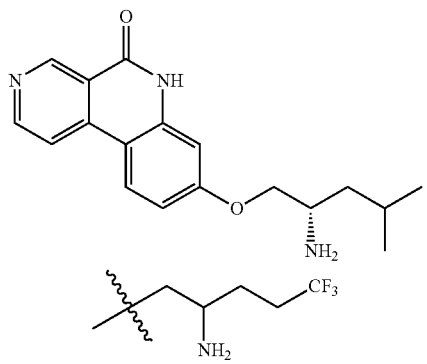

Part A. Methyl 4-chloronicotinate

A solution of 4-chloronicotinic acid (20 g, 127 mmol) in dichloromethane (600 mL) and DMF (15 mL), cooled to 0° C., was treated with oxalyl chloride (27.8 mL, 317 mmol) dropwise. After addition, the mixture was stirred for another 2 h at RT. The mixture was then cooled back to 0° C. and MeOH (30 mL) was added slowly. The reaction was warmed to RT and stirred for 0.5 h. The mixture was diluted with dichloromethane (500 mL) and saturated aqueous NaHCO$_3$ (100 mL) then extracted with DCM (3×1000 mL). The DCM layer was washed with brine (2×100 mL), dried over sodium sulfate and concentrated under reduced pressure. The crude product obtained as yellow oil (20 g, 92% yield) was taken to the next step without further purification. LC/MS (ESI) m/e 172.0 [(M+H)$^+$, calcd for C$_7$H$_7$ClNO$_2$: 172.6]; LC/MS retention time (method B): t$_R$=1.21 min. $^1$H NMR (400 MHz, CDCl$_3$) δ ppm 9.27 (s, 1H), 8.86 (bs, 1H), 7.98 (bs, 1H), 4.05 (s, 3H).

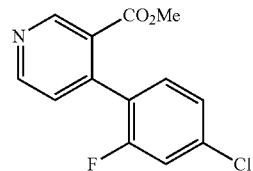 [SMILES: COC(=O)c1cnccc1-c1ccc(Cl)cc1F]

Part B. Methyl 4-(4-chloro-2-fluorophenyl)nicotinate

Methyl 4-chloronicotinate (20 g, 117 mmol), (4-chloro-2-fluorophenyl)boronic acid (22.4 g, 128 mmol), Pd(Ph$_3$P)$_4$ (9.4 g, 8.16 mmol) and Cs$_2$CO$_3$ (114 g, 350 mmol) were taken in a solvent mixture of 1,4-dioxane (400 mL) and water (30 mL) and purged with nitrogen for 5 min and heated to 85° C. After overnight stirring at this temperature the reaction mixture was diluted with ethyl acetate and filtered through a bed of diatomaceous earth (Celite®). The bed was further washed with ethyl acetate. Combined filtrate was washed with water (1×100 mL), dried (Na$_2$SO$_4$) and concentrated under reduced pressure to afford the crude product which was purified via combi flash (gradient of methanol and chloroform) to afford methyl 4-(4-chloro-2-fluorophenyl)nicotinate (13 g, 48.9 mmol, 42%, with purity of 77% by LC/MS) as a brown solid. LC/MS (ESI) m/e 266.0 [(M+H)$^+$, calcd for C$_{13}$H$_{10}$ClFNO$_2$ 266.1]; LC/MS retention time (method B): t$_R$=1.69 min.

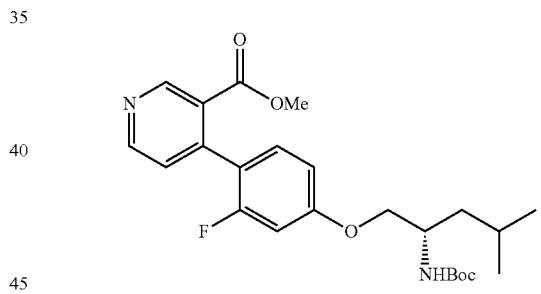

Part C. (S)-methyl 4-(4-((2-((tert-butoxycarbonyl)amino)-4-methylpentyl)oxy)-2-fluorophenyl)nicotinate Methyl 4-(4-chloro-2-fluorophenyl)nicotinate (50 mg, 0.188 mmol) in toluene (1 mL) was treated with cesium carbonate (92 mg, 0.282 mmol) and N-Boc-L-Leucinol (121 mg, 0.565 mmol). The mixture was purged with nitrogen gas for 5 min and treated with di-tert-butyl(2',4',6'-triisopropyl-[1,1'-biphenyl]-2-yl)phosphine (48.0 mg, 0.113 mmol). After purging the mixture with nitrogen for another 5 min, palladium(II)acetate (42.3 mg, 0.188 mmol) was added and nitrogen bubbled through for another 10 min. The mixture was sealed tightly and heated at 80° C. for 12 h. The mixture was filtered through a bed of diatomaceous earth (Celite®) and washed with ethyl acetate (2×3 mL). The washings were concentrated under reduced pressure. The residue was purified by combi flash (ethyl acetate and petroleum ether) to afford (S)-methyl 4-(4-((2-((tert-butoxycarbonyl)amino)-4-methylpentyl)oxy)-2-fluorophenyl)nicotinate (50 mg, 0.112 mmol, 60% yield). LC/MS (ESI) m/e 447.2 [(M+H)⁺, calcd for $C_{24}H_{32}FN_2O_5$ 447.2]; LC/MS retention time (method C): $t_R$=2.17 min.

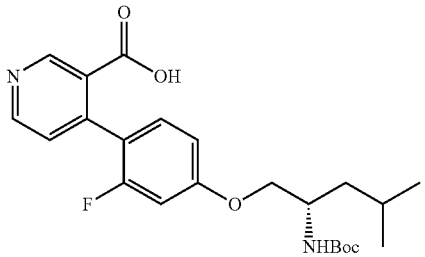 [SMILES: CC(C)C[C@@H](COc1ccc(-c2ccncc2C(=O)O)c(F)c1)NC(=O)OC(C)(C)C]

Part D. (S)-4-(4-((2-((tert-butoxycarbonyl)amino)-4-methylpentyl)oxy)-2-fluorophenyl)nicotinic Acid (S)-methyl-4-(4-((2-((tert-butoxycarbonyl)amino)-4-methylpentyl)oxy)-2-fluorophenyl)nicotinate (50.0 mg, 0.112 mmol) was taken in a mixture of tetrahydrofuran (1 mL), methanol (1 mL) and water (1 mL). To the solution was added lithium hydroxide (8.05 mg, 0.336 mmol) and the reaction mixture was stirred at RT for 2 h. The reaction mixture was concentrated under reduced pressure and the residue was diluted with water and the pH adjusted to 4 using 1.5N aqueous HCl. The crude product from the aqueous layer was extracted with ethyl acetate (3×5 mL). The combined organic layers were washed with brine (1×5 mL), dried (Na₂SO₄) and concentrated under reduced pressure to afford (S)-4-(4-((2-((tert-butoxycarbonyl)amino)-4-methylpentyl)oxy)-2-fluorophenyl)nicotinic acid (30 mg, 0.060 mmol, 53% yield) as an off-white solid. LC/MS (ESI) m/e 433.2 [(M+H)⁺, calcd for $C_{23}H_{30}FN_2O_5$ 433.2]; LC/MS retention time (method C): $t_R$=1.74 min.

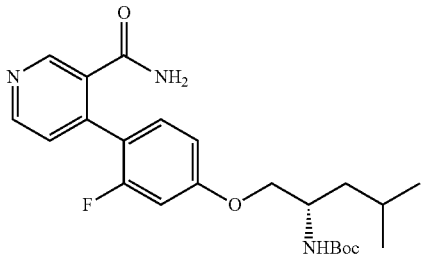 [SMILES: CC(C)C[C@@H](COc1ccc(-c2ccncc2C(N)=O)c(F)c1)NC(=O)OC(C)(C)C]

Part E. (S)-tert-butyl (1-(4-(3-carbamoylpyridin-4-yl)-3-fluorophenoxy)-4-methylpentan-2-yl)carbamate (S)-4-(4-((2-((tert-butoxycarbonyl)amino)-4-methylpentyl)oxy)-2-fluorophenyl)nicotinic acid (75 mg, 0.173 mmol) was taken in DMF (2 mL) and cooled to 0° C. To the solution was added EDC (49.9 mg, 0.260 mmol) and HOBT (53.1 mg, 0.347 mmol). After stirring the reaction mixture for 5 min, ammonium chloride (55.7 mg, 1.040 mmol) was added and the resultant mixture was stirred for 5 min. Diisopropylethylamine (0.121 mL, 0.694 mmol) was added and the mixture was allowed to stir at room temperature for an additional 12 h. The mixture was then quenched with ice and the residue was filtered and dried under vacuum to afford (S)-tert-butyl (1-(4-(3-carbamoylpyridin-4-yl)-3-fluorophenoxy)-4-methylpen-tan-2-yl)carbamate (50 mg, 0.098 mmol, 57% yield) as a light yellow solid. LC/MS (ESI) m/e 432.2 [(M+H)⁺, calcd for $C_{23}H_{31}FN_3O_4$ 432.2]; LC/MS retention time (method C): $t_R$=1.83 min.

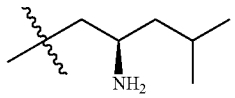 [SMILES: *C[C@H](N)CC(C)C]

Part F. (S)-tert-butyl (4-methyl-1-((5-oxo-5,6-dihydrobenzo[c][2,7]naphthyridin-8-yl)oxy)pentan-2-yl)carbamate Sodium hydride (5.56 mg, 0.232 mmol, 60% in mineral oil) was taken in tetrahydrofuran (1 mL) and cooled to 0° C. The suspension was treated with (S)-tert-butyl (1-(4-(3-carbamoylpyridin-4-yl)-3-fluorophenoxy)-4-methylpentan-2-yl)carbamate (50 mg, 0.116 mmol) in THF (1 mL) dropwise and the temperature was maintained at 0° C. for 30 min. The reaction mixture was then allowed to warm to room temperature and stirred for 2 h. The reaction was quenched with ice and extracted with ethyl acetate (3×5 mL). The combined organic layers were washed with brine (1×5 mL), dried (Na₂SO₄) and concentrated under reduced pressure to afford (S)-tert-butyl (4-methyl-1-((5-oxo-5,6-dihydrobenzo[c][2,7]naphthyridin-8-yl)oxy)pentan-2-yl)carbamate (40 mg, 0.097 mmol, 84% yield) as a colorless solid. LC/MS (ESI) m/e 412.2 [(M+H)⁺, calcd for $C_{23}H_{30}N_3O_4$ 412.2]; LC/MS retention time (method C): $t_R$=1.97 min.

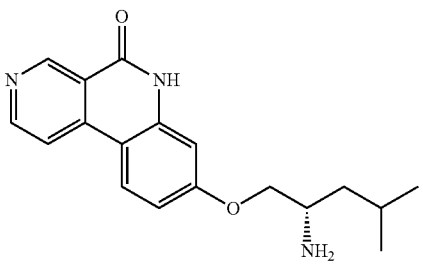 [SMILES: CC(C)C[C@H](N)COc1ccc2c(c1)[nH]c(=O)c1cnccc12]

Part G. (S)-8-(2-amino-4-methylpentyloxy)benzo[c][2,7]naphthyridin-5(6H)-one (S)-tert-butyl (4-methyl-1-((5-oxo-5,6-dihydrobenzo[c][2,7]naphthyridin-8-yl)oxy)pentan-2-yl)carbamate (10 mg, 0.024 mmol) in dichloromethane (1 mL) was cooled to 0° C. To the solution was added hydrogen chloride (0.886 mg, 0.012 mL, 0.024 mmol, 2M in diethyl ether) dropwise. The temperature of the reaction mixture was maintained at 0° C. for 30 min and then the reaction mixture was allowed to warm to room temperature and stirred for 2 h. The reaction mixture was then concentrated under reduced pressure to afford (S)-8-((2-amino-4-methylpentyl)oxy)benzo[c][2,7]naphthyridin-5(6H)-one (4 mg, 0.012 mmol, 49% yield) as a pale yellow solid. LC/MS (ESI) m/e 312.2 [(M+H)⁺, calcd for $C_{18}H_{22}N_3O_2$ 312.2]; LC/MS retention time (method A): $t_R$=1.1 min; HPLC retention time (method A): $t_R$=6.85 min; HPLC retention time (method B): $t_R$=7.51 min ¹H NMR (400 MHz, D₂O) δ ppm 9.30 (br. s., 1H), 8.77 (br. s., 1H), 8.36 (br. s., 1H), 8.07 (br. s., 1H), 6.95 (br. s., 1H), 6.72 (br. s., 1H), 4.41

(d, J=9.03 Hz, 1H), 4.26 (br. s., 1H), 3.89 (br. s., 1H), 3.38 (s, 1H), 1.72-1.88 (m, 2H), 1.05 (d, J=2.51 Hz, 6H).

Example 2

(S)-8-((2-amino-4-methylpentyl)oxy)-6-methylbenzo[c][2,7]naphthyridin-5(6H)-one

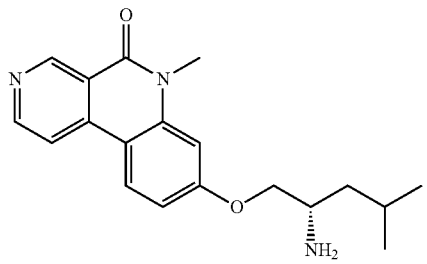

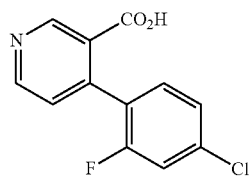

Part A. 4-(4-chloro-2-fluorophenyl)nicotinic Acid

To a solution of methyl 4-(4-chloro-2-fluorophenyl)nicotinate (15 g, 56.5 mmol) (as prepared in Ex 1, Part B) in a solvent mixture of methanol (150 mL) and water (150 mL) cooled to 0° C. was added sodium hydroxide (9.03 g, 226 mmol) and the mixture was warmed to room temperature and stirred for 1 h. The reaction mixture was concentrated under reduced pressure and pH of the resultant aqueous solution was adjusted to pH=4 using 1.5 N Hydrochloric acid during which time the product crashed out as a solid. Filtration of the mixture provided 4-(4-chloro-2-fluorophenyl)nicotinic acid (9 g, 35.8 mmol, 63% yield) as an off white solid. LC/MS (ESI) m/e 252.0 [(M+H)$^+$, calcd for $C_{12}H_8ClFNO_2$ 252.1]; LC/MS retention time (method A): $t_R$=0.97 min.

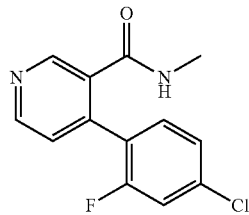 [SMILES: CNC(=O)c1cnccc1-c1ccc(Cl)cc1F]

Part B.
4-(4-chloro-2-fluorophenyl)-N-methylnicotinamide

To a solution of 4-(4-chloro-2-fluorophenyl)nicotinic acid (2 g, 7.95 mmol in dichloromethane (40 mL) cooled to 0° C. was added oxalyl chloride (2.09 mL, 23.8 mmol) followed by DMF (2 mL). The reaction mixture was allowed to warm to room temperature and stirred for 2 h. The reaction mixture was concentrated under reduced pressure and treated with dichloromethane (25 mL). This solution was added to a mixture of methylamine hydrochloride (5.37 g, 79 mmol) and triethylamine (11.08 mL, 79 mmol) in dichloromethane (25 mL) cooled to 0° C. The resultant mixture was stirred at room temperature for 3 h and then washed with a saturated solution of sodium bicarbonate. The organic layer was separated, dried (Na$_2$SO$_4$) and concentrated under reduced pressure to afford 4-(4-chloro-2-fluorophenyl)-N-methylnicotinamide (1.3 g, 4.91 mmol, 62%) as an off-white solid. LC/MS (ESI) m/e 265.1 [(M+H)$^+$, calcd for $C_{13}H_{11}ClFN_2O$ 265.1]; LC/MS retention time (method C): $t_R$=1.69 min.

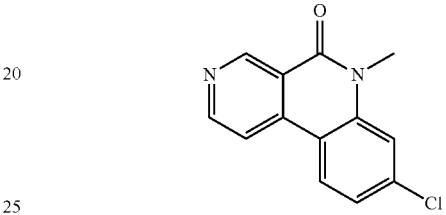

Part C. 8-chloro-6-methylbenzo[c][2,7]naphthyridin-5(6H)-one

Sodium hydride (80 mg, 3.32 mmol) was taken in THF (1 mL) and cooled to 0° C. To the suspension, 4-(4-chloro-2-fluorophenyl)-N-methylnicotinamide (440 mg, 1.66 mmol) in THF (1 mL) was added dropwise and the temperature was maintained at 0° C. for 30 min. The reaction mixture was then warmed to room temperature and stirred for 2 h. The reaction mixture was quenched with ice and extracted with ethyl acetate (3×5 mL). The combined organic layers were washed with brine (1×5 mL) dried (Na$_2$SO$_4$) and concentrated under reduced pressure to afford 8-chloro-6-methylbenzo[c][2,7]naphthyridin-5(6H)-one (440 mg, 1.798 mmol) as a light brown oil. LC/MS (ESI) m/e 245.1 [(M+H)$^+$, calcd for $C_{13}H_{10}ClN_2O$ 245.1]; LC/MS retention time (method C): $t_R$=1.79 min.

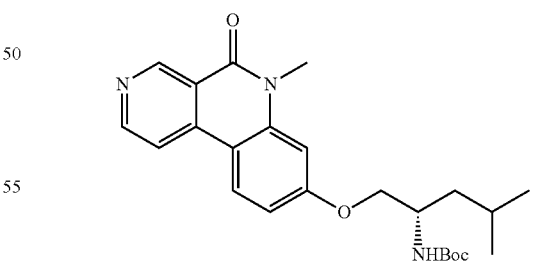

Part D. (S)-tert-butyl (4-methyl-1-((6-methyl-5-oxo-5,6 dihydrobenzo[c][2,7]naphthyridin-8-yl)oxy)pentan-2-yl)carbamate To a solution of 8-chloro-6-methylbenzo[c][2,7]naphthyridin-5(6H)-one (440 mg, 1.80 mmol) in toluene (8 mL) at room temperature, was added cesium carbonate (879 mg, 2.70 mmol) and di-tert-butyl(2',4',6'-triisopropyl-[1,1'-biphenyl]-2-yl)phosphine (458 mg, 1.079 mmol) and the mixture was degassed for 5 min. The mixture was then treated with N-Boc L-Leucinol (1160 mg, 5.39 mmol) followed by palladium(II)acetate (121 mg, 0.54 mmol) and the mixture degassed for another 10 min. The reaction mixture was sealed and heated at 80° C. After overnight stirring the reaction mixture was cooled to room temperature and filtered through diatomaceous earth (Celite®). The bed was washed with ethyl acetate and the combined filtrate was concentrated under reduced pressure to afford the crude product which was purified by combi flash (gradient of ethyl acetate and petroleum ether) to afford (S)-tert-butyl (4-methyl-1-((6-methyl-5-oxo-5,6 dihydrobenzo[c][2,7]naphthyridin-8-yl)oxy)pentan-2-yl)carbamate (190 mg, 0.34 mmol, 19% yield) as an off-white solid. LC/MS (ESI) m/e 426.2 [(M+H)$^+$, calcd for $C_{24}H_{32}N_3O_4$ 426.2]; LC/MS retention time (method C): $t_R$=2.10 min.

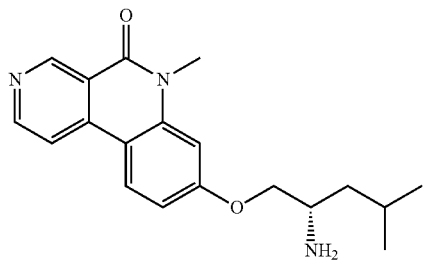 [SMILES: CC(C)C[C@H](N)COc1ccc2c3ccncc3c(=O)n(C)c2c1]

Part E. (S)-8-((2-amino-4-methylpentyl)oxy)-6-methylbenzo[c][2,7]naphthyridin-5(6H)-one To a solution of (S)-tert-butyl (4-methyl-1-((6-methyl-5-oxo-5,6-dihydrobenzo[c][2,7]naphthyridin-8-yl)oxy)pentan-2-yl)carbamate (190 mg, 0.447 mmol) in dichloromethane (4 mL) at 0° C. was added hydrogen chloride (81 mg, 0.558 mL, 2.233 mmol) in 1,4-dioxane (4 M) dropwise and the reaction mixture was stirred at 0° C. for 30 min then warmed to room temperature and allowed to stir for 2 h. The solvents were removed under reduced pressure to afford crude product which was purified by preparative HPLC (0.1% TFA in water) to afford (S)-8-((2-amino-4-methylpentyl) oxy)-6-methylbenzo[c][2,7]naphthyridin-5(6H)-one (51 mg, 0.157 mmol, 35% yield) as a yellow solid. LC/MS (ESI) m/e 326.2 [(M+H)$^+$, calcd for $C_{19}H_{24}N_3O_2$ 326.2]; LC/MS retention time (method A): $t_R$=1.21 min; HPLC retention time (method A): $t_R$=7.39 min; HPLC retention time (method B): $t_R$=7.40 min. $^1$H NMR (400 MHz, CD$_3$OD) δ ppm 9.48 (s, 1H), 8.77 (d, J=5.77 Hz, 1H), 8.43 (d, J=8.78 Hz, 1H), 8.26 (d, J=5.77 Hz, 1H), 7.09-7.16 (m, 2H), 4.20 (dd, J=9.41, 3.89 Hz, 1H), 4.02 (dd, J=9.29, 7.03 Hz, 1H), 3.81 (s, 3H), 3.35-3.39 (m, 1H), 1.81-1.91 (m, 1H), 1.41-1.56 (m, 2H), 0.98-1.05 (m, 6H).

Example 3

(S)-8-(2-amino-4-methylpentyloxy)-9-bromo-6-methylbenzo[c][2,7]naphthyridin-5(6H)-one

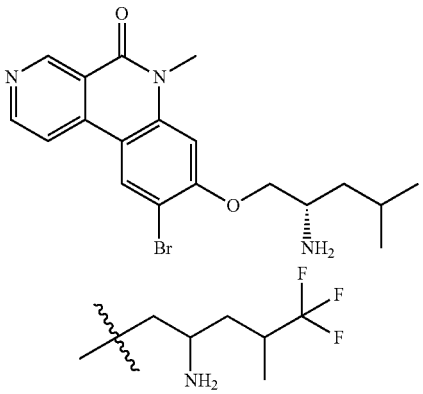

Part A. (S)-tert-butyl (1-((9-bromo-6-methyl-5-oxo-5,6-dihydrobenzo[c][2,7]naphthyridin-8-yl)oxy)-4-methylpentan-2-yl)carbamate To a solution of (S)-tert-butyl (4-methyl-1-((6-methyl-5-oxo-5,6-dihydrobenzo[c][2,7]naphthyridin-8-yl)oxy)pentan-2-yl)carbamate (0.100 g, 0.235 mmol) (as prepared in Ex. 2, Part D) in anhydrous acetonitrile (5 mL) was added N-bromosuccinimide (0.042 g, 0.235 mmol) and the mixture was heated at 85° C. for 5 h. The reaction mixture was diluted with water (10 mL), extracted with ethyl acetate (2×20 mL). The combined organic layers were dried over sodium sulfate and evaporated under reduced pressure to afford crude product which was purified by preparative TLC (gradient of ethyl acetate and petroleum ether) to afford (S)-tert-butyl (1-((9-bromo-6-methyl-5-oxo-5,6-dihydrobenzo[c][2,7]naphthyridin-8-yl)oxy)-4-methylpentan-2-yl)carbamate (80 mg, 0.159 mmol, 68% yield) as an off-white solid. LC/MS (ESI) m/e 504.2 [(M+H)$^+$, calcd for $C_{24}H_{31}BrN_3O_4$ 504.1]; LC/MS retention time (method A): $t_R$=2.23 min.

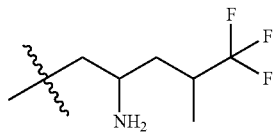

Part B. (S)-8-((2-amino-4-methylpentyl)oxy)-9-bromo-6-methylbenzo[c][2,7]naphthyridin-5(6H)-one To a solution of (S)-tert-butyl (1-((9-bromo-6-methyl-5-oxo-5,6-dihydrobenzo[c][2,7]naphthyridin-8-yl)oxy)-4-methylpentan-2-yl)carbamate (80 mg, 1.586 mmol) in anhydrous methanol (5 mL) was added a 4 M solution of HCl in 1,4-dioxane (2 mL, 8 mmol) dropwise at 0° C. The reaction mixture was warmed to room temperature and stirred for 2 h. The mixture was then was concentrated under reduced pressure to afford crude product which was purified by preparative HPLC (10 mM ammonium acetate in water; acetonitrile)

to afford (S)-8-((2-amino-4-methylpentyl)oxy)-9-bromo-6-methylbenzo[c][2,7]naphthyridin-5(6H)-one (20 mg, 0.049 mmol, 30% yield) as an off-white solid. LC/MS (ESI) m/e 404.1 [(M+H)+, calcd for $C_{19}H_{23}BrN_3O_2$ 404.1]; LC/MS retention time (method A): $t_R$=1.47 min; HPLC retention time (method A): $t_R$=9.55 min; HPLC retention time (method B): $t_R$=10.23 min; $^1$H NMR (400 MHz, $CD_3OD$) δ ppm 9.48 (s, 1H), 8.80 (d, J=5.77 Hz, 1H), 8.67 (s, 1H), 8.26 (d, J=5.77 Hz, 1H), 7.15 (s, 1H), 4.37 (dd, J=9.54, 3.76 Hz, 1H), 4.18 (dd, J=9.66, 6.40 Hz, 1H), 3.83 (s, 3H), 3.48-3.56 (m, 1H), 1.89 (m, 1H), 1.51-1.72 (m, 2H), 1.05 (t, J=6.27 Hz, 6H).

Example 4

(S)-8-((2-amino-4-methylpentyl)oxy)-6,9-dimethylbenzo[c][2,7]naphthyridin-5(6H)-one

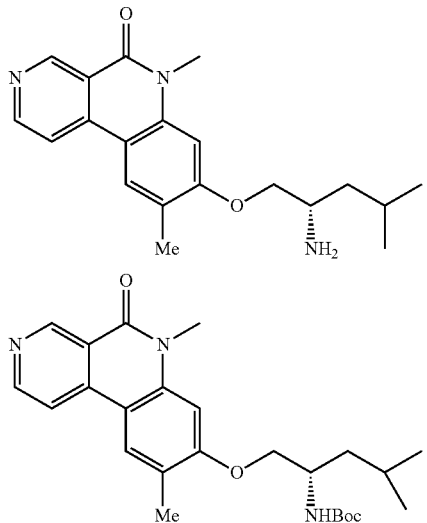

Part A. (S)-tert-butyl (1-((6,9-dimethyl-5-oxo-5,6-dihydrobenzo[c][2,7]naphthyridin-8-yl)oxy)-4-methylpentan-2-yl)carbamate In a 10 mL round-bottomed flask, (S)-tert-butyl (1-((9-bromo-6-methyl-5-oxo-5,6-dihydrobenzo[c][2,7]naphthyridin-8-yl)oxy)-4-methylpentan-2-yl)carbamate (as prepared in Ex. 3, Part A) (150 mg, 0.297 mmol), 2,4,6-trimethyl-1,3,5,2,4,6-trioxatriborinane (41.1 mg, 0.327 mmol), $Cs_2CO_3$ (291 mg, 0.892 mmol) and $PdCl_2(dppf)$ (21.76 mg, 0.030 mmol) were taken up in a mixture of 1,4-dioxane (2 mL) and water (0.1 mL). The reaction mixture was purged with nitrogen for 5 min and heated at 90° C. for 15 h. 1,4-dioxane was removed under reduced pressure and the residue was dissolved in ethyl acetate (20 mL). The ethyl acetate layer was washed with water (10×2 mL) and dried over sodium sulfate. Removal of the solvent gave crude product (0.08 g), which was filtered through silica-gel column (24 g silica-gel, MeOH—$CHCl_3$ mixture). The product was isolated as off-white solid (0.05 g, 0.11 mmol, 38% yield). LC/MS (ES-API) m/e 440.2 [(M+H)+, calcd for $C_{25}H_{34}N_3O_4$, 440.3]; LC/MS retention time (method B): $t_R$=1.95 min.

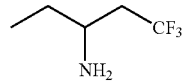

Part B. (S)-8-((2-amino-4-methylpentyl)oxy)-6,9-dimethylbenzo[c][2,7]naphthyridin-5(6H)-one In a 25 mL round-bottomed flask, (S)-tert-butyl (1-((6,9-dimethyl-5-oxo-5,6-dihydrobenzo[c][2,7]naphthyridin-8-yl)oxy)-4-methylpentan-2-yl)carbamate (80 mg, 0.182 mmol) was taken in MeOH (6 mL). The reaction mixture was cooled to 0° C. and a 4M solution of HCl in 1,4-dioxane (3.75 mL, 12 mmol) was added and the mixture stirred at RT for 2 h. The MeOH was removed and the crude product was dissolved in ethyl acetate (20 mL). The ethyl acetate layer was washed with water (10 mL) and dried over sodium sulfate. Removal of the solvent gave crude product which was purified by silica-gel column (MeOH—$CHCl_3$ mixture) to afford (S)-8-((2-amino-4-methylpentyl)oxy)-6,9-dimethylbenzo[c][2,7]naphthyridin-5(6H)-one (0.03 g, 0.09 mmol, 49% yield) as yellow solid. LC/MS (ESI) m/e 340.2 [(M+H)+, calcd for $C_{20}H_{26}N_3O_2$, 340.4]; LC/MS retention time (method B): $t_R$=1.33 min. HPLC retention time (method A): $t_R$=8.58 min; HPLC retention time (method B): $t_R$=8.12 min. $^1$H NMR (400 MHz, $CD_3OD$) δ ppm 9.51 (s, 1H), 8.79 (d, J=6.02 Hz, 1H), 8.40 (d, J=5.77 Hz, 1H), 8.33 (s, 1H), 7.10 (s, 1H), 4.50 (dd, J=10.67, 3.14 Hz, 1H), 4.36 (dd, J=10.67, 5.90 Hz, 1H), 3.77-3.87 (m, 4H), 2.46 (s, 3H), 1.79-1.92 (m, 2H), 1.66-1.77 (m, 1H), 1.08 (dd, J=6.27, 4.02 Hz, 6H).

Example 5

(S)-8-((2-amino-4-methylpentyl)oxy)-6-methyl-5-oxo-5,6 dihydrobenzo[c][2,7]naphthyridine-9-carbonitrile

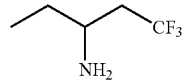

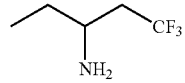

Part A. (S)-tert-butyl (1-((9-cyano-6-methyl-5-oxo-5,6-dihydrobenzo[c][2,7]naphthyridin-8-yl)oxy)-4-methylpentan-2-yl)carbamate In a 25 mL sealed tube, (S)-tert-butyl (1-((9-bromo-6-methyl-5-oxo-5,6-dihydrobenzo[c][2,7]naphthyridin-8-yl)oxy)-4-methylpentan-2-yl)carbamate (150 mg, 0.297 mmol) (as prepared in Ex. 3, Part A) was taken up in DMA (4 mL). To this mixture was added CuCN (53.3 mg, 0.595 mmol) and the mixture heated at 150° C. for 24 h. The reaction mixture was cooled to room temperature and diluted with ethyl acetate (20 mL) and filtered through diatomaceous earth (Celite®). The ethyl acetate solution was washed with brine (10 mL) and water (10 mL). The organic layer was dried over sodium sulfate and concentrated under reduced pressure to afford the crude product as gummy solid which was carried forward without further purification. LC/MS (ESI) m/e 451.2 [(M+H)$^+$, calcd for $C_{25}H_{31}N_4O_4$, 451.5]; LC/MS retention time (method B): $t_R$=2.02 min.

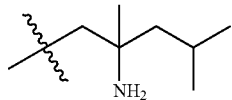

Part B. (S)-8-((2-amino-4-methylpentyl)oxy)-6-methyl-5-oxo-5,6 dihydrobenzo[c][2,7]naphthyridine-9-carbonitrile In a 25 mL round-bottomed flask, (S)-tert-butyl (1-((9-cyano-6-methyl-5-oxo-5,6-dihydrobenzo[c][2,7]naphthyridin-8-yl)oxy)-4-methylpentan-2-yl)carbamate (75 mg, 0.167 mmol) was taken up in MeOH (4 mL) and cooled to 0° C. The mixture was treated with 4M solution of HCl in 1,4-dioxane (2 mL, 8 mmol) and stirred for 2 h at RT. The MeOH was removed and the crude product was dissolved in EtOAc (20 mL). The ethyl acetate layer was washed with water (2×10 mL) and dried over sodium sulfate. Removal of the solvent gave crude product which was purified by silica-gel column (MeOH—CHCl$_3$ mixture) to obtain (S)-8-((2-amino-4-methylpentyl)oxy)-6-methyl-5-oxo-5,6 dihydrobenzo[c][2,7] naphthyridine-9-carbonitrile (4 mg, 0.01 mmol, 7% yield over 2 steps) as a yellow solid. LC/MS (ESI) m/e 351.2. [(M+H)$^+$, calcd for $C_{20}H_{23}N_4O_2$, 351.4]; LC/MS retention time (method B): $t_R$=1.43 min. HPLC retention time (method A): $t_R$=9.69 min; HPLC retention time (method B): $t_R$=9.31 min. $^1$H NMR (400 MHz, CD$_3$OD) δ ppm 9.56 (bs, 1H), 8.93 (s, 2H), 8.37 (d, J=4.77 Hz, 1H), 7.25 (s, 1H), 4.63 (dd, J=10.67, 3.14 Hz, 1H), 4.47 (dd, J=10.79, 6.02 Hz, 1H), 3.81-3.89 (m, 4H), 1.83-1.91 (m, 2H), 1.72 (t, J=6.53 Hz, 1H), 1.08 (d, J=5.02 Hz, 6H).

Example 6

(S)-8-((2-amino-4-methylpentyl)oxy)-9-cyclopropyl-6-methylbenzo[c][2,7]naphthyridin-5(6H)-one

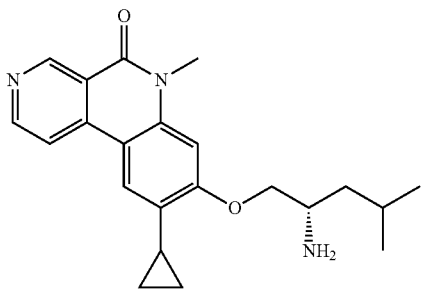 [SMILES: CC(C)C[C@H](N)COc1cc2c(cc1C1CC1)c1ccncc1c(=O)n2C]

-continued

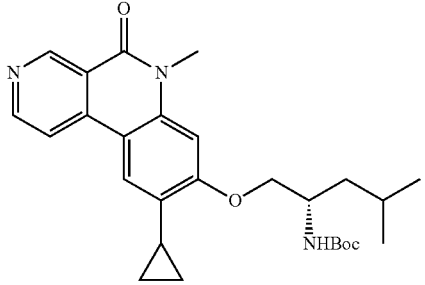

Part A: (S)-tert-butyl (1-((9-cyclopropyl-6-methyl-5-oxo-5,6-dihydrobenzo[c][2,7]naphthyridin-8-yl)oxy)-4-methylpentan-2-yl)carbamate A mixture of (S)-tert-butyl (1-((9-bromo-6-methyl-5-oxo-5,6-dihydrobenzo[c][2,7]naphthyridin-8-yl)oxy)-4-methylpentan-2-yl)carbamate (150 mg, 0.297 mmol) (as prepared in Ex. 3, Part A), cyclopropylboronic acid (28.1 mg, 0.327 mmol), tetrakis(triphenylphosphine)palladium (17.2 mg, 0.015 mmol) and Cs$_2$CO$_3$ (291 mg, 0.892 mmol) in toluene (5 mL) and water (0.43 mL) mixture was purged with nitrogen for 5 min then heated at 90° C. overnight (16 h). After cooling, toluene was removed under reduced pressure and the product was extracted with ethyl acetate (20 mL). The organic phase was washed with brine (2×20 mL), dried over Na$_2$SO$_4$, and concentrated under reduced pressure. The residue was purified by silica-gel column chromatography (EtOAc-hexane) to afford (S)-tert-butyl (1-((9-cyclopropyl-6-methyl-5-oxo-5,6-dihydrobenzo[c][2,7]naphthyridin-8-yl)oxy)-4-methylpentan-2-yl)carbamate (70 mg, 0.150 mmol, 51% yield) as an off-white gummy solid. LC/MS (ESI) m/z 466.4 [(M+H)$^+$, calcd for $C_{27}H_{36}N_3O_4$ 466.3]; LC/MS retention time (method E): $t_R$=1.19 min.

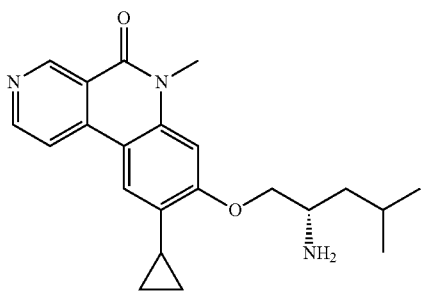

Part B: (S)-8-((2-amino-4-methylpentyl)oxy)-9-cyclopropyl-6-methylbenzo[c][2,7]naphthyridin-5(6H)-one To a solution of (S)-tert-butyl (1-((9-cyclopropyl-6-methyl-5-oxo-5,6-dihydrobenzo[c][2,7]naphthyridin-8-yl)oxy)-4-methylpentan-2-yl)carbamate (60 mg, 0.129 mmol) in MeOH (4 mL), at 0° C. was added a 4M solution of HCl in 1,4-dioxane (2 mL, 8 mmol). The resultant solution was stirred for 2 h at RT. The methanol was removed under reduced pressure and the residue was extracted with ethyl acetate (2×5 mL). The organic phase was washed with saturated aqueous NaHCO$_3$ (2×5 mL), dried over Na$_2$SO$_4$, and concentrated under reduced pressure. The residue was purified by silica-gel column (MeOH—CHCl₃) to afford (S)-8-((2-amino-4-methylpentyl)oxy)-9-cyclopropyl-6-methyl-benzo[c][2,7]naphthyridin-5(6H)-one (8 mg, 0.022 mmol, 17% yield) as an off-white solid. LC/MS (ESI) m/z 366.2 [(M+H)⁺, calcd for $C_{22}H_{28}N_3O_2$ 366.2]; LC/MS retention time (method B): $t_R$=1.34 min. HPLC retention time (method B): $t_R$=4.87 min and HPLC retention time (method A): $t_R$=9.18 min. ¹H NMR (400 MHz, CDCl₃) δ ppm 9.47 (s, 1H), 8.75 (d, J=5.7 Hz, 1H), 8.28 (d, J=5.7 Hz, 1H), 7.96 (s, 1H), 7.06 (s, 1H), 4.27 (m, 1H), 4.06-4.15 (m, 1H), 3.84 (s, 3H), 3.38-3.48 (m, 1H), 2.23-2.38 (m, 1H), 1.83-1.94 (m, 1H), 1.56-1.67 (m, 1H), 1.46-1.55 (m, 1H), 1.00-1.08 (m, 6H), 0.79-0.94 (m, 4H).

Example 7

(S)-8-(2-amino-4-methylpentyloxy)-9-hydroxy-6-methylbenzo[c][2,7]naphthyridin-5(6H)-one

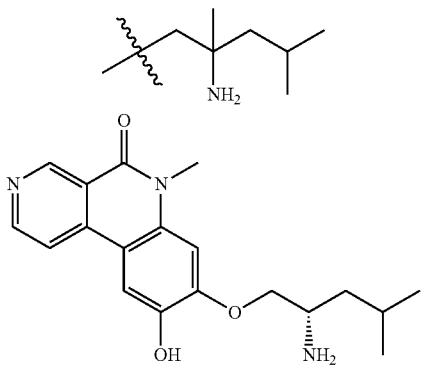

Part A. (S)-8-(2-amino-4-methylpentyloxy)-9-hydroxy-6 methylbenzo[c][2,7]naphthyridin-5(6H)-one A mixture of (S)-tert-butyl (1-((9-bromo-6-methyl-5-oxo-5,6-dihydrobenzo[c][2,7]naphthyridin-8-yl)oxy)-4-methyl-pentan-2-yl)carbamate (0.05 g, 0.099 mmol) (as prepared in Ex. 3, Part A), tetra-N-butylammonium hydroxide. 30H₂O (0.463 g, 1.784 mmol) and water (1.5 mL) was added over 0.1 h to a stirred solution of copper(I) iodide (1.89 mg, 9.91 µmol) and 2-methyl 8-quinolinol (3.16 mg, 0.020 mmol) in DMSO (1 mL). The reaction mixture was heated to 120° C. and stirred for 14 h. The resulting mixture was cooled to room temperature. The crude product was purified by reverse phase HPLC (10 mM ammonium acetate) to afford a (S)-8-((2-amino-4-methylpentyl)oxy)-9-hydroxy-6-methylbenzo[c][2,7]naphthyridin-5(6H)-one (0.004 g, 0.011 mmol, 12% yield) as a brown solid. LC/MS (ESI) m/e 342.2 [(M+H)⁺, calcd for $C_{19}H_{24}N_3O_3$, 342.2]; HPLC retention time (method F): $t_R$=1.62 min. HPLC retention time (method B): $t_R$=5.88 min. ¹H NMR (400 MHz, CD₃OD) δ 9.39 (s, 1H), 8.62 (d, J=6.00 Hz, 1H), 7.96 (d, J=5.60 Hz, 1H), 7.56 (s, 1H), 6.73 (s, 1H), 3.80 (s, 3H), 3.67-3.70 (m, 1H), 3.49-3.59 (m, 2H), 1.81-1.85 (m, 1H), 1.56-1.63 (m, 2H), 1.05 (d, J=6.80 Hz, 3H), 0.98 (d, J=6.80 Hz, 3H).

Example 8

(S)-8-((2-amino-4-methylpentyl)oxy)-6-isopropyl-benzo[c][2,7]naphthyridin-5(6H)-one

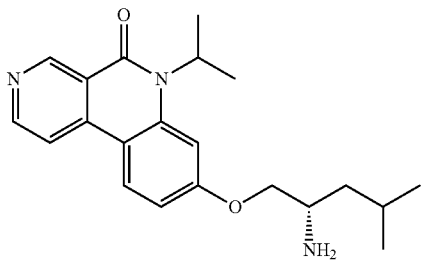

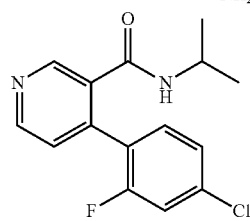

Part A. 4-(4-chloro-2-fluorophenyl)-N-isopropylnicotinamide

To a solution of 4-(4-chloro-2-fluorophenyl)nicotinic acid (400 mg, 1.590 mmol) (prepared as in Ex. 2, Part A) in DMF (6 mL) cooled to 0° C. was added EDC (457 mg, 2.384 mmol) and HOBT (487 mg, 3.18 mmol) and the mixture was stirred for 5 min. To the resultant solution DIPEA (0.83 mL, 4.77 mmol) followed by propan-2-amine (470 mg, 7.95 mmol) were added and the mixture was stirred at room temperature for 12 h. The reaction mixture was treated with ice and extracted with ethyl acetate (3×10 mL). The combined organic layers were washed with brine (1×10 mL), dried (Na₂SO₄) and concentrated under reduced pressure to afford 4-(4-chloro-2-fluorophenyl)-N-isopropylnicotinamide (480 mg, 1.64 mmol, 100%) as an off-white solid. LC/MS (ESI) m/e 293.2 [(M+H)⁺, calcd for $C_{15}H_{15}ClFN_2O$ 293.1]; LC/MS retention time (method C): $t_R$=1.84 min.

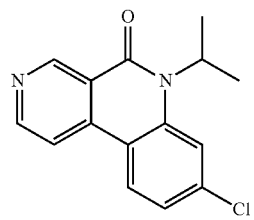 [SMILES: CC(C)n1c(=O)c2cnccc2c2ccc(Cl)cc21]

Part B. 8-chloro-6-isopropylbenzo[c][2,7]naphthyridin-5(6H)-one

To a suspension of sodium hydride (79 mg, 3.28 mmol) in THF (8 mL) at 0° C. was added a solution of 4-(4-chloro-2-fluorophenyl)-N-isopropylnicotinamide (480 mg, 1.640 mmol) in THF (10 mL) dropwise over a period of 10 min. The reaction mixture was stirred at 0° C. for 1 h and then warmed to room temperature and stirred for an additional 1 h. The reaction mixture was then treated with ice and extracted with ethyl acetate (3×5 mL). The combined organic layers were washed with brine (1×5 mL), dried (Na$_2$SO$_4$) and concentrated under reduced pressure to afford crude 8-chloro-6-isopropylbenzo[c][2,7]naphthyridin-5(6H)-one (250 mg, 0.917 mmol, 56% yield). LC/MS (ESI) m/e 273.0 [(M+H)$^+$, calcd for C$_{15}$H$_{14}$ClN$_2$O 273.1]; LC/MS retention time (method C): t$_R$=1.98 min; $^1$H NMR (400 MHz, CDCl$_3$) δ ppm 9.67 (s, 1H), 8.70 (d, J=6.0 Hz, 1H), 8.17-8.19 (d, J=8.4 Hz, 1H), 7.92-7.94 (d, J=5.6 Hz, 1H), 7.62 (d, J=1.6 Hz, 1H), 7.26-7.31 (dd, J=8.8, 2.0 Hz, 1H), 3.21-3.28 (m, 1H), 1.71 (d, J=6.8 Hz, 6H).

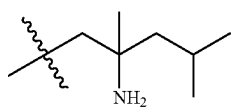

Part C. (S)-tert-butyl (1-((6-isopropyl-5-oxo-5,6-dihydrobenzo[c][2,7]naphthyridin-8-yl)oxy)-4-methylpentan-2-yl)carbamate To a solution 8-chloro-6-isopropylbenzo[c][2,7]naphthyridin-5(6H)-one (250 mg, 0.917 mmol) in toluene (2 mL) at room temperature was added cesium carbonate (448 mg, 1.375 mmol) and di-tert-butyl(2',4',6'-triisopropyl-[1',1'-biphenyl]-2-yl)phosphine (234 mg, 0.550 mmol) and the mixture was degassed for 5 min. The mixture was then treated with N-Boc-L-leucinol (591 mg, 2.75 mmol) followed by palladium(II)acetate (61.7 mg, 0.275 mmol) and degassed for another 10 min. The reaction mixture was sealed and heated at 80° C. The reaction mixture was then cooled to room temperature and filtered through diatomaceous earth (Celite®). The bed was washed with ethyl acetate and the combined filtrate was concentrated under reduced pressure to afford crude product which was purified by combi flash (gradient of ethyl acetate and petroleum ether) afford (S)-tert-butyl (1-((6-isopropyl-5-oxo-5,6-dihydrobenzo[c][2,7]naphthyridin-8-yl)oxy)-4-methylpentan-2-yl)carbamate (160 mg, 0.198 mmol, 21% yield) as an off-white solid. LC/MS (ESI) m/e 454.2 [(M+H)$^+$, calcd for C$_{26}$H$_{36}$N$_3$O$_4$ 454.3]; LC/MS retention time (method C): t$_R$=2.17 min.

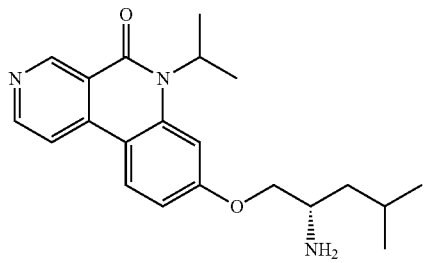 [SMILES: CC(C)C[C@H](N)COc1ccc2c3ccncc3c(=O)n(C(C)C)c2c1]

Part D. (S)-8-((2-amino-4-methylpentyl)oxy)-6-isopropylbenzo[c][2,7]naphthyridin-5(6H)-one To a solution of ((S)-tert-butyl (1-((6-isopropyl-5-oxo-5,6-dihydrobenzo[c][2,7]naphthyridin-8-yl)oxy)-4-methylpentan-2-yl)carbamate (160 mg, 0.353 mmol) in anhydrous dichloromethane (4 mL) was added a 2 M solution of HCl in diethyl ether (0.88 mL, 1.76 mmol) dropwise at 0° C. The reaction mixture was allowed to warm to room temperature and stirred for 2 h. The reaction mixture was then concentrated under reduced pressure to afford crude product which was purified by preparative HPLC (10 mM ammonium acetate in water; acetonitrile) to afford (S)-8-((2-amino-4-methylpentyl)oxy)-6-isopropylbenzo[c][2,7]naphthyridin-5(6H)-one (45 mg, 0.127 mmol, 36% yield) as an off-white solid. LC/MS (ESI) m/e 354.2 [(M+H)$^+$, calcd for C$_{21}$H$_{28}$N$_3$O$_2$ 354.2]; LC/MS retention time (method C): t$_R$=1.81 min; HPLC retention time (method A): t$_R$=8.85 min; HPLC retention time (method B): t$_R$=9.50 min. $^1$H NMR (400 MHz, CD$_3$OD) δ ppm 9.43 (d, J=0.75 Hz, 1H), 8.75 (d, J=5.77 Hz, 1H), 8.42 (d, J=9.04 Hz, 1H), 8.22 (d, J=5.52 Hz, 1H), 7.30 (d, J=2.26 Hz, 1H), 7.10 (dd, J=8.78, 2.26 Hz, 1H), 5.26-5.43 (m, 1H), 4.16 (dd, J=9.16, 3.89 Hz, 1H), 3.98 (dd, J=9.29, 7.03 Hz, 1H), 3.27-3.31 (m, 1H), 1.81-1.92 (m, 1H), 1.73 (d, J=7.03 Hz, 6H), 1.41-1.51 (m, 2H), 1.02 (dd, J=9.54, 6.53 Hz, 6H).

Example 9

(S)-6-allyl-8-((2-amino-4-methylpentyl)oxy)benzo[c][2,7]naphthyridin-5(6H)-one

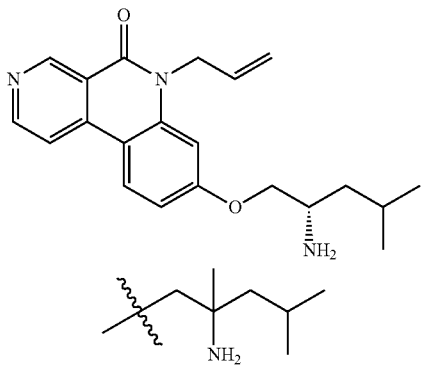

Part A. 4-(4-chloro-2-fluorophenyl)-N-cyclopropylnicotinamide

To a solution of 4-(4-chloro-2-fluorophenyl)nicotinic acid (500 mg, 1.987 mmol) (prepared as in Ex. 2, Part A) in DMF (6 mL) cooled to 0° C. was added EDC (571 mg, 2.98 mmol) and HOBT (609 mg, 3.97 mmol) and the mixture was stirred for 5 min. To the resultant solution DIPEA (1.04 mL, 5.96 mmol) followed by cyclopropanamine (567 mg, 9.93 mmol) was added and the mixture was stirred at room temperature for 12 h. The reaction mixture was treated with ice and extracted with ethyl acetate (3×10 mL). The combined organic layers were washed with brine (1×10 mL), dried (Na$_2$SO$_4$) and concentrated under reduced pressure to afford 4-(4-chloro-2-fluorophenyl)-N-cyclopropylnicotinamide (480 mg, 1.65 mmol, 83% yield). LC/MS (ESI) m/e 291.0 [(M+H)$^+$, calcd for C$_{15}$H$_{13}$ClFN$_2$O 291.1]; LC/MS retention time (method C): t$_R$=1.79 min.

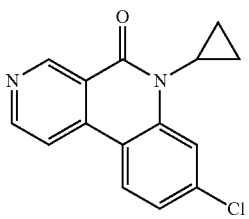 [SMILES: O=c1c2cnccc2c2ccc(Cl)cc2n1C1CC1]

Part B. 8-chloro-6-cyclopropylbenzo[c][2,7]naphthyridin-5(6H)-one

To a suspension of sodium hydride (72.6 mg, 3.03 mmol) in THF (8 mL) at 0° C. was added a solution of 4-(4-chloro-2-fluorophenyl)-N-cyclopropylnicotinamide (440 mg, 1.51 mmol) in THF (10 mL) dropwise over a period of 10 min. The reaction mixture was stirred at 0° C. for 1 h and then warmed to room temperature and stirred for another 1 h. The reaction mixture was then treated with ice and extracted with ethyl acetate (3×5 mL). The combined organic layers were washed with brine (2×5 mL), dried (Na$_2$SO$_4$) and concentrated under reduced pressure to afford crude 8-chloro-6-cyclopropylbenzo[c][2,7]naphthyridin-5(6H)-one (340 mg, 1.26 mmol, 83% yield) as an off-white solid. LC/MS (ESI) m/e 271.0 [(M+H)$^+$, calcd for C$_{15}$H$_{12}$ClN$_2$O 271.1]; LC/MS retention time (method C): t$_R$=1.89 min.

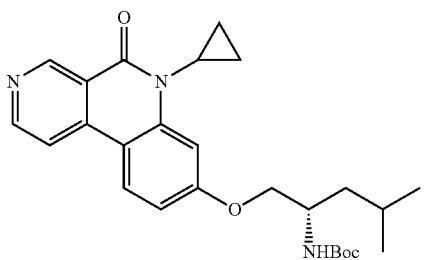 [SMILES: CC(C)C[C@@H](COc1ccc2c3ccncc3c(=O)n(C3CC3)c2c1)NC(=O)OC(C)(C)C]

Part C. (S)-tert-butyl (1-((6-cyclopropyl-5-oxo-5,6-dihydrobenzo[c][2,7]naphthyridin-8-yl)oxy)-4-methylpentan-2-yl)carbamate To a solution 8-chloro-6-cyclopropylbenzo[c][2,7]naphthyridin-5(6H)-one (200 mg, 0.739 mmol) in toluene (2 mL) at room temperature was added cesium carbonate (361 mg, 1.108 mmol) and di-tert-butyl(2',4',6'-triisopropyl-[1,1'-biphenyl]-2-yl)phosphine (188 mg, 0.443 mmol) and the mixture was degassed with nitrogen for 5 min. The mixture was then treated with N-Boc-L-leucinol (477 mg, 2.216 mmol) followed by palladium(II)acetate (49.8 mg, 0.222 mmol) and degassed for another 10 min. The reaction mixture was sealed and heated at 80° C. After overnight stirring the reaction mixture was cooled to room temperature and filtered through diatomaceous earth (Celite®). The bed was washed with ethyl acetate and the combined filtrate was concentrated under reduced pressure to afford crude product which was purified by combi flash (ethyl acetate and petroleum ether) to afford (S)-tert-butyl (1-((6-cyclopropyl-5-oxo-5,6-dihydrobenzo[c][2,7]naphthyridin-8-yl)oxy)-4-methylpentan-2-yl)carbamate (100 mg, 0.195 mmol, 26% yield) as an off-white solid. LC/MS (ESI) m/e 452.2 [(M+H)$^+$, calcd for C$_{26}$H$_{34}$N$_3$O$_4$ 452.3]; LC/MS retention time (method C): t$_R$=2.11 min.

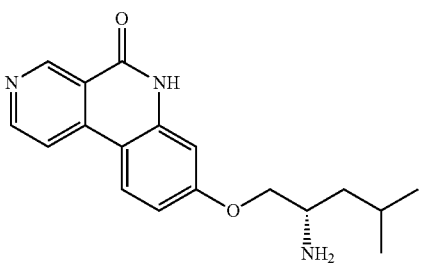

Part D. (S)-6-allyl-8-((2-amino-4-methylpentyl)oxy)benzo[c][2,7]naphthyridin-5(6H)-one To a solution of (S)-tert-butyl (1-((6-cyclopropyl-5-oxo-5,6-dihydrobenzo[c][2,7]naphthyridin-8-yl)oxy)-4-methylpentan-2-yl)carbamate (100 mg, 0.221 mmol) in anhydrous dichloromethane (2 mL) was added a 2 M solution of HCl in diethyl ether (0.176 mL, 0.353 mmol) dropwise at 0° C. The reaction mixture was allowed to warm to room temperature and stirred for 2 h. The reaction mixture was then concentrated under reduced pressure to afford crude product which was purified by preparative HPLC (0.1% TFA in water) to afford (S)-6-allyl-8-((2-amino-4-methylpentyl)oxy)benzo[c][2,7]naphthyridin-5(6H)-one (8 mg, 22.76 mmol, 10% yield) as a yellow solid. LC/MS (ESI) m/e 352.2 [(M+H)$^+$, calcd for C$_{21}$H$_{26}$N$_3$O$_2$ 352.2]; LC/MS retention time (method C): t$_R$=1.80 min; HPLC retention time (method A): t$_R$=8.06 min; HPLC retention time (method B): t$_R$=9.21 min. $^1$H NMR (400 MHz, CD$_3$OD) δ ppm 9.56 (s, 1H), 8.85 (d, J=6.27 Hz, 1H), 8.55 (d, J=9.04 Hz, 1H), 8.48 (d, J=6.27 Hz, 1H), 7.20 (dd, J=8.91, 2.38 Hz, 1H), 7.14 (d, J=2.26 Hz, 1H), 6.08 (dd, J=17.32, 10.54 Hz, 1H), 5.28 (dd, J=10.54, 1.00 Hz, 1H), 5.18 (dd, J=17.32, 1.25 Hz, 1H), 5.09-5.13 (m, 2H), 4.44 (dd, J=10.54, 3.26 Hz, 1H), 4.27 (dd, J=10.42, 6.40 Hz, 1H), 3.77 (dd, J=6.78, 3.51 Hz, 1H), 1.64-1.88 (m, 3H), 1.07 (dd, J=6.40, 4.89 Hz, 6H).

Example 10

(S)-8-((2-amino-4-methylpentyl)oxy)-7,9-dichloro-6-methylbenzo[c][2,7]naphthyridin-5(6H) one

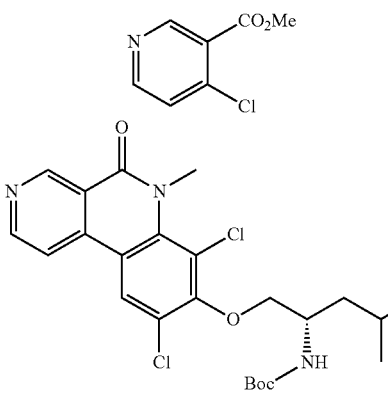

Part A. (S)-tert-butyl (1-((7,9-dichloro-6-methyl-5-oxo-5,6-dihydrobenzo[c][2,7]naphthyridin-8-yl)oxy)-4-methylpentan-2-yl)carbamate To a stirred solution of (S)-tert-butyl (4-methyl-1-((6-methyl-5-oxo-5,6-dihydrobenzo[c][2,7]naphthyridin-8-yl)oxy)

pentan-2-yl)carbamate (0.120 g, 0.282 mmol) (prepared as in Ex. 2, Part D) in anhydrous acetonitrile (2 mL) under nitrogen was added N-chlorosuccinimide (0.045 g, 0.338 mmol) and the solution was heated at 85° C. for 12 h. The reaction mixture was diluted with water (10 mL) and extracted with ethyl acetate (2×20 mL). The combined organic layers were dried over sodium sulfate and evaporated under reduced pressure to afford crude product which was purified by preparative TLC (ethyl acetate in petroleum ether) to afford (S)-tert-butyl (1-((7,9-dichloro-6-methyl-5-oxo-5,6-dihydrobenzo[c][2,7]naphthyridin-8-yl)oxy)-4-methylpentan-2-yl)carbamate (120 mg, 0.243 mmol, 86% yield, with 55% purity by LC/MS) as a yellow solid. LC/MS (ESI) m/e 494.2 [(M+H)$^+$, calcd for $C_{24}H_{30}Cl_2N_3O_4$ 494.1]; LC/MS retention time (method A): $t_R$=2.24 min.

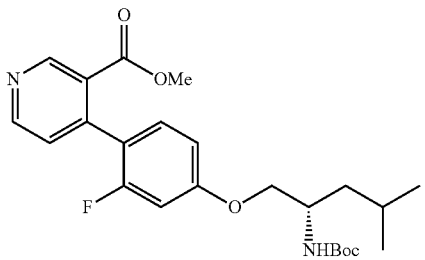 [SMILES: COC(=O)c1cnccc1-c1ccc(OC[C@H](CC(C)C)NC(=O)OC(C)(C)C)cc1F]

Part B. (S)-8-((2-amino-4-methylpentyl)oxy)-7,9-dichloro-6-methylbenzo[c][2,7]naphthyridin-5(6H)-one To a solution of (S)-tert-butyl (1-((7,9-dichloro-6-methyl-5-oxo-5,6-dihydrobenzo[c][2,7]naphthyridin-8-yl)oxy)-4-methylpentan-2-yl)carbamate (0.120 g, 0.243 mmol) in anhydrous methanol (5 mL) was added a 4M solution of HCl in 1,4-1,4-dioxane (2 mL, 8 mmol) dropwise at 0° C. The reaction mixture was allowed to warm to room temperature and stirred for 2 h. The reaction mixture was then concentrated under reduced pressure to afford crude compound which was purified by preparative HPLC (10 mM ammonium acetate in water; acetonitrile) to afford (S)-8-((2-amino-4-methylpentyl)oxy)-7,9-dichloro-6-methylbenzo[c][2,7]naphthyridin-5(6H)-one (28 mg, 0.063 mmol, 26% yield) as a yellow solid. LC/MS (ESI) m/e 394.2 [(M+H)$^+$, calcd for $C_{19}H_{22}Cl_2N_3O_2$ 394.1]; LC/MS retention time (method A): $t_R$=1.48 min; HPLC retention time (method A): $t_R$=5.21 min; HPLC retention time (method B): $t_R$=5.73 min. $^1$H NMR (400 MHz, CD$_3$OD) δ ppm 9.50 (d, J=0.75 Hz, 1H), 8.87 (d, J=5.52 Hz, 1H), 8.58 (s, 1H), 8.32 (d, J=5.27 Hz, 1H), 4.17 (dd, J=9.03, 4.02 Hz, 1H), 4.05 (dd, J=9.03, 7.28 Hz, 1H), 3.93 (s, 3H), 3.37-3.43 (m, 1H), 1.82-1.93 (m, 1H), 1.38-1.57 (m, 2H), 0.99-1.05 (m, 6H).

Example 11

(S)-8-((2-amino-4-methylpentyl)oxy)-6-benzylbenzo[c][2,7]naphthyridin-5(6H)-one

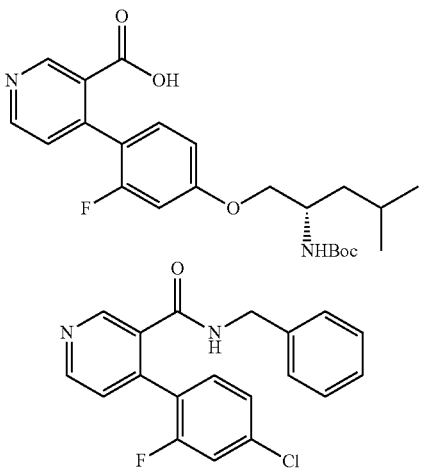

Part A.
N-benzyl-4-(4-chloro-2-fluorophenyl)nicotinamide

(S)-8-(2-amino-4-methylpentyloxy)-6-benzylbenzo[c][2,7]naphthyridin-5(6H)-one To a solution of 4-(4-chloro-2-fluorophenyl)nicotinic acid (600 mg, 2.38 mmol) (as prepared in Ex. 2, Part A) in DMF (6 mL) cooled to 0° C. was added EDC (457 mg, 2.38 mmol) and HOBT (365 mg, 2.38 mmol) and the mixture was stirred for 5 min. To the resultant solution was added DIPEA (0.416 mL, 2.384 mmol) followed by benzyl amine (307 mg, 2.86 mmol) and the mixture was stirred at room temperature for 12 h. The reaction mixture was treated with ice and extracted with ethyl acetate (3×10 mL). The combined organic layers were washed with brine (1×10 mL), dried (Na$_2$SO$_4$) and concentrated under reduced pressure to afford N-benzyl-4-(4-chloro-2-fluorophenyl)nicotinamide (680 mg, 2.00 mmol, 84% yield). LC/MS (ESI) m/e 341.0 [(M+H)$^+$, calcd for $C_{19}H_{15}ClFN_2O$ 341.1]; LC/MS retention time (method A): $t_R$=1.73 min.

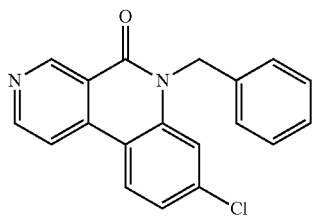 [SMILES: O=c1c2cnccc2c2ccc(Cl)cc2n1Cc1ccccc1]

Part B. 6-benzyl-8-chlorobenzo[c][2,7]naphthyridin-5(6H)-one

To a suspension of sodium hydride (96 mg, 3.99 mmol) in THF (13 mL) at 0° C. was added a solution of N-benzyl-4-(4-chloro-2-fluorophenyl)nicotinamide (680 mg, 1.995 mmol) in THF (10 mL) dropwise over a period of 10 min. The reaction mixture was stirred at 0° C. for 1 h and then warmed to room temperature and stirred for another 1 h. The reaction mixture was then treated with ice and extracted with ethyl acetate (3×5 mL). The combined organic layers were washed with brine (1×5 mL), dried (Na$_2$SO$_4$) and concentrated under reduced pressure to afford crude 6-benzyl-8-chlorobenzo[c][2,7]naphthyridin-5(6H)-one (640 mg, 2.00 mmol, 100%). LC/MS (ESI) m/e 321.0 [(M+H)$^+$, calcd for C$_{19}$H$_{14}$ClN$_2$O 321.0]; LC/MS retention time (method A): $t_R$=1.95 min.

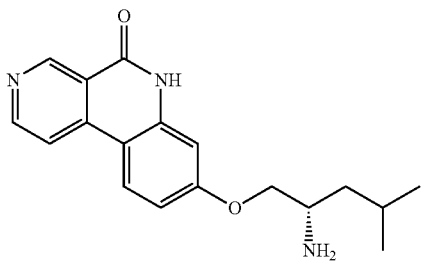

Part C. (S)-tert-butyl (1-((6-benzyl-5-oxo-5,6-dihydrobenzo[c][2,7]naphthyridin-8-yl)oxy)-4-methylpentan-2-yl)carbamate To a solution 6-benzyl-8-chlorobenzo[c][2,7]naphthyridin-5(6H)-one (640 mg, 2.00 mmol) in toluene (12 mL) at room temperature, was added cesium carbonate (975 mg, 2.99 mmol) and N-Boc L-Leucinol (1287 mg, 5.99 mmol) and the mixture was degassed with nitrogen for 5 min. The mixture was then treated with di-tert-butyl(2',4',6'-triisopropyl-[1',1'-biphenyl]-2-yl)phosphine (508 mg, 1.197 mmol) followed by palladium(II)acetate (448 mg, 2.00 mmol) and degassed for another 10 min. The reaction mixture was sealed and heated at 80° C. After overnight stirring the reaction mixture was cooled to room temperature and filtered through diatomaceous earth (Celite®). The bed was washed with ethyl acetate and the combined filtrate was concentrated under reduced pressure to afford crude product which was purified by combi flash (ethyl acetate/petroleum ether) to afford (S)-tert-butyl (1-((6-benzyl-5-oxo-5,6-dihydrobenzo[c][2,7]naphthyridin-8-yl)oxy)-4-methylpentan-2-yl)carbamate (500 mg, 0.738 mmol, 37% yield) as an off-white solid. LC/MS (ESI) m/e 502.3 [(M+H)$^+$, calcd for C$_{30}$H$_{36}$N$_3$O$_4$ 502.4]; LC/MS retention time (method D): $t_R$=1.26 min.

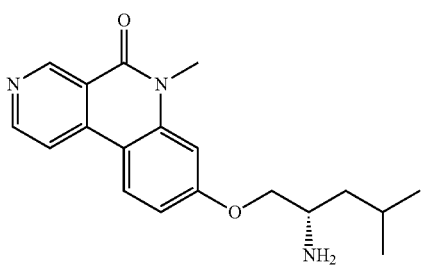 [SMILES: CC(C)C[C@H](N)COc1ccc2c3ccncc3c(=O)n(C)c2c1]

Part D. (S)-8-((2-amino-4-methylpentyl)oxy)-6-benzylbenzo[c][2,7]naphthyridin-5(6H)-one To a solution of (S)-tert-butyl (1-((6-benzyl-5-oxo-5,6-dihydrobenzo[c][2,7]naphthyridin-8-yl)oxy)-4-methylpentan-2-yl)carbamate (35 mg, 0.070 mmol) in anhydrous dichloromethane (1 mL) was added a 2 M solution of HCl in diethyl ether (0.17 mL, 0.349 mmol) dropwise at 0° C. The reaction mixture was allowed to warm to room temperature and stirred for 2 h. The reaction mixture was then concentrated under reduced pressure to afford crude product which was purified by preparative TLC (ethyl acetate in petroleum ether) to afford (S)-8-((2-amino-4-methylpentyl)oxy)-6-benzylbenzo[c][2,7]naphthyridin-5(6H)-one (10 mg, 0.024 mmol, 35% yield) as a light yellow solid. LC/MS (ESI) m/e 402.2 [(M+H)$^+$, calcd for C$_{25}$H$_{28}$N$_3$O$_2$ 402.2]; LC/MS retention time (method C): $t_R$=1.77 min; HPLC retention time (method A): $t_R$=5.54 min; HPLC retention time (method B): $t_R$=6.17 min. $^1$H NMR (400 MHz CD$_3$OD) δ ppm 9.61 (br. s., 1H), 8.87 (d, J=4.52 Hz, 1H), 8.53 (d, J=9.04 Hz, 1H), 8.47 (d, J=6.02 Hz, 1H), 7.28-7.38 (m, 5H), 7.15 (dd, J=8.91, 2.38 Hz, 1H), 7.04 (d, J=2.26 Hz, 1H), 5.72 (d, J=5.77 Hz, 2H), 4.27 (dd, J=10.54, 3.26 Hz, 1H), 4.10 (dd, J=10.42, 6.40 Hz, 1H), 3.69 (dd, J=6.65, 3.14 Hz, 1H), 1.68-1.81 (m, 1H), 1.57-1.67 (m, 2H), 1.00-1.05 (m, 6H).

Example 12

(S)-8-((2-amino-4-methylpentyl)oxy)-6-(2-methoxyethyl)benzo[c][2,7]naphthyridin-5(6H)-one

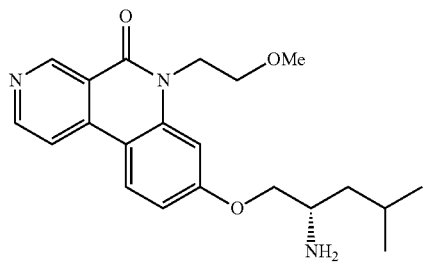

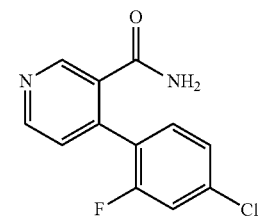

Part A. 4-(4-chloro-2-fluorophenyl)nicotinamide

To a stirred solution of 4-(4-chloro-2-fluorophenyl)nicotinic acid (1.1 g, 4.37 mmol) (as prepared in Ex. 2, Part A) in anhydrous DMF (10 mL) cooled to 0° C. was added HOBT (1.339 g, 8.74 mmol), EDC (1.257 g, 6.56 mmol), DIEA (3.05 mL, 17.49 mmol) followed by ammonium chloride (1.169 g, 21.86 mmol). The reaction mixture was allowed to warm to RT and stirred for 12 h under a nitrogen atmosphere. The reaction mixture was diluted with water (50 mL) and extracted with ethyl acetate (2×100 mL). The combined organic layers were dried over sodium sulfate and concentrated under reduced pressure to afford 4-(4-chloro-2-fluorophenyl)nicotinamide (0.900 g, 3.59 mmol, 82% yield) LC/MS (ESI) m/e 251 [(M+H)+, calcd for $C_{12}H_9ClFN_2O$ 251]; LC/MS retention time (method A): $t_R$=1.34 min.

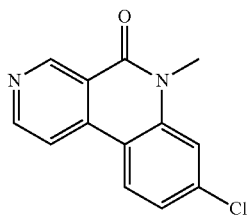 [SMILES: Cn1c(=O)c2cnccc2c2ccc(Cl)cc21]

Part B.
8-chlorobenzo[c][2,7]naphthyridin-5(6H)-one

To a solution of 4-(4-chloro-2-fluorophenyl)nicotinamide (0.9 g, 3.59 mmol) in THF (20 mL) at 0° C. was added sodium hydride (0.258 g, 10.77 mmol) and the reaction mixture was stirred at 0° C. for 1 h and then warmed to room temperature and stirred overnight (14 h). The reaction mixture was then quenched with ice and extracted with ethyl acetate (2×100 mL). The combined organic layers were washed with brine (1×100 mL), dried ($Na_2SO_4$) and concentrated under reduced pressure to afford crude 8-chlorobenzo[c][2,7]naphthyridin-5(6H)-one (0.80 g, 3.47 mmol, 97% yield). LC/MS (ESI) m/e 231.2 [(M+H)+, calcd for $C_{12}H_8ClN_2O$ 231]; LC/MS retention time (method D): $t_R$=0.61 min.

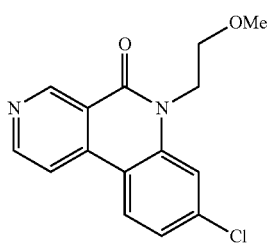 [SMILES: COCCn1c(=O)c2cnccc2c2ccc(Cl)cc21]

Part C. 8-chloro-6-(2-methoxyethyl)benzo[c][2,7]naphthyridin-5(6H)-one

To a stirred solution of 8-chlorobenzo[c][2,7]naphthyridin-5(6H)-one (0.150 g, 0.650 mmol) in anhydrous DMF (2 mL) at 0° C. was added 2-bromoethyl methyl ether (0.090 g, 0.650 mmol) under nitrogen. The reaction mixture was allowed to warm to RT and stirred for 12 h. The reaction mixture was diluted with water (10 mL) and extracted with ethyl acetate (2×20 mL). The combined organic layers were dried over sodium sulfate and concentrated under reduced pressure to afford 8-chloro-6-(2-methoxyethyl)benzo[c][2,7]naphthyridin-5(6H)-one (150 mg, 0.520 mmol, 80% yield). LC/MS (ESI) m/e 289.1 [(M+H)+, calcd for $C_{15}H_{13}ClN_2O_2$ 289.1]; LC/MS retention time (method A): $t_R$=1.65 min.

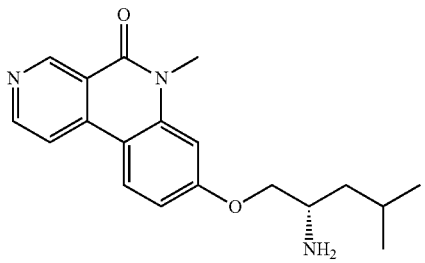 [SMILES: CC(C)C[C@H](N)COc1ccc2c3ccncc3c(=O)n(C)c2c1]

Part D. (S)-tert-butyl (1-((6-(2-methoxyethyl)-5-oxo-5,6-dihydrobenzo[c][2,7]naphthyridin-8-yl)oxy)-4-methylpentan-2-yl)carbamate To a solution 8-chloro-6-cyclopropylbenzo[c][2,7]naphthyridin-5(6H)-one (100 mg, 0.346 mmol) in toluene (5 mL) at room temperature was added cesium carbonate (169 mg, 0.520 mmol) and N-Boc-L-leucinol (226 mg, 1.039 mmol) and the mixture was degassed with nitrogen for 5 min. The mixture was then treated with di-tert-butyl(2',4',6'-triisopropyl-[1,1'-biphenyl]-2-yl)phosphine (47.8 mg, 0.208 mmol) followed by palladium(II)acetate (23.3 mg, 0.104 mmol) and degassed for another 10 min. The reaction mixture was sealed and heated at 80° C. After overnight stirring the reaction mixture was cooled to room temperature and filtered through diatomaceous earth (Celite®). The bed was washed with ethyl acetate (15 mL) and the filtrate was concentrated under reduced pressure to afford crude product which was purified by combi flash (gradient of ethyl acetate and petroleum ether) afford (S)-tert-butyl (1-((6-(2-methoxyethyl)-5-oxo-5,6-dihydrobenzo[c][2,7]naphthyridin-8-yl)oxy)-4-methylpentan-2-yl)carbamate (80 mg, 0.170 mmol, 49% yield) as a brown gum. LC/MS (ESI) m/e 470.3 [(M+H)+, calcd $C_{26}H_{36}N_3O_5$ 470.3]; LC/MS retention time (method A): $t_R$=2.02 min.

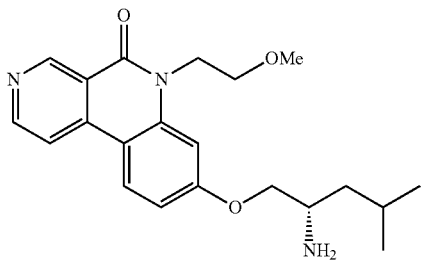 [SMILES: COCCn1c(=O)c2cnccc2c2ccc(OC[C@@H](N)CC(C)C)cc21]

Part E. (S)-8-((2-amino-4-methylpentyl)oxy)-6-(2 methoxyethyl)benzo[c][2,7]naphthyridin-5(6H)-one To a solution of (S)-tert-butyl (1-((6-(2-methoxyethyl)-5-oxo-5,6-dihydrobenzo[c][2,7]naphthyridin-8-yl)oxy)-4-methylpentan-2-yl)carbamate (0.080 g, 0.170 mmol) in anhydrous methanol (5 mL) was added a 4M solution of HCl in 1,4-dioxane (0.21 mL, 0.85 mmol) dropwise at 0° C. The reaction mixture was allowed to warm to room temperature and stirred for 2 h. The reaction mixture was concentrated under reduced pressure to afford crude compound which was purified by preparative HPLC (10 mM ammonium acetate in water:acetonitrile) to afford (S)-8-((2-amino-4-methylpentyl)oxy)-6-(2-methoxyethyl)benzo[c][2,7]naphthyridin-5(6H)-one (20 mg, 0.054 mmol, 32% yield) a white solid. LC/MS (ESI) m/e 370.2 [(M+H)+, calcd for $C_{21}H_{28}N_3O_3$ 370.2]; LC/MS retention time (method A): $t_R$=1.34 min; HPLC retention time (method A): $t_R$=8.36 min; HPLC retention time (method B): $t_R$=8.78 min. $^1$H NMR (400 MHz, $CD_3OD$) δ ppm 9.45 (s, 1H), 8.76 (d, J=5.77 Hz, 1H), 8.40 (d, J=9.03 Hz, 1H,), 8.23 (d, J=6.02 Hz, 1H), 7.29 (d, J=2.26 Hz, 1H), 7.11 (d, J=8.78 Hz, 1H), 4.61 (t, J=5.65 Hz, 2H), 4.36 (s, 1H), 4.20 (s, 1H), 3.81 (t, J=5.77 Hz, 2H), 3.63-3.71 (m, 1H), 3.37 (s, 3H), 1.86 (m, 1H), 1.67 (qt, J=14.01, 7.09 Hz, 2H), 1.06 (d, J=5.77 Hz, 6H).

Example 13

(S)-8-((2-amino-4-methylpentyl)oxy)-6-(cyclopropylmethyl)benzo[c][2,7]naphthyridin-5(6H)-one

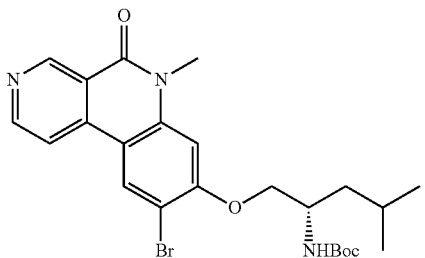

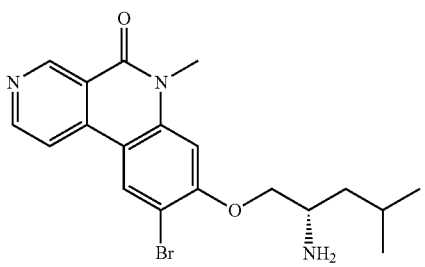

Part A. 8-chloro-6-(cyclopropylmethyl)benzo[c][2,7]naphthyridin-5(6H)-one

To a stirred solution of 8-chlorobenzo[c][2,7]naphthyridin-5(6H)-one (100 mg, 0.434 mmol) (as prepared in Ex. 12, Part B) in anhydrous DMF (2 mL) at 0° C. was added cyclopropyl methyl bromide (0.088 g, 0.650 mmol) under nitrogen. The reaction mixture was allowed to warm to RT and stirred for 12 h. The reaction mixture was diluted with water (10 mL) and extracted with ethyl acetate (2×20 mL). The combined organic layers were dried over sodium sulfate and concentrated under reduced pressure to 8-chloro-6-(cyclopropylmethyl)benzo[c][2,7]naphthyridin-5(6H)-one (100 mg, 0.351 mmol, 81% yield, 53% pure by LC/MS). LC/MS (ESI) m/e 285.1 [(M+H)+, calcd for $C_{16}H_{14}ClN_2O$ 285.1]; LC/MS retention time (method D): $t_R$=0.91 min.

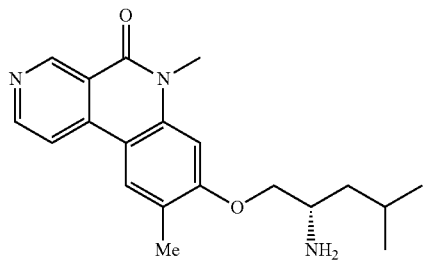 [SMILES: Cc1cc2c3ccncc3c(=O)n(C)c2cc1OC[C@@H](N)CC(C)C]

Part B. (S)-tert-butyl (1-((6-(cyclopropylmethyl)-5-oxo-5,6-dihydrobenzo[c][2,7]naphthyridin-8-yl)oxy)-4-methylpentan-2-yl)carbamate To a solution 8-chloro-6-(cyclopropylmethyl)benzo[c][2,7]naphthyridin-5(6H)-one (100 mg, 0.351 mmol) in anhydrous toluene (5 mL) at room temperature was added cesium carbonate (172 mg, 0.527 mmol) and Boc-L-leucinol (229 mg, 1.054 mmol) and the mixture was degassed with nitrogen for 5 min. The mixture was then treated with di-tert-butyl(2',4',6'-triisopropyl-[1,1'-biphenyl]-2-yl)phosphine (48.5 mg, 0.211 mmol) followed by palladium(II)acetate (23.65 mg, 0.105 mmol) and degassed for another 10 min. The reaction mixture was sealed and heated at 80° C. After overnight stirring the reaction mixture was cooled to room temperature and filtered through diatomaceous earth (Celite®). The bed was washed with ethyl acetate (15 mL) and the filtrate was concentrated under reduced pressure to afford crude compound which was purified by preparative HPLC (ethyl acetate in petroleum ether) to afford (S)-tert-butyl (1-((6-(cyclopropylmethyl)-5-oxo-5,6-dihydrobenzo[c][2,7]naphthyridin-8-yl)oxy)-4-methylpentan-2-yl)carbamate (80 mg, 0.172 mmol, 49% yield) as a brown gummy solid. LC/MS (ESI) m/e 466.3 [(M+H)+, calcd $C_{27}H_{36}N_3O_4$ 466.3]; LC/MS retention time (method A): $t_R$=2.199 min.

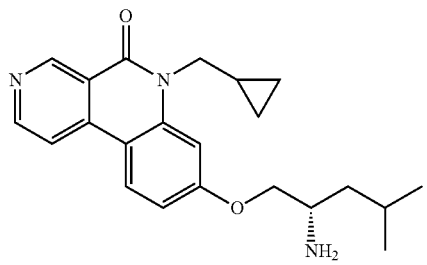 [SMILES: CC(C)C[C@H](N)COc1ccc2c3ccncc3c(=O)n(CC3CC3)c2c1]

Part C. (S)-8-((2-amino-4-methylpentyl)oxy)-6-(cyclopropylmethyl)benzo[c][2,7]naphthyridin-5(6H)-one To a solution of (S)-tert-butyl (1-((6-(cyclopropylmethyl)-5-oxo-5,6-dihydrobenzo[c][2,7]naphthyridin-8-yl)oxy)-4-methylpentan-2-yl)carbamate (0.08 g, 0.172 mmol) in anhydrous methanol (5 mL) was added a 4M solution of HCl in 1,4-dioxane (2 mL, 65.8 mmol) dropwise at 0° C. The reaction mixture was allowed to warm to room temperature and stirred for 2 h. The reaction mixture was concentrated under reduced pressure to afford crude compound which was purified by preparative HPLC (10 mM ammonium acetate in water:acetonitrile) to afford (S)-8-((2-amino-4-methylpentyl)oxy)-6-(cyclopropylmethyl)benzo[c][2,7]naphthyridin-5(6H)-one (22 mg, 0.060 mmol, 35% yield) as a yellow gum. LC/MS (ESI) m/e 366.2 [(M+H)$^+$, calcd for $C_{22}H_{28}N_3O_2$ 366.2]; LC/MS retention time (method A): $t_R$=1.47 min; HPLC retention time (method A): $t_R$=9.470 min; HPLC retention time (method B): $t_R$=5.250 min. $^1$H NMR (400 MHz, CD$_3$OD) δ ppm 9.47 (d, J=0.50 Hz, 1H), 8.78 (d, J=5.77 Hz, 1H), 8.46 (d, J=9.04 Hz, 1H), 8.26 (d, J=5.52 Hz, 1H), 7.28 (d, J=2.26 Hz, 1H), 7.14 (dd, J=9.03, 2.26 Hz, 1H), 4.39 (d, J=6.78 Hz, 2H), 4.31 (dd, J=9.79, 3.76 Hz, 1H), 4.13 (dd, J=9.79, 6.78 Hz, 1H), 3.53 (dd, J=7.15, 3.64 Hz, 1H), 1.87 (m, 1H), 1.59 (q, J=13.72, 7.03 Hz, 2H), 1.36-1.45 (m, 1H), 1.04 (dd, J=7.28, 6.78 Hz, 6H), 0.57-0.63 (m, 4H).

Example 14

(S)-8-((2-amino-4-methylpentyl)oxy)-9-fluoro-6-methylbenzo[c][2,7]naphthyridin-5(6H)-one

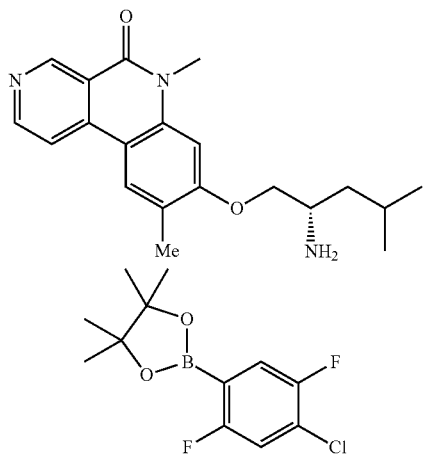

Part A. 2-(4-chloro-2,5-difluorophenyl)-4,4,5,5-tetramethyl-1,3,2-dioxaborolane

To a solution of 1-bromo-4-chloro-2,5-difluorobenzene (200 mg, 0.879 mmol) in THF (10 mL) cooled to –10° C. was added isopropylmagnesium bromide (1M in THF, 1.055 mL, 1.055 mmol) dropwise and the reaction mixture was stirred at this temperature for 1 h. The reaction mixture was then warmed to 0° C. and stirred for another 1 h. The resultant mixture was again cooled to –10° C. and treated dropwise with a solution of 2-isopropoxy-4,4,5,5-tetramethyl-1,3,2-dioxaborolane (196 mg, 1.055 mmol). The reaction mixture was allowed to warm up to room temperature and treated with a saturated solution of ammonium chloride (3 mL). The layers were separated and aqueous layer was extracted with dichloromethane (2×2 mL). The combined organic layer was dried over sodium sulfate, filtered and concentrated under reduced pressure to afford crude compound which was purified by column chromatography on a silica (7:3-Ethyl acetate:hexane) to afford 2-(4-chloro-2,5-difluorophenyl)-4,4,5,5-tetramethyl-1,3,2-dioxaborolane (150 mg, 0.546 mmol, 62% yield) as an oil. $^1$H NMR (400 MHz, DMSO-d$_6$) δ ppm 7.46-7.49 (m, 1H), 7.09-7.13 (m, 1H), 1.35 (s, 12H).

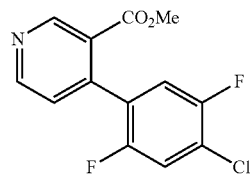 [SMILES: COC(=O)c1cnccc1-c1cc(F)c(Cl)cc1F]

Part B. Methyl 4-(4-chloro-2,5-difluorophenyl)nicotinate

To a stirred solution of methyl 4-chloronicotinate (100 mg, 0.583 mmol) in a solvent mixture of 1,4-dioxane:water (4:1, 20 mL) at room temperature under nitrogen atmosphere was added potassium carbonate (62.6 mg, 0.453 mmol) followed by tetrabutylammonium bromide (73.0 mg, 0.226 mmol). The resultant mixture was degassed with nitrogen for 10 min and treated with N-(6-chloro-4-(trimethylstannyl)pyridin-2-yl)acetamide (60.4 mg, 0.181 mmol) followed by bis(triphenylphosphine)palladium(II)chloride (10.60 mg, 0.015 mmol). The mixture was degassed again for 1o min and heated at 80° C. for 8 h. The reaction mixture was then cooled to room temperature and quenched with water (20 mL) and extracted with ethyl acetate (5 mL). The organic layer was separated and washed with water (3×5 mL), dried (Na$_2$SO$_4$) and concentrated under reduced pressure to afford crude methyl 4-(4-chloro-2,5-difluorophenyl)nicotinate (400 mg, 0.592 mmol, 20% yield, 42% pure by LC/MS). This was taken to the next step without further purification. LC/MS (ESI) m/e 284.0 [(M+H)$^+$, calcd for $C_{13}H_9ClF_2NO_2$ 284.02]; LC/MS retention time (method A): $t_R$=1.82 min.

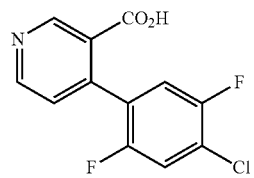

Part C. 4-(4-chloro-2,5-difluorophenyl)nicotinic Acid

To a solution of methyl 4-(4-chloro-2,5-difluorophenyl)nicotinate (400 mg, 1.41 mmol) in water:THF (1:1, 8 mL) was added LiOH (67.5 mg, 2.82 mmol) and the reaction mixture was stirred at room temperature for 4 h. The reaction mixture was quenched with water (5 mL) and washed with ethyl acetate (2×5 mL). The aqueous layer was separated and acidified with 1.5N HCl and concentrated under reduced pressure to afford 4-(4-chloro-2,5-difluorophenyl)nicotinic acid (180 mg, 0.541 mmol, 38% yield) as a solid. LC/MS (ESI) m/e 270 [(M+H)$^+$, calcd for $C_{12}H_7ClF_2NO_2$ 270]; LC/MS retention time (method B): $t_R$=1.48 min.

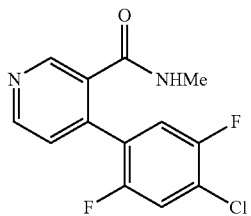 [SMILES: CNC(=O)c1cnccc1-c1cc(F)c(Cl)cc1F]

Part D. 4-(4-chloro-2,5-difluorophenyl)-N-methylnicotinamide 4-(4-chloro-2,5-difluorophenyl)nicotinic acid (170 mg, 0.630 mmol) was taken in thionyl chloride (0.14 mL, 1.89 mmol) and heated at 65° C. for 1 h. The solvent was evaporated under reduced pressure to afford a crude oil which was dissolved in dichloromethane and added to a mixture of methanamine hydrochloride (63.9 mg, 0.946 mmol) and DIEA (0.11 mL, 0.63 mmol) in DCM (8 mL) dropwise at 0° C. The reaction mixture was then allowed to warm to room temperature and stirred for 7 h. The reaction mixture was diluted with DCM (5 mL) and washed with water (3×5 mL) followed by brine (1×10 mL). The combined organic extracts were dried over sodium sulfate and concentrated under reduced pressure to provide the crude product which was purified by preparative thin layer chromatography (3:2 Ethyl acetate:hexane) to afford 4-(4-chloro-2,5-difluorophenyl)-N-methylnicotinamide (90 mg, 0.264 mmol, 42% yield) as a white solid. LC/MS (ESI) m/e 283.0 [(M+H)$^+$, calcd for $C_{13}H_{10}ClF_2N_2O$ 283.0]; LC/MS retention time (method A): $t_R$=1.46 min.

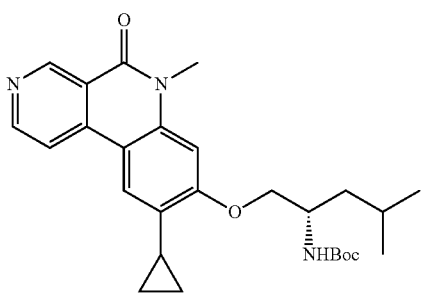

Part E. 8-chloro-9-fluoro-6-methylbenzo[c][2,7]naphthyridin-5(6H)-one

To a suspension of sodium hydride (56.6 mg, 1.42 mmol) in THF (5 mL) at 0° C. was slowly added 4-(4-chloro-2,5-difluorophenyl)-N-methylnicotinamide (100 mg, 0.354 mmol) in THF (5 mL). The resultant mixture was stirred at room temperature for 1 h. The reaction was then quenched by addition of cold water (1 mL) and extracted with ethyl acetate (2×2 mL). The combined organic extracts were dried with sodium sulfate and concentrated under reduced pressure. The residue was purified by column chromatography (1:1 ethyl acetate in petroleum ether) to afford 8-chloro-9-fluoro-6-methylbenzo[c][2,7]naphthyridin-5(6H)-one (82 mg, 0.297 mmol, 84% yield) as white solid. LC/MS (ESI) m/e 262.5 [(M+H)$^+$, calcd for $C_{13}H_9ClFN_2O$ 263.0]; LC/MS retention time (method D): $t_R$=1.79 min; HPLC retention time (method A): $t_R$=7.35 min; HPLC retention time (method B): $t_R$=7.07 min.

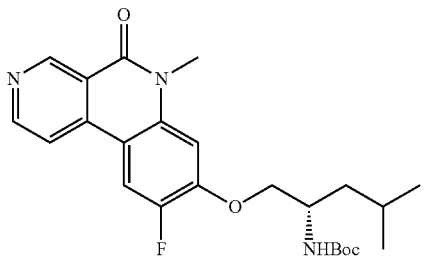 [SMILES: CC(C)C[C@@H](COc1cc2c(cc1F)c1ccncc1c(=O)n2C)NC(=O)OC(C)(C)C]

Part F. (S)-tert-butyl (1-((9-fluoro-6-methyl-5-oxo-5,6-dihydrobenzo[c][2,7]naphthyridin-8-yl)oxy)-4-methylpentan-2-yl)carbamate To a stirred suspension of 8-chloro-9-fluoro-6-methylbenzo[c][2,7]naphthyridin-5(6H)-one (40 mg, 0.152 mmol), (S)-tert-butyl (1-hydroxy-4-methylpentan-2-yl)carbamate (39.7 mg, 0.183 mmol), di-tert-butyl(2',4',6'-triisopropyl-[1',1'-biphenyl]-2-yl)phosphine (38.8 mg, 0.091 mmol) and cesium carbonate (74.4 mg, 0.228 mmol) in toluene (4 mL) was added palladium(II)acetate (10.26 mg, 0.046 mmol). Nitrogen gas was bubbled through the mixture for 5 min, and then the reaction mixture was heated to 85° C. for 8 h. The reaction mixture was cooled to room temperature and diluted with ethyl acetate (2 mL) and filtered through diatomaceous earth (Celite®). The filtrate was washed with water (2×2 mL) and brine (2×2 mL), dried over sodium sulfate and concentrated under reduced pressure. The residue was purified via silica gel column chromatography (60% ethyl acetate in hexanes) to afford (S)-tert-butyl (1-((9-fluoro-6-methyl-5-oxo-5,6-dihydrobenzo[c][2,7]naphthyridin-8-yl)oxy)-4-methylpentan-2-yl)carbamate (28 mg, 0.023 mmol, 15% yield). LC/MS (ESI) m/e 444.2 [(M+H)$^+$, calcd for $C_{24}H_{31}IFN_3O_4$ 444.2]; LC/MS retention time (method A): $t_R$=2.02 min.

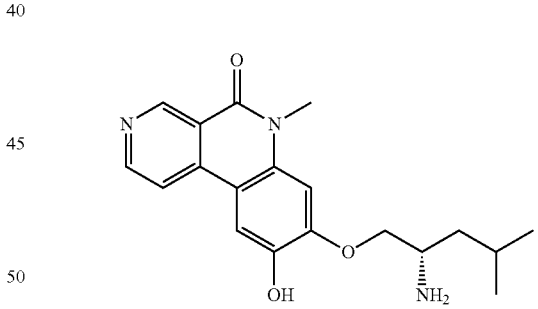

Part G. (S)-8-((2-amino-4-methylpentyl)oxy)-9-fluoro-6-methylbenzo[c][2,7]naphthyridin-5(6H)-one To a stirred solution of (S)-tert-butyl (1-((9-fluoro-6-methyl-5-oxo-5,6-dihydrobenzo[c][2,7]naphthyridin-8-yl)oxy)-4-methylpentan-2-yl)carbamate (25 mg, 0.056 mmol) in diethyl ether (4 mL) was added a 2M solution of hydrochloric acid in diethyl ether (42.5 μl, 0.085 mmol) at 0° C. dropwise over 10 min. The ice bath was removed and the reaction mixture was stirred at room temperature for 2 h. The solvent was removed and the crude material was taken up in water (5 mL). The aqueous layer was washed with ethyl acetate (3 mL) and treated with 10% NaHCO$_3$ (20 mL). The resultant solution was extracted with ethyl acetate (3×10 mL). The combined organic layers were washed with water (2×10 mL), dried (sodium sulfate), filtered and concentrated under reduced pressure to afford crude material which was purified via preparative TLC (40% Ethyl acetate in Hexane) to afford (S)-8-((2-amino-4-methylpentyl)oxy)-9-fluoro-6-methylbenzo[c][2,7]naphthyridin-5(6H)-one (15 mg, 0.041 mmol, 73% yield) as a white solid. LC/MS (ESI) m/e 344.2 [(M+H)$^+$, calcd for C$_{19}$H$_{23}$FN$_3$O$_2$ 344.2]; LC/MS retention time (method A): t$_R$=1.35 min; HPLC retention time (method A): t$_R$=8.31 min; HPLC retention time (method B): t$_R$=8.85 min; $^1$H NMR (400 MHz, CD$_3$OD) δ ppm 9.66-9.71 (m, 1H), 8.83-8.87 (m, 1H), 7.90-7.95 (m, 1H), 7.79-7.83 (m, 1H), 6.91-6.95 (m, 1H), 4.10-4.14 (m, 1H), 3.89-3.95 (m, 1H), 3.76-3.80 (m, 3H), 3.35-3.44 (m, 1H), 1.78-1.86 (m, 1H), 1.39 (t, J=7.00 Hz, 2H), 0.96-1.03 (m, 6H).

Example 15

8-(2-amino-5,5,5-trifluoropentyloxy)-6-methylbenzo[c][2,7]naphthyridin-5(6H)-one

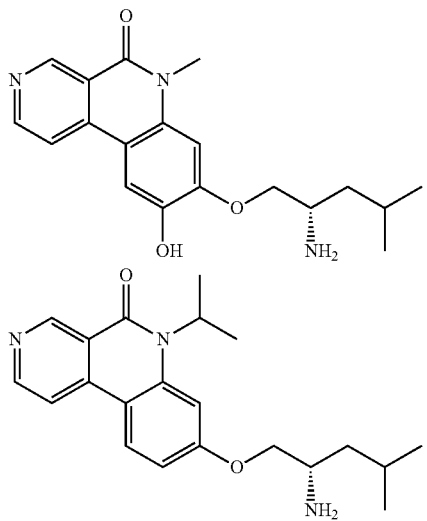

Part A. Tert-butyl 2-(diphenylmethyleneamino)-5,5,5-trifluoropentanoate

To a stirred solution of tert-butyl 2-((diphenylmethylene)amino)acetate (1 g, 3.39 mmol) in THF (20 mL) cooled to −78° C. under nitrogen atmosphere was added a 2M solution of LDA in THF (2.54 mL, 5.08 mmol) dropwise for 30 min. To this mixture was then added 3,3,3-trifluoropropyl trifluoromethanesulfonate (1.083 g, 4.40 mmol). The reaction was gradually warmed to rt and stirred for 4 h. The reaction mixture was quenched by addition of saturated aqueous ammonium chloride at 0° C. The reaction mixture was then extracted with ethyl acetate (3×10 mL). The combined organic extracts were washed with water (1×10 mL) and brine (1×10 mL), dried over sodium sulfate and then concentrated under reduced pressure. The crude oil was purified by silica gel column chromatography (2% ethyl acetate in hexane) to afford tert-butyl 2-((diphenylmethylene)amino)-5,5,5-trifluoropentanoate (800 mg, 2.02 mmol, 60% yield) as a yellow oil. LC/MS (ESI) m/e 391.9 [(M+H)$^+$, calcd for C$_{22}$H$_{25}$F$_3$NO$_2$, 392.2]; LC/MS retention time (method E): t$_R$=2.49 min.

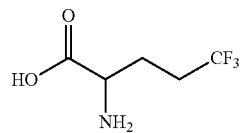

Part B. 2-amino-5,5,5-trifluoropentanoic Acid (Hydrochloride Salt)

A stirred solution of tert-butyl 2-((diphenylmethylene)amino)-5,5,5-trifluoropentanoate (800 mg, 2.023 mmol) in 50% aqueous HCl (0.123 mL, 2.023 mmol) was refluxed at 100° C. for 8 h. The reaction mixture was cooled to rt and concentrated under reduced pressure to afford 2-amino-5,5,5-trifluoropentanoic acid hydrochloride (400 mg, 1.82 mmol, 90% yield, 78% pure by LC/MS) as a white solid. LC/MS (ESI) m/e 171.7 [(M+H)$^+$, calcd for C$_5$H$_7$F$_3$O$_2$, 172.1]; LC/MS retention time (method E): t$_R$=0.80 min.

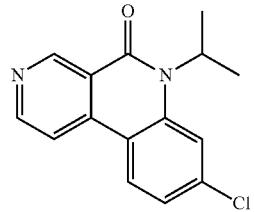 [SMILES: CC(C)n1c(=O)c2cnccc2c2ccc(Cl)cc21]

Part C. 2-(tert-butoxycarbonylamino)-5,5,5-trifluoropentanoic Acid

To a stirred solution of 2-amino-5,5,5-trifluoropentanoic acid hydrochloride (400 mg, 1.503 mmol, 78% by LC/MS) in THF (8 mL) and water (8 mL) at rt was added K$_2$CO$_3$ (831 mg, 6.01 mmol) and the solution stirred for 10 min. To this mixture was added Boc$_2$O (656 mg, 3.01 mmol). The reaction mixture was stirred for 8 h at rt then concentrated under reduced pressure. The aqueous layer was washed with ethyl acetate (3×5 mL). The aqueous layer was acidified with saturated citric acid solution (5 mL) and extracted with ethyl acetate (3×8 mL). The combined organic layers were washed with water (3×5 mL) followed by brine solution (1×10 mL), dried over sodium sulfate and concentrated under reduced pressure to afford 2-((tert-butoxycarbonyl)amino)-5,5,5-trifluoropentanoic acid (500 mg, 1.84 mmol, 100% yield) as a colorless oil. The material was taken into the next step without further purification. $^1$H NMR (400 MHz, CDCl$_3$) δ 5.04 (s, 1H), 4.38 (s, 1H), 2.15-2.28 (m, 2H), 1.91-1.95 (m, 2H), 1.46 (s, 9H).

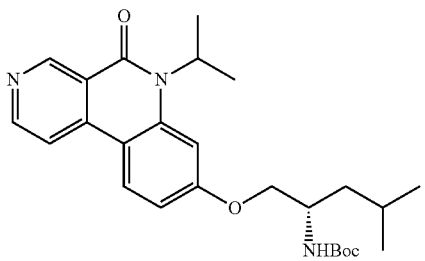 [SMILES: CC(C)C[C@@H](COc1ccc2c3ccncc3c(=O)n(C(C)C)c2c1)NC(=O)OC(C)(C)C]

Part D. Tert-butyl 5,5,5-trifluoro-1-hydroxypentan-2-ylcarbamate

To a stirred solution of 2-((tert-butoxycarbonyl)amino)-5,5,5-trifluoropentanoic acid (500 mg, 1.843 mmol) in THF (15 mL) cooled to −10° C. under nitrogen atmosphere was added N-methylmorphline (0.223 mL, 2.028 mmol) followed by isobutyl chloroformate (0.266 mL, 2.028 mmol) dropwise. The solution was then stirred for 30 min then filtered. The filtrate was added to sodium borohydride (147 mg, 3.87 mmol) in water (10 mL), stirred for 5 min and diluted with ethyl acetate (10 mL). The organic layer was separated and washed with brine (2×10 mL), dried (Na$_2$SO$_4$) and evaporated under reduced pressure to afford tert-butyl (5,5,5-trifluoro-1-hydroxypentan-2-yl)carbamate (400 mg, 1.555 mmol, 84% yield) as a white solid which was taken to the next step without further purification. $^1$H NMR (400 MHz, MeOD) δ 3.44-3.56 (m, 3H), 2.16-2.26 (m, 2H), 1.83-1.92 (m, 1H), 1.57-1.67 (m, 1H), 1.47 (s, 9H).

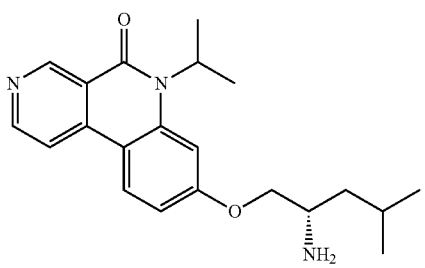 [SMILES: CC(C)C[C@H](N)COc1ccc2c3ccncc3c(=O)n(C(C)C)c2c1]

Part E. Tert-butyl 5,5,5-trifluoro-1-(6-methyl-5-oxo-5,6-dihydrobenzo[c][2,7]naphthyridin-8-yloxy)pentan-2-ylcarbamate The reaction was carried out as in Ex. 2, Part D to yield product tert-butyl (5,5,5-trifluoro-1-((6-methyl-5-oxo-5,6-dihydrobenzo[c][2,7]naphthyridin-8-yl)oxy)pentan-2-yl)carbamate (160 mg, 0.237 mmol, 23% yield) as a white solid. LC/MS (ESI) m/e 466.31 [(M+H)$^+$, calcd for C$_{23}$H$_{27}$F$_3$N$_3$O$_4$, 466.19]; LC/MS retention time (method D): t$_R$=1.04 min.

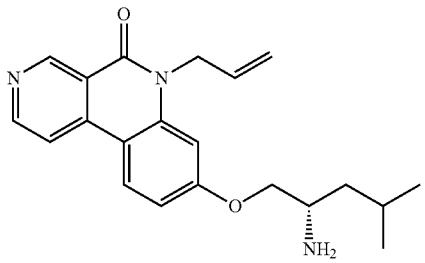 [SMILES: C=CCn1c(=O)c2cnccc2c2ccc(OC[C@@H](N)CC(C)C)cc21]

Part F. 8-(2-amino-5,5,5-trifluoropentyloxy)-6-methylbenzo[c][2,7]naphthyridin-5(6H)-one To a solution of tert-butyl (5,5,5-trifluoro-1-((6-methyl-5-oxo-5,6-dihydrobenzo[c][2,7]naphthyridin-8-yl)oxy)pentan-2-yl)carbamate (150 mg, 0.322 mmol) in diethyl ether (10 mL) under nitrogen atmosphere, cooled to 0° C. was added 4M HCl in 1,4-dioxane (0.098 mL, 0.392 mmol) slowly over a period of 5 min. The light yellow reaction mixture was stirred at 0° C. for 5 min then warmed to room temperature and allowed to stir for 12 h. The solvent was removed under reduced pressure. The residual yellow oil was diluted with water (3 mL) and extracted with EtOAc (2×4 mL). The aqueous layer was separated and treated with sat. Na$_2$CO$_3$ solution (3 mL). The resultant aqueous layer was extracted with EtOAc (3×5 mL). The combined organic layer s were separated and washed with water (2×5 mL), brine (1×5 mL) and dried over sodium sulfate. The filtrate was evaporated under reduced pressure and purified by SFC (CO$_2$ and 0.5% DEA in Methanol) to afford 8-((2-amino-5,5,5-trifluoropentyl)oxy)-6-methylbenzo[c][2,7]naphthyridin-5(6H)-one (102.8 mg, 0.278 mmol, 86% yield) as a white solid. LC/MS (ESI) m/e 366.2 [(M+H)$^+$, calcd for C$_{18}$H$_{19}$F$_3$N$_3$O$_2$ 366.13]; LC/MS retention time (method C): t$_R$=1.77 min; HPLC retention time (method A): t$_R$=7.79 min; HPLC retention time (method B): t$_R$=8.20 min. $^1$H NMR (400 MHz, MeOD) δ 9.48 (d, J=0.80 Hz, 1H), 8.78 (d, J=5.60 Hz, 1H), 8.44 (d, J=8.80 Hz, 1H), 8.27 (d, J=5.60 Hz, 1H), 7.17 (d, J=2.40 Hz, 1H), 7.12 (dd, J=2.40, 8.80 Hz, 1H), 4.17-4.20 (m, 1H), 4.09 (dd, J=6.00, 9.40 Hz, 1H), 3.82 (s, 3H), 3.28-3.28 (m, 1H), 2.33-2.49 (m, 2H), 1.92-1.99 (m, 1H), 1.73-1.80 (m, 1H).

Example 16

(S)-8-((2-amino-4-methylpentyl)oxy)-4,6-dimethylbenzo[c][2,7]naphthyridin-5(6H)-one

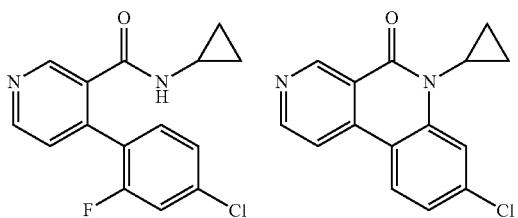

Part A: 2,4-dichloronicotinic Acid

To a solution of 2,4-dichloropyridine (7 g, 47.3 mmol) in THF (70 mL) at −78° C. was added a 2M solution of LDA in THF (28.4 mL, 56.8 mmol) and stirred for 30 min. The reaction mixture was quenched with excess dry ice and stirred for 30 min at RT. After neutralizing with 1.5N HCl, the reaction mixture was diluted with ethyl acetate (100 mL) and washed with brine (2×50 mL) and water (100 mL). The organic layer was separated, dried over Na₂SO₄ and concentrated under reduced pressure to afford 2,4-dichloronicotinic acid (4.5 g, 23.44 mmol, 50% yield) as a brown solid. ¹H NMR (400 MHz, DMSO-d₆) δ ppm 8.47 (d, 1H), 7.74 (d, 1H).

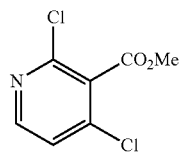 [SMILES: COC(=O)c1c(Cl)ccnc1Cl]

Part B: Methyl 2,4-dichloronicotinate

To a solution of 2,4-dichloronicotinic acid (500 mg, 2.60 mmol) in acetonitrile (10 mL) cooled to 0° C. was added DBU (0.981 mL, 6.51 mmol) followed by methyl iodide (0.814 mL, 13.0 mmol). The reaction mixture was stirred at RT overnight (14 h). After the reaction completion, the solvent was removed under reduced pressure. The residue was taken up in ethyl acetate (10 mL) and washed with water (1×5 mL), dried over Na₂SO₄, and concentrated under reduced pressure. The residue was purified by silica gel column chromatography (EtOAc-hexane) to afford methyl 2,4-dichloronicotinate (260 mg, 1.262 mmol, 49% yield) as pale yellow oil. LC/MS, (ESI) m/z 206.1 [(M+H)⁺, calcd for $C_7H_6Cl_2NO_2$ 205.97]; LC/MS retention time (method D): $t_R$=0.85 min. ¹H NMR (300 MHz, CD₃OD) δ ppm 8.42 (d, J=5.4 Hz, 1H), 7.59 (d, J=5.4 Hz, 1H), 3.99 (s, 3H).

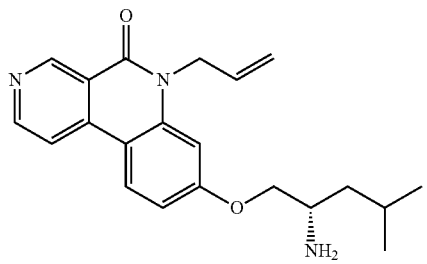 [SMILES: C=CCn1c(=O)c2cnccc2c2ccc(OC[C@@H](N)CC(C)C)cc21]

Part C: Methyl 4-chloro-2-methylnicotinate

A mixture of methyl 2,4-dichloronicotinate (2 g, 9.71 mmol), trimethylboroxine (1.462 g, 11.65 mmol), Cs₂CO₃ (6.33 g, 19.42 mmol) and PdCl₂(dppf) (0.710 g, 0.971 mmol) in 1,4-dioxane (30 mL) and water (2 mL) was purged with nitrogen for 5 min and heated at 70° C. for 16 h. The reaction was concentrated under reduced pressure and purified by silica gel column chromatography (EtOAc-hexane mixture) to afford methyl 4-chloro-2-methylnicotinate (550 mg, 2.94 mmol, 31% yield) as a red oil. ¹H NMR (300 MHz, CD₃OD) δ ppm 8.44 (d, J=5.7 Hz, 1H), 7.43 (d, J=5.7 Hz, 1H), 3.98 (s, 3H), 2.54 (s, 3H).

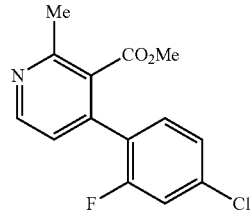 [SMILES: COC(=O)c1c(-c2ccc(Cl)cc2F)ccnc1C]

Part D: Methyl 4-(4-chloro-2-fluorophenyl)-2-methylnicotinate

A mixture of methyl 4-chloro-2-methylnicotinate (4 g, 21.55 mmol), (4-chloro-2-fluorophenyl)boronic acid (4.13 g, 23.71 mmol), tricyclohexylphosphine (1.813 g, 6.47 mmol), Pd(OAc)₂ (0.484 g, 2.155 mmol) and Cs₂CO₃ (14.04 g, 43.1 mmol) in DMA (15 mL) was purged with nitrogen for 5 min and heated at 100° C. overnight (14 h). After cooling, the reaction mixture was filtered through diatomaceous earth (Celite®). DMA was removed under reduced pressure and the residue was diluted with ethyl acetate (10 mL). The organic phase was concentrated under reduced pressure and purified by silica gel column chromatography (EtOAc-hexane) to afford methyl 4-(4-chloro-2-fluorophenyl)-2-methylnicotinate (1 g, 3.58 mmol, 17% yield) as a red oil. LC/MS, (ESI) m/z 280.1 [(M+H)⁺, calcd for $C_{14}H_{12}ClFNO_2$ 280.0]; LC/MS retention time (method D): $t_R$=0.80 min.

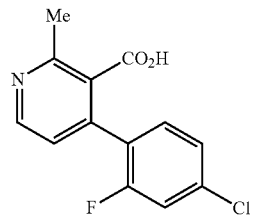 [SMILES: Cc1nccc(-c2ccc(Cl)cc2F)c1C(=O)O]

Part E: 4-(4-chloro-2-fluorophenyl)-2-methylnicotinic Acid

To a solution of methyl 4-(4-chloro-2-fluorophenyl)-2-methylnicotinate (40 mg, 0.143 mmol) in MeOH (2 mL) and water (3 mL) was added NaOH (11.44 mg, 0.286 mmol) and the reaction mixture was stirred at RT for 14 h. The reaction mixture was concentrated under reduced pressure and acidified with 1.5N HCl the extracted with ethyl acetate (5 mL). The organic layer was washed with saturated NaHCO₃ (2×10 mL) and water (10 mL); dried over Na₂SO₄ and concentrated under reduced pressure to afford crude 4-(4-chloro-2-fluorophenyl)-2-methylnicotinic acid (30 mg, 0.113 mmol, 79% yield) as brown solid. This was taken into the next step without further purification. LC/MS, (ESI) m/z 266.1 [(M+H)⁺, calcd for $C_{13}H_{10}ClFNO_2$. 266.0]; LC/MS retention time (method D): $t_R$=0.64 min.

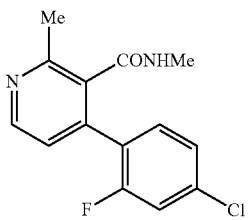

Part F: 4-(4-chloro-2-fluorophenyl)-N,2-dimethylnicotinamide

To a solution of 4-(4-chloro-2-fluorophenyl)-2-methylnicotinic acid (180 mg, 0.678 mmol) in DCM (5 mL) and DMF (0.2 mL) at 0° C., was added oxalyl chloride (0.178 mL, 2.033 mmol). The reaction mixture was stirred for 3 h at RT then diluted with DCM (5 mL) and treated with a solution of methylamine hydrochloride (457 mg, 6.78 mmol) in DCM (5 mL) cooled to 0° C. The mixture was stirred for another 1 h at RT. The solution was extracted with DCM (20 mL), washed with saturated NaHCO$_3$ (2×10 mL) and water (20 mL); dried over Na$_2$SO$_4$ and concentrated under reduced pressure to afford 4-(4-chloro-2-fluorophenyl)-N,2-dimethylnicotinamide (50 mg, 0.179 mmol, 27% yield) as a brown gum. LC/MS, (ESI) m/z 279.2 [(M+H)$^+$, calcd for C$_{14}$H$_{13}$ClFN$_2$O 279.1]; LC/MS retention time (method D): t$_R$=0.62 min.

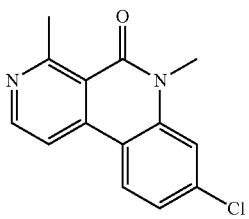 [SMILES: Cc1nccc2c1c(=O)n(C)c1cc(Cl)ccc21]

Part G: 8-chloro-4,6-dimethylbenzo[c][2,7]naphthyridin-5(6H)-one

To a solution of 4-(4-chloro-2-fluorophenyl)-N,2-dimethylnicotinamide (40 mg, 0.144 mmol) in THF (3 mL) cooled to 0° C. was added NaH (10.33 mg, 0.431 mmol) and the reaction mixture was stirred for 4 h. After the reaction completion, the reaction mixture was quenched with ice water and the product was extracted with ethyl acetate (20 mL). The organic layer was dried over Na$_2$SO$_4$ and concentrated under reduced pressure to afford 8-chloro-4,6-dimethylbenzo[c][2,7]naphthyridin-5(6H)-one (30 mg, 0.116 mmol, 81% yield) as an off-white solid. LC/MS, (ESI) m/z 259.2 [(M+H)$^+$, calcd for C$_{14}$H$_{12}$ClN$_2$O 259.1]; LC/MS retention time (Method D): t$_R$=0.65 min.

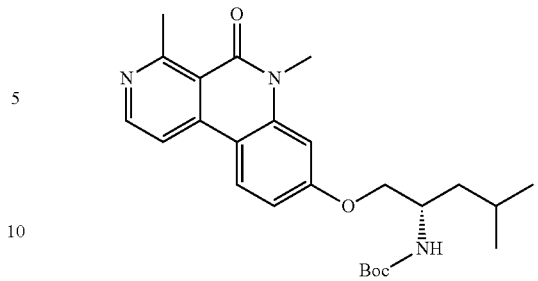

Part H: (S)-tert-butyl (1-((4,6-dimethyl-5-oxo-5,6-dihydrobenzo[c][2,7]naphthyridin-8-yl)oxy)-4-methylpentan-2-yl)carbamate A mixture of 8-chloro-4,6-dimethylbenzo[c][2,7]naphthyridin-5(6H)-one (60 mg, 0.232 mmol), (S)-tert-butyl (1-hydroxy-4-methylpentan-2-yl)carbamate (101 mg, 0.464 mmol), Cs$_2$CO$_3$ (113 mg, 0.348 mmol), Pd(OAc)$_2$ (15.6 mg, 0.070 mmol) and 2-di-t-butylphosphino-2',4',6'-tri-i-propyl-1,1'-biphenyl (5.91 mg, 0.014 mmol) in toluene (5 mL) was purged with nitrogen for 5 min and heated at 100° C. overnight (14 h). After cooling, the reaction mixture was filtered through diatomaceous earth (Celite®), concentrated under reduced pressure and dissolved in ethyl acetate (5 mL). The organic layer was washed with brine (2×10 mL) and water (20 mL); dried over Na$_2$SO$_4$ and concentrated under reduced pressure to afford (S)-tert-butyl (1-((4,6-dimethyl-5-oxo-5,6-dihydrobenzo[c][2,7]naphthyridin-8-yl)oxy)-4-methylpentan-2-yl)carbamate (55 mg crude) as a gummy solid. The crude product was used in the next step without further purification. LC/MS, (ESI) m/z 440.4 [(M+H)$^+$, calcd for C$_{25}$H$_{34}$N$_3$O$_4$, 440.2]; LC/MS retention time (method D): t$_R$=0.89 min.

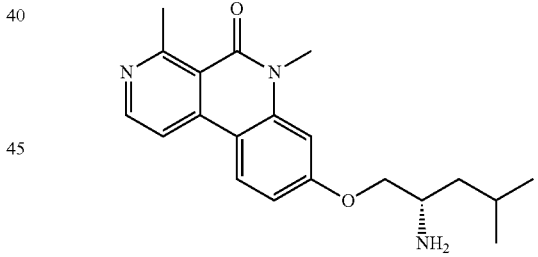

Part I: (S)-8-((2-amino-4-methylpentyl)oxy)-4,6-dimethylbenzo[c][2,7]naphthyridin-5(6H)-one To a solution of (S)-tert-butyl (1-((4,6-dimethyl-5-oxo-5,6-dihydrobenzo[c][2,7]naphthyridin-8-yl)oxy)-4-methylpentan-2-yl)carbamate (30 mg, 0.068 mmol) in MeOH (3 mL) at 0° C. was added HCl (4N in 1,4-dioxane, 3 mL, 12.00 mmol). The solution was warmed to room temperature and stirred for 2 h. The reaction mixture was then concentrated under reduced pressure and the residue dissolved in ethyl acetate (10 mL). The organic layer was washed with saturated NaHCO$_3$ (2×10 mL) and water (20 mL); dried over Na$_2$SO$_4$, and concentrated under reduced pressure. The residue was purified by preparative TLC (DCM-MeOH mixture) to afford (S)-8-((2-amino-4-methylpentyl)oxy)-4,6-dimethylbenzo[c][2,7]naphthyridin-5(6H)-one (8 mg, 0.021 mmol, 31% yield)

as a brown solid. LC/MS, (ESI) m/z 340.2 [(M+H)⁺, calcd for $C_{20}H_{26}N_3O_2$, 340.2]; LC/MS retention time (method B): $t_R$=1.27 min. HPLC retention time (method A): $t_R$=8.30 and HPLC retention time (method B): $t_R$=8.97 min. ¹H NMR (400 MHz, CD₃OD) δ ppm 8.53 (d, J=5.77 Hz, 1H), 8.33 (d, J=9.54 Hz, 1H), 8.08 (d, J=5.77 Hz, 1H), 7.00-7.06 (m, 2H), 4.21 (m, 1H), 4.02 (m, 1H), 3.73 (s, 3H), 3.47-3.52 (m, 1H), 3.06 (s, 3H), 1.82-1.93 (m, 1H), 1.67-1.76 (m, 2H), 1.26-1.56 (m, 6H).

Example 17

(S)-4-amino-8-(2-amino-4-methylpentyloxy)-6-methylbenzo[c][2,7]naphthyridin-5(6H)-one

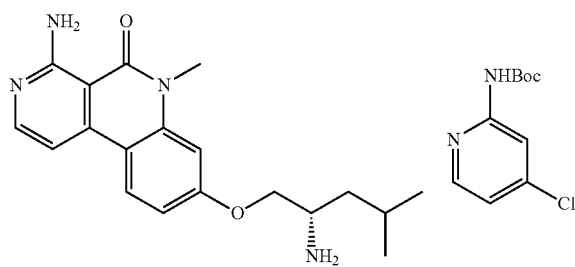

Part A. tert-butyl (4-chloropyridin-2-yl)carbamate

To a solution of LHMDS (1M in THF, 17.11 mL, 17.11 mmol) in THF (5 mL) at −5° C. was added a solution of 4-chloropyridin-2-amine (1 g, 7.78 mmol) in THF (5 mL) and the mixture was stirred for 5 min. To this mixture was added a solution of Boc₂O (1.898 mL, 8.18 mmol) in THF (5 mL). The mixture was stirred at 0° C. for 2 h and quenched by addition of aqueous NH₄Cl. The pH of the solution was adjusted to 6 by addition of 1.5N HCl and extracted with ethyl acetate (3×15 mL). The combined organic extracts were washed with sodium bicarbonate (15 mL), water (15 mL) and brine (15 mL). The combined organic extracts were dried over sodium sulfate and concentrated under reduced pressure. The residue was purified by silica gel column chromatography (ethyl acetate, petroleum ether gradient) to yield tert-butyl (4-chloropyridin-2-yl)carbamate (1.435 g, 6.28 mmol, 81% yield). ¹H NMR. ¹H NMR (400 MHz, DMSO-d₆) δ 10.10 (s, 1H), 8.23 (d, J=5.20 Hz, 1H), 7.88 (d, J=2.00 Hz, 1H), 7.15 (dd, J=2.00, 5.20 Hz, 1H), 1.48 (s, 9H).

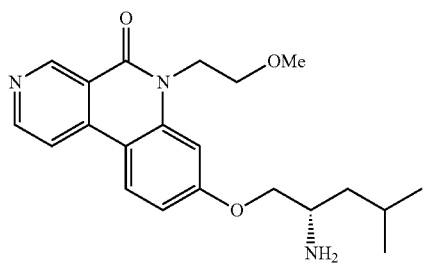 [SMILES: COCCn1c(=O)c2cnccc2c2ccc(OC[C@@H](N)CC(C)C)cc21]

Part B. tert-Butyl 4-chloro-3-formylpyridin-2-ylcarbamate

To a stirred solution of tert-butyl (4-chloropyridin-2-yl) carbamate (1.00 g, 4.37 mmol) in THF (30 mL) cooled to −78° C. was added n-butyllithium (2.55 M in hexane, 4.1 mL, 10.06 mmol) dropwise. After complete addition the solution was stirred at −78° C. for 1 h. DMF (1.591 mL, 20.55 mmol) was added dropwise and the resultant solution stirred at −78° C. for an additional 1 h. The reaction mixture was then quenched by addition of saturated aqueous ammonium chloride solution (20 mL) and extracted with ethyl acetate (2×25 mL). The combined organic extracts were washed with brine (1×20 mL), dried over sodium sulfate and concentrated under reduced pressure. The crude residue was purified via neutral alumina chromatography (ethyl acetate/hexanes) to yield tert-butyl (4-chloro-3-formylpyridin-2-yl)carbamate (530 mg, 2.06 mmol, 27% yield) as a yellow solid. ¹H NMR (400 MHz, CDCl₃) δ 10.73 (s, 1H), 10.55 (s, 1H), 8.52 (d, J=5.3 Hz, 1H), 7.06 (d, J=5.3 Hz, 1H), 1.56 (s, 9H); LC/MS (ESI) m/e 255.2 [(M−H)⁻, calcd for $C_{11}H_{12}ClN_2O_3$ 255.1]. LC/MS retention time (method A): $t_R$=1.75 min.

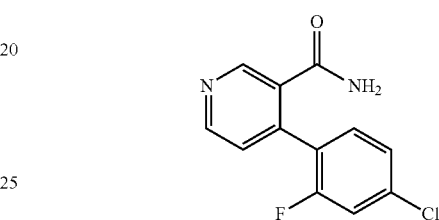

Part C. tert-Butyl 4-(4-chloro-2-fluorophenyl)-3-formylpyridin-2-ylcarbamate

To a stirred suspension of tert-butyl (4-bromo-3-formylpyridin-2-yl)carbamate (100 mg, 0.332 mmol), (4-chloro-2-fluorophenyl)boronic acid (57.9 mg, 0.332 mmol) and cesium carbonate (216 mg, 0.664 mmol) in THF (50 mL) and water (8 mL), was added Pd(PPh₃)₄ (19.19 mg, 0.017 mmol) and the reaction mixture was heated to 85° C. overnight (14 h). The reaction mixture was cooled to room temperature, diluted with water (30 mL) and extracted with ethyl acetate (2×25 mL). The combined organic extracts were washed with brine (1×25 mL), dried over sodium sulfate and concentrated under reduced pressure. The crude residue was purified via silica gel chromatography (ethyl acetate/hexanes) to afford tert-butyl 4-(4-chloro-2-fluorophenyl)-3-formylpyridin-2-ylcarbamate (60 mg, 0.17 mmol, 35% yield). LC/MS (ESI) m/e 351.2 [(M+H)⁺, calcd for $C_{17}H_{17}ClFN_2O_3$ 351.1]. LC/MS retention time (method A): $t_R$=2.07 min.

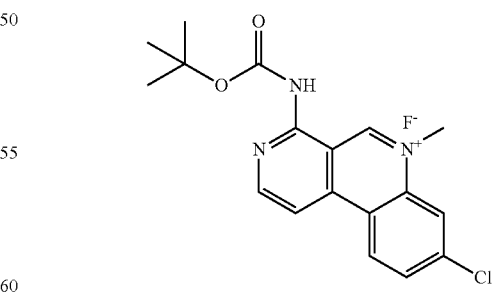

Part D. 4-((tert-butoxycarbonyl)amino)-8-chloro-6-methylbenzo[c][2,7]naphthyridin-6-ium Fluoride To a solution of tert-butyl (4-(4-chloro-2-fluorophenyl)-3-formylpyridin-2-yl)carbamate (700 mg, 1.996 mmol)

in ethanol (10 mL) at 0° C. was added methylamine (8M in EtOH) (620 mg, 2.49 mL, 19.96 mmol) and the reaction was stirred at rt for 5 h. After the consumption of starting material, solvent was removed under reduced pressure. The residue was washed with hexane (50 mL) and the solid so obtained was dried under vacuum to yield the fluoride salt of 4-((tert-butoxycarbonyl)amino)-8-chloro-6-methylbenzo[c][2,7]naphthyridin-6-ium fluoride (900 mg, 1.69 mmol, 84% yield) as a yellow solid. LC/MS (ESI) m/e 344.2 [(M)$^+$, calcd for $C_{18}H_{19}ClN_3O_2$ 344.1]; LC/MS retention time (method C): $t_R$=1.90 min.

DCM (2×30 mL). The combined organic layers were washed with brine (30 mL), dried over sodium sulfate, and concentrated under reduced pressure. The residue was purified by prep. HPLC (0.1% TFA in MeOH) to yield 4-amino-8-chloro-6-methylbenzo[c][2,7]naphthyridin-5(6H)-one (30 mg, 0.110 mmol, 27% yield) as a mono TFA salt. LC/MS (ESI) m/e 260.0 [(M+H)$^+$, calcd for $C_{13}H_{11}ClN_3O$ 260.05]; LC/MS retention time (method B): $t_R$=1.18 min; HPLC retention time (method A): $t_R$=5.24 min; HPLC retention time (method B): $t_R$=6.31 min; 400 MHz, $^1$H NMR (DMSO-d$_6$) δ 9.95 (s, 1H), 8.75 (s, 1H), 8.56 (d, J=8.80 Hz, 1H), 8.23 (d, J=6.80 Hz, 1H), 7.82 (dd, J=6.80, 7.20 Hz, 2H), 7.54 (dd, J=2.00, 8.80 Hz, 1H), 3.72 (s, 3H).

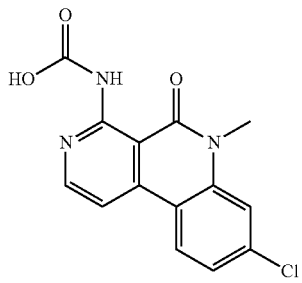 [SMILES: Cn1c(=O)c2c(NC(=O)O)nccc2c2ccc(Cl)cc21]

Part E. 8-chloro-6-methyl-5-oxo-5,6-dihydrobenzo[c][2,7]naphthyridin-4-ylcarbamic Acid To a stirred solution of 4-((tert-butoxycarbonyl)amino)-8-chloro-6-methylbenzo[c][2,7]naphthyridin-6-ium fluoride (0.35 g, 0.65 mmol) and NaOH (0.162 g, 4.06 mmol) in a mixture of DCM (10 mL) and water (10 mL) was added KMnO$_4$ (0.642 g, 4.06 mmol) in portions at rt and the reaction was heated to 90° C. for 1 h. The solution was diluted with water (10 mL) and extracted with DCM (2×20 mL). The combined organic layers were washed with water 50 mL, dried over sodium sulfate, and concentrated under reduced pressure to yield (8-chloro-6-methyl-5-oxo-5,6-dihydrobenzo[c][2,7]naphthyridin-4-yl)carbamic acid (305 mg, 0.422 mmol, 65% yield) as a yellow solid, which carried on without further purification. LC/MS (ESI) m/e 304.1 [(M+H)$^+$, calcd for $C_{14}H_{11}ClN_3O_3$ 304.04]; LC/MS retention time (Method D): $t_R$=1.01 min.

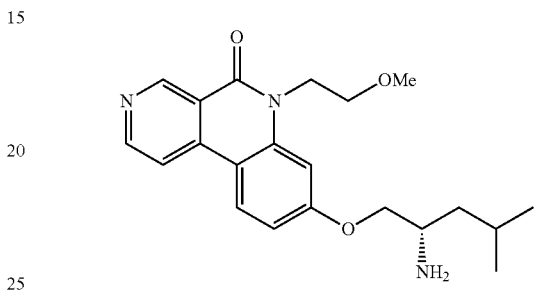

Part G. 8-chloro-4-(4-methoxybenzylamino)-6-methylbenzo[c][2,7]naphthyridin-5(6H)-one To a stirred solution of 4-amino-8-chloro-6-methylbenzo[c][2,7]naphthyridin-5(6H)-one (30 mg, 0.059 mmol) in DMF (10 mL) at 0° C. was added NaH (7.09 mg, 0.295 mmol) and the reaction was stirred for 5 min. To this mixture, 1-(chloromethyl)-4-methoxybenzene (0.026 mL, 0.191 mmol) was added and stirred at rt for 16 h. The reaction was quenched by addition of ice and the reaction mixture extracted with ethyl acetate (2×10 mL). The combined organic layers were washed with water (25 mL), dried over sodium sulfate, and concentrated under reduced pressure to yield 8-chloro-4-((4-methoxybenzyl)amino)-6-methylbenzo[c][2,7]naphthyridin-5(6H)-one (29 mg, 0.044 mmol, 75% yield). LC/MS (ESI) m/e 380.27 [(M+H)$^+$, calcd for $C_{21}H_{19}ClN_3O_2$ 380.11]; LC/MS retention time (Method D): $t_R$=0.86 min.

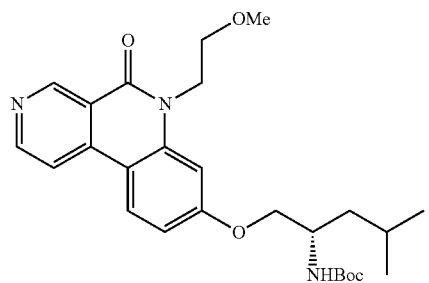 [SMILES: COCCn1c(=O)c2cnccc2c2ccc(OC[C@H](CC(C)C)NC(=O)OC(C)(C)C)cc21]

Part F. 4-amino-8-chloro-6-methylbenzo[c][2,7]naphthyridin-5(6H)-one

A solution of (8-chloro-6-methyl-5-oxo-5,6-dihydrobenzo[c][2,7]naphthyridin-4-yl)carbamic acid (300 mg, 0.415 mmol) in conc. HCl (15 mL, 494 mmol) was heated at 90° C. for 2 h. The pH of the reaction mixture was adjusted to 8 with saturated sodium bicarbonate solution and extracted with

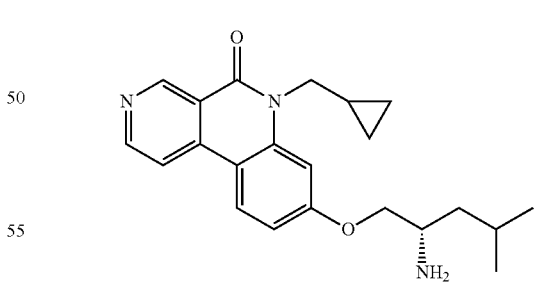

Part H. (S)-tert-butyl 1-(4-(4-methoxybenzylamino)-6-methyl-5-oxo-5,6-dihydrobenzo[c][2,7]naphthyridin-8-yloxy)-4-methylpentan-2-ylcarbamate The reaction was carried out as in Ex. 2, Part D to afford crude product which was purified by silica gel column using (ethyl acetate and hexane) to yield (S)-tert-butyl (1-((4-((4-methoxybenzyl)amino)-6-methyl-5-oxo-5,6-dihydrobenzo

[c][2,7]naphthyridin-8-yl)oxy)-4-methylpentan-2-yl)carbamate (0.29 g, 0.422 mmol, 61% yield) as a yellow oil. LC/MS (ESI) m/e 561.5 [(M+H)+, calcd for $C_{32}H_{41}N_4O_5$ 561.3]; LC/MS retention time (Method D): $t_R$=1.03 min.

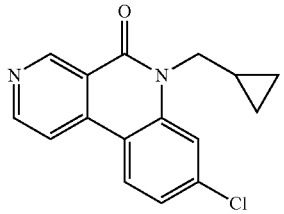

Part I. (S)-4-amino-8-(2-amino-4-methylpentyloxy)-6-methylbenzo[c][2,7]naphthyridin-5(6H)-one To a stirred solution of (S)-tert-butyl (1-((4-((4-methoxybenzyl)amino)-6-methyl-5-oxo-5,6-dihydrobenzo[c][2,7]naphthyridin-8-yl)oxy)-4-methylpentan-2-yl)carbamate (100 mg, 0.145 mmol) in DCM (10 mL) at rt was added TFA (4 mL, 51.9 mmol) dropwise and the reaction was heated at 45° C. for 12 h. After the completion of reaction, the volatile organics were evaporated under reduced pressure and the residue obtained was purified by prep. HPLC (0.1% TFA in water/acetonitrile as mobile phase) to yield (S)-4-amino-8-((2-amino-4-methylpentyl)oxy)-6-methylbenzo[c][2,7]naphthyridin-5(6H)-one (16 mg, 0.046 mmol, 32% yield) as a mono TFA salt as an offwhite solid. LC/MS (ESI) m/e 341.2 [(M+H)+, calcd for $C_{19}H_{25}N_4O_2$ 341.2]; LC/MS retention time (method B): $t_R$=1.08 min; HPLC retention time (method A): $t_R$=8.02 min; HPLC retention time (method B): $t_R$=8.40 min; 1H NMR (400 MHz, MeOD) δ 8.44 (d, J=8.80 Hz, 1H), 8.00 (d, J=7.20 Hz, 1H), 7.71 (d, J=7.20 Hz, 1H), 7.24 (d, J=2.40 Hz, 1H), 7.21-7.22 (m, 1H), 4.51 (dd, J=3.20, 10.80 Hz, 1H), 4.34 (dd, J=6.40, 10.40 Hz, 1H), 3.84 (s, 3H), 3.78-3.82 (m, 1H), 1.65-1.89 (m, 3H), 1.08 (d, J=4.40 Hz, 3H), 1.06 (d, J=4.40 Hz, 3H).

Example 18

(S)—N-(8-(2-amino-4-methylpentyloxy)-6-methyl-5-oxo-5,6 dihydrobenzo[c][2,7]naphthyridin-2-yl)acetamide

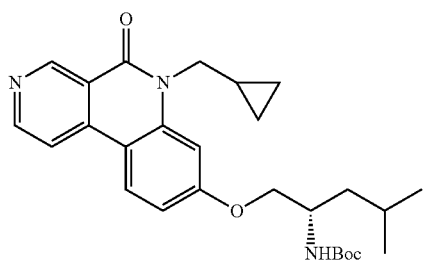

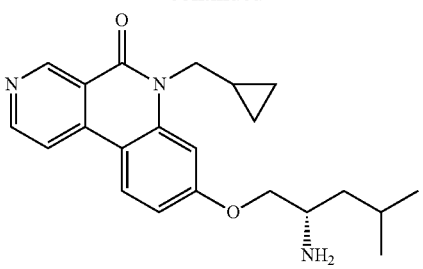 [SMILES: CC(C)C[C@H](N)COc1ccc2c3ccncc3c(=O)n(CC3CC3)c2c1]

Part A. 4-chloropyridin-2-amine

To a stirred solution of 4-chloropyridin-2-amine (8 g, 62.2 mmol) in acetonitrile (600 mL) at rt was added N-bromosuccinimide (11.08 g, 62.2 mmol) in portions and the reaction was stirred for 14 h. The reaction mixture was concentrated under reduced pressure. The residue was diluted with water (50 mL) and extracted with EtOAc (3×50 mL). The combined organic layers were washed with water (100 mL), brine (100 mL) and dried over sodium sulfate. The organics were concentrated under reduced pressure to afford 5-bromo-4-chloropyridin-2-amine as yellow solid (13 g, 99%) that was used as is without further purification. LC/MS (ESI) m/e 207.0 [(M+H)+, calcd for $C_5H_5BrClN_2$ 206.9]; LC/MS retention time (method B): $t_R$=0.8 min.

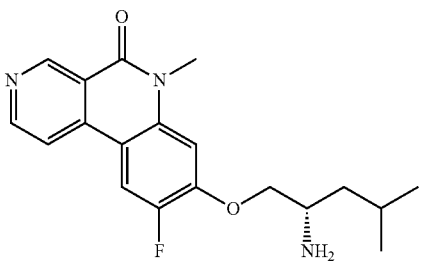

Part B. N-(5-bromo-4-chloropyridin-2-yl)acetamide

To a stirred solution of 5-bromo-4-chloropyridin-2-amine (11.6 g, 55.9 mmol) in pyridine (100 mL) at 0° C. was added acetyl chloride (3.98 mL, 55.9 mmol) and the reaction was stirred at rt for 3 h. The reaction mixture was quenched with cold water and concentrated under reduced pressure. The residue was diluted with water (50 mL) and extracted with EtOAc (3×50 mL). The combined organic layers were washed with water (100 mL), brine (100 mL) and dried over sodium sulfate. The organics were concentrated under reduced pressure to afford N-(5-bromo-4-chloropyridin-2-yl)acetamide (14.6 g, 55.9 mmol, 100% yield) as a white solid that was carried on without further purification. LC/MS (ESI) m/e 249 [(M+H)+, calcd for $C_7H_7BrClN_2O$ 248.9], LC/MS retention time (method B): $t_R$=1.64 min; 1H NMR (400 MHz, DMSO-$d_6$) δ 10.87 (s, 1H), 8.58 (s, 1H), 8.33 (s, 1H), 2.11 (s, 3H).

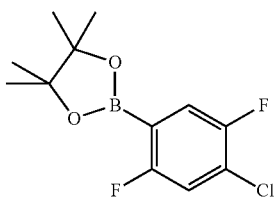 [SMILES: CC1(C)OB(c2cc(F)c(Cl)cc2F)OC1(C)C]

Part C. N-(4-chloro-5-vinylpyridin-2-yl)acetamide

To a stirred solution of N-(5-bromo-4-chloropyridin-2-yl)acetamide (7 g, 28.1 mmol), 2,4,6-trivinyl-1,3,5,2,4,6-trioxatriborinane complex with pyridine (1:1) (8.78 g, 36.5 mmol), sodium carbonate (5.95 g, 56.1 mmol) solution in 7 mL of water and tetrakis(triphenylphosphine)palladium (0.973 g, 0.842 mmol) in a mixture of Toluene (50 mL) and Ethanol (8 mL), nitrogen gas was bubbled for 5 min. The reaction mixture was heated at 85° C. for 14 hours. After the completion, the reaction was diluted with EtOAc (50 mL), filtered through diatomaceous earth (Celite®). The filtrate was diluted with water and the organic layer was separated, washed with brine solution, dried over sodium sulfate. The organics were concentrated under reduced pressure and residue so obtained was purified by comb flash column 120 g using hexane/ethyl acetate. Product eluted at 30% EtOAc in hexane and required fractions were concentrated to yield N-(4-chloro-5-vinylpyridin-2-yl)acetamide (5.92 g, 27.7 mmol, 99% yield) as yellow solid. LC/MS (ESI) m/e 197.2 [(M+H)$^+$, calcd for $C_9H_{10}ClN_2O$ 197.04] LC/MS retention time (method A): $t_R$=1.50 min; $^1$H NMR (400 MHz, DMSO-d$_6$) δ 10.79 (s, 1H), 8.64 (s, 1H), 8.18 (d, J=6.40 Hz, 1H), 6.88 (dd, J=11.20, 17.60 Hz, 1H), 5.99 (dd, J=0.80, 17.60 Hz, 1H), 5.47 (dd, J=0.80, 11.40 Hz, 1H), 2.12 (s, 3H).

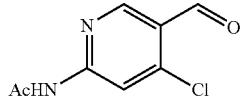

Part D. N-(4-chloro-5-formylpyridin-2-yl)acetamide

To a stirred solution of N-(4-chloro-5-vinylpyridin-2-yl)acetamide (6 g, 30.5 mmol) and 2,6-lutidine (7.11 mL, 61.0 mmol) in a mixture of 1,4-dioxane (110 mL) and water (25 mL) at 0° C. was added osmium tetroxide (2.5% in 2-methyl-2-propanol, 9.58 mL, 30.5 mmol) followed by the addition of sodium periodate (19.58 g, 92 mmol) and the reaction was stirred for 4 h. The reaction mixture was diluted with water and extracted with EtOAc (2×100 mL). The combined organic layers were washed with brine solution, dried over sodium sulfate, concentrated under reduced pressure and residue so obtained was purified by comb flash column 120 g silica column using hexane/EtOAc as eluant. The desired product was isolated at 30% EtOAc in hexane. The required fractions were concentrated under reduced pressure to yield N-(4-chloro-5-formylpyridin-2-yl)acetamide as a off-white solid (5.8 g, 28.1 mmol, 92% yield). LC/MS (ESI) m/e 197.0 [(M)$^-$, calcd for $C_8H_6ClN_2O_2$ 197.04] LC/MS retention time (method A): $t_R$=1.21 min; $^1$H NMR (400 MHz, DMSO-d$_6$) δ 11.20 (s, 1H), 10.18 (s, 1H), 8.76 (s, 1H), 8.27 (s, 1H), 2.16 (s, 3H).

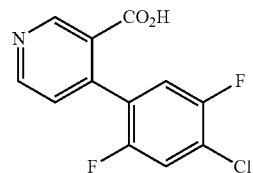 [SMILES: O=C(O)c1cnccc1-c1cc(F)c(Cl)cc1F]

Part E. N-(4-(4-chloro-2-fluorophenyl)-5-formylpyridin-2-yl)acetamide

To a stirred solution of N-(4-chloro-5-formylpyridin-2-yl)acetamide (3 g, 15.11 mmol), (4-chloro-2-fluorophenyl)boronic acid (2.63 g, 15.11 mmol), cesium carbonate (9.84 g, 30.2 mmol) in a mixture of water (8 mL) and THF (25 mL) was added tetrakis(triphenylphosphine)palladium (19.19 mg, 0.017 mmol) and the reaction was heated to 85° C. overnight (14 h). The reaction mixture was diluted with water (25 mL) and extracted with EtOAc (2×25 mL). The combined organic layers were washed with water (25 mL), brine (25 mL), dried over sodium sulfate, and concentrated under reduced pressure. The residue was purified by silica gel chromatography (hexane/EtOAc as eluant), yielding N-(4-(4-chloro-2-fluorophenyl)-5-formylpyridin-2-yl)acetamide as an off-white solid (2.8 g, 9.01 mmol, 60% yield). LC/MS (ESI) m/e 291.0 [(M)$^-$, calcd for $C_{14}H_9ClFN_2O_2$ 291.0], LC/MS retention time (method A): $t_R$=1.69 min; $^1$H NMR (400 MHz, DMSO-d$_6$) δ 11.14 (s, 1H), 9.84 (d, J=Hz, 1H), 8.88 (s, 1H), 8.13 (s, 1H), 7.61 (dd, J=2.00, 10.00 Hz, 1H), 7.46-7.48 (m, 2H), 2.11 (s, 3H).

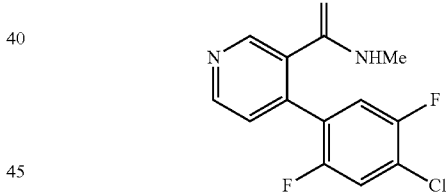

Part F. 2-Acetamido-8-chloro-6-methylbenzo[c][2,7]naphthyridin-6-ium Fluoride To a stirred solution of N-(4-(4-chloro-2-fluorophenyl)-5-formylpyridin-2-yl)acetamide (0.39 g, 1.332 mmol) and 4 Å molecular sieves (50 mg) in dichloromethane (35 mL) at 0° C. was added methyl amine (8M in EtOH, 0.041 g, 0.166 mL, 1.332 mmol) dropwise and the reaction was stirred at rt overnight (12 h). The reaction mixture was diluted with DCM (40 mL) and filtered through a bed of diatomaceous earth (Celite®). The filtrate was concentrated under reduced pressure to afford 2-acetamido-8-chloro-6-methylbenzo[c][2,7]naphthyridin-6-ium fluoride (450 mg, 1.24 mmol, 93% yield) as a yellow solid that was used in the next step without purification. LC/MS (ESI) m/e 286.1 [(M)$^+$, calcd for $C_{15}H_{13}ClN_3O$ 286.1]; LC/MS retention time (Method D): $t_R$=0.71 min.

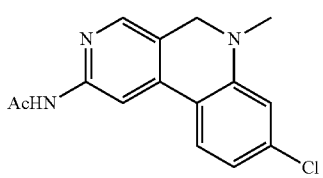 [SMILES: CC(=O)Nc1cc2c(cn1)CN(C)c1cc(Cl)ccc1-2]

Part G. N-(8-chloro-6-methyl-5,6-dihydrobenzo[c][2,7]naphthyridin-2-yl)acetamide To a stirred solution of 2-acetamido-8-chloro-6-methyl-benzo[c][2,7]naphthyridin-6-ium fluoride (2.1 g, 2.47 mmol) in a mixture of THF (20 mL) and MeOH (5 mL) at 0° C. was added NaBH$_4$ (0.199 g, 5.27 mmol) in three portions and the reaction was stirred at rt for 45 min. The volatile organics were removed under reduced pressure; saturated ammonium chloride solution (30 mL) was added and the solution extracted with ethyl acetate (2×30 mL). The combined organic layers were washed with brine (25 mL), dried over sodium sulfate, and concentrated under reduced pressure. The residue was purified by silica gel column chromatography (hexane/ethyl acetate) to afford N-(8-chloro-6-methyl-5,6-dihydrobenzo[c][2,7]naphthyridin-2-yl)acetamide (0.71 g, 2.29 mmol, 93% yield) as a yellow solid. LC/MS (ESI) m/e 288.2 [(M+H)$^+$, calcd for C$_{15}$H$_{15}$ClN$_3$O 288.1]; LC/MS retention time (method C); t$_R$=1.87 min; HPLC retention time (method A): t$_R$=12.76 min; HPLC retention time (method B): t$_R$=13.07 min; $^1$H NMR (400 MHz, DMSO-d$_6$) δ 10.46 (s, 1H), 8.36 (s, 1H), 8.16 (d, J=0.40 Hz, 1H), 7.63 (d, J=8.40 Hz, 1H), 6.88 (dd, J=2.00, 8.00 Hz, 1H), 6.82 (d, J=2.00 Hz, 1H), 4.26 (s, 2H), 2.89 (s, 3H), 2.11 (s, 3H).

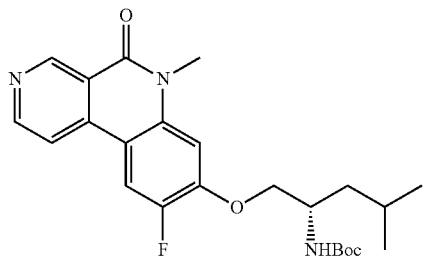 [SMILES: CC(C)C[C@@H](COc1cc2c(cc1F)c1ccncc1c(=O)n2C)NC(=O)OC(C)(C)C]

Part H. N-(8-chloro-6-methyl-5-oxo-5,6-dihydrobenzo[c][2,7]naphthyridin-2-yl)acetamide To a stirred solution of N-(8-chloro-6-methyl-5,6-dihydrobenzo[c][2,7]naphthyridin-2-yl)acetamide (0.6 g, 1.199 mmol) in DCM (20 mL) at rt was added barium manganate (1.536 g, 5.99 mmol) in three portions and the reaction was heated at 45° C. for 60 h. After the completion of reaction, the reaction mixture was diluted with DCM (70 mL) and passed through diatomaceous earth (Celite®). The filtrate was concentrated under reduced pressure. The residue was purified by silica gel column chromatography (DCM/MeOH as an eluant) to yield N-(8-chloro-6-methyl-5-oxo-5,6-dihydrobenzo[c][2,7]naphthyridin-2-yl)acetamide (0.4 g, 1.071 mmol, 89% yield) as an off white solid. LC/MS (ESI) m/e 302.1 [(M+H)$^+$, calcd for C$_{15}$H$_{13}$ClN$_3$O$_2$ 302.1]; LC/MS retention time (method C): t$_R$=1.88 min; HPLC retention time (method A); t$_R$=8.82 min; HPLC retention time (method B): t$_R$=7.99 min; $^1$H NMR (400 MHz, DMSO-d$_6$) δ 11.01 (s, 1H), 9.24 (s, 1H), 8.92 (s, 1H), 8.26 (d, J=8.80 Hz, 1H), 7.69 (d, J=2.00 Hz, 1H), 7.48 (dd, J=2.00, 8.80 Hz, 1H), 3.68 (s, 3H), 2.20 (s, 3H).

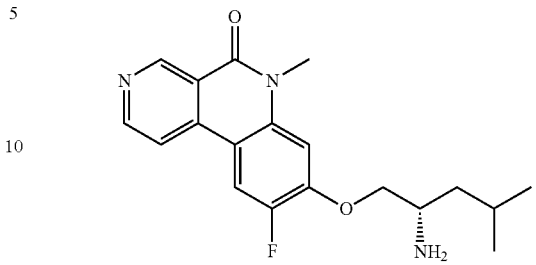

Part I. (S)-tert-butyl 1-(2-acetamido-6-methyl-5-oxo-5,6-dihydrobenzo[c][2,7]naphthyridin-8-yloxy)-4-methylpentan-2-ylcarbamate The reaction was carried out as in Ex. 2, Part D to afford crude (S)-tert-butyl 1-(2-acetamido-6-methyl-5-oxo-5,6-dihydrobenzo[c][2,7]naphthyridin-8-yloxy)-4-methylpentan-2-ylcarbamate (160 mg, 0.33 mmol, 20.5% pure by LC/MS) as a brown oil. This was taken to the next step without purification. LC/MS (ESI) m/e 483.34 [(M+H)$^+$, calcd for C$_{26}$H$_{35}$N$_4$O$_5$ 483.25]; LC/MS retention time (Method E): t$_R$=1.13 min.

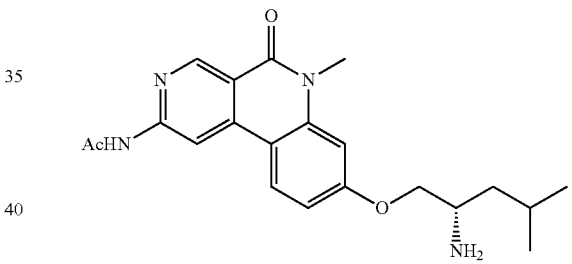

Part J. (S)—N-(8-(2-amino-4-methylpentyloxy)-6-methyl-5-oxo-5,6-dihydrobenzo[c][2,7]naphthyridin-2-yl)acetamide To a stirred solution of (S)-tert-butyl (1-((2-acetamido-6-methyl-5-oxo-5,6-dihydrobenzo[c][2,7]naphthyridin-8-yl)oxy)-4-methylpentan-2-yl)carbamate (140 mg, 0.059 mmol) in CH$_2$Cl$_2$ (15 mL) at 0° C. was added TFA (1.2 mL, 15.58 mmol) and the reaction mixture was stirred at RT for 40 min. After the completion of reaction, the volatile organics were evaporated under reduced pressure and the residue was purified by preparative HPLC (0.1% TFA in water/Acetonitrile) to yield (S)—N-(8-((2-amino-4-methylpentyl)oxy)-6-methyl-5-oxo-5,6-dihydrobenzo[c][2,7]naphthyridin-2-yl)acetamide (2 mg, 3.93 µmol, 6.6% yield) as a mono TFA salt. LC/MS (ESI) m/e 383.2 [(M+H)$^+$, calcd for C$_{21}$H$_{22}$N$_4$O$_3$ 383.2]; LC/MS retention time (method C): t$_R$=1.80 min; HPLC retention time (method A): t$_R$=5.14 min; HPLC retention time (method B): t$_R$=5.62 min; $^1$H NMR (400 MHz, CD$_3$OD) δ 9.28 (s, 1H), 8.93 (s, 1H), 8.35 (d, J=8.80 Hz, 1H), 7.17 (s, 1H), 7.15 (d, J=2.00 Hz, 1H), 4.46 (d, J=8.80 Hz, 1H), 4.28 (dd, J=6.40, 10.80 Hz, 1H), 3.76-3.79 (m, 4H), 2.29 (s, 3H), 1.65-1.88 (m, 3H), 1.08 (d, J=4.40 Hz, 3H), 1.07 (d, J=4.40 Hz, 3H).

Example 19

(R)-8-((2-amino-4-methylpentyl)oxy)-4,6-dimethyl-benzo[c][2,7]naphthyridin-5(6H)-one

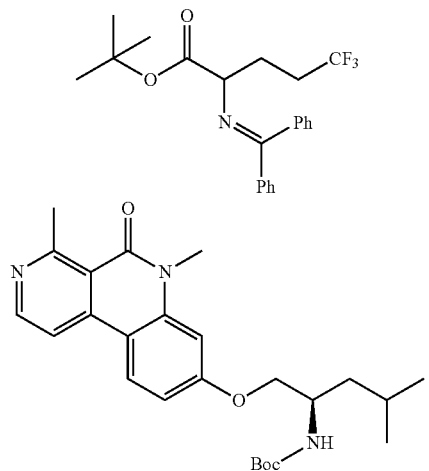

Part A. (R)-tert-butyl (1-((4,6-dimethyl-5-oxo-5,6-dihydrobenzo[c][2,7]naphthyridin-8-yl)oxy)-4-methylpentan-2-yl)carbamate The title compound was prepared as described in Example 16 using (R)-tert-butyl (1-hydroxy-4-methylpentan-2-yl)carbamate in part H to afford (R)-tert-butyl (1-((4,6-dimethyl-5-oxo-5,6-dihydrobenzo[c][2,7]naphthyridin-8-yl)oxy)-4-methylpentan-2-yl)carbamate (620 mg, 0.564 mmol, 49% yield) as a yellow solid. LC/MS, (ESI) m/z 440.3 [(M+H)$^+$, calcd for $C_{25}H_{34}N_3O_4$ 440.3].

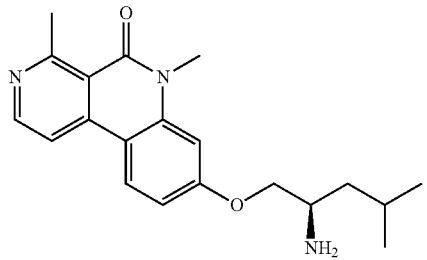

Part B. (R)-8-((2-amino-4-methylpentyl)oxy)-4,6-dimethylbenzo[c][2,7]naphthyridin-5(6H)-one An ambient temperature solution of (R)-tert-butyl (1-((4,6-dimethyl-5-oxo-5,6-dihydrobenzo[c][2,7]naphthyridin-8-yl)oxy)-4-methylpentan-2-yl)carbamate (102 mg, 0.232 mmol) in dichloromethane (1 mL) was treated with HCl (1.160 mL, 4.64 mmol) and stirred for 1 h. The resulting mixture was concentrated to an oil and purified by reverse phase high performance liquid chromatography (Phenomenex Luna C18 30×100 mm 10 micron; water/methanol/0.1% TFA gradient elution). Fractions containing product were neutralized with saturated aqueous sodium bicarbonate and concentrated under reduced pressure. The residue was partitioned between ethyl acetate and brine and the layers were separated. The aqueous was extracted twice more with ethyl acetate and the pooled organics were washed once with brine, dried over magnesium sulfate, filtered, and concentrated to afford (R)-8-((2-amino-4-methylpentyl)oxy)-4,6-dimethylbenzo[c][2,7]naphthyridin-5(6H)-one (11.5 mg, 0.033 mmol, 14% yield) as a milky oil. LC/MS, (ESI) m/z 340.2 [(M+H)$^+$, calcd for $C_{20}H_{26}N_3O_2$ 340.2]; HPLC retention time (method C): $t_R$=13.02 min; HPLC retention time (method D): $t_R$=13.05 min; $^1$H NMR (500 MHz, METHANOL-$d_4$) δ 8.68-8.63 (m, 2H), 8.58 (d, J=9.0 Hz, 1H), 7.22 (dd, J=9.0, 2.3 Hz, 1H), 7.20 (d, J=2.3 Hz, 1H), 4.52 (dd, J=10.5, 3.3 Hz, 1H), 4.34 (dd, J=10.7, 6.6 Hz, 1H), 3.82 (s, 3H), 3.80-3.75 (m, 1H), 3.25 (s, 3H), 1.91-1.81 (m, 1H), 1.80-1.73 (m, 1H), 1.72-1.64 (m, 1H), 1.07 (d, J=5.8 Hz, 3H), 1.06 (d, J=5.8 Hz, 3H).

Example 20

(R)-8-((2-amino-4-methylpentyl)oxy)-9-chloro-4,6-dimethylbenzo[c][2,7]naphthyridin-5(6H)-one

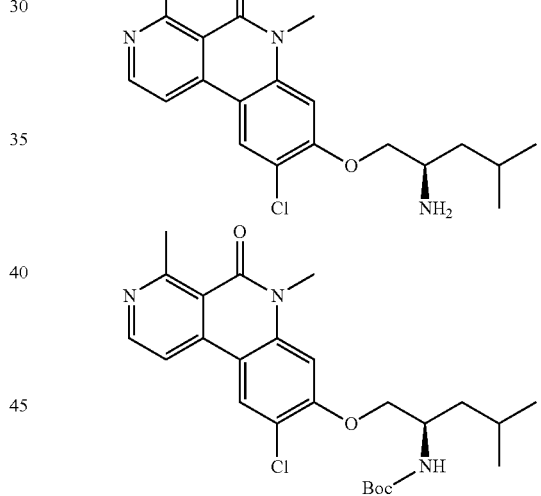

Part A. (R)-tert-butyl (1-((9-chloro-4,6-dimethyl-5-oxo-5,6-dihydrobenzo[c][2,7]naphthyridin-8-yl)oxy)-4-methylpentan-2-yl)carbamate A mixture of (R)-tert-butyl (1-((4,6-dimethyl-5-oxo-5,6-dihydrobenzo[c][2,7]naphthyridin-8-yl)oxy)-4-methylpentan-2-yl)carbamate (248 mg, 0.564 mmol) prepared as described in Example 19, Part A, NCS (151 mg, 1.128 mmol), and acetonitrile (5 mL) was heated at 90° C. for 1 h and then stirred at room temperature overnight. The crude material was concentrated under reduced pressure to afford (R)-tert-butyl (1-((9-chloro-4,6-dimethyl-5-oxo-5,6-dihydrobenzo[c][2,7]naphthyridin-8-yl)oxy)-4-methylpentan-2-yl)carbamate (15 mg, 0.032 mmol, 6% crude yield). The mixture was carried on without further purification. LC/MS, (ESI) m/z 474.2 [(M+H)$^+$, calcd for $C_{25}H_{33}ClN_3O_4$ 474.2].

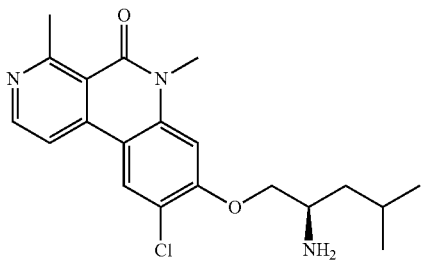 [SMILES: Cc1nccc2c1c(=O)n(C)c1cc(OC[C@H](N)CC(C)C)c(Cl)cc21]

Part B. (R)-8-((2-amino-4-methylpentyl)oxy)-9-chloro-4,6-dimethylbenzo[c][2,7]naphthyridin-5(6H)-one An ambient temperature solution of (R)-tert-butyl (1-((9-chloro-4,6-dimethyl-5-oxo-5,6-dihydrobenzo[c][2,7]naphthyridin-8-yl)oxy)-4-methylpentan-2-yl)carbamate (15 mg, 0.032 mmol) in dichloromethane (0.5 mL) was treated with HCl (4M in 1,4-dioxane) (0.396 mL, 1.58 mmol) and stirred for 1 h. The resulting mixture was concentrated and the residue was purified by reverse phase high performance liquid chromatography (Phenomenex Luna C18 30×100 mm 10 micron; water/acetonitrile/10 mM ammonium acetate gradient elution). Fractions containing product were concentrated under reduced pressure to afford (R)-tert-butyl (1-((9-chloro-4,6-dimethyl-5-oxo-5,6-dihydrobenzo[c][2,7]naphthyridin-8-yl)oxy)-4-methylpentan-2-yl)carbamate one (9.0 mg, 0.023 mmol, 73% yield) as a white solid. LC/MS, (ESI) m/z 373.2 [(M+H)$^+$, calcd for $C_{20}H_{25}ClN_3O_2$ 373.2]; HPLC retention time (method C): $t_R$=14.21 min; HPLC retention time (method D): $t_R$=14.30 min; $^1$H NMR (400 MHz, CHLOROFORM-d) δ 8.70 (d, J=5.8 Hz, 1H), 8.21 (s, 1H), 7.79 (d, J=5.8 Hz, 1H), 6.83 (s, 1H), 4.18 (dd, J=8.8, 3.8 Hz, 1H), 4.04-3.97 (m, 1H), 3.76 (s, 3H), 3.48 (qd, J=6.9, 3.5 Hz, 1H), 3.17 (s, 3H), 1.84 (dquin, J=13.7, 6.7 Hz, 1H), 1.49 (t, J=7.0 Hz, 2H), 1.03 (d, J=6.5 Hz, 3H), 1.01 (d, J=6.5 Hz, 3H).

Example 21

(S)-8-(2-amino-3-cyclopropylpropoxy)-4,6-dimethylbenzo[c][2,7]naphthyridin-5(6H)-one

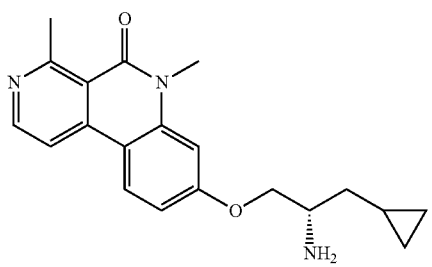 [SMILES: Cc1nccc2c1c(=O)n(C)c1cc(OC[C@@H](N)CC3CC3)ccc21]

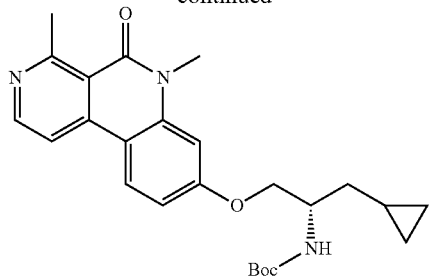

Part A: (S)-tert-butyl (1-cyclopropyl-3-((4,6-dimethyl-5-oxo-5,6-dihydrobenzo[c][2,7]naphthyridin-8-yl)oxy)propan-2-yl)carbamate The title compound was prepared as described in Example 16 using (S)-tert-butyl (1-cyclopropyl-3-hydroxypropan-2-yl)carbamate (0.287 g, 1.334 mmol) in Part H to afford (S)-tert-butyl (1-cyclopropyl-3-((4,6-dimethyl-5-oxo-5,6-dihydrobenzo[c][2,7]naphthyridin-8-yl)oxy)propan-2-yl)carbamate (230 mg, 0.526 mmol, 59% yield) as a colorless oil. LC/MS, (ESI) m/z 438.3 [(M+H)$^+$, calcd for $C_{25}H_{32}N_3O_4$ 438.2]; $^1$H NMR (400 MHz, CHLOROFORM-d) δ 8.61 (d, J=5.5 Hz, 1H), 8.09 (d, J=8.8 Hz, 1H), 7.77 (d, J=5.5 Hz, 1H), 6.96-6.79 (m, 2H), 4.92 (br. s., 1H), 4.35-3.98 (m, 3H), 3.70 (s, 3H), 3.13 (s, 3H), 1.63 (t, J=6.9 Hz, 2H), 1.47 (s, 9H), 0.83-0.70 (m, 1H), 0.61-0.42 (m, 2H), 0.21-0.04 (m, 2H).

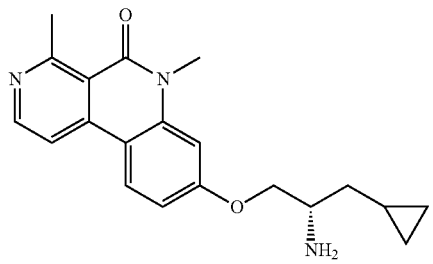

Part B: (S)-8-(2-amino-3-cyclopropylpropoxy)-4,6-dimethylbenzo[c][2,7]naphthyridin-5(6H)-one An ambient temperature suspension of (S)-tert-butyl (1-cyclopropyl-3-((4,6-dimethyl-5-oxo-5,6-dihydrobenzo[c][2,7]naphthyridin-8-yl)oxy)propan-2-yl)carbamate (50 mg, 0.114 mmol) (prepared as described in Example 16 using (S)-tert-butyl (1-cyclopropyl-3-hydroxypropan-2-yl)carbamate (0.287 g, 1.334 mmol) in Part H) in diethyl ether (1 mL) was treated with HCl (4M in 1,4-dioxane) (0.571 mL, 2.286 mmol) and stirred for 1 h. The resulting mixture was concentrated under reduced pressure to a yellow solid. The crude material was purified by reverse phase high performance liquid chromatography (Phenomenex Luna C18 30×100 mm 10 micron; water/methanol/TFA gradient elution). Fractions containing product were concentrated under reduced pressure. The resulting residue was partitioned between saturated aqueous sodium bicarbonate and ethyl acetate. The layers were separated and the aqueous was extracted twice more with ethyl acetate. The pooled organics were washed once with brine, dried over magnesium sulfate, filtered, and concentrated to afford (S)-8-(2-amino-3-cyclopropylpropoxy)-4,6-dimethylbenzo[c][2,7]naphthyridin-5 (6H)-one (9.0 mg, 0.025 mmol, 22% yield for the final step) as a white solid. LC/MS, (ESI) m/z 338.2 [(M+H)$^+$, calcd for $C_{20}H_{24}N_3O_2$ 338.2]; HPLC retention time (method C): $t_R$=13.05 min; HPLC retention time (method D): $t_R$=13.88 min; $^1$H NMR (400 MHz, CHLOROFORM-d) δ 8.65 (d, J=5.8 Hz, 1H), 8.16 (d, J=8.8 Hz, 1H), 7.83 (d, J=5.5 Hz, 1H), 6.92 (dd, J=8.9, 2.4 Hz, 1H), 6.87 (d, J=2.3 Hz, 1H), 4.15 (dd, J=8.9, 3.9 Hz, 1H), 3.97 (dd, J=8.8, 7.0 Hz, 1H), 3.75 (s, 3H), 3.48-3.35 (m, 1H), 3.17 (s, 3H), 1.59-1.42 (m, 2H), 0.87-0.74 (m, 1H), 0.64-0.47 (m, 2H), 0.25-0.17 (m, 1H), 0.16-0.10 (m, 1H).

Example 22

(S)-8-(2-amino-3-cyclobutylpropoxy)-4,6-dimethylbenzo[c][2,7]naphthyridin-5(6H)-one

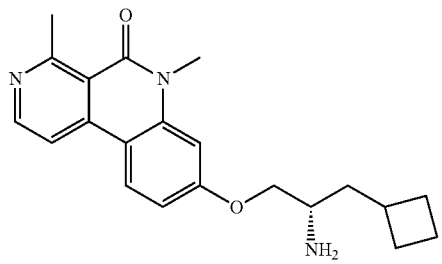 [SMILES: Cc1nccc2c1c(=O)n(C)c1cc(OC[C@@H](N)CC3CCC3)ccc21]

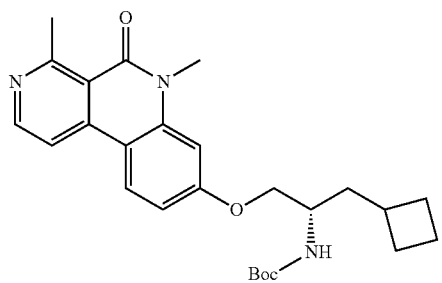

Part A: (S)-tert-butyl (1-cyclobutyl-3-((4,6-dimethyl-5-oxo-5,6-dihydrobenzo[c][2,7]naphthyridin-8-yl)oxy)propan-2-yl)carbamate The title compound was prepared as described in Example 16 using (S)-tert-butyl (1-cyclobutyl-3-hydroxypropan-2-yl)carbamate (0.359 g, 1.566 mmol) in Part H to afford (S)-tert-butyl (1-cyclobutyl-3-((4,6-dimethyl-5-oxo-5,6-dihydrobenzo[c][2,7]naphthyridin-8-yl)oxy)propan-2-yl)carbamate (400 mg, 0.886 mmol, 85% yield) as a colorless oil. LC/MS, (ESI) m/z 452.3 [(M+H)$^+$, calcd for $C_{26}H_{34}N_3O_4$ 452.3]; $^1$H NMR (400 MHz, CHLOROFORM-d) δ 8.62 (d, J=5.8 Hz, 1H), 8.11 (d, J=8.8 Hz, 1H), 7.79 (d, J=5.5 Hz, 1H), 6.94-6.79 (m, 2H), 4.76 (d, J=7.5 Hz, 1H), 4.07 (d, J=3.5 Hz, 2H), 3.93 (br. s., 1H), 3.71 (s, 3H), 3.14 (s, 3H), 2.55-2.35 (m, 1H), 2.15-2.05 (m, 2H), 1.97-1.59 (m, 7H), 1.47 (s, 9H).

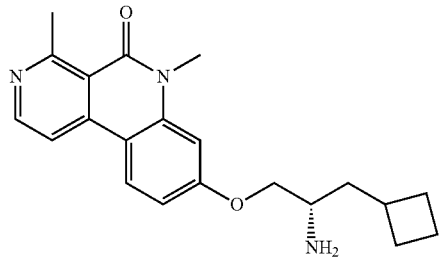

Part B: (S)-8-(2-amino-3-cyclobutylpropoxy)-4,6-dimethylbenzo[c][2,7]naphthyridin-5(6H)-one An ambient temperature suspension of (S)-tert-butyl (1-cyclobutyl-3-((4,6-dimethyl-5-oxo-5,6-dihydrobenzo[c][2,7]naphthyridin-8-yl)oxy)propan-2-yl)carbamate (70 mg, 0.155 mmol) in diethyl ether (1 mL) was treated with HCl (4M in 1,4-dioxane) (0.775 mL, 3.10 mmol) and stirred for 1 h. The resulting mixture was concentrated under reduced pressure to a yellow solid. The crude material was purified by reverse phase high performance liquid chromatography (Phenomenex Luna C18 30×100 mm 10 micron; water/methanol/TFA gradient elution). Fractions containing product were concentrated under reduced pressure. The resulting residue was partitioned between saturated aqueous sodium bicarbonate and ethyl acetate. The layers were separated and the aqueous was extracted twice more with ethyl acetate. The pooled organics were washed once with brine, dried over magnesium sulfate, filtered, and concentrated under reduced pressure to afford (S)-8-(2-amino-3-cyclobutylpropoxy)-4,6-dimethylbenzo[c][2,7]naphthyridin-5(6H)-one (17 mg, 0.046 mmol, 30% yield) as a white solid. LC/MS, (ESI) m/z 352.3 [(M+H)$^+$, calcd for $C_{21}H_{26}N_3O_2$ 352.2]; HPLC retention time (method C): $t_R$=14.15 min; HPLC retention time (method D): $t_R$=14.78 min; $^1$H NMR (400 MHz, CHLOROFORM-d) δ 8.64 (d, J=5.8 Hz, 1H), 8.15 (d, J=9.0 Hz, 1H), 7.82 (d, J=5.8 Hz, 1H), 6.89 (dd, J=8.9, 2.4 Hz, 1H), 6.84 (d, J=2.3 Hz, 1H), 4.04 (dd, J=8.9, 3.9 Hz, 1H), 3.86 (dd, J=8.8, 7.5 Hz, 1H), 3.73 (s, 3H), 3.23 (tdd, J=7.5, 5.5, 3.8 Hz, 1H), 3.16 (s, 3H), 2.60-2.43 (m, 1H), 2.21-2.08 (m, 2H), 2.01-1.81 (m, 2H), 1.80-1.55 (m, 4H).

Example 23

(S)-8-(2-amino-3-cyclopropylpropoxy)-9-chloro-4,6-dimethylbenzo[c][2,7]naphthyridin-5(6H)-one

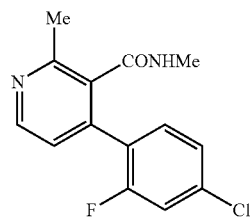

The title compound was prepared as described in Example 20 to afford (S)-8-(2-amino-3-cyclopropylpropoxy)-9- chloro-4,6-dimethylbenzo[c][2,7]naphthyridin-5(6H)-one (12.5 mg, 0.030 mmol, 24% yield for the final step) as a pale yellow solid. LC/MS, (ESI) m/z 372.2 [(M+H)⁺, calcd for $C_{20}H_{23}ClN_3O_2$ 372.2]; HPLC retention time (method C): $t_R$=14.16 min; HPLC retention time (method D): $t_R$=15.03 min; ¹H NMR (400 MHz, CHLOROFORM-d) δ 8.66 (d, J=5.5 Hz, 1H), 8.17 (s, 1H), 7.74 (d, J=5.8 Hz, 1H), 6.81 (s, 1H), 4.22 (dd, J=8.7, 3.9 Hz, 1H), 4.05 (dd, J=8.5, 7.0 Hz, 1H), 3.73 (s, 3H), 3.49 (qd, J=6.8, 4.0 Hz, 1H), 3.20-3.12 (m, 3H), 1.63-1.46 (m, 2H), 0.89-0.75 (m, 1H), 0.67-0.45 (m, 2H), 0.25-0.18 (m, 1H), 0.17-0.10 (m, 1H).

Example 24

(S)-8-(2-amino-3-cyclobutylpropoxy)-9-chloro-4,6-dimethylbenzo[c][2,7]naphthyridin-5(6H)-one

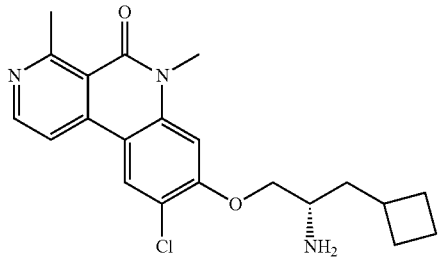 [SMILES: Cc1nccc2c1c(=O)n(C)c1cc(OC[C@@H](N)CC3CCC3)c(Cl)cc21]

The title compound was prepared as described in Example 20 to afford (S)-8-(2-amino-3-cyclobutylpropoxy)-9-chloro-4,6-dimethylbenzo[c][2,7]naphthyridin-5(6H)-one (10.5 mg, 0.027 mmol, 24% yield for the final step) as a colorless solid. LC/MS, (ESI) m/z 386.2 [(M+H)⁺, calcd for $C_{21}H_{25}ClN_3O_2$ 386.2]; HPLC retention time (method C): $t_R$=14.92 min; HPLC retention time (method D): $t_R$=15.61 min; ¹H NMR (400 MHz, CHLOROFORM-d) δ 8.68 (d, J=5.5 Hz, 1H), 8.20 (s, 1H), 7.77 (d, J=5.8 Hz, 1H), 6.81 (s, 1H), 4.14 (dd, J=8.7, 3.9 Hz, 1H), 4.01-3.91 (m, 1H), 3.75 (s, 3H), 3.34 (d, J=4.5 Hz, 1H), 3.17 (s, 3H), 2.62-2.44 (m, 1H), 2.22-2.06 (m, 2H), 2.01-1.82 (m, 2H), 1.82-1.63 (m, 4H).

Example 25

(S)-8-(2-amino-3-cyclopropylpropoxy)-4,6,9-trimethylbenzo[c][2,7]naphthyridin-5(6H)-one

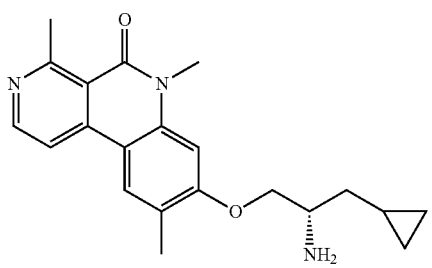

Part A: (S)-tert-butyl (1-((9-bromo-4,6-dimethyl-5-oxo-5,6-dihydrobenzo[c][2,7]naphthyridin-8-yl)oxy)-3-cyclopropylpropan-2-yl)carbamate A mixture of (S)-tert-butyl (1-cyclopropyl-3-((4,6-dimethyl-5-oxo-5,6-dihydrobenzo[c][2,7]naphthyridin-8-yl)oxy)propan-2-yl)carbamate (100 mg, 0.229 mmol) prepared as described in Example 21, Part A in acetonitrile (5 mL) was heated to 90° C. for 1 h resulting in a homogeneous orange solution. The solution was treated with saturated aqueous sodium bicarbonate and concentrated under reduced pressure. The residue was partitioned between brine and ethyl acetate and the layers were separated. The aqueous layer was extracted twice more with ethyl acetate and the pooled organics were washed once with brine, dried over magnesium sulfate, filtered, and concentrated to a solid. The solid was purified via silica gel chromatography (1% ammonia in methanol/dichloromethane) to afford (S)-tert-butyl (1-((9-bromo-4,6-dimethyl-5-oxo-5,6-dihydrobenzo[c][2,7]naphthyridin-8-yl)oxy)-3-cyclopropylpropan-2-yl)carbamate (53 mg, 0.103 mmol, 45% yield) as a colorless oil which solidified upon standing. LC/MS, (ESI) m/z 516.2, 518.2 Br pattern [(M+H)⁺, calcd for $C_{25}H_{31}BrN_3O_4$ 516.2].

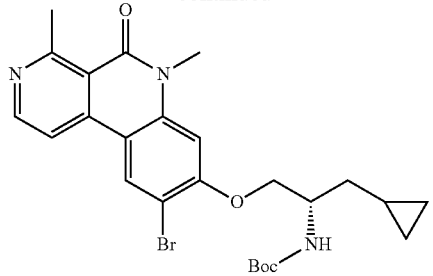

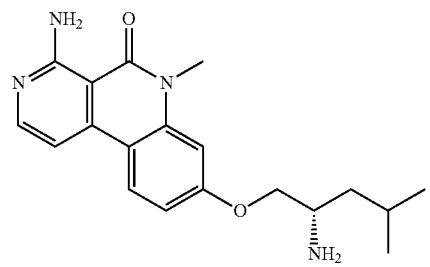 [SMILES: CC(C)C[C@H](N)COc1ccc2c3ccnc(N)c3c(=O)n(C)c2c1]

Part B: (S)-tert-butyl (1-cyclopropyl-3-((4,6,9-trimethyl-5-oxo-5,6-dihydrobenzo[c][2,7]naphthyridin-8-yl)oxy)propan-2-yl)carbamate An ambient temperature mixture of (S)-tert-butyl (1-((9-bromo-4,6-dimethyl-5-oxo-5,6-dihydrobenzo[c][2,7]naphthyridin-8-yl)oxy)-3-cyclopropylpropan-2-yl)carbamate (51 mg, 0.099 mmol), trimethylboroxine (0.015 mL, 0.109 mmol), $PdCl_2$(dppf)-$CH_2Cl_2$ Adduct (8.06 mg, 9.88 μmol), cesium carbonate (64.4 mg, 0.198 mmol), 1,4-dioxane (1 mL), and water (0.33 mL) was charged to a pressure rated vial and purged with a stream of nitrogen for 10 minutes. The vial was sealed and stirred under nitrogen at 75° C. for 12 h. The resulting mixture was cooled to room temperature and vacuum filtered. The filtrate was concentrated under reduced pressure and the residue was partitioned between ethyl acetate and brine. The layers were separated and the aqueous layer was extracted twice more with ethyl acetate. The pooled organics were dried over magnesium sulfate, filtered, and concentrated to an oil. The oil was purified via silica gel chromatography (1% 2M ammonia in methanol/dichloromethane) to afford (S)-tert-butyl (1-cyclopropyl-3-((4,6,9-trimethyl-5-oxo-5,6-dihydrobenzo[c][2,7]naphthyridin-8-yl)oxy)propan-2-yl)carbamate (41 mg, 0.091 mmol, 92% yield) as a colorless oil. LC/MS, (ESI) m/z 452.3 [(M+H)$^+$, calcd for $C_{26}H_{34}N_3O_4$ 452.3]; $^1$H NMR (400 MHz, CHLOROFORM-d) δ 8.59 (d, J=5.8 Hz, 1H), 7.90 (s, 1H), 7.78 (d, J=5.8 Hz, 1H), 6.74 (s, 1H), 4.91 (d, J=7.3 Hz, 1H), 4.35-4.04 (m, 3H), 3.71 (s, 3H), 3.14 (s, 3H), 2.31 (s, 3H), 1.72-1.59 (m, 2H), 1.48 (s, 9H), 0.86-0.70 (m, 1H), 0.60-0.44 (m, 2H), 0.21-0.00 (m, 2H).

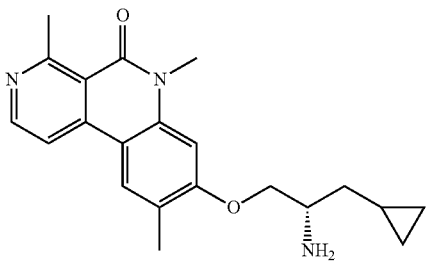 [SMILES: Cc1cc2c3ccnc(C)c3c(=O)n(C)c2cc1OC[C@@H](N)CC1CC1]

Part C: (S)-8-(2-amino-3-cyclopropylpropoxy)-4,6,9-trimethylbenzo[c][2,7]naphthyridin-5(6H)-one An ambient temperature solution of (S)-tert-butyl (1-cyclopropyl-3-((4,6,9-trimethyl-5-oxo-5,6-dihydrobenzo[c][2,7]naphthyridin-8-yl)oxy)propan-2-yl)carbamate (41 mg, 0.091 mmol) in methanol (0.5 mL) was treated with HCl (4M in 1,4-dioxane) (0.454 mL, 1.816 mmol) and stirred for 1 h. The resulting mixture was concentrated under reduced pressure to yellow solid. The crude material was purified by reverse phase high performance liquid chromatography (Phenomenex Luna C18 30×100 mm 10 micron; water/methanol/TFA gradient elution). Product containing fractions were neutralized with saturated aqueous sodium bicarbonate and concentrated under reduced pressure. The resulting residue was partitioned between water and ethyl acetate and the layers were separated. The aqueous was extracted twice more with ethyl acetate and the pooled organics were dried over magnesium sulfate, filtered, and concentrated to afford (S)-8-(2-amino-3-cyclopropylpropoxy)-4,6,9-trimethylbenzo[c][2,7]naphthyridin-5(6H)-one (10.7 mg, 0.028 mmol, 93% yield) as a colorless solid. LC/MS, (ESI) m/z 352.2 [(M+H)$^+$, calcd for $C_{21}H_{26}N_3O_2$ 352.2]; HPLC retention time (method C): $t_R$=13.71 min; HPLC retention time (method D): $t_R$=14.29 min; $^1$H NMR (400 MHz, CHLOROFORM-d) δ 8.63 (d, J=5.5 Hz, 1H), 7.98 (s, 1H), 7.84 (d, J=5.8 Hz, 1H), 6.74 (s, 1H), 4.15 (dd, J=8.8, 4.0 Hz, 1H), 4.00 (dd, J=8.7, 6.9 Hz, 1H), 3.76 (s, 3H), 3.50-3.37 (m, 1H), 3.17 (s, 3H), 2.37 (s, 3H), 1.61-1.44 (m, 2H), 1.02-0.74 (m, 1H), 0.68-0.45 (m, 2H), 0.30-0.06 (m, 2H).

Example 26

(S)-8-(2-amino-3-cyclopropylpropoxy)-4,6,9-trimethylbenzo[c][2,7]naphthyridin-5(6H)-one

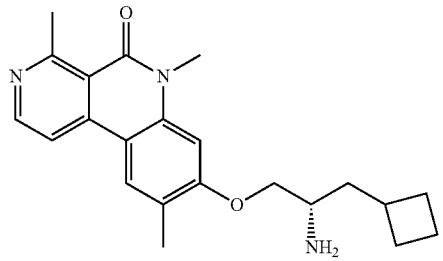

The title compound was prepared as described in Example 25 starting from (S)-tert-butyl (1-cyclobutyl-3-((4,6-dimethyl-5-oxo-5,6-dihydrobenzo[c][2,7]naphthyridin-8-yl)oxy)propan-2-yl)carbamate, prepared as described in Example 22, Part A to afford (S)-8-(2-amino-3-cyclobutylpropoxy)-4,6,9-trimethylbenzo[c][2,7]naphthyridin-5(6H)-one (18 mg, 0.046 mmol, 26% yield for the final step) as a hazy film. LC/MS, (ESI) m/z 366.3 [(M+H)$^+$, calcd for $C_{22}H_{28}N_3O_2$ 366.2]; HPLC retention time (method C): $t_R$=14.65 min; HPLC retention time (method D): $t_R$=15.04 min; $^1$H NMR (400 MHz, CHLOROFORM-d) δ 8.62 (d, J=5.8 Hz, 1H), 7.95 (s, 1H), 7.82 (d, J=5.8 Hz, 1H), 6.69 (s, 1H), 4.05 (dd, J=8.8, 4.0 Hz, 1H), 3.88 (dd, J=8.5, 7.3 Hz, 1H), 3.74 (s, 3H), 3.34-3.20 (m, 1H), 3.16 (s, 3H), 2.63-2.46 (m, 1H), 2.36 (s, 3H), 2.23-2.08 (m, 2H), 2.01-1.59 (m, 6H).

Example 27

(S)-8-((2-amino-4-methylpentyl)oxy)-9-(difluoromethyl)-4,6-dimethylbenzo[c][2,7]naphthyridin-5(6H)-one

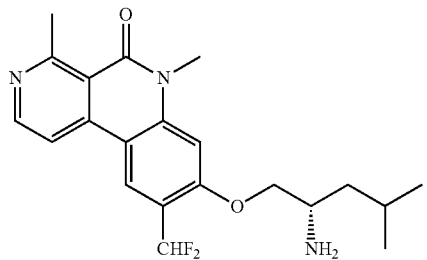 [SMILES: Cc1nccc2c1c(=O)n(C)c1cc(OC[C@@H](N)CC(C)C)c(C(F)F)cc21]

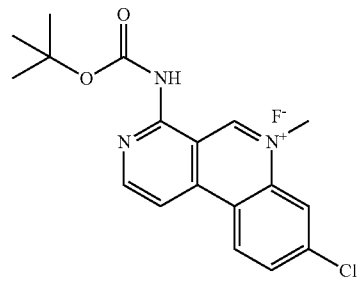

Part A: 8-chloro-9-iodo-4,6-dimethylbenzo[c][2,7]naphthyridin-5(6H)-one

To a solution of 8-chloro-4,6-dimethylbenzo[c][2,7]naphthyridin-5(6H)-one (1 g, 3.87 mmol) prepared as described in Example 16, Part G, in acetic acid (30 mL) was added $H_2SO_4$ (0.021 mL, 0.387 mmol) and periodic acid (0.881 g, 3.87 mmol). The solution was heated at 80° C. for 20 min then iodine (0.294 g, 1.160 mmol) was added. The mixture was stirred for another 3 h at 80° C. The solution was cooled to room temperature then concentrated under reduced pressure. EtOAc was added to the residue and the layer was washed with saturated aqueous $NaHCO_3$ then $H_2O$. The combined organic layers were dried over $Na_2SO_4$, filtered and concentrated under reduced pressure to afford 8-chloro-9-iodo-4,6-dimethylbenzo[c][2,7]naphthyridin-5(6H)-one (1.2 g, 3.12 mmol, 81% crude yield) as an off-white solid. The material was carried on without further purification. LC/MS (ESI) m/e 385.0 [(M+H)$^+$, calcd for $C_{14}H_{11}ClIN_2O$, 385.0]; LC/MS retention time (method B): $t_R$=1.09 min.

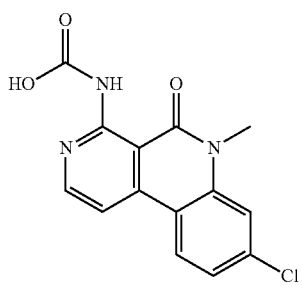 [SMILES: Cn1c(=O)c2c(NC(=O)O)nccc2c2ccc(Cl)cc21]

Part B: 8-chloro-4,6-dimethyl-9-vinylbenzo[c][2,7]naphthyridin-5(6H)-one

A solution of 8-chloro-9-iodo-4,6-dimethylbenzo[c][2,7]naphthyridin-5(6H)-one (1.2 g, 2.71 mmol), 2,4,6-trivinylcyclotriboroxane pyridine complex (0.784 g, 3.26 mmol), tetrakis(triphenylphosphine)palladium (0.157 g, 0.136 mmol) and $Na_2CO_3$ (0.575 g, 5.43 mmol) in toluene (30 mL) and water (0.5 mL) was purged with nitrogen and heated at 90° C. for 16 h. After cooling to room temperature, the mixture was concentrated under reduced pressure. The residue was taken up in ethyl acetate and filtered through diatomaceous earth (Celite®). The EtOAc layer was washed with brine and water. The combined organic layers were dried over $Na_2SO_4$, filtered and concentrated under reduced pressure. The crude material was purified by silica gel flash chromatography using EtOAc-hexane as the eluent to afford 8-chloro-4,6-dimethyl-9-vinylbenzo[c][2,7]naphthyridin-5(6H)-one (0.6 g, 1.43 mmol, 68% yield)) as brown gummy solid. LC/MS (ESI) m/e 285.0 [(M+H)$^+$, calcd for $C_{16}H_{14}ClN_2O$, 285.1]; LC/MS retention time (method B): $t_R$=2.25 min.

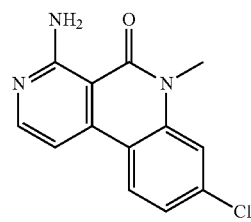 [SMILES: Cn1c(=O)c2c(N)nccc2c2ccc(Cl)cc21]

Part C: 8-chloro-4,6-dimethyl-5-oxo-5,6-dihydrobenzo[c][2,7]naphthyridine-9-carbaldehyde To a solution of 8-chloro-4,6-dimethyl-9-vinylbenzo[c][2,7]naphthyridin-5(6H)-one (600 mg, 2.107 mmol), osmium tetroxide (2.5% in 2-methyl-2-propanol) (0.794 mL, 0.063 mmol), and 2,6-dimethylpyridine (0.491 mL, 4.21 mmol) in 1,4-dioxane (30 mL) and water (30 mL) cooled to 0° C. was added sodium periodate (1803 mg, 8.43 mmol). The mixture was warmed to room temperature and stirred for 3 h. The mixture was diluted with ethyl acetate and filtered through diatomaceous earth (Celite®). The organic layer was concentrated under reduced pressure to afford a brown solid. The solid was washed with hexane (3×20 mL) and dried under vacuum to afford 8-chloro-4,6-dimethyl-5-oxo-5,6-dihydrobenzo[c][2,7]naphthyridine-9-carbaldehyde 0.6 g, 2.107 mmol, 84% yield) as a gummy brown solid. LC/MS (ESI) m/e 287.0 [(M+H)$^+$, calcd for $C_{15}H_{12}ClN_2O_2$, 287.1]; LC/MS retention time (method B): $t_R$=2.03 min.

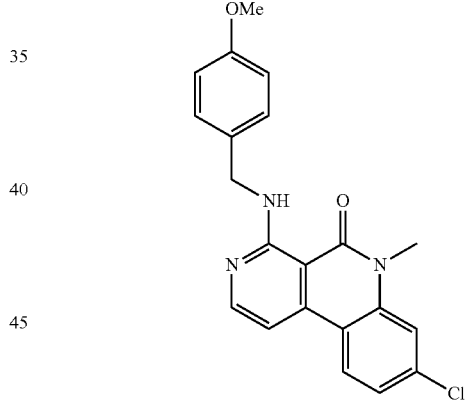

Part D: 8-chloro-9-(difluoromethyl)-4,6-dimethylbenzo[c][2,7]naphthyridin-5(6H)-one To a solution of 8-chloro-4,6-dimethyl-5-oxo-5,6-dihydrobenzo[c][2,7]naphthyridine-9-carbaldehyde (600 mg, 1.779 mmol) in DCM (15 mL) was added bis-(2-methoxyethyl)aminosulfur trifluoride (Deoxo-Fluor) (1.968 g, 8.89 mmol). The mixture was then heated at 40° C. for 3 h. After cooling to room temperature, the reaction mixture was diluted with DCM and the DCM layer washed with saturated aqueous $NaHCO_3$ then $H_2O$, dried over $Na_2SO_4$, filtered and concentrated under reduced pressure. The residue was purified by silica gel flash chromatography using EtOAc-hexane as the eluent to afford 8-chloro-9-(difluoromethyl)-4,6-dimethylbenzo[c][2,7]naphthyridin-5(6H)-one (0.7 g, 1.519 mmol, 84% yield) as an off-white solid. LC/MS (ESI) m/e 309.0 [(M+H)$^+$, calcd for $C_{15}H_{12}ClF_2N_2O$, 309.1]; LC/MS retention time (method B): $t_R$=2.38 min. $^1$H NMR (400 MHz, METHANOL-$d_4$) δ ppm 8.68-8.74 (m, 2H), 8.32 (d, 1H), 7.78 (s, 1H), 7.00-7.33 (m, 1H), 3.79 (s, 3H), 3.13 (s, 3H).

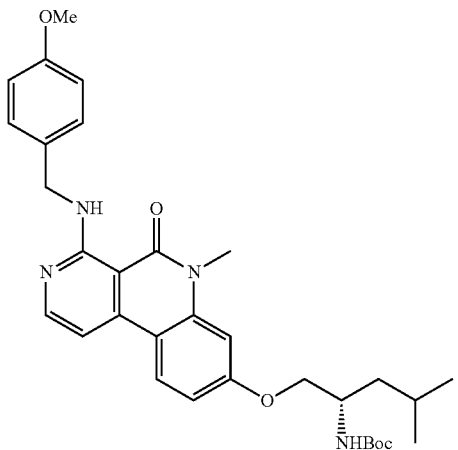 [SMILES: COc1ccc(CNc2nccc3c2c(=O)n(C)c2cc(OC[C@H](CC(C)C)NC(=O)OC(C)(C)C)ccc32)cc1]

Part E: (S)-tert-butyl (1-((9-(difluoromethyl)-4,6-dimethyl-5-oxo-5,6-dihydrobenzo[c][2,7]naphthyridin-8-yl)oxy)-4-methylpentan-2-yl)carbamate A solution of 8-chloro-9-(difluoromethyl)-4,6-dimethylbenzo[c][2,7]naphthyridin-5(6H)-one (700 mg, 1.519 mmol), (S)-tert-butyl (1-hydroxy-4-methylpentan-2-yl)carbamate (660 mg, 3.04 mmol), 2-di-t-butylphosphino-2',4',6'-tri-i-propyl-1,1'-biphenyl (387 mg, 0.912 mmol), PdOAc$_2$ (34.1 mg, 0.152 mmol) and Cs$_2$CO$_3$ (990 mg, 3.04 mmol) in toluene (20 mL) was heated at 80° C. for 16 h. After cooling to room temperature, the mixture was concentrated under reduced pressure. The residue was taken up in ethyl acetate and filtered through diatomaceous earth (Celite®). The organic layer was washed with brine and water; dried over Na$_2$SO$_4$, filtered and concentrated under reduced pressure. The residue was purified by silica gel flash chromatography using EtOAc-hexane as the eluent to afford (S)-tert-butyl (1-((9-(difluoromethyl)-4,6-dimethyl-5-oxo-5,6-dihydrobenzo[c][2,7]naphthyridin-8-yl)oxy)-4-methylpentan-2-yl)carbamate (0.6 g, 0.58 mmol, 54% yield) as a brown gummy solid. LC/MS (ESI) m/e 490.2 [(M+H)$^+$, calcd for C$_{26}$H$_{34}$F$_2$N$_3$O$_4$, 490.2]; LC/MS retention time (method B): $t_R$=2.72 min.

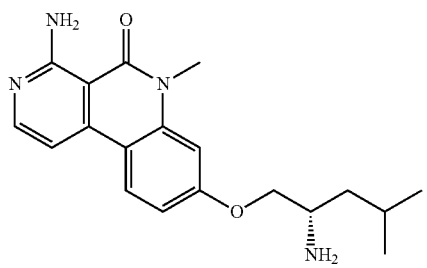 [SMILES: CC(C)C[C@H](N)COc1ccc2c3ccnc(N)c3c(=O)n(C)c2c1]

Part F: (S)-8-((2-amino-4-methylpentyl)oxy)-9-(difluoromethyl)-4,6-dimethylbenzo[c][2,7]naphthyridin-5(6H)-one To a solution of (S)-tert-butyl (1-((9-(difluoromethyl)-4,6-dimethyl-5-oxo-5,6-dihydrobenzo[c][2,7]naphthyridin-8-yl)oxy)-4-methylpentan-2-yl)carbamate (500 mg, 0.480 mmol) in MeOH (10 mL) at 0° C. was added 4N HCl in 1,4-dioxane (20 mL, 80 mmol). The solution was warmed to room temperature and stirred for 2 h. The mixture was then was concentrated under reduced pressure. The residue was taken up in EtOAc and the EtOAc layer was washed with saturated aqueous NaHCO$_3$ then H$_2$O, dried over Na$_2$SO$_4$, filtered and concentrated under reduced pressure. The residue was purified by prep. HPLC to afford (S)-8-((2-amino-4-methylpentyl)oxy)-9-(difluoromethyl)-4,6-dimethylbenzo[c][2,7]naphthyridin-5(6H)-one (60 mg, 0.149 mmol, 31% yield) as pale yellow solid. LC/MS (ESI) m/e 390.2 [(M+H)$^+$, calcd for C$_{21}$H$_{26}$F$_2$N$_3$O$_2$, 390.2]; LC/MS retention time (method A): $t_R$=2.09 min; HPLC retention time (method A): $t_R$=10.1 min; HPLC retention time (method B): $t_R$=9.18 min; $^1$H NMR (400 MHz, METHANOL-$d_4$) δ ppm 8.73 (s, 1H), 8.66 (s, 2H), 7.07-7.41 (m, 2H), 4.66-4.53 (m, 1H), 4.52-4.49 (m, 1H), 3.78-3.89 (m, 4H), 3.22 (s, 3H), 1.74-1.88 (m, 2H), 1.63-1.71 (m, 1H), 1.04 (m, 6H).

Example 28 tert-butyl (2,4-dimethyl-1-((6-methyl-5-oxo-5,6-dihydrobenzo[c][2,7]naphthyridin-8-yl)oxy)pentan-2-yl)carbamate

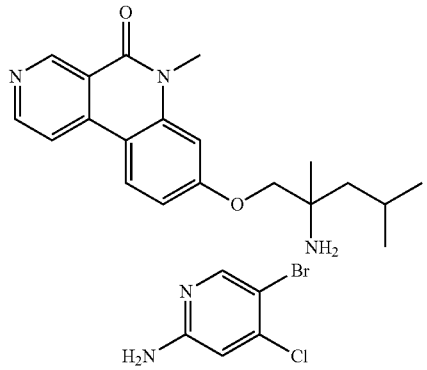

Part A. tert-butyl (2,4-dimethyl-1-((6-methyl-5-oxo-5,6-dihydrobenzo[c][2,7]naphthyridin-8-yl)oxy)pentan-2-yl)carbamate 8-Chloro-6-methylbenzo[c][2,7]naphthyridin-5(6H)-one (0.15 g, 0.613 mmol), prepared as described in Example 2, Part C, and tert-butyl (1-hydroxy-2,4-dimethylpentan-2-yl)carbamate (0.284 g, 1.226 mmol) were subjected to ether synthesis as described in Example 2, Part D, to afford tert-butyl(2,4-dimethyl-1-((6-methyl-5-oxo-5,6-dihydrobenzo[c][2,7]naphthyridin-8-yl)oxy)pentan-2-yl)carbamate (0.3 g, 28% yield) as pale yellow solid. LC/MS (ESI) m/e 440.2 [(M+H)$^+$, calcd for C$_{25}$H$_{34}$N$_3$O$_4$ 440.2]; LC/MS retention time (method C): $t_R$=2.67 min.

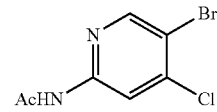

Part B. 8-((2-amino-2,4-dimethylpentyl)oxy)-6-methylbenzo[c][2,7]naphthyridin-5(6H)-one tert-Butyl (2,4-dimethyl-1-((6-methyl-5-oxo-5,6 dihydrobenzo[c][2,7]naphthyridin-8-yl)oxy)pentan-2-yl)carbamate was taken further for deprotection of Boc as described in example 2, part E to afford 8-((2-amino-2,4-dimethylpentyl)oxy)-6-methylbenzo[c][2,7]naphthyridin-5(6H)-one (30 mg, 12% yield) as off white solid. LC/MS (ESI) m/e 340.0 [(M+H)$^+$, calcd for $C_{20}H_{26}N_3O_2$, 340.2]; LC/MS retention time (method G): $t_R$=1.88 min. $^1$H NMR (400 MHz, METHANOL-$d_4$) δ ppm 9.43 (s, 1H), 8.73 (d, J=6.0 Hz, 1H), 8.35 (d, J=8.5 Hz, 1H), 8.19 (d, J=6.0 Hz, 1H), 7.12-7.01 (m, 2H), 4.05-3.92 (m, 2H), 3.77 (s, 3H), 1.95-1.80 (m, 1H), 1.58 (qd, J=14.2, 5.5 Hz, 2H), 1.30 (s, 3H), 1.04 (d, J=6.5 Hz, 3H), 1.01 (d, J=6.5 Hz, 3H). Chiral HPLC (Method CHIRALPAK AD-H (250×4.6) mm, 5 micron, Mob. Phase CO$_2$ (65%), Co-solvent 0.3% DEA in MeOH (35%), Back pressure 101), Chiral SFC retention time $t_{R1}$=5.44 min; Chiral SFC retention time $t_{R2}$=7.77 min.

Example 29

8-((2-amino-2,4-dimethylpentyl)oxy)-7-fluoro-4,6-dimethylbenzo[c][2,7]naphthyridin-5(6H)-one

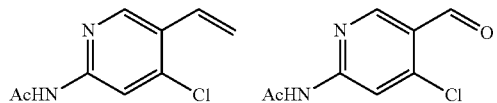

Part A. Methyl 4-chloro-2-methylnicotinate

To a solution of methyl 2,4-dichloronicotinate (10.0 g, 48.5 mmol) in a solvent mixture of 1,4-dioxane (400 mL) and water (40 mL) was added trimethylboroxine (6.79 mL, 48.5 mmol) followed by PdCl$_2$(dppf)-CH$_2$Cl$_2$ adduct (1.982 g, 2.427 mmol) and cesium carbonate (31.6 g, 97 mmol). The reaction mixture was degassed with argon for 5 minutes. The reaction mixture was heated to reflux for 8 h. The reaction mixture was cooled to room temperature and filtered through diatomaceous earth (Celite®). The bed was washed with ethyl acetate and the combined filtrate was concentrated under reduced pressure to afford the crude product which was purified by silica gel column chromatography (gradient of ethyl acetate and petroleum ether) to afford methyl 4-chloro-2-methylnicotinate (5.20 g, 28 mmol, 58% yield) as a yellow liquid. LC/MS (ESI) m/e 185.7 [(M+H)$^+$, calcd for $C_8H_8ClNO_2$ 185.6]; LC/MS retention time (method G): $t_R$=1.90 min.

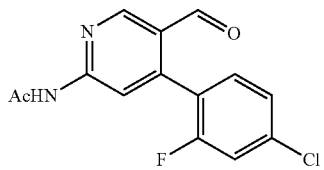 [SMILES: CC(=O)Nc1cc(-c2ccc(Cl)cc2F)c(C=O)cn1]

Part B. Methyl 4-iodo-2-methylnicotinate

To a solution of methyl 4-chloro-2-methylnicotinate (6.00 g, 32.3 mmol) in acetonitrile (80 mL) was added acetyl chloride (3.45 mL, 48.5 mmol) followed by sodium iodide (48.5 g, 323 mmol). The reaction mixture was heated at 80° C. for 16 hrs. The reaction mixture was evaporated to dryness and the residue was adjusted to pH 6 by adding saturated potassium carbonate solution. The product was extracted with dichloromethane (250 mL). The organic phase was washed with brine (2×100 mL), dried over Na$_2$SO$_4$, and concentrated under reduced pressure to afford methyl 4-iodo-2-methylnicotinate (2.00 g, 7.22 mmol, 22% crude yield) as colorless semisolid which was carried on without further purifications. LC/MS (ESI) m/e 278.0 [(M+H)$^+$, calcd for $C_8H_9INO_2$ 278.0]; LC/MS retention time (method C): $t_R$=2.13 min.

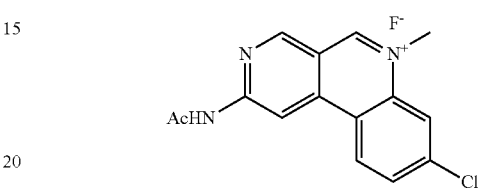

Part C. Methyl 4-(4-bromo-2,3-difluorophenyl)-2-methylnicotinate

In a microwave vessel, methyl 4-iodo-2-methylnicotinate (1.00 g, 3.61 mmol) was taken in a mixture of 1,4-dioxane (18 mL) and water (2 mL) under inert atmosphere. (4-bromo-2,3-difluorophenyl)boronic acid (1.03 g, 4.33 mmol) and Na$_2$CO$_3$ (765 mg, 7.22 mmol) were added to the reaction mixture and degassed for 5 minutes. Pd(Ph$_3$P)$_4$ (83 mg, 0.072 mmol) was added to the reaction mixture and heated in microwave at 110° C. for 90 min. The reaction mixture was diluted with water (150 mL) and extracted with ethyl acetate (200 mL). The organic phase was washed with brine (2×100 mL), dried over Na$_2$SO$_4$, and concentrated under reduced pressure. The residue was purified by silica gel chromatography (gradient of ethyl acetate and petroleum ether) to afford methyl 4-(4-bromo-2,3-difluorophenyl)-2-methylnicotinate (540 mg, 1.58 mmol, 44% yield) as a yellow liquid. LC/MS (ESI) m/e 344.0 [(M+2H)$^+$, calcd for $C_{14}H_{12}BrF_2NO_2$ 344.1]; LC/MS retention time (method C): $t_R$=2.48 min.

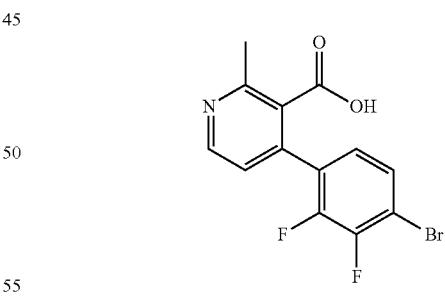

Part D. 4-(4-bromo-2,3-difluorophenyl)-2-methylnicotinic Acid

To a solution of methyl 4-(4-bromo-2,3-difluorophenyl)-2-methylnicotinate (800 mg, 2.34 mmol) in MeOH (10 mL) was added NaOH (935 mg, 23.38 mmol) in Water (10 mL). The reaction mixture was stirred at room temperature for 16 hrs. The reaction mixture was evaporated under reduced pressure and the residue obtained was adjusted to pH ~3 by adding 1.5N HCl solution. The product was extracted with dichloromethane and the layers were separated. The organic phase was dried over Na$_2$SO$_4$, and concentrated under reduced pressure to afford 4-(4-bromo-2,3-difluorophenyl)-2-methylnicotinic acid (700 mg, 2.133 mmol, 91% crude yield) as an off-white solid which was carried on without further purification. LC/MS (ESI) m/e 330.0 [(M+2H)$^+$, calcd for C$_{13}$H$_{10}$BrF$_2$NO$_2$ 330.1]; LC/MS retention time (method C): t$_R$=1.34 min.

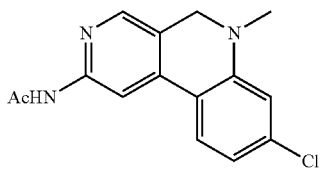 [SMILES: CC(=O)Nc1cc2c(cn1)CN(C)c1cc(Cl)ccc1-2]

Part E. 4-(4-bromo-2,3-difluorophenyl)-N,2-dimethylnicotinamide

To a solution of 4-(4-bromo-2,3-difluorophenyl)-2-methylnicotinic acid (700 mg, 2.13 mmol) in dichloromethane (20 mL) at 0° C. was added oxalyl chloride (0.56 mL, 6.40 mmol) drop wise followed by DMF (0.03 mL, 0.43 mmol). The reaction mixture was heated to 45° C. for 4 h. The reaction mixture was evaporated to dryness. The residue was taken in dichloromethane (50 mL) at 0° C. and methylamine hydrochloride (1.56 g, 23.08 mmol) was added to it followed by triethylamine (4.83 mL, 34.6 mmol). The reaction mixture was stirred at room temperature for 2 h. The reaction mixture was diluted with water (50 mL) and extracted with dichloromethane (100 mL). The organic layer was separated, dried over Na$_2$SO$_4$ and concentrated under reduced pressure to afford 4-(4-bromo-2,3-difluorophenyl)-N,2-dimethylnicotinamide (600 mg, 1.76 mmol, 76% crude yield) as yellow semi-solid which was carried on without further purification. LC/MS (ESI) m/e 343.0 [(M+2H)$^+$, calcd for C$_{14}$H$_{13}$BrF$_2$N$_2$O 343.0]; LC/MS retention time (method C): t$_R$=1.61 min.

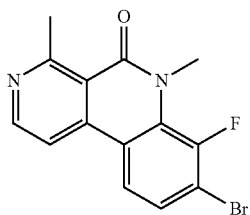 [SMILES: Cc1nccc2c1c(=O)n(C)c1c(F)c(Br)ccc21]

Part F. 8-bromo-7-fluoro-4,6-dimethylbenzo[c][2,7]naphthyridin-5(6H)-one

To a solution of 4-(4-bromo-2,3-difluorophenyl)-N,2-dimethylnicotinamide (600 mg, 1.76 mmol) in tetrahydrofuran (20 mL) at 0° C. was added NaH (176 mg, 4.40 mmol) and the reaction mixture was brought to room temperature gradually. The reaction mixture was stirred at room temperature for 15 h. The reaction mixture was diluted with water (50 mL) and extracted with ethyl acetate (100 mL). The organic layer was separated, dried over Na$_2$SO$_4$ and concentrated under reduced pressure to afford 8-bromo-7-fluoro-4,6-dimethylbenzo[c][2,7]naphthyridin-5(6H)-one (400 mg, 1.24 mmol, 71% yield) as yellow solid. LC/MS (ESI) m/e 322.8 [(M+2H)$^+$, calcd for C$_{14}$H$_{12}$BrFN$_2$O 322.9]; LC/MS retention time (method G): t$_R$=2.21 min.

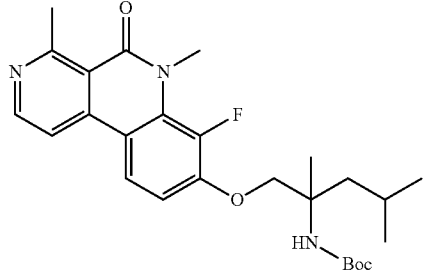 [SMILES: Cc1nccc2c1c(=O)n(C)c1c(F)c(OCC(C)(CC(C)C)NC(=O)OC(C)(C)C)ccc21]

Part G. tert-butyl (1-((7-fluoro-4,6-dimethyl-5-oxo-5,6-dihydrobenzo[c][2,7]naphthyridin-8-yl)oxy)-2,4-dimethylpentan-2-yl)carbamate To a stirred solution of 8-bromo-7-fluoro-4,6-dimethylbenzo[c][2,7]naphthyridin-5(6H)-one (350 mg, 1.090 mmol) and tert-butyl (1-hydroxy-2,4-dimethylpentan-2-yl)carbamate (504 mg, 2.180 mmol) in toluene (10 mL) was added cesium carbonate (355 mg, 1.09 mmol) and 2-Di-t-butylphosphino-2',4',6'-tri-i-propyl-1,1'-biphenyl (28 mg, 0.065 mmol). The reaction mixture was degassed with argon for 5 min and then palladium acetate (7.34 mg, 0.033 mmol) was added to it. The reaction mixture was heated to 100° C. for 18 h. Then, it was filtered through diatomaceous earth (Celite®) and the filtrate was evaporated to afford tert-butyl (1-((7-fluoro-4,6-dimethyl-5-oxo-5,6-dihydrobenzo[c][2,7]naphthyridin-8-yl)oxy)-2,4-dimethylpentan-2-yl)carbamate which was taken to next step without purification. LC/MS (ESI) m/e 472.2 [(M+H)$^+$, calcd for C$_{26}$H$_{35}$FN$_3$O$_4$ 472.2]; LC/MS retention time (method C): t$_R$=2.17 min.

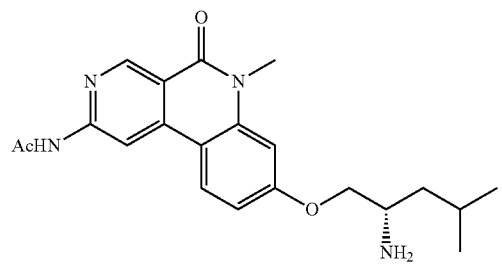 [SMILES: CC(=O)Nc1cc2c(cn1)c(=O)n(C)c1cc(OC[C@@H](N)CC(C)C)ccc21]

Part H. 8-((2-amino-2,4-dimethylpentyl)oxy)-7-fluoro-4,6-dimethylbenzo[c][2,7]naphthyridin-5(6H)-one To a solution of tert-butyl (1-((7-fluoro-4,6-dimethyl-5-oxo-5,6 dihydrobenzo[c][2,7]naphthyridin-8-yl)oxy)-2,4-dimethylpentan-2-yl)carbamate (200 mg, 0.424 mmol) in MeOH (6 mL) at 0° C. was added 4M HCl in 1,4-dioxane (3 mL, 99.0 mmol). The reaction mixture was stirred at 0° C. for 2 h. After 2 h, the reaction mixture was concentrated under reduced pressure to afford crude product which was purified by preparative HPLC to afford 8-((2-amino-2,4-dimethylpentyl)oxy)-7-fluoro-4,6-dimethylbenzo[c][2,7]naphthyridin-5(6H)-one (10 mg, 0.024 mmol, 6% yield) as an off-white solid. LC/MS (ESI) m/e 372.0 [(M+H)$^+$, calcd for $C_{21}H_{27}FN_3O_2$ 372.2]; LC/MS retention time (method G): $t_R$=1.99 min. HPLC retention time (method A): $t_R$=8.37 min; HPLC retention time (method B): $t_R$=9.72 min. $^1$H NMR (400 MHz, METHANOL-$d_4$) δ ppm 8.58 (d, J=6 Hz, 1H), 8.22 (dd, J=9.2 Hz, J=2 Hz, 1H), 8.14 (d, J=6 Hz, 1H), 7.23 (m, 1H), 4.31 (d, J=10 Hz, 1H), 4.23 (d, J=10.4 Hz, 1H), 3.88 (d, J=9.2 Hz, 3H), 3.06 (s, 3H), 1.90 (m, 2H), 1.73 (m, 1H), 1.52 (s, 3H), 1.05 (m, 6H).

Example 30 & Example 31

8-(((S)-2-amino-4-methylpentyl)oxy)-9-(1-hydroxyethyl)-4,6 dimethylbenzo[c][2,7]naphthyridin-5(6H)-one

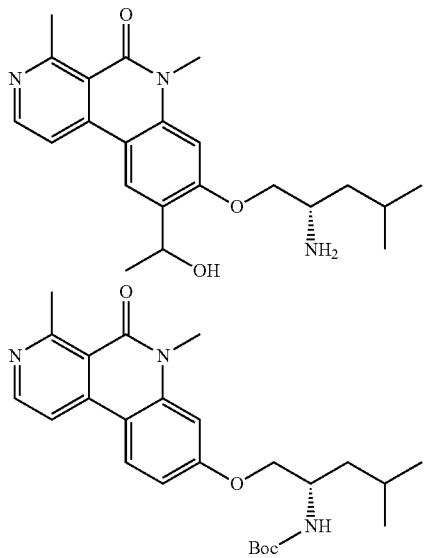

Part A. (S)-tert-butyl 1-(4,6-dimethyl-5-oxo-5,6-dihydrobenzo[c][2,7]naphthyridin-8-yloxy)-4-methylpentan-2-ylcarbamate Preparation as described in Example 16, Part H.

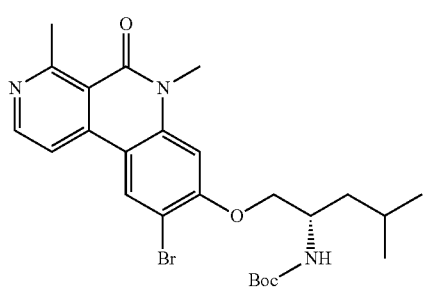 [SMILES: Cc1nccc2c1c(=O)n(C)c1cc(OC[C@H](CC(C)C)NC(=O)OC(C)(C)C)c(Br)cc21]

Part A. (S)-tert-butyl (1-((9-bromo-4,6-dimethyl-5-oxo 5,6-dihydrobenzo[c][2,7]naphthyridin-8-yl)oxy)-4-methylpentan-2-yl)carbamate (S)-tert-Butyl (1-((4,6-dimethyl-5-oxo-5,6-dihydrobenzo[c][2,7]naphthyridin-8-yl)oxy)-4-methylpentan-2-yl)carbamate, prepared as described in Example 16, Part H, was subjected to bromination following the condition mentioned in Example 3, Part A to afford (S)-tert-butyl (1-((9-bromo-4,6-dimethyl-5-oxo 5,6dihydrobenzo[c][2,7]naphthyridin-8-yl)oxy)-4-methylpentan-2-yl)carbamate (1.6 g, 2.62 mmol, 77% yield) as pale yellow solid. LC/MS (ESI) m/e 518.2 [(M)$^+$, calcd for $CH_{33}BrN_3O_4$ 518.1]; LC/MS retention time (method C): $t_R$=2.46 min.

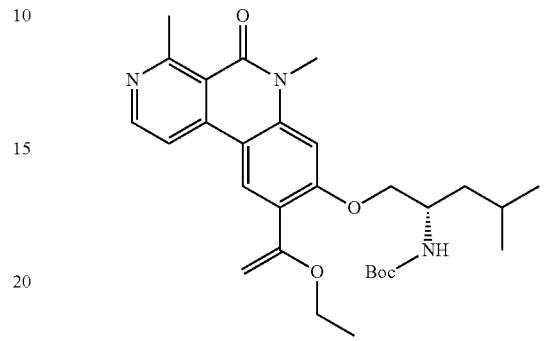

Part B. (S)-tert-butyl (1-((9-(1-ethoxyvinyl)-4,6 dimethyl-5-oxo-5,6-dihydrobenzo[c][2,7]naphthyridin-8-yl)oxy)-4-methylpentan-2yl)carbamate To a solution of (S)-tert-butyl (1-((9-bromo-4,6-dimethyl-5-oxo-5,6 dihydrobenzo[c][2,7]naphthyridin-8-yl)oxy)-4-methylpentan-2-yl)carbamate (500 mg, 0.964 mmol) in 1,4-dioxane (5 mL), tributyl(1-ethoxyvinyl)stannane (697 mg, 1.929 mmol), tris(dibenzylideneacetone)dipalladium (0) (88 mg, 0.096 mmol) and DPPF (53.5 mg, 0.096 mmol) were added. The reaction mixture was allowed to stir at 100° C. for 12 h. The reaction mixture was diluted with water and extracted in ethyl acetate. The organic layer was dried over sodium sulfate and concentrated which afforded (S)-tert-butyl (1-((9-(1-ethoxyvinyl)-4,6 dimethyl-5-oxo-5,6-dihydrobenzo[c][2,7]naphthyridin-8-yl)oxy)-4-methylpentan-2-yl)carbamate (0.3 g, 0.33 mmol, 34% crude yield) as brown solid which was carried on without further purification. LC/MS (ESI) m/e 510.2 [(M+H)$^+$, calcd for $C_{29}H_{40}N_3O_5$, 510.3]; LC/MS retention time (Method=C): $t_R$=2.60 min.

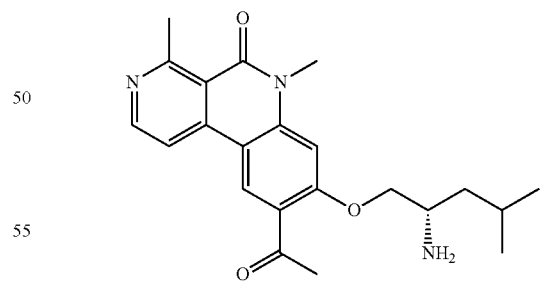

Part C. (S)-9-acetyl-8-((2-amino-4-methylpentyl)oxy)-4,6-dimethylbenzo[c][2,7]naphthyridin-5(6H)-one (S)-tert-Butyl (1-((9-(1-ethoxyvinyl)-4,6-dimethyl-5-oxo-5,6 dihydrobenzo[c][2,7]naphthyridin-8-yl)oxy)-4-methylpentan-2-yl)carbamate (200 mg, 0.392 mmol) was treated with hydrochloric acid in 1,4-dioxane (981 μL, 3.92 mmol) at 0° C. The reaction mixture was allowed to stir at RT for 2 h and then evaporated to dryness. The crude material was neutralized with aqueous 10% NaHCO$_3$ and extracted with ethyl acetate. The organic layer was dried over Na$_2$SO$_4$ and concentrated which afforded (S)-9-acetyl-8-((2-amino-4-methylpentyl)oxy)-4,6-dimethylbenzo[c][2,7]naphthyridin-5(6H)-one (0.11 g, 0.164 mmol, 42% yield) as brown solid. The material was carried on without further purification. LC/MS (ESI) m/e 382.2 [(M+H)$^+$, calcd for C$_{22}$H$_{28}$N$_3$O$_3$, 382.2]; LC/MS retention time (method E): t$_R$=0.78 min.

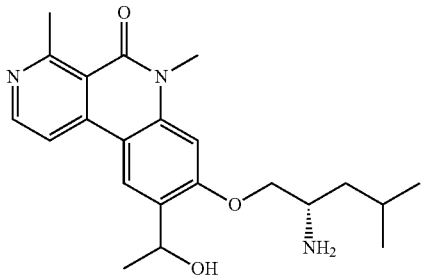 [SMILES: Cc1nccc2c1c(=O)n(C)c1cc(OC[C@@H](N)CC(C)C)c(C(C)O)cc21]

Part D. 8-(((S)-2-amino-4-methylpentyl)oxy)-9-(1-hydroxyethyl)-4,6-dimethylbenzo[c][2,7]naphthyridin-5(6H)-one To a solution of (S)-9-acetyl-8-((2-amino-4-methylpentyl)oxy)-4,6 dimethylbenzo[c][2,7]naphthyridin-5(6H)-one (100 mg, 0.257 mmol) in Ethanol (2 mL) was added NaBH$_4$ (97 mg, 2.57 mmol) at 0° C. The reaction mixture was allowed to stir at RT for 16 h. Then, it was quenched with NH$_4$Cl, diluted with water and extracted in ethyl acetate. The combined organic layers were dried over Na$_2$SO$_4$ and concentrated. The crude reaction mixture was purified by prep. HPLC which afforded 8-(((S)-2-amino-4-methylpentyl)oxy)-9-(1-hydroxyethyl)-4,6-dimethylbenzo[c][2,7]naphthyridin-5(6H)-one (0.03 g, 27% yield) as pale yellow semi-solid. LC/MS (ESI) m/e 384.1 [(M+H)$^+$, calcd for C$_{22}$H$_{30}$N$_3$O$_3$, 384.2]; LC/MS retention time (method E): t$_R$=0.73 min.

96533-072—Chiral separation was done which afforded two diastereomers as off-white solid. Diastereomer-1 was eluted at retention time (HPLC Column: (250×30×5µ) M. Phase A: 0.2% DEA Hexane; M, phase B: Ethanol): t$_R$=21.9 min.

96533-072-11—$^1$H NMR (400 MHz, METHANOL-d$_4$): ppm 1.01-1.07 (m, 6H), 1.55 (d, J=6.46 Hz, 4H), 1.58-1.68 (m, 1H), 1.83-1.92 (m, 1H), 3.09 (s, 3H), 3.35 (d, J=1.69 Hz, 1H), 3.80 (s, 3H), 4.13-4.19 (m, 1H), 4.28-4.34 (m, 1H), 5.32 (d, J=6.46 Hz, 1H), 7.04 (s, 1H), 8.16 (d, J=5.84 Hz, 1H), 8.47 (s, 1H), 8.58 (d, J=5.77 Hz, 1H).

Diastereomer-2 was eluted at retention time (HPLC Column: (250×30×5µ) M. Phase A: 0.2% DEA Hexane; M, phase B: Ethanol) t$_R$=24.9 min.

96533-072-12—$^1$H NMR (400 MHz, METHANOL-d$_4$): ppm 1.03 (t, J=6.84 Hz, 6H), 1.43-1.58 (m, 5H), 1.88 (dt, J=13.73, 6.97 Hz, 1H), 3.09 (s, 3H), 3.35 (d, J=1.69 Hz, 1H), 3.80 (s, 3H), 4.03-4.13 (m, 1H), 4.21-4.29 (m, 1H), 5.31 (d, J=6.40 Hz, 1H), 7.03 (s, 1H), 8.15 (d, J=5.84 Hz, 1H), 8.47 (s, 1H), 8.57 (d, J=5.77 Hz, 1H).

Example 32

8-((2-amino-2,4-dimethylpentyl)oxy)-4,6-dimethylbenzo[c][2,7]naphthyridin-5(6H)-one

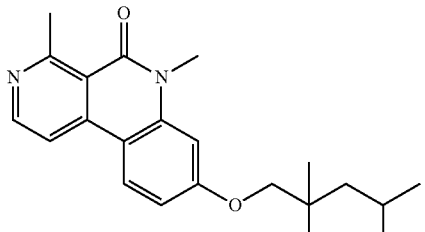

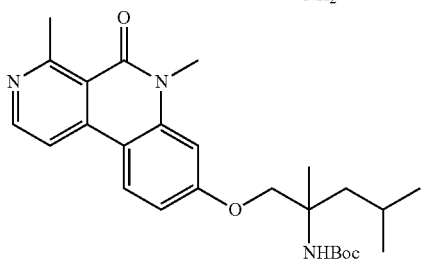

Part A. tert-butyl(1-((4,6-dimethyl-5-oxo-5,6-dihydrobenzo[c][2,7]naphthyridin-8-yl)oxy)-2,4-dimethylpentan-2-yl)carbamate 8-Chloro-4,6-dimethylbenzo[c][2,7]naphthyridin-5(6H)-one (0.15 g, 0.580 mmol), prepared as described in Example 16, Part G, and tert-butyl (1-hydroxy-2,4-dimethylpentan-2-yl)carbamate (0.161 g, 0.696 mmol) were subjected to the Buchwald coupling as described in Example 16, Part H, to afford tert-butyl(1-((4,6-dimethyl-5-oxo-5,6-dihydrobenzo[c][2,7]naphthyridin-8-yl)oxy)-2,4-dimethylpentan-2-yl)carbamate (0.22 g, 0.199 mmol, 34% crude yield). Crude product was used for next step without further purification. LC/MS (ESI) m/e 454.1 [(M+H)$^+$, calcd for C$_{26}$H$_{36}$N$_3$O$_4$, 454.3]; LC/MS retention time (method D): t$_R$=0.93 min.

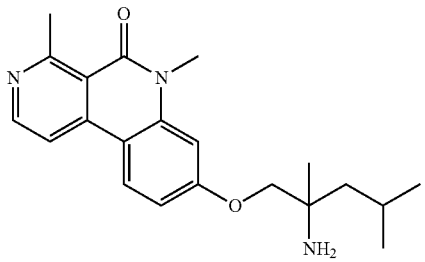 [SMILES: Cc1nccc2c1c(=O)n(C)c1cc(OCC(C)(N)CC(C)C)ccc21]

Part B. 8-((2-amino-2,4-dimethylpentyl)oxy)-4,6-dimethylbenzo[c][2,7]naphthyridin-5(6H)-one tert-Butyl (1-((4,6-dimethyl-5-oxo-5,6-dihydrobenzo[c][2,7]naphthyridin-8-yl)oxy)-2,4-dimethylpentan-2-yl)carbamate (0.22 g, 0.199 mmol) was subjected to de-protection of the Boc group using the procedure described in Example 2, Part E to give 8-((2-amino-2,4-dimethylpentyl)oxy)-4,6 dimethylbenzo[c][2,7]naphthyridin-5(6H)-one (8 mg, 0.022 mmol, 11% yield) as white solid. LC/MS (ESI) m/e 354.2 [(M+H)+, calcd for $C_{21}H_{28}N_3O_2$, 354.2]; LC/MS retention time (method C): $t_R$=1.57 min. HPLC retention time (method A): $t_R$=8.67 min; HPLC retention time (method B): $t_R$=9.46 min. $^1$H NMR (400 MHz, METHANOL-d4) ppm δ 8.54 (s, 1H), 8.34-8.36 (bs, 1H), 8.10 (bs, 1H), 7.06 (s, 1H), 4.11-4.17 (m, 2H), 3.73 (s, 3H), 3.06 (s, 3H), 1.70-1.98 (m, 2H), 1.68 (bs, 1H), 1.45 (s, 3H), 1.02-1.08 (m, 6H).

Example 33

8-(((2S,3S)-3-amino-5-methylhexan-2-yl)oxy)-4,6-dimethylbenzo[c][2,7]naphthyridin-5(6H)-one

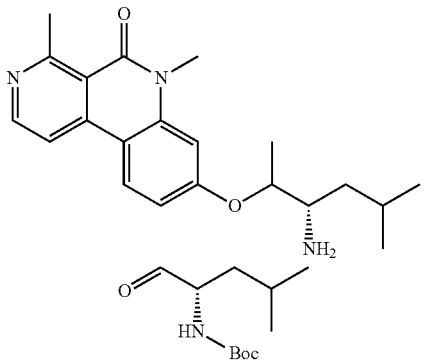

Part A. (S)-tert-butyl (4-methyl-1-oxopentan-2-yl) carbamate

To a solution of (S)-tert-butyl (1-hydroxy-4-methylpentan-2-yl)carbamate (2 g, 9.20 mmol) in DCM (30 mL) was added Dess-Martin Periodinane (5.86 g, 13.81 mmol) at 0° C. The reaction mixture was allowed to stir at RT for 16 h. The reaction mixture was quenched with NaHCO$_3$, diluted with water and extracted in ethyl acetate. Organic layer was dried over Na$_2$SO$_4$ and concentrated which afforded (S)-tert-butyl (4-methyl-1-oxopentan-2-yl)carbamate as colorless oil (1.4 g, 6.50 mmol, 71% crude yield). The material was carried on without further purification. $^1$H NMR (300 MHz, DMSO-d6): δ 0.8-0.96 (m, 6H), 1.31-1.49 (m, 11H), 1.57-1.66 (m, 1H), 3.81-3.89 (m, 1H). 7.27 (d, 1H), 9.43 (s, 1H).

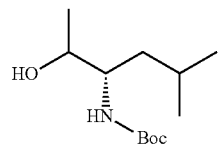 [SMILES: CC(C)C[C@H](NC(=O)OC(C)(C)C)C(C)O]

Part B. tert-butyl ((3S)-2-hydroxy-5-methylhexan-3-yl)carbamate

A solution of (S)-tert-butyl (4-methyl-1-oxopentan-2-yl) carbamate (1.3 g, 6.04 mmol) in diethyl ether (50 mL) was cooled to −78° C. and treated with methyl magnesium bromide (1.4 M in diethyl ether) (8.63 mL, 12.08 mmol). The slurry was stirred at 0° C. for 1 h and then stirred for an additional hour at RT. The reaction mixture was quenched with NH$_4$Cl. The reaction mixture was extracted with diethyl ether (3×100 mL). The combined organic layers were washed with brine, dried over MgSO$_4$, and concentrated to afford the product, tert-butyl ((3S)-2-hydroxy-5-methylhexan-3-yl)carbamate (1 g, 4.32 mmol, 72% crude yield) as colorless oil. The material was carried on without further purification. $^1$H NMR (300 MHz, DMSO-d6): δ 0.78-0.93 (m, 6H), 0.98 (d, 3H), 1.11-1.41 (m, 2H), 1.42 (s, 9H), 1.45-1.64 (m, 1H), 3.30-3.63 (m, 2H), 4.37 (d, 1H), 6.19 (d, 1H).

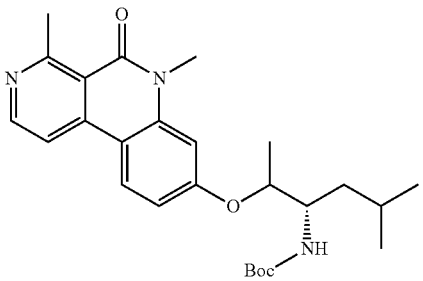

Part C. tert-butyl ((3S)-2-((4,6-dimethyl-5-oxo-5,6-dihydrobenzo[c][2,7]naphthyridin-8-yl)oxy)-5-methylhexan-3-yl)carbamate A mixture of 8-chloro-4,6-dimethylbenzo[c][2,7]naphthyridin-5(6H)-one (0.05 g, 0.193 mol), tert-butyl ((3S)-2-hydroxy-5-methylhexan-3-yl)carbamate (0.067 g, 0.290 mmol), Cs$_2$CO$_3$ (0.315 g, 0.966 mol), 2-di-t-butylphosphino-2',4',6'-tri-i-propyl-1,1'-biphenyl (8.21 mg, 0.019 mol) and Pd(OAc)$_2$ (2.60 mg, 0.012 mol) were taken in Toluene (2 mL) and heated overnight at 90° C. After cooling the reaction mixture was concentrated, then diluted with ethyl acetate and water. Ethyl acetate layer was collected, dried over Na$_2$SO$_4$, filtered and concentrated which afforded tert-butyl((3S)-2-((4,6-dimethyl-5-oxo-5,6-dihydrobenzo[c][2,7]naphthyridin-8-yl)oxy)-5-methylhexan-3-yl)carbamate, (70 mg, 0.154 mmol, 80% crude yield) as brown solid. The crude product was used for next step without further purification. LC/MS (ESI) m/e 454.2 [(M+H)+, calcd for $C_{26}H_{36}N_3O_4$, 454.3]; LC/MS retention time (method D): $t_R$=0.91 min.

Part D. 8-(((3S)-3-amino-5-methylhexan-2-yl)oxy)-4,6-dimethylbenzo[c][2,7]naphthyridin-5(6H)-one tert-Butyl ((3S)-2-((4,6-dimethyl-5-oxo-5,6-dihydrobenzo[c][2,7]naphthyridin-8-yl)oxy)-5-methylhexan-3-yl)carbamate (0.16 g, 0.353 mmol) was subjected to deprotection of the Boc group (procedure described in Example 2, Part E) which afforded the diastereomeric mixture 8-(((3S)-

3-amino-5-methylhexan-2-yl)oxy)-4,6-dimethylbenzo[c][2,7]naphthyridin-5(6H)-one (17 mg, 0.017 mmol, 5% yield) as a white solid. LC/MS (ESI) m/e 354.2 [(M+H)$^+$, calcd for $C_{21}H_{28}N_3O_2$, 354.2]; LC/MS retention time (method C): $t_R$=1.56 min. HPLC retention time (method A): $t_R$=9.40 min; HPLC retention time (method B): $t_R$=9.36 min. $^1$H NMR (400 MHz, METHANOL-d$_4$) 8.57 (d, J=5.5 Hz, 1H), 8.41 (d, J=9.0 Hz, 1H), 8.15 (d, J=6.0 Hz, 1H), 7.15-7.06 (m, 2H), 4.68 (quin, J=5.9 Hz, 1H), 3.76 (s, 4H), 3.09 (s, 3H), 1.88-1.50 (m, 3H), 1.44 (s, 3H), 1.03 (d, J=6.5 Hz, 3H), 0.98 (d, J=6.5 Hz, 3H).

Example 34

8-((2-amino-2,4-dimethylpentyl)oxy)-9-methoxy-4,6-dimethylbenzo[c][2,7]naphthyridin-5(6H)-one

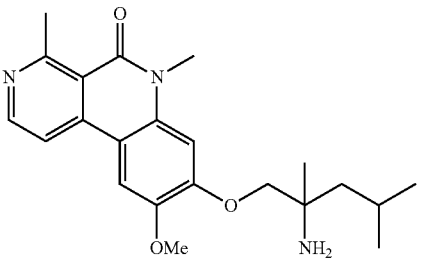

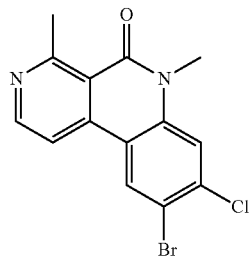

Part A. 9-bromo-8-chloro-4,6-dimethylbenzo[c][2,7]naphthyridin-5(6H)-one

To a solution of 8-chloro-4,6-dimethylbenzo[c][2,7]naphthyridin-5(6H)-one (0.2 g, 0.773 mmol) in acetonitrile (4 mL) at −30° C. was added trifluoroacetic acid (0.089 mL, 1.160 mmol) and 1-bromopyrrolidine-2,5-dione (0.151 g, 0.850 mmol). The mixture was heated to 80° C. overnight. The reaction mixture was concentrated, diluted with ethyl acetate and excess aqueous 10% NaHCO$_3$. The ethyl acetate layer was concentrated. The residue was purified by prep. HPLC to afforded 9-bromo-8-chloro-4,6 dimethylbenzo[c][2,7]naphthyridin-5(6H)-one (120 mg, 0.351 mmol, 45% yield) as white solid. LC/MS (ESI) m/e 337.0 [(M+H)$^+$, calcd for $C_{14}H_{11}BrClN_2O$, 337.0]; LC/MS retention time (Method C): $t_R$=2.55 min; $^1$H NMR (400 MHz, METHANOL-d$_4$) ppm 3.11 (s, 3H), 3.75 (s, 3H), 7.81 (s, 1H), 8.20-8.26 (m, 1H), 8.68 (d, J=5.6 Hz, 1H), 8.79 (s, 1H).

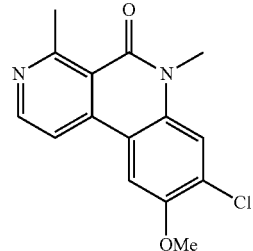 [SMILES: COc1cc2c3ccnc(C)c3c(=O)n(C)c2cc1Cl]

Part B. 8-chloro-9-methoxy-4,6-dimethylbenzo[c][2,7]naphthyridin-5(6H)-one

A mixture of 9-bromo-8-chloro-4,6-dimethylbenzo[c][2,7]naphthyridin-5(6H)-one (0.05 g, 0.148 mmol), copper(I) iodide (0.031 g, 0.163 mmol), L-proline (0.020 g, 0.178 mmol), sodium methoxide (0.040 g, 0.741 mmol) and K$_2$CO$_3$ (0.041 g, 0.296 mmol) were stirred in DMSO (1.5 mL). The mixture was heated to 80° C. for 16 h. After cooling, the crude reaction mixture was diluted with methanol, filtered through diatomaceous earth (Celite®) and concentrated under reduced pressure to afford 8-chloro-9-methoxy-4,6-dimethylbenzo[c][2,7]naphthyridin-5(6H)-one, as brown solid (40 mg). LC/MS (ESI) m/e 289.0 [(M)$^+$, calcd for $C_{15}H_{14}ClN_2O_2$, 289.1]; LC/MS retention time (method D): $t_R$=0.89 min.

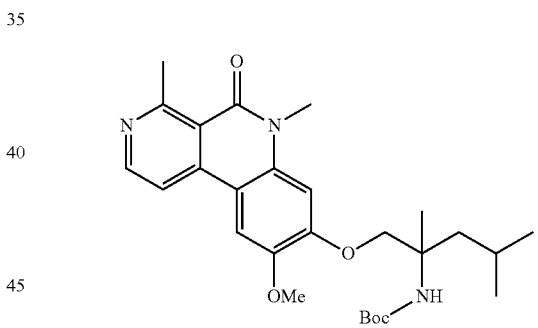

Part C. tert-butyl(1-((9-methoxy-4,6-dimethyl-5-oxo-5,6-dihydrobenzo[c][2,7]naphthyridin-8-yl)oxy)-2,4-dimethylpentan-2-yl)carbamate 8-Chloro-9-methoxy-4,6-dimethylbenzo[c][2,7]naphthyridin-5(6H)-one (0.04 g, 0.139 mmol) was subjected to Buchwald coupling (Example 16, Part H) with tert-butyl (1-hydroxy-2,4-dimethylpentan-2-yl)carbamate (0.048 g, 0.208 mmol) which afforded tert-butyl(1-((9-methoxy-4,6-dimethyl-5-oxo-5,6-dihydrobenzo[c][2,7]naphthyridin-8-yl)oxy)-2,4-dimethylpentan-2-yl)carbamate as white solid (15 mg, 0.029 mmol, 21% yield). LC/MS (ESI) m/e 484.2 [(M+H)$^+$, calcd for $C_{22}H_{38}N_3O_5$, 484.3]; LC/MS retention time (Method C): $t_R$=2.42 min.

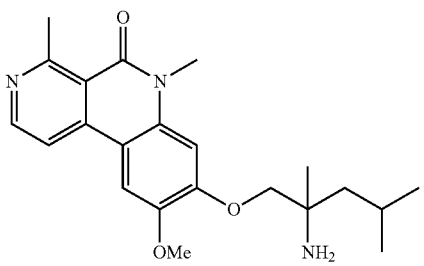 [SMILES: COc1cc2c3ccnc(C)c3c(=O)n(C)c2cc1OCC(C)(N)CC(C)C]

Part D. 8-((2-amino-2,4-dimethylpentyl)oxy)-9-methoxy-4,6 dimethylbenzo[c][2,7]naphthyridin-5(6H)-one tert-Butyl (1-((9-methoxy-4,6-dimethyl-5-oxo-5,6-dihydrobenzo[c][2,7]naphthyridin-8-yl)oxy)-2,4-dimethylpentan-2-yl)carbamate (0.015 g, 0.031 mmol) was subjected to deprotection of the Boc group as per Example 2, Part E to afford 8-((2-amino-2,4-dimethylpentyl)oxy)-9-methoxy-4,6 dimethylbenzo[c][2,7]naphthyridin-5(6H)-one (8 mg, 0.02 mmol, 63% yield) as a yellow solid. LC/MS (ESI) m/e 384.2 [(M+H)$^+$, calcd for $C_{22}H_{30}N_3O_3$, 384.5]; LC/MS retention time (Method C), $t_R$=6.57 min. $^1$H NMR (400 MHz, METHANOL-$d_4$) 8.63 (d, J=6.0 Hz, 1H), 8.51 (br. s., 1H), 8.02 (s, 1H), 7.23 (s, 1H), 4.39 (d, J=10.5 Hz, 1H), 4.32-4.24 (m, 1H), 4.10 (s, 3H), 3.83 (s, 3H), 3.19 (s, 3H), 1.99-1.86 (m, 2H), 1.73 (d, J=9.0 Hz, 1H), 1.55 (s, 3H), 1.09 (d, J=6.5 Hz, 3H), 1.05 (d, J=6.5 Hz, 3H).

Example 35

(S)-8-((2-amino-4-methylpentyl)oxy)-9-(2-hydroxypropan-2-yl)-4,6-dimethylbenzo[c][2,7]naphthyridin-5(6H)-one

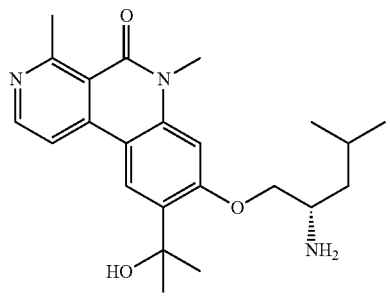

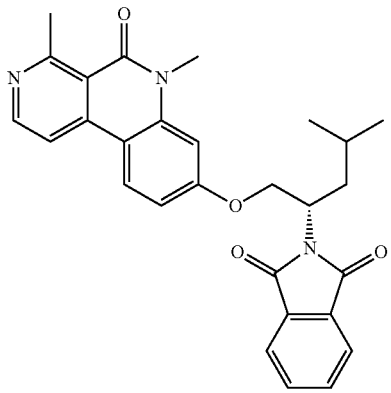

Part A. (S)-2-(1-((4,6-dimethyl-5-oxo-5,6-dihydrobenzo[c][2,7]naphthyridin-8-yl)oxy)-4-methylpentan-2-yl)isoindoline-1,3-dione 8-Chloro-4,6-dimethylbenzo[c][2,7]naphthyridin-5(6H)-one (1.4 g, 5.41 mmol) and (S)-2-(1-hydroxy-4-methylpentan-2-yl)isoindoline-1,3-dione (4.01 g, 16.23 mmol) were subjected to Buchwald coupling as described in Example 16, Part H) to give (S)-2-(1-((4,6-dimethyl-5-oxo 5,6-dihydrobenzo[c][2,7]naphthyridin-8-yl)oxy)-4-methylpentan-2-yl)isoindoline-1,3-dione as yellow solid (1.4 g, 2.62 mmol, 49% yield). LC/MS (ESI) m/e 470.2 [(M+H)$^+$, calcd for $C_{28}H_{28}N_3O_4$ 470.2]; LC/MS retention time (method C): $t_R$=2.05 min.

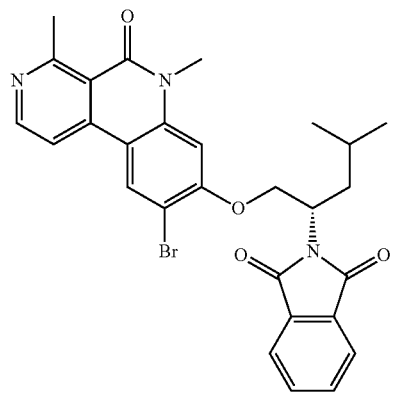 [SMILES: Cc1nccc2c1c(=O)n(C)c1cc(OC[C@H](CC(C)C)N3C(=O)c4ccccc4C3=O)c(Br)cc21]

Part B. (S)-2-(1-((9-bromo-4,6-dimethyl-5-oxo-5,6-dihydrobenzo[c][2,7]naphthyridin-8-yl)oxy)-4-methylpentan-2-yl)isoindoline-1,3-dione To a solution of (S)-2-(1-((4,6-dimethyl-5-oxo-5,6-dihydrobenzo[c][2,7]naphthyridin-8-yl)oxy)-4-methylpentan-2-yl)isoindoline-1,3-dione (1 g, 1.917 mmol) in acetonitrile (20 mL) was added NBS (0.341 g, 1.917 mmol) and the solution heated to 80° C. overnight to afford (S)-2-(1-((9-bromo-4,6-dimethyl-5-oxo-5,6-dihydrobenzo[c][2,7]naphthyridin-8-yl)oxy)-4-methylpentan-2-yl)isoindoline-1,3-dione (1.2 g, 1.69 mmol, 88% crude yield) as brown solid. The material was carried forward without further purification. LC/MS (ESI) m/e 548.0 [(M+H)$^+$, calcd for $C_{28}H_{27}BrN_3O_4$ 548.1; LC/MS retention time (method D): $t_R$=0.76 min.

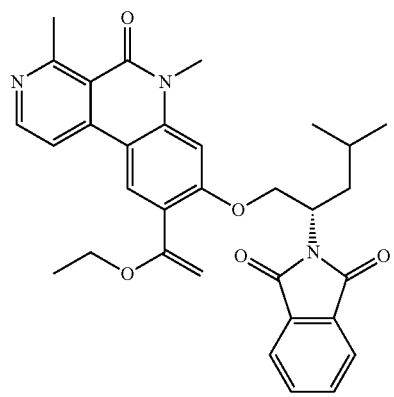 [SMILES: C=C(OCC)c1cc2c3ccnc(C)c3c(=O)n(C)c2cc1OC[C@H](CC(C)C)N1C(=O)c2ccccc2C1=O]

Part C. (S)-2-(1-((9-(1-ethoxyvinyl)-4,6-dimethyl-5-oxo-5,6-dihydrobenzo[c][2,7]naphthyridin-8-yl)oxy)-4-methylpentan-2-yl)isoindoline-1,3-dione A solution of (S)-2-(1-((9-bromo-4,6-dimethyl-5-oxo-5,6-dihydrobenzo[c][2,7]naphthyridin-8-yl)oxy)-4-methylpentan-2-yl)isoindoline-1,3-dione (100 mg, 0.182 mmol), tributyl(1-ethoxyvinyl)stannane (132 mg, 0.365 mmol), DPPF (20.22 mg, 0.036 mmol) and Pd$_2$(dba)$_3$ (16.70 mg, 0.018 mmol) in 1,4-dioxane (5 mL) was purged with nitrogen for 5 min then heated at 100° C. overnight. After cooling to ambient temperature, the volatiles were concentrated under reduced pressure. The residue was taken up in ethyl acetate and filtered through diatomaceous earth (Celite®). The organic filtrate was washed with H$_2$O, then brine, dried over Na$_2$SO$_4$ and concentrated under reduced pressure to afford (S)-2-(1-((9-(1-ethoxyvinyl)-4,6-dimethyl-5-oxo-5,6-dihydrobenzo[c][2,7]naphthyridin-8-yl)oxy)-4-methylpentan-2-yl)isoindoline-1,3-dione (0.15 g, 0.131 mmol, 72% crude yield) as a black gummy solid. The material was carried forward without further purification. LC/MS (ESI) m/e 540.3 [(M+H)$^+$, calcd for C$_{32}$H$_{34}$N$_3$O$_5$ 540.2; LC/MS retention time (method G): $t_R$=1.21 min.

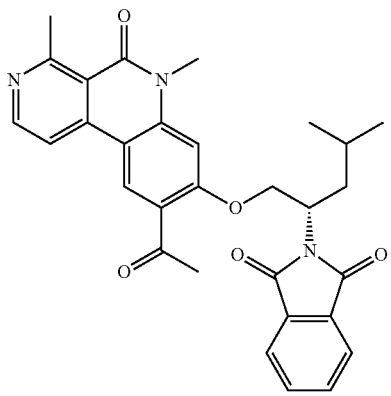 [SMILES: CC(=O)c1cc2c3ccnc(C)c3c(=O)n(C)c2cc1OC[C@H](CC(C)C)N1C(=O)c2ccccc2C1=O]

Part D. (S)-2-(1-((9-acetyl-4,6-dimethyl-5-oxo-5,6-dihydrobenzo[c][2,7]naphthyridin-8-yl)oxy)-4-methylpentan-2-yl)isoindoline-1,3-dione (S)-2-(1-((9-(1-ethoxyvinyl)-4,6-dimethyl-5-oxo-5,6-dihydrobenzo[c][2,7]naphthyridin-8-yl)oxy)-4-methylpentan-2-yl)isoindoline-1,3-dione (150 mg, 0.278 mmol) was subjected to acid hydrolysis to afford (S)-2-(1-((9-acetyl-4,6-dimethyl-5-oxo-5,6-dihydrobenzo[c][2,7]naphthyridin-8-yl)oxy)-4-methylpentan-2-yl)isoindoline-1,3-dione (0.1 g, 0.14 mmol, 51% yield) as brown solid. The crude material was carried forward without further purification. LC/MS (ESI) m/e 512.1 [(M+H)$^+$, calcd for C$_{30}$H$_{30}$N$_3$O$_5$ 512.2; LC/MS retention time (method D): $t_R$=0.89 min.

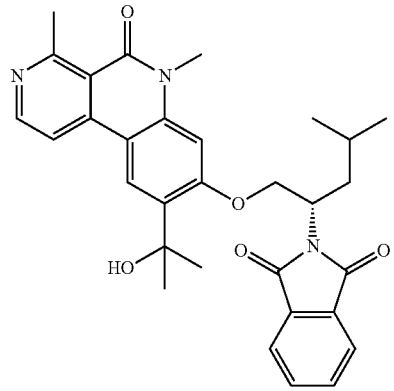 [SMILES: Cc1nccc2c1c(=O)n(C)c1cc(OC[C@H](CC(C)C)N3C(=O)c4ccccc4C3=O)c(C(C)(C)O)cc21]

Part E. (S)-2-(1-((9-(2-hydroxypropan-2-yl)-4,6-dimethyl-5-oxo-5,6-dihydrobenzo[c][2,7]naphthyridin-8-yl)oxy)-4-methylpentan-2-yl)isoindoline-1,3-dione To a solution of (S)-2-(1-((9-acetyl-4,6-dimethyl-5-oxo-5,6-dihydrobenzo[c][2,7]naphthyridin-8-yl)oxy)-4-methylpentan-2-yl)isoindoline-1,3-dione (220 mg, 0.430 mmol) in THF (6 mL) was added methyl magnesium bromide (1.4 M in diethyl ether) (0.922 mL, 1.290 mmol) at −10° C. and stirred for overnight at RT. The reaction mixture was carefully quenched with water and diluted with EtOAc. The organic layer was separated, dried over sodium sulphate and concentrated under reduced pressure. The residue was purified via silica gel chromatography to afford (S)-2-(1-((9-(2-hydroxypropan-2-yl)-4,6-dimethyl-5-oxo-5,6-dihydrobenzo[c][2,7]naphthyridin-8-yl)oxy)-4-methylpentan-2-yl)isoindoline-1,3-dione (0.2 g, 0.152 mmol, 35% yield) as a brown gummy solid. LC/MS (ESI) m/e 528.2 [(M+H)$^+$, calcd for C$_{31}$H$_{34}$N$_3$O$_5$ 528.2; LC/MS retention time (method D): $t_R$=0.89 min.

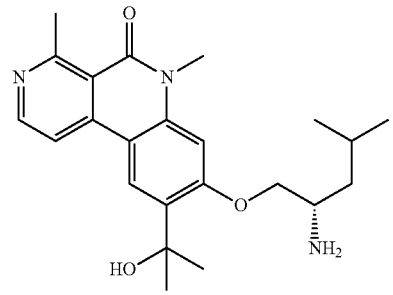 [SMILES: Cc1nccc2c1c(=O)n(C)c1cc(OC[C@@H](N)CC(C)C)c(C(C)(C)O)cc21]

Part F. (S)-8-((2-amino-4-methylpentyl)oxy)-9-(2-hydroxypropan-2-yl)-4,6-dimethylbenzo[c][2,7]naphthyridin-5(6H)-one To a solution of (S)-2-(1-((9-(2-hydroxypropan-2-yl)-4,6-dimethyl-5-oxo-5,6-dihydrobenzo[c][2,7]naphthyridin-8-yl)oxy)-4-methylpentan-2-yl)isoindoline-1,3-dione (200 mg, 0.152 mmol) in ethanol (5 mL), was added hydrazine (4.76 µl, 0.152 mmol) at RT then the mixture was heated to 60° C. for 4 h. The reaction mixture was filtered, concentrated and purified by prep. HPLC to afford (S)-8-((2-amino-4-methylpentyl)oxy)-9-(2-hydroxypropan-2-yl)-4,6-dimethylbenzo[c][2,7]naphthyridin-5(6H)-one as white solid (9 mg, 0.021 mmol, 14% yield). LC/MS (ESI) m/e 398.0 [(M+H)+, calcd for $C_{23}H_{32}N_3O_3$ 398.2]; LC/MS retention time (method G): $t_R$=1.99 min. HPLC retention time (method A): $t_R$=8.63 min; HPLC retention time (method B): $t_R$=9.79 min. $^1$H NMR (400 MHz, METHANOL-$d_4$) ppm 0.94-1.10 (m, 6H), 1.25-1.37 (m, 1H), 1.49-1.78 (m, 7H), 1.82-1.93 (m, 1H), 2.96-3.19 (m, 2H), 3.56-3.65 (m, 1H), 3.80 (s, 3H), 4.16-4.29 (m, 1H), 4.34-4.49 (m, 1H), 7.01-7.15 (m, 1H), 8.10-8.22 (m, 1H), 8.51-8.64 (m, 2H).

Example 36

(S)-8-((2-amino-4-methylpentyl)oxy)-9-ethyl-4,6-dimethylbenzo[c][2,7]naphthyridin-5(6H)-one

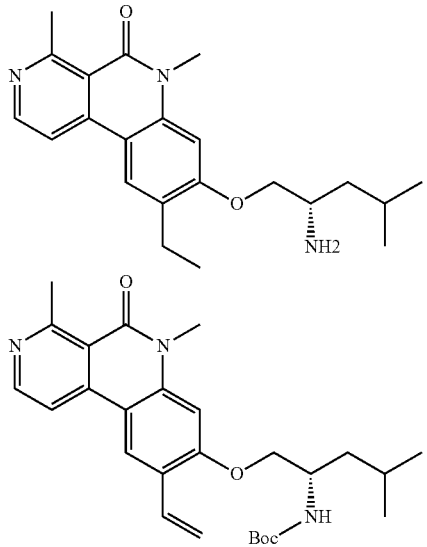

Part A: (S)-tert-butyl (1-((4,6-dimethyl-5-oxo-9-vinyl-5,6-dihydrobenzo[c][2,7]naphthyridin-8-yl)oxy)-4-methylpentan-2-yl)carbamate To the solution of (S)-tert-butyl (1-((9-bromo-4,6-dimethyl-5-oxo-5,6-dihydrobenzo[c][2,7]naphthyridin-8-yl)oxy)-4-methylpentan-2-yl)carbamate (300 mg, 0.579 mmol), prepared as described in Example 3, Part A, in the solvent mixture toluene (10 mL), water (0.5 mL) and ethanol (2 mL) was added sodium carbonate (184 mg, 1.736 mmol), tetrakis(triphenylphosphine)palladium (33.4 mg, 0.029 mmol) and 2,4,6-trivinyl-1,3,5,2,4,6-trioxatriborinane with pyridine (1:1) (167 mg, 0.694 mmol). The reaction mixture was degassed for 30 min. Then the reaction mixture was allowed to stir at 90° C. for 16 h. After cooling to room temperature the mixture was filtered through diatomaceous earth (Celite®) eluting with EtOAc. The filtrate was concentrated under reduced pressure. The residue was taken up in EtOAc and water. The solution was extracted with ethyl acetate (2×15 mL). The combined organic layers were washed with water (10 mL), brine (10 mL), dried over sodium sulfate, filtered and concentrated under reduced pressure. The residue was purified by silica gel column chromatography (60% Ethyl acetate in hexane) to afford (S)-tert-butyl (1-((4,6-dimethyl-5-oxo-9-vinyl-5,6-dihydrobenzo[c][2,7]naphthyridin-8-yl)oxy)-4-methylpentan-2-yl)carbamate (300 mg, 0.110 mmol, 19% yield) as a pale yellow semi solid. LC/MS, (ESI) m/z 466.5 [(M+H)+, calcd for $C_{27}H_{36}N_3O_4$ 466.3]; LC/MS retention time (method E): $t_R$=1.18 min.

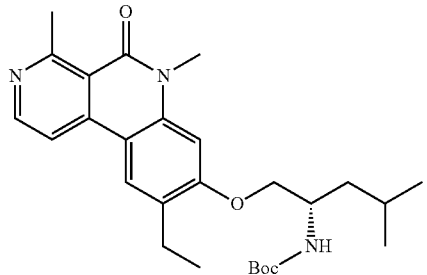 [SMILES: CCc1cc2c3ccnc(C)c3c(=O)n(C)c2cc1OC[C@H](CC(C)C)NC(=O)OC(C)(C)C]

Part B: (S)-tert-butyl (1-((9-ethyl-4,6-dimethyl-5-oxo-5,6-dihydrobenzo[c][2,7]naphthyridin-8-yl)oxy)-4-methylpentan-2-yl)carbamate A solution of (S)-tert-butyl (1-((4,6-dimethyl-5-oxo-9-vinyl-5,6-dihydrobenzo[c][2,7]naphthyridin-8-yl)oxy)-4-methylpentan-2-yl)carbamate (50 mg, 0.107 mmol) in MeOH (3 mL) was degassed with nitrogen for 5 min, then palladium on carbon (1.143 mg, 10.74 μmol) was added. The reaction mixture was allowed to stir under a balloon of hydrogen for 16 h. The reaction mixture was then filtered through diatomaceous earth (Celite®) and the filtrate was concentrated under reduced pressure. The residue was purified by preparative TLC (2% MeOH in MDC) to afford (S)-tert-butyl (1-((9-ethyl-4,6-dimethyl-5-oxo-5,6-dihydrobenzo[c][2,7]naphthyridin-8-yl)oxy)-4-methylpentan-2-yl)carbamate (31 mg, 0.058 mmol, 54% yield) as pale yellow solid. LC/MS, (ESI) m/z 468.5 [(M+H)+, calcd for $C_{27}H_{38}N_3O_4$ 468.3]; LC/MS retention time (method D): $t_R$=1.31 min.

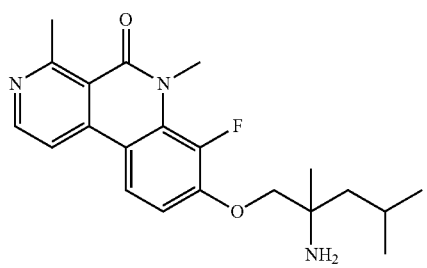 [SMILES: Cc1nccc2c1c(=O)n(C)c1c(F)c(OCC(C)(N)CC(C)C)ccc21]

Part C: (S)-8-((2-amino-4-methylpentyl)oxy)-9-ethyl-4,6-dimethylbenzo[c][2,7]naphthyridin-5(6H)-one Prepared as described in Example 2, Part E to afford the title compound (4 mg, 10.62 μmoles, 33% yield) as a pale yellow gum. LC/MS, (ESI) m/z 368.4 [(M+H)+, calcd for $C_{22}H_{30}N_3O_2$ 368.2]; LC/MS retention time (method B): $t_R$=2.18 min. HPLC retention time (method A): $t_R$=8.87 min; HPLC retention time (method B): $t_R$=9.53 min. $^1$H NMR (400 MHz, MeOH-$d_4$) δ ppm 8.51 (d, J=5.60 Hz, 1H) 8.17 (s, 1H) 8.13 (d, J=5.60 Hz, 1H) 6.97 (s, 1H) 4.17-4.20 (m, 1H) 4.04-4.04 (m, 1H) 3.76 (s, 3H) 3.31-3.38 (m, 1H) 3.06 (s, 3H)

2.80-2.82 (m, 2H) 1.81-1.89 (m, 1H) 1.53-1.58 (m, 1H) 1.45-1.50 (m, 1H) 1.27-1.31 (m, 3H), 0.98-1.02 (m, 6H).

Example 37 (Enantiomer 1) and Example 38 (Enantiomer 2)

(R)-8-((2-amino-2,4-dimethylpentyl)oxy)-4,6-dimethylbenzo[c][2,7]naphthyridin-5(6H)-one and (S)-8-((2-amino-2,4-dimethylpentyl)oxy)-4,6-dimethylbenzo[c][2,7]naphthyridin-5(6H)-one

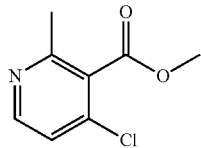

The resolution of 8-((2-amino-2,4-dimethylpentyl)oxy)-4,6 dimethylbenzo[c][2,7]naphthyridin-5(6H)-one, prepared in Example 2 32, was carried out by chiral HPLC (Method: Co-solvent: 0.3% DEA in methanol, Column: Chiralpak AD H (250×21) mm 5 u) resulting into two enantiomers. The absolute stereochemistry of each enantiomer was not determined.

Enantiomer-1: LC/MS (ESI) m/e 354.2 [(M+H)$^+$, calcd for C$_{21}$H$_{28}$N$_3$O$_2$, 354.2]; LC/MS retention time (method C): $t_R$=1.57 min. HPLC retention time (method A): $t_R$=8.67 min; HPLC retention time (method B): $t_R$=9.46 min. $^1$H NMR (400 MHz, METHANOL-d4) ppm δ 8.54 (s, 1H), 8.34-8.36 (bs, 1H), 8.10 (bs, 1H), 7.06 (s, 1H), 4.11-4.17 (m, 2H), 3.73 (s, 3H), 3.06 (s, 3H), 1.70-1.98 (m, 2H), 1.68 (bs, 1H), 1.45 (s, 3H), 1.02-1.08 (m, 6H); Chiral HPLC retention time, $t_R$=9.36 min Enantiomer-2: LC/MS (ESI) m/e 354.2 [(M+H)$^+$, calcd for C$_{21}$H$_{28}$N$_3$O$_2$, 354.2]; LC/MS retention time (method C): $t_R$=1.57 min. HPLC (Method B) retention time (method A): $t_R$=8.67 min; HPLC retention time (method B): $t_R$=9.46 min. $^1$H NMR (400 MHz, METHANOL-d4) ppm δ 8.54 (s, 1H), 8.34-8.36 (bs, 1H), 8.10 (bs, 1H), 7.06 (s, 1H), 4.11-4.17 (m, 2H), 3.73 (s, 3H), 3.06 (s, 3H), 1.70-1.98 (m, 2H), 1.68 (bs, 1H), 1.45 (s, 3H), 1.02-1.08 (m, 6H); Chiral HPLC (Method B) retention time: $t_R$=10.68 min.

Example 39

(S)-8-((2-(dimethylamino)-4-methylpentyl)oxy)-6-methylbenzo[c][2,7]naphthyridin-5(6H)-one

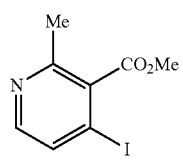

To a stirred solution of (S)-8-((2-amino-4-methylpentyl)oxy)-6-methylbenzo[c][2,7]naphthyridin-5(6H)-one (0.06 g, 0.184 mmol) (synthesis described in Example 2, Part E) in formic acid (0.035 mL, 0.922 mmol) was added formaldehyde (0.025 mL, 0.922 mmol) at ambient temperature. Then reaction mixture was then heated to reflux for 16 h. The reaction mixture was concentrated under reduced pressure. The residue was diluted with 50 mL of water and extracted with 80 mL of dichloromethane. The organic layer was separated, dried over sodium sulphate, and concentrated under reduced pressure. The residue was purified by reverse phase HPLC (acetonitrile/water/10 mM NH$_4$OAc) to afford (S)-8-((2-(dimethylamino)-4-methylpentyl)oxy)-6 methylbenzo[c][2,7]naphthyridin-5(6H)-one (8 mg, 0.021 mmol, 11% yield) as a white solid. LC/MS (ESI) m/e 354.0 [(M+H)$^+$, calcd for C$_{21}$H$_{28}$N$_3$O$_2$, 354.5]; LC/MS retention time (method C): $t_R$=1.85 min. HPLC retention time (method A): $t_R$=8.02 min; HPLC retention time (method B): $t_R$=9.19 min $^1$H NMR (400 MHz, METHANOL-d$_4$) δ ppm 1.01 (d, J=6.80 Hz, 6H), 1.50-1.61 (m, 2H), 1.73-1.80 (m, 1H), 2.52 (s, 1H), 3.15-3.16 (m, 1H), 3.73 (s, 3H), 4.23-4.31 (m, 2H), 7.04 (d, J=8.00 Hz, 2H), 8.15 (s, 1H), 8.30 (d, J=8.00 Hz, 1H), 8.71 (s, 1H), 8.39 (s, 1H).

Example 40

(S)-8-((2-(dimethylamino)-4-methylpentyl)oxy)-4,6-dimethylbenzo[c][2,7]naphthyridin-5(6H)-one

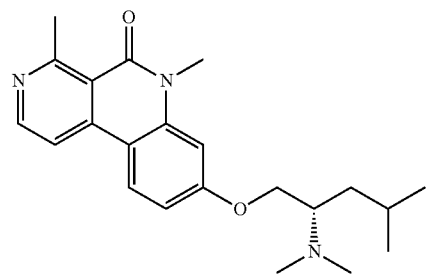 [SMILES: Cc1nccc2c1c(=O)n(C)c1cc(OC[C@H](CC(C)C)N(C)C)ccc21]

To a slurry of (S)-8-((2-amino-4-methylpentyl)oxy)-4,6 dimethylbenzo[c][2,7]naphthyridin-5(6H)-one (0.1 g, 0.295 mmol) (synthesis described in Example 16, part I) in formic acid (0.011 mL, 0.295 mmol) was added formaldehyde (8.12 μL, 0.295 mmol) at RT. The reaction mixture was heated to 100° C. for 16 h in a sealed tube. After cooling to room temperature, the mixture concentrated under reduced pressure. The residue was then partitioned between water (50 mL) and dichloromethane (80 mL). The organic layer was separated, dried over sodium sulfate and concentrated under reduced pressure. The residue was purified by reverse phase HPLC (10 mM ammonium acetate/AcCN) to afford (S)-8-((2-(dimethylamino)-4-methylpentyl)oxy)-4,6-dimethylbenzo[c][2,7]naphthyridin-5(6H)-one (30 mg, 0.078 mmol, 26% yield) as a white solid. LC/MS (ESI) m/e 368.0 [(M+H)$^+$, calcd for C$_{22}$H$_{30}$N$_3$O$_2$, 368.2]; LC/MS retention time (Method C): $t_R$=1.86 min. HPLC retention time (method A): $t_R$=7.98 min; HPLC retention time (method B): $t_R$=9.44 min. $^1$H NMR (400 MHz, METHANOL-d$_4$) ppm δ 1.01 (d, J=6.80 Hz, 6H), 1.61-1.95 (m, 3H), 2.66-2.69 (m, 6H), 3.06 (s, 3H), 3.37-3.43 (m, 1H), 3.74 (s, 3H), 4.37 (d, J=4.80 Hz, 2H), 7.04-7.08 (m, 2H), 8.10 (d, J=5.60 Hz, 1H), 8.36 (d, J=8.80 Hz, 1H), 8.53 (d, J=5.60 Hz, 1H).

Example 41

8-((2-amino-2,4-dimethylpentyl)oxy)-9-chloro-4,6-dimethylbenzo[c][2,7]naphthyridin-5(6H)-one

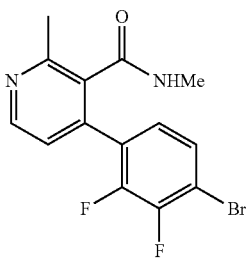 [SMILES: CNC(=O)c1c(-c2ccc(Br)c(F)c2F)ccnc1C]

To the stirred solution of 8-((2-amino-2,4-dimethylpentyl)oxy)-4,6 dimethylbenzo[c][2,7]naphthyridin-5(6H)-one (Prepared in Example 32, Part B) (0.08 g, 0.226 mmol) in acetonitrile (5 mL) was added NCS (0.030 g, 0.226 mmol)) at RT and the reaction mixture was stirred for 2 h. The mixture was then evaporated to dryness. The residue was purified by reverse phase HPLC (0.1% TFA in water/AcCN) to afford 8-((2-amino-2,4-dimethylpentyl)oxy)-9-chloro-4,6-dimethylbenzo[c][2,7]naphthyridin-5(6H)-one (12 mg, 0.030 mmol, 13% yield). LC/MS (ESI) m/e 388.0 [(M+H)$^+$, calcd for $C_{21}H_{27}ClN_3O_2$, 388.2] as an off-white solid. LC/MS retention time (method C): $t_R$=2.13 min. HPLC retention time (method A): $t_R$=8.97 min; HPLC retention time (method B): $t_R$=10.16 min. $^1$H NMR (400 MHz, METHANOL-d$_4$) δ ppm 0.99-1.02 (m, 6H), 1.30 (s, 3H), 1.54-1.66 (m, 2H), 1.84-1.90 (m, 1H), 3.05 (s, 1H), 3.73 (s, 1H), 4.04 (q, J=23.20 Hz, 2H), 7.03 (s, 1H), 8.06 (d, J=6.00 Hz, 1H), 8.39 (s, 1H), 8.54 (d, J=6.00 Hz, 1H).

Example 42

(S)-8-(2-amino-4-methylpentyloxy)-4-methoxy-6-methylbenzo[c][2,7]naphthyridin-5(6H)-one

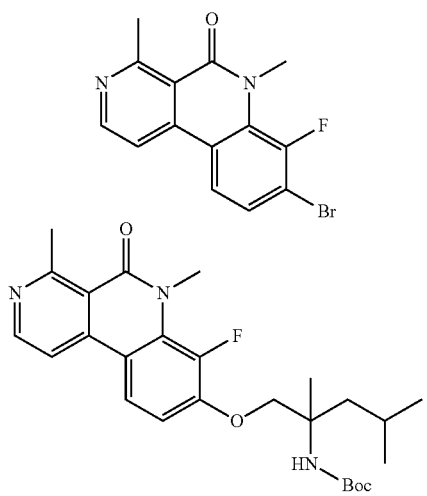

Part A. 8-chloro-6-methylbenzo[c][2,7]naphthyridin-5(6H)-one

Preparation as described in Example 2, Part C.

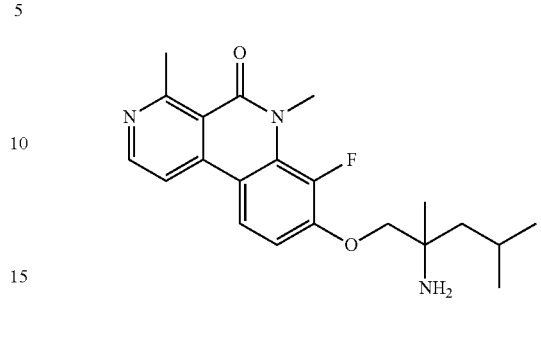

Part A. 8-chloro-6-methyl-5-oxo-5,6-dihydrobenzo[c][2,7]naphthyridine 3-oxide To the stirred solution of 8-chloro-6-methylbenzo[c][2,7]naphthyridin-5(6H)-one (1.0 g, 4.09 mmol), prepared as described in Example 2, Part C, in DCM (20 mL) cooled to 0° C. was added m-CPBA (1.763 g, 10.22 mmol). The reaction mixture was then warmed to ambient temperature and stirred for 4 h. Reaction mixture was then diluted with dichloromethane (100 mL) and washed with saturated sodium bicarbonate solution (200 mL), brine solution (50 mL). The organics were then dried over sodium sulphate, filtered and concentrate to afford 8-chloro-6-methyl-5-oxo-5,6-dihydrobenzo[c][2,7]naphthyridine 3-oxide (1.0 g, 3.84 mmol, 94% crude yield) as a yellow solid. The material was carried on without further purification. LC/MS (ESI) m/e 261.0, [(M+H)$^+$, calcd for $C_{13}H_{10}ClN_2O_2$, 261.0]; LC/MS retention time (method C): $t_R$=1.65 min.

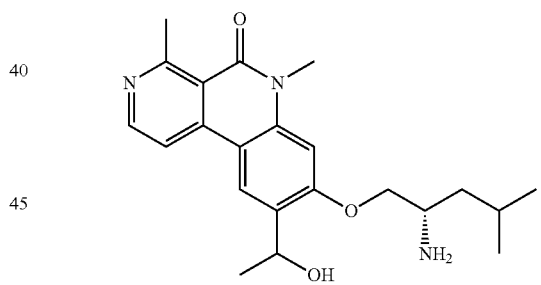

Part B. 4,8-dichloro-6-methylbenzo[c][2,7]naphthyridin-5(6H)-one

A stirred solution of 8-chloro-6-methyl-5-oxo-5,6-dihydrobenzo[c][2,7]naphthyridine 3-oxide (0.5 g, 1.918 mmol) in POCl$_3$ (3.58 mL, 38.4 mmol) was heated to reflux for 6 h. The reaction mixture was concentrated under reduced pressure. The residue was then partitioned between dichloromethane (100 mL) and saturated sodium bicarbonate solution (200 mL). The organic layer was separated and washed again with brine solution (50 mL), dried over sodium sulphate, and concentrated to afford 4,8-dichloro-6 methylbenzo[c][2,7]naphthyridin-5(6H)-one (0.3 g, 1.075 mmol, 56% crude yield). The material was carried on without further purification. LC/MS (ESI) m/e 280.8, [(M+2H)$^+$, calcd for $C_{13}H_9Cl_2N_2O$, 280.8]; LC/MS retention time (method C): $t_R$=2.06 min.

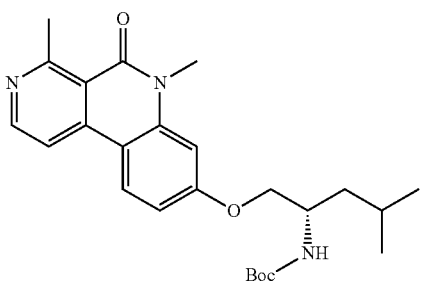

Part C. 8-chloro-4-methoxy-6-methylbenzo[c][2,7]naphthyridin-5(6H)-one

To a solution of 4,8-dichloro-6-methylbenzo[c][2,7]naphthyridin-5(6H)-one (1.0 g, 3.58 mmol) in MeOH (1 mL) was added sodium methoxide (0.806 mL, 3.58 mmol). The resultant mixture was heated in a microwave at 80° C. for 25 min. The reaction mixture was then diluted with water (20 mL) and extracted with ethyl acetate (30 mL). The organic layer was separated, dried over sodium sulphate and evaporated to dryness to afford 8-chloro-4-methoxy-6-methylbenzo[c][2,7]naphthyridin-5(6H)-one (0.4 g, 1.391 mmol, 39% crude yield) as a brown solid. The material was carried on without further purification. LC/MS (ESI) m/e 274.8 [(M+H)$^+$, calcd for $C_{14}H_{12}ClN_2O_2$, 275.0]; LC/MS retention time (method C): $t_R$=2.06 min.

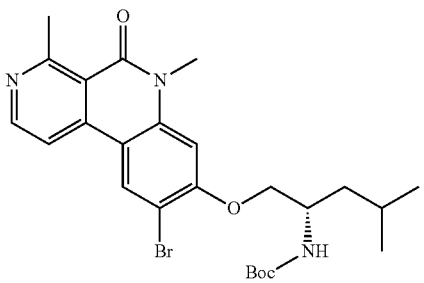 [SMILES: Cc1nccc2c1c(=O)n(C)c1cc(OC[C@H](CC(C)C)NC(=O)OC(C)(C)C)c(Br)cc21]

Part D. (S)-tert-butyl (1-((4-methoxy-6-methyl-5-oxo-5,6-dihydrobenzo[c][2,7]naphthyridin-8-yl)oxy)-4-methylpentan-2-yl)carbamate Prepared as described in Example 16, Part H to afford the title product (0.1 g, 0.135 mmol, 62% yield) as a semi solid. LC/MS (ESI) m/e 456.0, [(M+H)$^+$, calcd for $C_{25}H_{34}N_3O_5$, 456.2]; LC/MS retention time (method C): $t_R$=2.26 min.

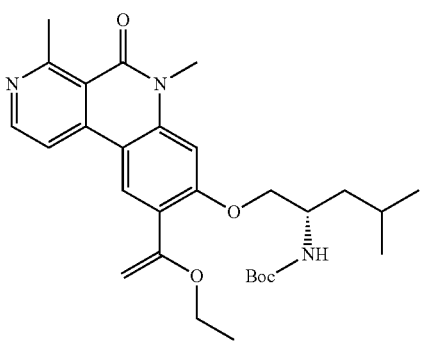 [SMILES: C=C(OCC)c1cc2c3ccnc(C)c3c(=O)n(C)c2cc1OC[C@H](CC(C)C)NC(=O)OC(C)(C)C]

Part E. (S)-8-((2-amino-4-methylpentyl)oxy)-4-methoxy-6 methylbenzo[c][2,7]naphthyridin-5(6H)-one Prepared as described in Example 2, Part E to afford the title product (10 mg, 0.027 mmol, 20% yield) as a gum. LC/MS (ESI) m/e 356.0, [(M+H)$^+$, calcd for $C_{20}H_{26}N_3O_3$, 356.4]; LC/MS retention time (method C): $t_R$=1.83 min. HPLC retention time (method A): $t_R$=8.48 min; HPLC retention time (method B): $t_R$=7.61 min. $^1$H NMR (400 MHz, METHANOL-$d_4$) δ ppm 8.24 (d, J=6.0 Hz, 1H), 8.13 (d, J=9.0 Hz, 1H), 7.62 (d, J=6.0 Hz, 1H), 6.99-6.91 (m, 1H), 6.90 (d, J=2.5 Hz, 1H), 4.11 (dd, J=9.5, 4.0 Hz, 1H), 4.06 (s, 3H), 3.92 (dd, J=9.3, 7.3 Hz, 1H), 3.65 (s, 3H), 1.93-1.81 (m, 1H), 1.45 (td, J=7.7, 6.3 Hz, 2H), 1.03 (d, J=6.5 Hz, 3H), 1.01 (d, J=6.5 Hz, 3H).

Example 43

(S)-8-((2-amino-4-methylpentyl)oxy)-9-chloro-6-methylbenzo[c][2,7]naphthyridin-5(6H)-one

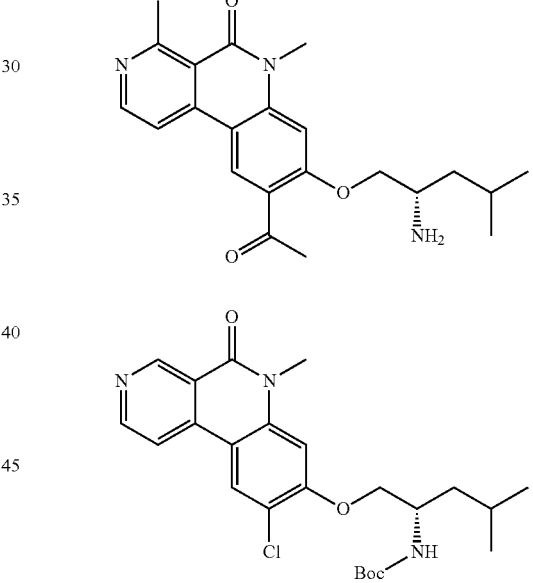

Part A. (S)-tert-butyl (1-((9-chloro-6-methyl-5-oxo-5,6-dihydrobenzo[c][2,7]naphthyridin-8-yl)oxy)-4-methylpentan-2-yl)carbamate (S)-tert-butyl (4-methyl-1-((6-methyl-5-oxo-5,6-dihydrobenzo[c][2,7]naphthyridin-8-yl)oxy)pentan-2-yl)carbamate (0.4 g, 0.714 mmol), prepared as described in Example 19, Part B, was subjected to chlorination using NCS as described in Example 41, to afford (S)-tert-butyl (1-((9-chloro-6-methyl-5-oxo-5,6-dihydrobenzo[c][2,7]naphthyridin-8-yl)oxy)-4-methylpentan-2-yl)carbamate (0.3 g, 0.437 mmol, 61% yield) as a yellow solid. LC/MS (ESI) m/e 460.2 [(M+H)$^+$, calcd for $C_{24}H_{31}ClN_3O_4$, 460.2]; LC/MS retention time (Method C) $t_R$=2.17 min.

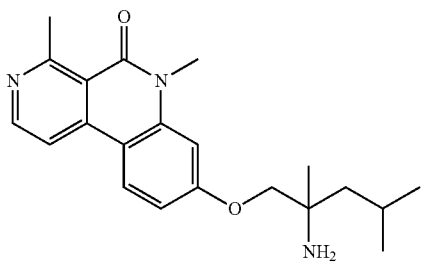 [SMILES: Cc1nccc2c1c(=O)n(C)c1cc(OCC(C)(N)CC(C)C)ccc21]

Part B. (S)-8-((2-amino-4-methylpentyl)oxy)-9-chloro-6 methylbenzo[c][2,7]naphthyridin-5(6H)-one (S)-tert-Butyl (1-((9-chloro-6-methyl-5-oxo-5,6-dihydrobenzo[c][2,7]naphthyridin-8-yl)oxy)-4-methylpentan-2-yl)carbamate was subjected to deprotection of Boc, as described in Example 2, Part E, to afford (S)-8-((2-amino-4-methylpentyl)oxy)-9-chloro-6 methylbenzo[c][2,7]naphthyridin-5(6H)-one (0.1 g, 0.27 mmol, 72% yield) as an off-white solid. LC/MS (ESI) m/e 360.2 [(M+H)+, calcd for $C_{19}H_{23}ClN_3O_2$, 360.1]; HPLC retention time (method A): $t_R$=8.94 min; HPLC retention time (method B): $t_R$=5.4 min. $^1$H NMR (400 MHz, METHANOL-d4) ppm 9.43 (d, J=0.50 Hz, 1H), 8.76 (d, J=5.52 Hz, 1H), 8.42 (s, 1H), 8.16-8.20 (m, 1H), 7.10 (s, 1H), 4.23-4.27 (m, 1H), 4.02-4.08 (m, 1H), 3.78 (s, 3H), 3.34-3.40 (m, 1H), 1.84-1.94 (m, 1H), 1.42-1.58 (m, 2H), 1.03 (dd, J=8.66, 6.65 Hz, 6H).

Example 44

(S)-8-(2-amino-4-methylpentyloxy)-6-(2-hydroxyethyl)benzo[c][2,7]naphthyridin-5(6H)-one

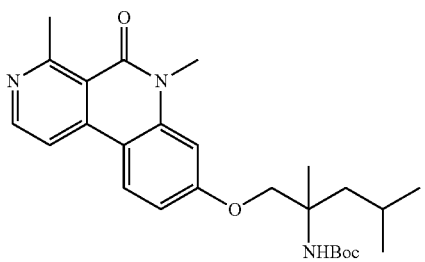

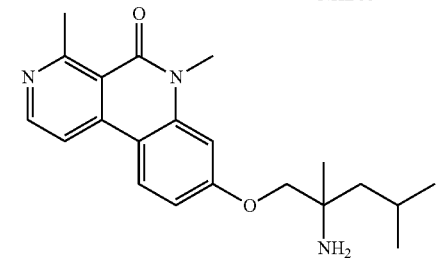

Part A. 8-chloro-6-(2-hydroxyethyl)benzo[c][2,7]naphthyridin-5(6H)-one

To a stirred solution of 8-chlorobenzo[c][2,7]naphthyridin-5(6H)-one (80 mg, 0.347 mmol) in anhydrous DMF (5 mL) under a nitrogen atmosphere was added ethyl carbonate (122 mg, 1.387 mmol), $K_2CO_3$ (96 mg, 0.694 mmol), and 18-crown-6 (18.31 mg, 0.069 mmol). The reaction mixture was heated to 80° C. for 12 h. The reaction mixture was diluted with water (10 mL) and extracted with ethyl acetate (2×20 mL). The combined ethyl acetate layers were dried over sodium sulphate and concentrated under reduced pressure to afford 8-chloro-6-(2-hydroxyethyl)benzo[c][2,7]naphthyridin-5(6H)-one (80 mg, 0.291 mmol, 84% crude yield) The material was carried on without further purification. LC/MS (ESI) m/e 275.0 [(M+H)+, calcd for $C_{14}H_{12}ClN_2O_2$, 275.1]; $^1$H NMR (400 MHz, MeOD) δ 9.55 (s, 1H), 8.87 (d, J=5.6 Hz, 1H), 8.50 (d, J=8.8 Hz, 1H), 8.34 (d, J=5.6 Hz, 1H), 7.88 (d, J=1.6 Hz, 1H), 7.44 (dd, J=8.4, 2.0 Hz, 1H), 4.57 (t, J=6.0 Hz, 2H), 3.96 (t, J=6.0 Hz, 2H).

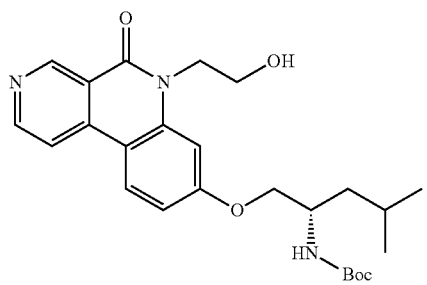 [SMILES: CC(C)C[C@@H](COc1ccc2c3ccncc3c(=O)n(CCO)c2c1)NC(=O)OC(C)(C)C]

Part B. (S)-tert-butyl (1-((6-(2-hydroxyethyl)-5-oxo-5,6-dihydrobenzo[c][2,7]naphthyridin-8-yl)oxy)-4-methylpentan-2-yl)carbamate Prepared as described in Example 16, Part H to afford (S)-tert-butyl (1-((6-(2-hydroxyethyl)-5-oxo-5,6-dihydrobenzo[c][2,7]naphthyridin-8-yl)oxy)-4-methylpentan-2-yl)carbamate (60 mg, 0.132 mmol, 45% yield) as a white oil, LC/MS (ESI) m/e 456.2, [(M+H)+, calcd for $C_{25}H_{34}N_3O_5$, 456.2]; LC/MS retention time (method C): $t_R$=1.81 min.

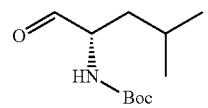

Part C. (S)-8-((2-amino-4-methylpentyl)oxy)-6-(2-hydroxyethyl)benzo[c][2,7]naphthyridin-5(6H)-one Prepared as described in Example 2, Part E to afford (S)-8-((2-amino-4-methylpentyl)oxy)-6-(2-hydroxyethyl)benzo[c][2,7]naphthyridin-5(6H)-one (6 mg, 0.015 mmol, 12% yield) as a yellow solid. LC/MS (ESI) m/e 356.2, [(M+H)+, calcd for C20H26N3O3, 356.2]; LC/MS retention time (method C): $t_R$=1.59 min. HPLC retention time (method A): $t_R$=7.66 min; HPLC retention time (method B): $t_R$=7.99 min. $^1$H NMR (400 MHz, MeOD) δ 9.50 (s, 1H), 8.79 (d, J=6.0 Hz, 1H), 8.47 (d, J=8.8 Hz, 1H), 8.29 (d, J=5.6 Hz, 1H), 7.34 (d, J=2.0 Hz, 1H), 7.14 (dd, J=8.8, 2.4 Hz, 1H), 4.59 (t, J=6.4 Hz, 2H), 4.34 (dd, J=10.0, 3.6 Hz, 1H), 4.17 (dd, J=10.0, 6.4 Hz, 1H), 3.98 (t, J=6.0 Hz, 2H), 3.63-3.53 (m, 1H), 1.92-1.80 (m, 1H), 1.66-1.59 (m, 2H), 1.06-1.03 (m, 6H).

Example 45

(S)-8-(2-amino-4-methylpentyloxy)-6-(2,2,2-trifluoroethyl)benzo[c][2,7]naphthyridin-5(6H)-one

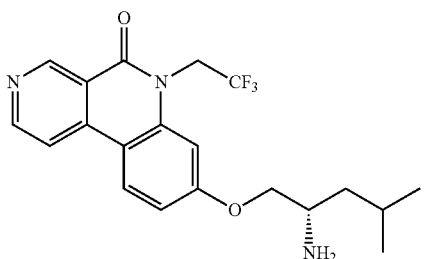

Part A. 4-(4-chloro-2-fluorophenyl)-N-(2,2,2-trifluoroethyl)nicotinamide

To stirred solution of 4-(4-chloro-2-fluorophenyl)nicotinic acid (300 mg, 1.192 mmol), prepared as described in Example 2, Part A, in anhydrous DMF (2 mL) under nitrogen was added HOBT (365 mg, 2.384 mmol), DIEA (0.927 mL, 4.77 mmol) and EDC (343 mg, 1.788 mmol). The reaction mixture was cooled to 0° C. and treated with 2,2,2-trifluoroethanamine (236 mg, 2.384 mmol) drop wise and warmed to RT and allowed to stir for 12 h. The reaction mixture was diluted with water (20 mL) and extracted with ethyl acetate (2×50 mL). The combined organic layers were dried over sodium sulphate and concentrated under reduced pressure to afford 4-(4-chloro-2-fluorophenyl)-N-(2,2,2-trifluoroethyl) nicotinamide (200 mg, 0.601 mmol, 50% crude yield) as a yellow solid. LC/MS (ESI) m/e 333.2, [(M+H)$^+$, calcd for $C_{14}H_{10}ClF_4N_2O$, 333.0]; LC/MS retention time (method A): $t_R$=1.66 min.

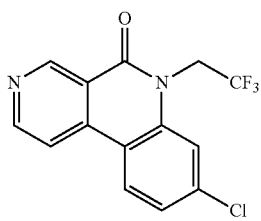 [SMILES: O=c1c2cnccc2c2ccc(Cl)cc2n1CC(F)(F)F]

Part B. 8-chloro-6-(2,2,2-trifluoroethyl)benzo[c][2,7]naphthyridin-5(6H)-one Prepared as described in Example 2, Part C to afford 8-chloro-6-(2,2,2-trifluoroethyl)benzo[c][2,7]naphthyridin-5(6H)-one (150 mg, 0.480 mmol, 80% yield) LC/MS (ESI) m/e 313.1, [(M+H)$^+$, calcd for $C_{14}H_9ClF_3N_2O$, 313.0]; LC/MS retention time (method D): $t_R$=0.95 min.

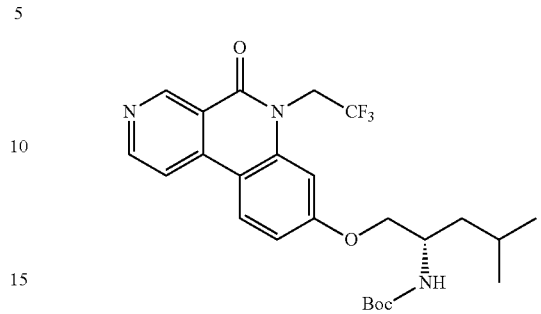

Part C. (S)-tert-butyl (4-methyl-1-((5-oxo-6-(2,2,2-trifluoroethyl)-5,6-dihydrobenzo[c][2,7]naphthyridin-8-yl)oxy)pentan-2-yl)carbamate Prepared as described in Example 16, Part H to afford (S)-tert-butyl (4-methyl-1-((5-oxo-6-(2,2,2-trifluoroethyl)-5,6-dihydrobenzo[c][2,7]naphthyridin-8-yl)oxy)pentan-2-yl)carbamate (100 mg, 0.203 mmol, 42% yield) as a brown solid. LC/MS (ESI) m/e 494.5, [(M+H)$^+$, calcd for $C_{25}H_{31}F_3N_3O_4$ 494.2]; LC/MS retention time (method C): $t_R$=2.17 min.

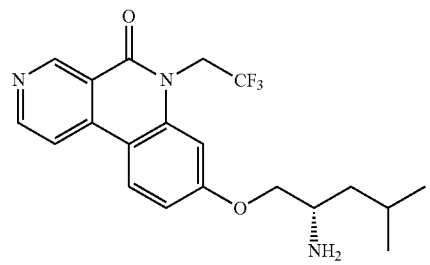 [SMILES: CC(C)C[C@H](N)COc1ccc2c3ccncc3c(=O)n(CC(F)(F)F)c2c1]

Part D. (S)-8-((2-amino-4-methylpentyl)oxy)-6-(2,2,2-trifluoroethyl)benzo[c][2,7]naphthyridin-5(6H)-one Prepared as described in Example 2, Part E to afford (S)-8-((2-amino-4-methylpentyl)oxy)-6-(2,2,2-trifluoroethyl)benzo[c][2,7]naphthyridin-5(6H)-one (25 mg, 0.061 mmol, 30% yield), white solid. LC/MS (ESI) m/e 394.2, [(M+H)$^+$, calcd for $C_{20}H_{23}F_3N_3O_2$, 394.2]; LC/MS retention time (method C): $t_R$=1.78 min. HPLC retention time (method A): $t_R$=5.26 min; HPLC retention time (method B): $t_R$=5.60 min. $^1$H NMR (400 MHz, MeOD) δ 9.49 (s, 1H), 8.81 (d, J=5.6 Hz, 1H), 8.46 (d, J=8.8 Hz, 1H), 8.28 (d, J=5.6 Hz, 1H), 7.23 (br s, 1H), 7.15 (dd, J=8.8, 2.0 Hz, 1H), 5.32 (dd, J=8.8, 6.4 Hz, 2H), 4.21 (dd, J=9.2, 3.6 Hz, 1H), 4.03 (dd, J=9.2, 7.2 Hz, 1H), 3.40-3.33 (m, 1H), 1.92-1.80 (quin, J=6.8, 1H), 1.52-1.46 (m, 2H), 1.02 (d, J=6.4 Hz, 3H), 1.00 (d, J=6.4 Hz, 3H).

Example 46

(S)-8-(2-amino-4-methylpentyloxy)-9-ethyl-6-methylbenzo[c][2,7]naphthyridin-5(6H)-one

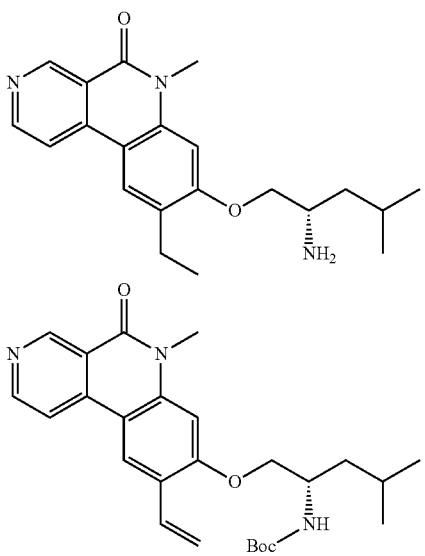

Part A. (S)-tertbutyl (4-methyl-1-((6-methyl-5-oxo-9-vinyl-5,6 dihydrobenzo[c][2,7]naphthyridin-8-yl)oxy)pentan-2-yl)carbamate A mixture of (S)-tert-butyl (1-((9-bromo-6-methyl-5-oxo-5,6-dihydrobenzo[c][2,7]naphthyridin-8-yl)oxy)-4-methylpentan-2-yl)carbamate (0.250 g, 0.496 mmol) (prepared as described in Example 3, Part B) 2,4,6-trivinylcyclotriboroxane pyridine complex (0.239 g, 0.991 mmol), Na$_2$CO$_3$ (0.158 g, 1.487 mmol) and Pd(PPh$_3$)$_4$ (0.029 g, 0.025 mmol) in toluene (1 mL) water (0.1 mL), and ethanol (0.3 mL) was purged with nitrogen gas and heated at 90° C. for 16 h. After cooling, the reaction mixture was transferred to separatory funnel containing water (10 mL) and extracted with ethyl acetate (3×10 mL). The combined organic layers were dried over sodium sulphate and concentrated under reduced pressure. The residue was purified by column chromatography on silica gel (60% ethyl acetate: petroleum ether) to afford a (S)-tert-butyl(4-methyl-1-((6-methyl-5-oxo-9-vinyl-5,6-dihydrobenzo[c][2,7]naphthyridin-8-yl)oxy)pentan-2-yl)carbamate (0.150 g, 0.166 mmol, 34% yield) as a yellow solid. LC/MS (ESI) m/e 452.4, [(M+H)$^+$, calcd for C$_{26}$H$_{34}$N$_3$O$_4$, 452.2]; LC/MS retention time (method D): t$_R$=0.95 min.

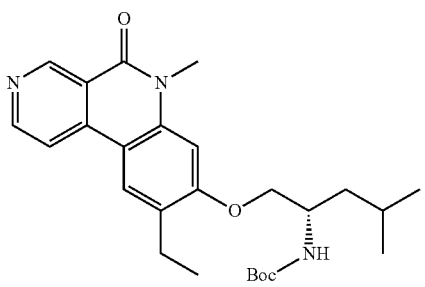 [SMILES: CCc1cc2c3ccncc3c(=O)n(C)c2cc1OC[C@H](CC(C)C)NC(=O)OC(C)(C)C]

Part B. (S)-tert-butyl (1-((9-ethyl-6-methyl-5-oxo-5,6-dihydrobenzo[c][2,7]naphthyridin-8-yl)oxy)-4-methylpentan 2-yl)carbamate A mixture of (S)-tert-butyl (4-methyl-1-((6-methyl-5-oxo-9-vinyl-5,6-dihydrobenzo[c][2,7]naphthyridin-8-yl)oxy)pentan-2-yl)carbamate (0.15 g, 0.332 mmol) and palladium on carbon (0.075 g, 0.070 mmol) in MeOH (3 mL) and ethyl acetate (3 mL) was stirred at RT under a balloon of hydrogen gas for 24 h. The reaction mixture was filtered through diatomaceous earth (Celite®) and the filtrate was concentrated under reduced pressure. The residue was purified by prep TLC (60% ethyl acetate and petroleum ether) to afford (S)-tert-butyl (1-((9-ethyl-6-methyl-5-oxo-5,6-dihydrobenzo[c][2,7]naphthyridin-8-yl)oxy)-4-methylpentan 2-yl)carbamate (0.11 g, 0.133 mmol, 40% yield) as a yellow semi solid. LC/MS (ESI) m/e 454.4, [(M+H)$^+$, calcd for C$_{26}$H$_{36}$N$_3$O$_4$, 454.3]; LC/MS retention time (method D): t$_R$=0.96 min.

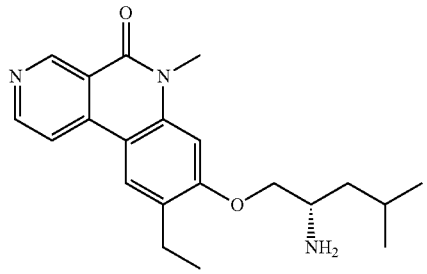 [SMILES: CCc1cc2c3ccncc3c(=O)n(C)c2cc1OC[C@@H](N)CC(C)C]

Part C. (S)-8-((2-amino-4-methylpentyl)oxy)-9-ethyl-6-methylbenzo[c][2,7]naphthyridin-5(6H)-one Prepared as described in Example 2, Part E to afford the title compound (55 mg, 0.155 mmol, 64% yield) as a yellow solid. LC/MS (ESI) m/e 354.2, [(M+H)$^+$, calcd for C$_{21}$H$_{28}$N$_3$O$_2$, 354.2]; LC/MS retention time (method C): t$_R$=1.94 min. HPLC retention time (method A): t$_R$=8.76 min; HPLC retention time (method B): t$_R$=5.19 min. $^1$H NMR (400 MHz, MeOD) δ 9.52 (s, 1H), 8.81 (d, J=6.0 Hz, 1H), 8.51 (d, J=8.8 Hz, 1H), 8.33 (s, 1H), 7.11 (s, 1H), 4.52 (m, 1H), 4.36 (m, 1H), 3.86 (s, 3H), 3.76-3.84 (m, 1H), 2.86-2.93 (m, 2H), 1.81-1.90 (m, 2H), 1.63-1.81 (m, 1H), 1.35 (m, 3H), 1.05 (m, 6H).

Example 47

(S)-8-(2-amino-4-methylpentyloxy)-9-isopropyl-6-methylbenzo[c][2,7]naphthyridin-5(6H)-one

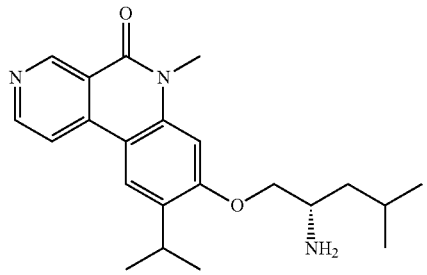

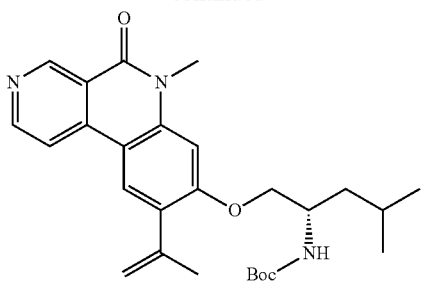

Part A. (S)-tert-butyl (4-methyl-1-((6-methyl-5-oxo-9-(prop-1-en-2-yl)-5,6-dihydrobenzo[c][2,7]naphthyridin-8-yl)oxy)pentan-2-yl)carbamate Prepared as described in Example 46, Parts A and B to afford (S)-tert-butyl (4-methyl-1-((6-methyl-5-oxo-9-(prop-1-en-2-yl)-5,6-dihydrobenzo[c][2,7]naphthyridin-8-yl)oxy)pentan-2-yl)carbamate (100 mg, 0.215 mmol, 90% yield) as a solid. LC/MS (ESI) m/e 466.4, [(M+H)⁺, calcd for $C_{27}H_{36}N_3O_4$, 466.3]; LC/MS retention time (method C): $t_R$=2.22 min.

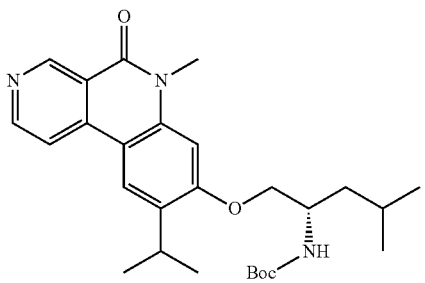 [SMILES: CC(C)C[C@@H](COc1cc2c(cc1C(C)C)c1ccncc1c(=O)n2C)NC(=O)OC(C)(C)C]

Part B. (S)-tert-butyl (1-((9-isopropyl-6-methyl-5-oxo-5,6 dihydrobenzo[c][2,7]naphthyridin-8-yl)oxy)-4-methylpentan-2-yl)carbamate A mixture of (S)-tert-butyl (4-methyl-1-((6-methyl-5-oxo-9-(prop-1-en-2-yl)-5,6-dihydrobenzo[c][2,7]naphthyridin-8-yl)oxy)pentan-2-yl)carbamate (0.1 g, 0.215 mmol) and palladium on carbon (0.07 g, 0.066 mmol) in MeOH (3 mL) and ethyl acetate (3 mL) was stirred at RT under a balloon of hydrogen gas for 24 h. The reaction mixture was filtered through diatomaceous earth (Celite®) and the filtrate was concentrated under reduced pressure to afford (S)-tert-butyl (1-((9-isopropyl-6-methyl-5-oxo-5,6-dihydrobenzo[c][2,7]naphthyridin-8-yl)oxy)-4-methylpentan-2-yl)carbamate (0.04 g, 2.464 mmol, 1% yield) as a brown oil, which was carried on without further purification. LC/MS (ESI) m/e 468.4, [(M+H)⁺, calcd for $C_{27}H_{38}N_3O_4$, 468.3]; LC/MS retention time (method D): $t_R$=1.00 min.

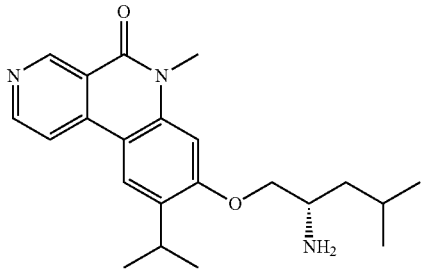 [SMILES: CC(C)C[C@H](N)COc1cc2c(cc1C(C)C)c1ccncc1c(=O)n2C]

Part C. (S)-8-(2-amino-4-methylpentyloxy)-9-isopropyl-6-methylbenzo[c][2,7]naphthyridin-5(6H)-one Prepared as described in Example 2, Part E to afford the title product (12.05 mg, 0.033 mmol, 99% (purity) as a yellow solid. LC/MS (ESI) m/e 368.2, [(M+H)⁺, calcd for $C_{22}H_{30}N_3O_2$, 368.2]; LC/MS retention time (method C): $t_R$=1.97 min. HPLC retention time (method A): $t_R$=7.28 min; HPLC retention time (method B): $t_R$=10.15 min. ¹H NMR (400 MHz, MeOD) δ ppm 9.54 (s, 1H), 8.82 (d, J=6.0 Hz, 1H), 8.60 (d, J=8.8 Hz, 1H), 8.36 (s, 1H), 7.12 (s, 1H), 4.52 (m, 1H), 4.41 (m, 1H), 3.86 (s, 3H), 3.74-3.84 (m, 1H), 3.61 (m, 1H), 1.80-1.90 (m, 2H), 1.64-1.81 (m, 1H), 1.35-1.43 (m, 6H), 1.02-1.11 (m, 6H).

Example 48

(S)-8-(2-amino-4-methylpentyloxy)-6-methyl-9-(oxazol-5-yl)benzo[c][2,7]naphthyridin-5(6H)-one

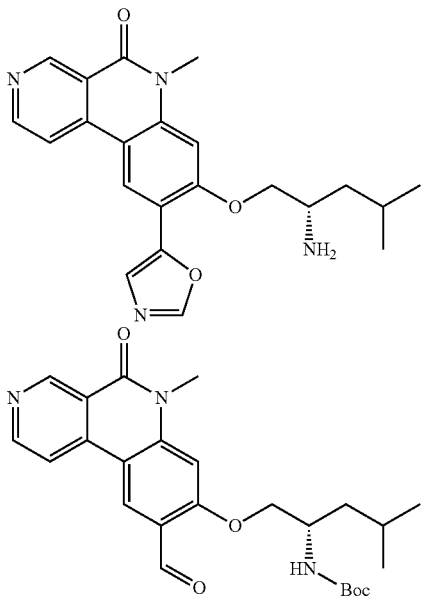

Part A. (S)-tert-butyl 1-(9-formyl-6-methyl-5-oxo-5,6-dihydrobenzo[c][2,7]naphthyridin-8-yloxy)-4-methylpentan-2-ylcarbamate A mixture of (S)-tert-butyl (4-methyl-1-((6-methyl-5-oxo-9-vinyl-5,6-dihydrobenzo[c][2,7]naphthyridin-8-yl)oxy)

pentan-2-yl)carbamate (300 mg, 0.664 mmol) (prepared as described in Example 46, Part A) osmium tetroxide (2.5% in 2-methyl-2-propanol) (4.17 μl, 0.013 mmol), and 2,6-dimethylpyridine (0.155 mL, 1.329 mmol) in 1,4-dioxane (5 mL) and water (2 mL), cooled to 0° C., was stirred for 15 min. Sodium metaperiodate (568 mg, 2.66 mmol) was added and the reaction was warmed to room temperature and stirred for 2 h. The reaction mixture was filtered through diatomaceous earth (Celite®), eluting with EtOAc. The EtOAc layer was washed with saturated aqueous $NaHCO_3$, $H_2O$, then brine. The organic layer was dried with $Na_2SO_4$, filtered and concentrated under reduced pressure. The residue was purified by silica gel chromatography (EtOAc/petroleum ether) to afford (S)-tert-butyl (1-((9-formyl-6-methyl-5-oxo-5,6-dihydrobenzo[c][2,7]naphthyridin-8-yl)oxy)-4-methylpentan-2-yl)carbamate (160 mg, 0.353 mmol, 53% yield) as a gummy solid. LC/MS (ESI) m/e 454.1, $[(M+H)^+$, calcd for $C_{25}H_{32}N_3O_5$, 454.2].

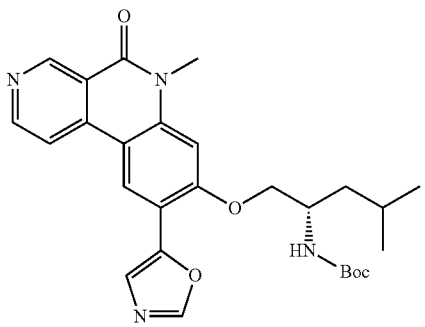 [SMILES: CC(C)C[C@@H](COc1cc2c(cc1-c1cnco1)c1ccncc1c(=O)n2C)NC(=O)OC(C)(C)C]

Part B. (S)-tert-butyl (4-methyl-1-((6-methyl-9-(oxazol-5-yl)-5-oxo-5,6-dihydrobenzo[c][2,7]naphthyridin-8-yl)oxy)pentan-2-yl)carbamate A mixture of (S)-tert-butyl (1-((9-formyl-6-methyl-5-oxo-5,6-dihydrobenzo[c][2,7]naphthyridin-8-yl)oxy)-4-methylpentan-2-yl)carbamate (100 mg, 0.220 mmol), $K_2CO_3$ (33.5 mg, 0.243 mmol) and TOSMIC (47.4 mg, 0.243 mmol) in MeOH (5 mL) was heated at 60° C. for 2 h. After cooling, the MeOH was removed under reduced pressure and residue was taken up in ethyl acetate. The organic layer was washed with $H_2O$, followed by saturated $NaHCO_3$, dried over $Na_2SO_4$ and concentrated under reduced pressure to afford (S)-tert-butyl (4-methyl-1-((6-methyl-9-(oxazol-5-yl)-5-oxo-5,6-dihydrobenzo[c][2,7]naphthyridin-8-yl)oxy)pentan-2-yl)carbamate (50 mg, 0.054 mmol, 24% crude yield) as a gum. The material was carried on without further purification. LC/MS (ESI) m/e 493.4, $[(M+H)^+$, calcd for $C_{27}H_{33}N_4O_5$, 493.6]; LC/MS retention time (method E): $t_R$=1.08 min.

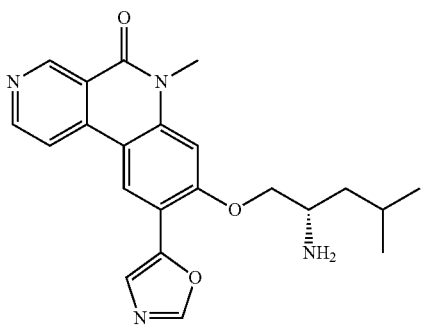 [SMILES: CC(C)C[C@H](N)COc1cc2c(cc1-c1cnco1)c1ccncc1c(=O)n2C]

Part C. (S)-8-(2-amino-4-methylpentyloxy)-6-methyl-9-(oxazol-5-yl)benzo[c][2,7]naphthyridin-5(6H)-one Prepared as described in Example 2, Part E to afford (S)-8-(2-amino-4-methylpentyloxy)-6-methyl-9-(oxazol-5-yl)benzo[c][2,7]naphthyridin-5(6H)-one (15 mg, 0.038 mmol, 29% yield) as a yellow solid. LC/MS (ESI) m/e 393.2, $[(M+H)^+$, calcd for $C_{22}H_{25}N_4O_3$, 393.2]; LC/MS retention time (method C): $t_R$=1.70 min. HPLC retention time (method A): $t_R$=8.89 min; HPLC retention time (method B): $t_R$=9.12 min. $^1$H NMR (400 MHz, METHANOL-d4) δ ppm 1.07-1.13 (m, 6H) 1.75 (d, J=6.78 Hz, 1H) 1.81-1.93 (m, 2H) 3.91 (s, 3H) 3.94-4.00 (m, 1H) 4.55 (dd, J=11.04, 6.53 Hz, 1H) 4.67 (dd, J=10.92, 3.39 Hz, 1H) 7.30 (s, 1H) 7.71 (s, 1H) 8.43 (s, 1H) 8.55 (d, J=5.52 Hz, 1H) 8.90 (s, 2H) 9.59 (s, 1H).

Example 49

(S)-8-(2-amino-4-methylpentyloxy)-9-bromo-4-methylbenzo[c][2,7]naphthyridin-5(6H)-one

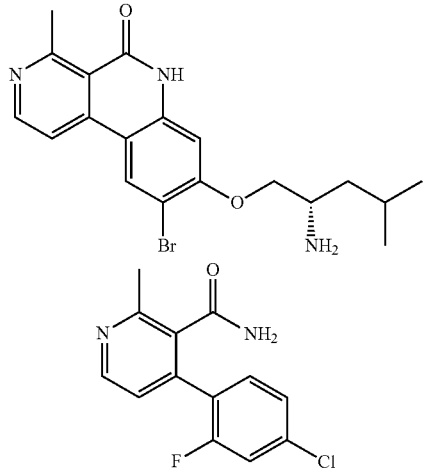

Part A.
4-(4-chloro-2-fluorophenyl)-2-methylnicotinamide 4-(4-Chloro-2-fluorophenyl)-2-methylnicotinic acid (9 g, 33.9 mmol) (previous described in Example 16, Part E) was taken in DCM (50 mL) and cooled to 0° C. The solution was treated with oxalyl chloride (14.83 mL, 169 mmol) followed by slow addition of DMF (1 mL). The mixture was heated at 40° C. for 3 h. After cooling, the volatiles were removed under reduced pressure. The residue taken up in DCM (25 mL) was cooled to 0° C., and TEA (22.08 mL, 158 mmol) and ammonium chloride (16.94 g, 317 mmol) were added slowly. After stirring at room temperature for 1 h, the reaction mixture was washed with saturated aqueous NaHCO3 (10 mL), water (10 mL), and brine (10 mL). The organic layer was separated and dried with $Na_2SO_4$ to afford the 4-(4-chloro-2-fluorophenyl)-2-methylnicotinamide (3.5 g, 13.2 mmol, 42% crude yield) as a brown solid. The material was carried forward without further purification. LC/MS (ESI) m/e 264.4 $[(M)^+$, calcd for $C_{13}H_{10}ClFN_2O$ 264.0] LC/MS retention time (method C): $t_R$=1.58 min.

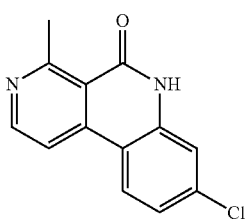 [SMILES: Cc1nccc2c1c(=O)[nH]c1cc(Cl)ccc12]

Part B. 8-chloro-4-methylbenzo[c][2,7]naphthyridin-5(6H)-one

Prepared as described in Example 2, Part C to afford 8-chloro-4-methylbenzo[c][2,7]naphthyridin-5(6H)-one (800 m g, 3.14 mmol, 24% yield, 96% purity) as a yellow solid. LC/MS (ESI) m/e 245.1 [(M+H)$^+$, calcd for $C_{13}H_{10}ClN_2O$ 245.04] LC/MS retention time (method D): $t_R$=0.52 min.

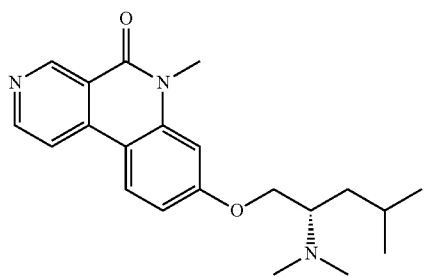 [SMILES: CC(C)C[C@@H](COc1ccc2c3ccncc3c(=O)n(C)c2c1)N(C)C]

Part C. 8-chloro-6-(4-methoxybenzyl)-4-methylbenzo[c][2,7]naphthyridin-5(6H)-one Prepared as described in Example 17, Part G to afford 8-chloro-6-(4-methoxybenzyl)-4-methylbenzo[c][2,7]naphthyridin-5(6H)-one (710 m g, 1.362 mmol, 56% yield) as a brown gum. LC/MS (ESI) m/e 365.1 [(M+H)$^+$, calcd for $C_{21}H_{18}ClN_2O_2$ 365.1] LC/MS retention time (method D): $t_R$=0.8 min.

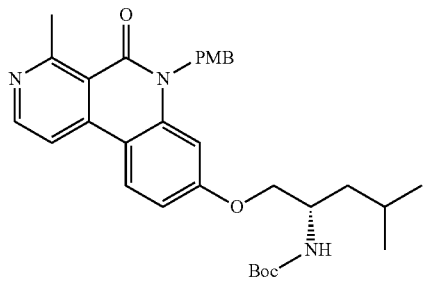

Part D. (S)-tert-butyl 1-(6-(4-methoxybenzyl)-4-methyl-5-oxo-5,6-dihydrobenzo[c][2,7]naphthyridin-8-yloxy)-4-methylpentan-2-ylcarbamate Prepared as described in Example 16, Part H to afford (S)-tert-butyl 1-(6-(4-methoxybenzyl)-4-methyl-5-oxo-5,6-dihydrobenzo[c][2,7]naphthyridin-8-yloxy)-4-methylpentan-2-ylcarbamate (130 mg, 0.21 mmol, 31% yield, 88% purity) as a brown gum. LC/MS (ESI) m/e 546.2 [(M+H)$^+$, calcd for $C_{32}H_{40}FN_3O_5$ 546.3] LC/MS retention time (method D): $t_R$=0.94 min.

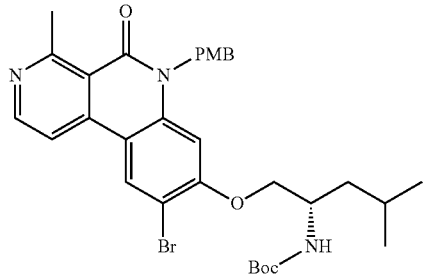

Part E. (S)-tert-butyl 1-(9-bromo-6-(4-methoxybenzyl)-4-methyl-5-oxo-5,6-dihydrobenzo[c][2,7]naphthyridin-8-yloxy)-4-methylpentan-2-ylcarbamate Prepared as described in Example 3, Part A to afford (S)-tert-butyl 1-(9-bromo-6-(4-methoxybenzyl)-4-methyl-5-oxo-5,6-dihydrobenzo[c][2,7]naphthyridin-8-yloxy)-4-methylpentan-2-ylcarbamate (140 mg, 0.146 mmol, 61% yield, 65% purity) as an orange red solid. LC/MS (ESI) m/e 624.2 [(M+H)$^+$, calcd for $C_{32}H_{39}BrN_3O_5$ 624.2] LC/MS retention time (method D): $t_R$=0.98 min.

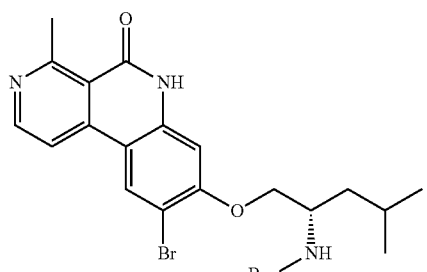

Part F. (S)-tert-butyl 1-(9-bromo-4-methyl-5-oxo-5,6-dihydrobenzo[c][2,7]naphthyridin-8-yloxy)-4-methylpentan-2-ylcarbamate PMB deprotection carried out using ceric ammonium nitrate as described in *Protective Groups in organic synthesis* (Greene, Wuts; 3$^{rd}$ ed., 1999, John Wiley & Sons, Inc.) afford (S)-tert-butyl 1-(9-bromo-4-methyl-5-oxo-5,6-dihydrobenzo[c][2,7]naphthyridin-8-yloxy)-4-methylpentan-2-ylcarbamate (60 mg, 0.12 mmol, 93% yield) as a red solid. LC/MS (ESI) m/e 504.1 [(M+H)$^+$, calcd for $C_{24}H_{31}BrN_3O_4$ 504.14] LC/MS retention time (method D): $t_R$=0.91 min.

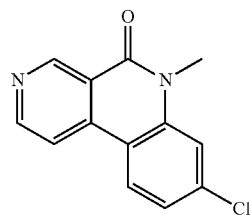 [SMILES: Cn1c(=O)c2cnccc2c2ccc(Cl)cc21]

145

Part G. (S)-8-(2-amino-4-methylpentyloxy)-9-bromo-4-methylbenzo[c][2,7]naphthyridin-5(6H)-one Prepared as described in Example 2, Part E to afford (S)-8-(2-amino-4-methylpentyloxy)-9-bromo-4-methylbenzo[c][2,7]naphthyridin-5(6H)-one (12 mg, 0.029 mmol, 35% yield, 98% purity) as a off-white solid. LC/MS (ESI) m/e 402.0 [(M)$^-$, calcd for $C_{19}H_{21}BrN_3O_2$ 402.1] LC/MS retention time (method C): $t_R$=2.19 min. HPLC retention time (method A): $t_R$=8.52 min and HPLC retention time (method B): $t_R$=9.02 min. $^1$H NMR (400 MHz, METHANOL-d$_4$) δ ppm 8.67 (s, 1H), 8.64 (d, J=6.0 Hz, 1H), 8.30 (d, J=6.0 Hz, 1H), 6.98 (s, 1H), 4.85-4.43 (m, 1H), 4.31-4.27 (m, 1H), 3.82-3.80 (m, 1H), 3.13 (s, 3H), 1.88-1.80 (m, 2H), 1.76-1.71 (m, 1H), 1.09 (d, J=6.4 Hz, 3H), 1.07 (d, J=6.4 Hz, 3H).

Example 50

(S)-8-((2-amino-4-methylpentyl)oxy)-4-((4-methoxybenzyl)amino)-6-methylbenzo[c][2,7]naphthyridin-5(6H)-one

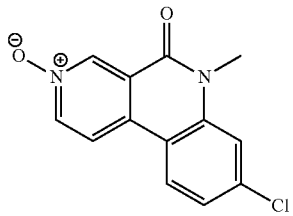 [SMILES: Cn1c(=O)c2c[n+]([O-])ccc2c2ccc(Cl)cc21]

Prepared as described in Example 17, Part H and Example 2, Part E to afford (S)-8-((2-amino-4-methylpentyl)oxy)-4-((4-methoxybenzyl)amino)-6-methylbenzo[c][2,7]naphthyridin-5(6H)-one hydrochloride (19 mg, 0.038 mmol, 26% yield) as a pale yellow solid. LC/MS (ESI) m/e 461 [(M+H)$^+$, calcd for $C_{27}H_{33}N_4O_3$, 461.25]; LC/MS retention time (method B): $t_R$=1.42 min. HPLC retention time (method A): $t_R$=11.09 min; HPLC retention time (method B): $t_R$=12.68 min. $^1$H NMR (400 MHz, DMSO-d$_6$) δ 10.09 (br. s. 1H), 8.40 (d, J=8.8 Hz, 1H), 8.24 (d, J=6.0 Hz, 1H), 8.07 (s, 3H), 7.45 (d, J=6.0 Hz, 1H), 7.33 (d, J=8.4 Hz, 2H), 7.07-7.06 (m, 2H), 6.95-6.91 (m, 2H), 4.67 (d, J=5.2 Hz, 1H), 4.38 (dd, J=10.4, 3.2 Hz, 2H), 4.21 (dd, J=10.8, 6.8 Hz, 1H), 3.75 (s, 3H), 3.68 (s, 3H), 3.62 (br s, 1H), 1.80 (quin, J=6.8, 1H), 1.59-1.55 (m, H), 0.95 (d, J=6.4 Hz, 3H), 0.94 (d, J=6.4 Hz, 3H).

Example 51

(S)-8-((2-amino-4-methylpentyl)oxy)-9-(4-fluorophenyl)-6 methylbenzo[c][2,7]naphthyridin-5(6H)-one

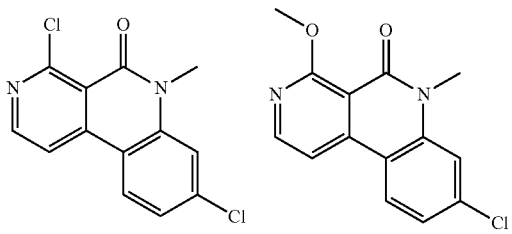 [SMILES: Cn1c(=O)c2c(Cl)nccc2c2ccc(Cl)cc21 ; COc1nccc2c1c(=O)n(C)c1cc(Cl)ccc21]

146

Part A. (S)-tert-butyl (1-((9-(4-fluorophenyl)-6-methyl-5-oxo-5,6-dihydrobenzo[c][2,7]naphthyridin-8-yl)oxy)-4-methylpentan-2-yl)carbamate (S)-tert-Butyl (1-((9-bromo-6-methyl-5-oxo-5,6-dihydrobenzo[c][2,7]naphthyridin-8-yl)oxy)-4-methylpentan-2-yl)carbamate (150 mg, 0.297 mmol) (prepared as described in Example 3, Part A) 4-fluorophenylboronic acid (49.9 mg, 0.357 mmol), $Cs_2CO_3$ (291 mg, 0.892 mmol) and $PdCl_2$(dppf)-$CH_2Cl_2$ adduct (12.14 mg, 0.015 mmol) in 1,4-dioxane (8 mL) and water (0.4 mL) was degassed with nitrogen gas for 5 min then heated at 80° C. overnight. The reaction mixture was cooled to room temperature and concentrated under reduced pressure. The residue was taken up in dichloromethane (10 mL) and water (8 mL). The organic layer was separated, dried with sodium sulfate, filtered and concentrated under reduced pressure to afford (S)-tert-butyl (1-((9-(4-fluorophenyl)-6-methyl-5-oxo-5,6-dihydrobenzo[c][2,7]naphthyridin-8-yl)oxy)-4-methylpentan-2-yl)carbamate (0.13 g, 0.09 mmol, 31% yield) as a brown gum. The material was carried forward without further purification. LC/MS, (ESI) m/z 520.4 [(M+H)$^+$, calcd for $C_{30}H_{35}FN_3O_4$ 520.25]; LC/MS retention time (method D): $t_R$=1.08 min.

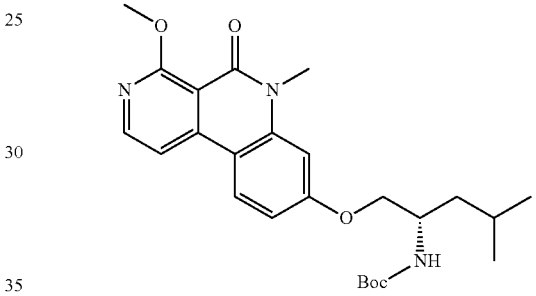

Part B. (S)-8-((2-amino-4-methylpentyl)oxy)-9-(4-fluorophenyl)-6 methylbenzo[c][2,7]naphthyridin-5(6H)-one Prepared as described in Example 2, Part E to afford (S)-8-((2-amino-4-methylpentyl)oxy)-9-(4-fluorophenyl)-6 methylbenzo[c][2,7]naphthyridin-5(6H)-one (19 mg, 0.043 mmol, 47% yield) as a pale yellow solid. LC/MS, (ESI) m/z 420.0 [(M+H)$^+$, calcd for $C_{25}H_{27}FN_3O_2$, 420.3]; LC/MS retention time (method C'): $t_R$=1.61 min. $^1$H NMR (400 MHz, METHANOL-d$_4$) δ ppm 9.40 (s, 1H), 8.69 (m, 1H), 8.24 (s, 1H), 8.18 (m, 1H), 7.62 (m, 2H), 7.22 (m, 2H), 7.04 (s, 1H), 4.16 (m, 1H), 3.98 (m, 1H), 3.78 (s, 3H), 3.20 (m, 1H), 1.78 (m, 1H), 1.35 (m, 2H), 0.90-0.98 (m, 6H).

Example 52

(S)-4-amino-8-(2-amino-4-methylpentyloxy)-9-fluoro-6-methylbenzo[c][2,7]naphthyridin-5(6H)-one

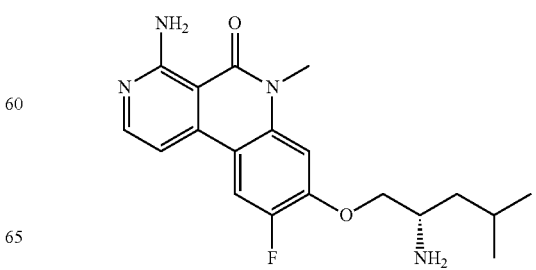

-continued

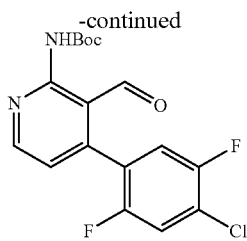

Part A. tert-butyl 4-(4-chloro-2,5-difluorophenyl)-3-formylpyridin-2-ylcarbamate Prepared as described in Example 17, Part C by Suzuki coupling between 2-(4-chloro-2,5-difluorophenyl)-4,4,5,5-tetramethyl-1,3,2-dioxaborolane) preparation described in Example 14, Part A) and tert-butyl 4-chloro-3-formylpyridin-2-ylcarbamate (Preparation described in Example 17, Part B) to afford tert-butyl 4-(4-chloro-2,5-difluorophenyl)-3-formylpyridin-2-ylcarbamate (3.7 g, 8.91 mmol, 76% yield) as a yellow solid. LC/MS (ESI) m/e 367.1 [(m)⁻, calcd for $C_{17}H_{16}ClF_2N_2O_3$ 367.1] LC/MS retention time (method E): $t_R$=1.07 min.

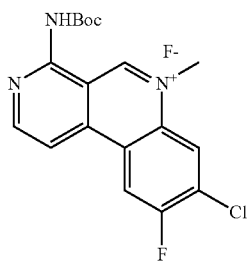

Part B: 4-(tert-butoxycarbonylamino)-8-chloro-9-fluoro-6-methylbenzo[c][2,7]naphthyridin-6-ium To a stirred solution of tert-butyl (4-(4-chloro-2,5-difluorophenyl)-3-formylpyridin-2-yl)carbamate (2.6 g, 6.26 mmol) in DCM (10 mL) at 0° C. was added dropwise methanamine (2M in MeOH) (75 mL, 6.26 mmol) and the reaction mixture was stirred at rt for 18 hours. The reaction mixture concentrated under reduced pressure. The residue was triturated with EtOAc/hexane and the solid obtained was collected by vacuum filtration to yield 4-((tert-butoxycarbonyl)amino)-8-chloro-9-fluoro-6-methylbenzo[c][2,7]naphthyridin-6-ium (2.7 g, 2.399 mmol, 38% yield) as a yellow solid. Sample was taken to the next step without further purification. LC/MS (ESI) m/e 362.2 [(M+H)⁺, calcd for $C_{18}H_{18}ClFN_3O_2$ 362.1] LC/MS retention time (method E): $t_R$=0.66 min.

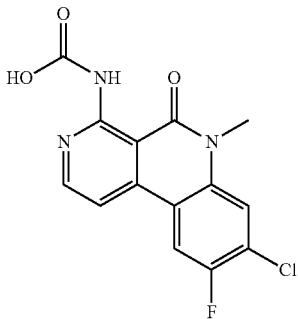 [SMILES: Cn1c(=O)c2c(NC(=O)O)nccc2c2cc(F)c(Cl)cc21]

Part C: 8-chloro-9-fluoro-6-methyl-5-oxo-5,6-dihydrobenzo[c][2,7]naphthyridin-4-ylcarbamic Acid To a stirred solution of 4-((tert-butoxycarbonyl)amino)-8-chloro-9-fluoro-6-methylbenzo[c][2,7]naphthyridin-6-ium (2.6 g, 2.310 mmol) in a mixture of DCM (10 mL) and water (50 mL) was added NaOH (0.370 g, 9.24 mmol) in three portions, followed by the addition of KMnO₄ (1.461 g, 9.24 mmol) in five portions and the reaction was heated to 90° C. for 5 h. After cooling, the solvent was removed under reduced pressure. The residue was taken up in EtOAc (50 mL) and MeOH (50 mL) and stirred for 10 min. The reaction mixture was then passed through diatomaceous earth (Celite®), eluting with EtOAc. The filtrate was concentrated to yield (8-chloro-9-fluoro-6-methyl-5-oxo-5,6-dihydrobenzo[c][2,7]naphthyridin-4-yl)carbamic acid (2.35 g, 2.082 mmol, 90% crude yield) as a yellow solid which was taken to the next step without purification. LC/MS (ESI) m/e 322.1 [(M+H)⁺, calcd for $C_{14}H_{10}ClFN_3O_3$ 322.0] LC/MS retention time (method E): $t_R$=1.05 min.

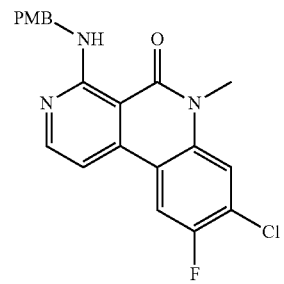

Part D: 8-chloro-9-fluoro-4-(4-methoxybenzylamino)-6-methylbenzo[c][2,7]naphthyridin-5(6H)-one Prepared as described in Example 17, Part F to give the 4-amino-8-chloro-9-fluoro-6-methylbenzo[c][2,7]naphthyridin-5(6H)-one which was then protected with PMB as per procedure described in Example 17, Part G to afford the title product (0.45 g, 0.755 mmol, 17% yield) as a yellow oil. LC/MS (ESI) m/e 398.2 [(M+H)⁺, calcd for $C_{21}H_{18}ClFN_3O_2$ 398.1] LC/MS retention time (method E): $t_R$=1.23 min.

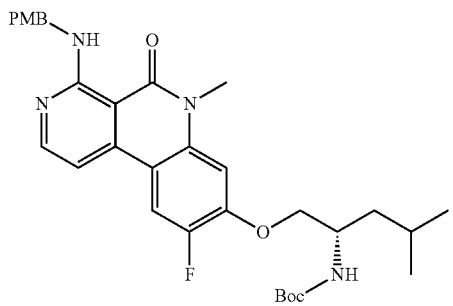

Part E: (S)-tert-butyl 1-(9-fluoro-4-(4-methoxybenzylamino)-6-methyl-5-oxo-5,6-dihydrobenzo[c][2,7]naphthyridin-8-yloxy)-4-methylpentan-2-ylcarbamate Prepared as described in Example 16, Part H to afford the title product (910 mg, 0.405 mmol, 54% yield) as a yellow oil.

LC/MS (ESI) m/e 579.5 [(M+H)+, calcd for $C_{32}H_{40}FN_4O_5$ 579.3] LC/MS retention time (method E): $t_R$=1.37 min.

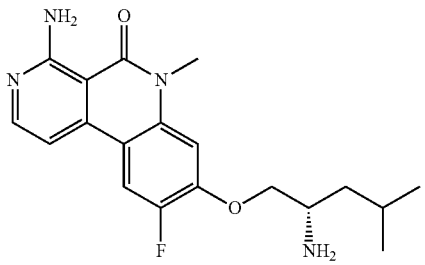

Part F: (S)-4-amino-8-(2-amino-4-methylpentyloxy)-9-fluoro-6-methylbenzo[c][2,7]naphthyridin-5(6H)-one Prepared as described in Example 2, Part E to afford the title product (27 mg, 0.045 mmol, 11% yield) pale yellow solid in the form of TFA salt. LC/MS (ESI) m/e 359.2 [(M+H)+, calcd for $C_{19}H_{24}FN_4O_2$ 359.2] LC/MS retention time (method C): $t_R$=1.53 min. HPLC retention time (method A): $t_R$=8.01 min and HPLC retention time (method B): $t_R$=9.13 min. $^1$H NMR (400 MHz, METHANOL-$d_4$) δ ppm 8.33 (d, J=12.0 Hz, 1H), 8.02 (d, J=7.0 Hz, 1H), 7.67 (d, J=7.3 Hz, 1H), 7.34 (d, J=7.3 Hz, 1H), 4.60 (dd, J=10.7, 3.1 Hz, 1H), 4.46 (dd, J=10.8, 6.0 Hz, 1H), 3.87 (s, 3H), 3.86-3.78 (m, 1H), 1.95-1.64 (m, 3H), 1.08 (d, J=4.3 Hz, 3H), 1.07 (d, J=4.3 Hz, 3H).

Example 53

(S)-8-(2-amino-3-isopropoxypropoxy)-6-methyl-benzo[c][2,7]naphthyridin-5(6H)-one

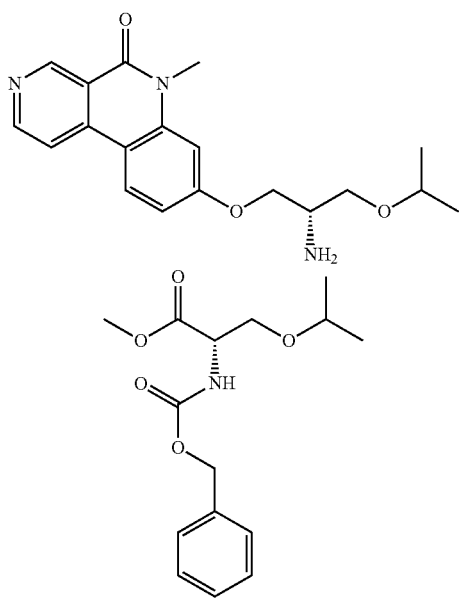

Part A. (S)-methyl 2-(((benzyloxy)carbonyl)amino)-3-isopropoxypropanoate

Prepared as described in literature Steven, M. S. et. al. Bioorg Med. Chem. Lett., 2009, 19, 981-985.

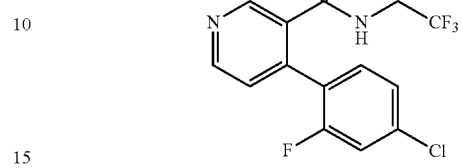

Part B. (R)-benzyl (1-hydroxy-3-isopropoxypropan-2-yl)carbamate (S)-Methyl 2-(((benzyloxy)carbonyl)amino)-3-isopropoxypropanoate (0.02 g, 0.068 mmol) was taken in 2-propanol (4 mL) and then NaBH$_4$ (7.69 mg, 0.203 mmol) was added and the mixture stirred for overnight at 50° C. After cooling to 0° C., the mixture was quenched with 1N HCl and then extracted with diethyl ether (10 mL). The diethyl ether layer was collected and concentrated under reduced pressure to afford (R)-benzyl (1-hydroxy-3 isopropoxypropan-2-yl) carbamate) (14 mg, 0.058 mmol, 86% crude yield) as colorless oil. The product was carried on without further purification. $^1$H NMR (400 MHz, MeOD) δ 7.31-7.48 (m, 5H), 5.12 (s, 1H), 4.81 (bs, 1H), 3.41-3.91 (m, 6H), 1.12-1.26 (m, 6H).

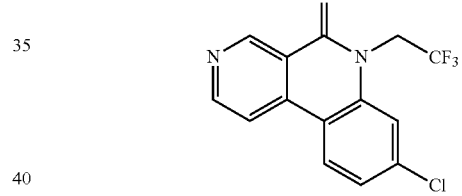

Part C: (S)-benzyl (1-isopropoxy-3-((6-methyl-5-oxo-5,6-dihydrobenzo[c][2,7]naphthyridin-8-yl)oxy)propan-2-yl)carbamate Prepared as described in Example 16, Part H to afford the title product (S)-benzyl (1-isopropoxy-3-((6-methyl-5-oxo-5,6-dihydrobenzo[c][2,7]naphthyridin-8-yl)oxy)propan-2-yl)carbamate (220 mg, 0.130 mmol, 10% yield) as a light yellow solid. LC/MS (ESI) m/e 476.4, [(M+H)+, calcd for $C_{27}H_{30}N_3O_5$, 476.2]; LC/MS retention time (method E): $t_R$=1.04 min.

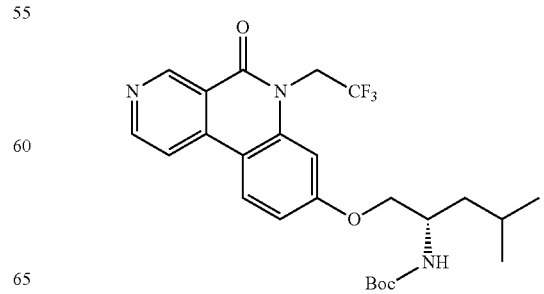

Part D: (S)-8-(2-amino-3-isopropoxypropoxy)-6-methylbenzo[c][2,7]naphthyridin-5(6H)-one A solution of (S)-benzyl (1-isopropoxy-3-((6-methyl-5-oxo-5,6-dihydrobenzo[c][2,7]naphthyridin-8-yl)oxy)propan-2-yl)carbamate (220 mg, 0.130 mmol) in MeOH (12 mL) was degassed with $N_2$ for 5 min. Pd/C (68.9 mg, 0.065 mmol) was added and the mixture stirred under a balloon of $H_2$ for 12 h. The reaction mixture was filtered through diatomaceous earth (Celite®), eluting with methanol and the filtrate was concentrated under reduced pressure. The residue was purified by reverse phase HPLC (10 MM ammonium acetate in water/AcCN) to afford (S)-8-(2-amino-3-isopropoxypropoxy)-6-methylbenzo[c][2,7]naphthyridin-5(6H)-one (90 mg, 0.108 mmol, 83% yield) as an off-white solid. LC/MS (ESI) m/e 342.2, $[(M+H)^+$, calcd for $C_{19}H_{24}N_3O_3$, 342.2]; LC/MS retention time (method C): $t_R$=1.50 min. HPLC retention time (method A): $t_R$=7.20 min; HPLC retention time (method B): $t_R$=8.00 min. $^1$H NMR (400 MHz, MeOD) δ ppm 9.54 (s, 1H), 8.23 (d, J=4.4 Hz, 1H), 8.52 (d, J=8.8 Hz, 1H), 8.44 (d, J=6.0 Hz, 1H), 7.20 (s, 1H), 7.18 (d, J=6.0 Hz, 1H), 4.52 (dd, J=10.4, 3.6 Hz, 1H), 4.43 (dd, J=10.4, 6.8 Hz, 1H), 3.88-3.75 (m, 7H), 1.26 (d, J=6.4 Hz, 3H), 1.25 (d, J=6.4 Hz, 3H).

Example 54

(S)-6-methyl-8-((4-methyl-2-(methylamino)pentyl)oxy)benzo[c][2,7]naphthyridin-5(6H)-one

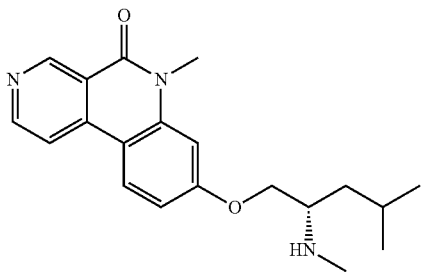

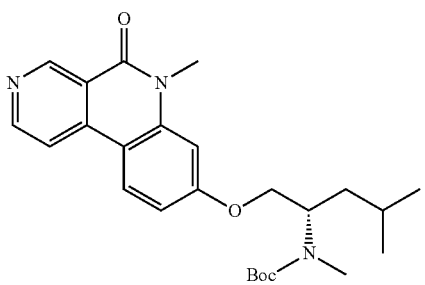

Part A. (S)-tert-butyl methyl(4-methyl-1-(6-methyl-5-oxo-5,6-dihydrobenzo[c][2,7]naphthyridin-8-yloxy)pentan-2-yl)carbamate To a solution of (S)-tert-butyl (4-methyl-1-((6-methyl-5-oxo-5,6-dihydrobenzo[c][2,7]naphthyridin-8-yl)oxy)pentan-2-yl)carbamate (200 mg, 0.470 mmol) (Preparation description in Example 2, Part D) in THF (4 mL) at 0° C. was added NaH (37.6 mg, 0.940 mmol). The reaction was stirred at 0° C. for 30 min then MeI (0.044 mL, 0.705 mmol) was added. The reaction mixture was then stirred at 0° C. for 16 h. The reaction mixture was quenched with ice cold water (50 mL) and extracted with ethyl acetate (3×30 mL). The combined organic layers and washed with brine (1×50 mL), dried over $Na_2SO_4$, filtered and concentrated under reduced pressure. The crude product was purified by silica gel chromatography using petroleum ether: ethyl acetate mobile phase to afford (S)-tert-butyl methyl(4-methyl-1-(6-methyl-5-oxo-5,6-dihydrobenzo[c][2,7]naphthyridin-8-yloxy)pentan-2-yl)carbamate (180 mg, 0.409 mmol, 87% yield) as a yellow solid. LC/MS (ESI) m/e 440.4, $[(M+H)^+$, calcd for $C_{25}H_{34}N_3O_4$, 440.3]; LC/MS retention time (method I): $t_R$=2.4 min.

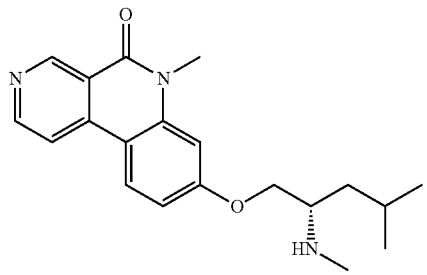 [SMILES: CN[C@H](COc1ccc2c3ccncc3c(=O)n(C)c2c1)CC(C)C]

Part B: (S)-6-methyl-8-((4-methyl-2-(methylamino)pentyl)oxy)benzo[c][2,7]naphthyridin-5(6H)-one To the solution of (S)-tert-butyl methyl(4-methyl-1-((6-methyl-5-oxo-5,6-dihydrobenzo[c][2,7]naphthyridin-8-yl)oxy)pentan-2-yl)carbamate (180 mg, 0.078 mmol) in dichloromethane (4 mL) cooled to 0° C. was added HCl in ether (4 mL, 4.00 mmol) slowly over a period of 1 min. The reaction mixture was stirred at 0° C. for 5 min then warmed to room temperature and stirred for 4 h. The volatiles were then removed under reduced pressure. The residue was purified via reverse phase HPLC (0.1% TFA in water:acetonitrile) to afford (S)-6-methyl-8-((4-methyl-2-(methylamino)pentyl)oxy)benzo[c][2,7]naphthyridin-5(6H)-one (15 mg, 0.025 mmol, 32% yield) as a yellow solid. LC/MS (ESI) m/e 340.2, $[(M+H)^+$, calcd for $C_{20}H_{26}N_3O_2$, 340.2]; LC/MS retention time (method I): $t_R$=1.6 min. HPLC retention time (method A): $t_R$=7.59 min; HPLC retention time (method B): $t_R$=8.08 min. $^1$H NMR (400 MHz, METHANOL-$d_4$) δ ppm 9.54 (s, 1H), 8.83 (d, J=5.8 Hz, 1H), 8.53 (d, J=8.8 Hz, 1H), 8.46 (d, J=6.0 Hz, 1H), 7.27-7.16 (m, 2H), 4.57 (dd, J=11.3, 3.0 Hz, 1H), 4.44 (dd, J=11.3, 5.3 Hz, 1H), 3.84 (s, 3H), 3.78-3.68 (m, 1H), 2.84 (s, 3H), 1.95-1.78 (m, 2H), 1.75-1.61 (m, 1H), 1.08 (d, J=6.5 Hz, 6H).

Example 55

(S)-8-((2-amino-4,4-difluoropentyl)oxy)-6-methyl-benzo[c][2,7]naphthyridin-5(6H)-one

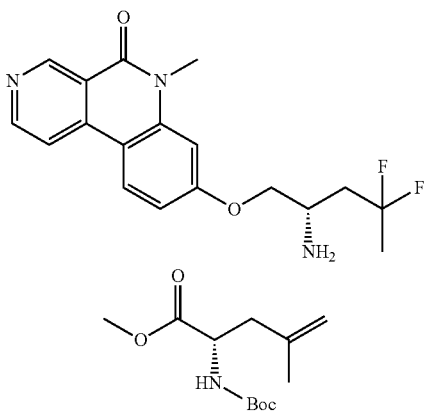

Part A: (S)-methyl 2-((tert-butoxycarbonyl)amino)-4-methylpent-4-enoate

To a solution of (S)-2-((tert-butoxycarbonyl)amino)-4-methylpent-4-enoic acid (550 mg, 2.399 mmol) in tetrahydrofuran (11 mL) at 0° C., was added TMS-diazomethane (4.80 mL, 4.80 mmol) dropwise over 5 min. The reaction mixture was then stirred at 0° C. for 15 min. After gradually warmed to room temperature, the mixture was stirred for 16 h. The reaction mixture was evaporated to dryness to afford (S)-methyl 2-((tert-butoxycarbonyl)amino)-4-methylpent-4-enoate (580 mg, 2.386 mmol, 99% crude yield) as a dark yellow oil which was taken to the next step without purification. $^1$H NMR (400 MHz, CDCl$_3$): δ ppm 4.91 (s, 1H), 4.85 (s, 1H), 4.75 (s, 1H), 4.38 (q, J=16.00 Hz, 1H), 3.73 (s, 3H), 2.33-2.53 (m, 2H), 1.71 (s, 3H), 1.43 (s, 9H).

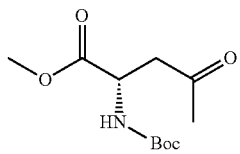

Part B: (S)-methyl 2-((tert-butoxycarbonyl)amino)-4-oxopentanoate

To a solution of (S)-methyl 2-((tert-butoxycarbonyl)amino)-4-methylpent-4-enoate (500 mg, 2.055 mmol) in a solvent mixture of 1,4-dioxane (10 mL) and water (2.5 mL) at 0° C., was added 2,6-lutidine (0.479 mL, 4.11 mmol) and osmium tetroxide (2.5% in 2-methyl-2-propanol) (0.516 mL, 0.041 mmol), followed by sodium metaperiodate (1.758 g, 8.22 mmol). The reaction mixture was stirred at 0° C. for 15 min and warmed to room temperature and stirred for an additional 3 h. The mixture was diluted with ethyl acetate (150 mL) and washed with 10% aqueous NaHCO$_3$. The organic layer was separated, dried over sodium sulphate and concentrated under reduced pressure to afford (S)-methyl 2-((tert-butoxycarbonyl)amino)-4-oxopentanoate (500 mg, 2.040 mmol, 100% crude yield) as a yellow liquid. The material was carried on without further purification. $^1$H NMR (400 MHz, CDCl$_3$): δ ppm 5.48 (s, 1H), 4.51 (t, J=8.00 Hz, 1H), 3.75 (s, 3H), 3.23 (d, J=4.00 Hz, 1H), 3.17 (d, J=4.00 Hz, 1H), 2.18 (s, 3H), 1.46 (s, 9H).

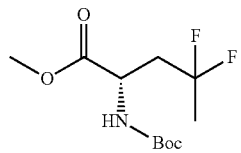 [SMILES: COC(=O)[C@H](CC(C)(F)F)NC(=O)OC(C)(C)C]

Part C: (S)-methyl 2-((tert-butoxycarbonyl)amino)-4,4-difluoropentanoate

To (S)-methyl 2-((tert-butoxycarbonyl)amino)-4-oxopentanoate (300 mg, 1.223 mmol) at 0° C., was added DAST (M in) (323 µL, 2.446 mmol) dropwise. The reaction mixture was stirred at room temperature for 84 h. The reaction mixture was cooled to 0° C. and then quenched with aqueous 10% NaHCO$_3$ solution. The resulting suspension was extracted with ethyl acetate (3×25 mL). The organic layer was washed with brine (15 mL), dried over Na$_2$SO4, filtered, and concentrated under reduced pressure. The crude product was purified by silica gel chromatography to afford (S)-methyl 2-((tert-butoxycarbonyl)amino)-4,4-difluoropentanoate (70 mg, 0.26 mmol, 19% yield) as a yellow oil. $^1$H NMR (400 MHz, CDCl$_3$): δ ppm 5.15 (s, 1H), 4.50 (s, 1H), 3.75 (s, 3H), 3.23 (t, J=8.00 Hz, 1H), 2.30-2.45 (m, 2H), 1.60 (s, 3H), 1.44 (s, 9H).

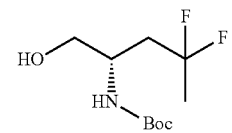 [SMILES: CC(F)(F)C[C@@H](CO)NC(=O)OC(C)(C)C]

Part D: (S)-tert-butyl (4,4-difluoro-1-hydroxypentan-2-yl)carbamate

To a solution of (S)-methyl 2-((tert-butoxycarbonyl)amino)-4,4-difluoropentanoate (70 mg, 0.262 mmol) in tetrahydrofuran (4 mL) at −10° C., was added Lithium aluminum hydride, 2M in THF (0.262 mL, 0.524 mmol). The reaction mixture was stirred at −10° C. for 2 h, then quenched with aqueous ammonium chloride (5 mL) and extracted with ethyl acetate (2×10 mL). The combined organic layers were washed with brine (15 mL), dried over Na$_2$SO$_4$, filtered, and concentrated under reduced pressure to afford (S)-tert-butyl (4,4-difluoro-1-hydroxypentan-2-yl)carbamate (38 mg, 0.159 mmol, 61% crude yield) as colorless oil. The material was carried forward without further purification. $^1$H NMR (400 MHz, CDCl$_3$): δ ppm 3.89 (d, J=4.00 Hz, 2H), 2.10-2.14 (m, 1H), 1.61-1.66 (m, 2H), 1.51 (s, 3H), 1.44 (s, 9H).

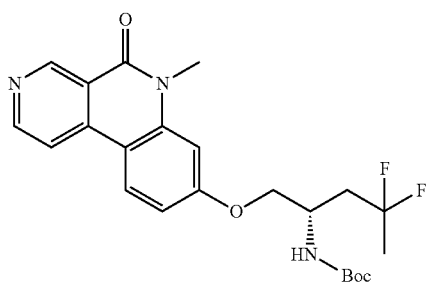 [SMILES: Cn1c(=O)c2cnccc2c2ccc(OC[C@H](CC(C)(F)F)NC(=O)OC(C)(C)C)cc21]

Part E: (S)-tert-butyl (4,4-difluoro-1-((6-methyl-5-oxo-5,6-dihydrobenzo[c][2,7]naphthyridin-8-yl)oxy)pentan-2-yl)carbamate In a sealed tube containing 8-chloro-6-methylbenzo[c][2,7]naphthyridin-5(6H)-one (30 mg, 0.123 mmol) and (S)-tert-butyl (4,4-difluoro-1-hydroxypentan-2-yl)carbamate (35.2 mg, 0.147 mmol) was added toluene (3 mL). Di-tert-butyl(2',4',6'-triisopropyl-[1,1'-biphenyl]-2-yl)phosphine (31.2 mg, 0.074 mmol) and cesium carbonate (59.9 mg, 0.184 mmol) were added to the reaction mixture followed by palladium (II)acetate (8.26 mg, 0.037 mmol). The reaction mixture was then heated at 85° C. for 16 h. The reaction mixture was cooled to room temperature, diluted with ethyl acetate and filtered through diatomaceous earth (Celite®), eluting with ethyl acetate. The filtrate was evaporated under reduced pressure and the crude product was purified by silica gel chromatography to afford (S)-tert-butyl (4,4-difluoro-1-((6-methyl-5-oxo-5,6-dihydrobenzo[c][2,7]naphthyridin-8-yl)oxy)pentan-2-yl)carbamate (12 mg, 0.027 mmol, 22% yield) as yellow solid. LC/MS (ESI) m/e 448.3 [(M+H)$^+$, calcd for $C_{23}H_{28}F_2N_3O_4$ 448.2]; LC/MS retention time (method E): $t_R$=0.96 min.

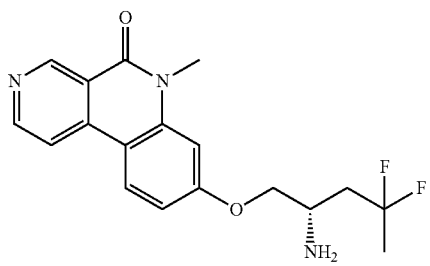 [SMILES: Cn1c(=O)c2cnccc2c2ccc(OC[C@@H](N)CC(C)(F)F)cc21]

Part F: (S)-8-((2-amino-4,4-difluoropentyl)oxy)-6-methylbenzo[c][2,7]naphthyridin-5(6H)-one To a solution of (S)-tert-butyl (4,4-difluoro-1-((6-methyl-5-oxo-5,6-dihydrobenzo[c][2,7]naphthyridin-8-yl)oxy)pentan-2-yl)carbamate (15 mg, 0.024 mmol) in dichloromethane (2 mL) at 0° C. was added 4M HCl in diethyl ether (2 mL, 2.00 mmol) dropwise over a period of 5 min. The reaction mixture was stirred at 0° C. for 5 min and warmed to room temperature and stirred for 3 h. The volatiles were removed under reduced pressure. The residue was dissolved in water (10 mL) and washed with ethyl acetate (2×5 mL). The aqueous layer was lyophilized to afford (S)-8-((2-amino-4,4-difluoropentyl)oxy)-6-methylbenzo[c][2,7]naphthyridin-5(6H)-one, 2HCl (6 mg, 0.018 mmol, 72% yield, 93% purity) as a brown sticky solid. LC/MS (ESI) m/e 348.2 [(M+H)$^+$, calcd for $C_{18}H_{20}F_2N_3O_2$ 348.1]; LC/MS retention time (method E): $t_R$=0.56 min. HPLC retention time (method A): $t_R$=6.60 min; HPLC retention time (method B): $t_R$=6.53 min; $^1$H NMR (400 MHz, METHANOL-$d_4$) δ ppm 9.60 (br. s., 1H), 8.88 (br. s., 1H), 8.73 (br. s., 1H), 8.60 (br. s., 1H), 7.23 (br. s., 2H), 4.63-4.36 (m, 2H), 4.13-4.06 (m, 1H), 3.84 (br. s., 3H), 2.75-2.40 (m, 2H), 1.78 (t, J=18.8 Hz, 3H).

Example 56

8-((2-amino-5,5,5-trifluoropentyl)oxy)-6-methyl-5-oxo-5,6 dihydrobenzo[c][2,7]naphthyridine-9-carbonitrile

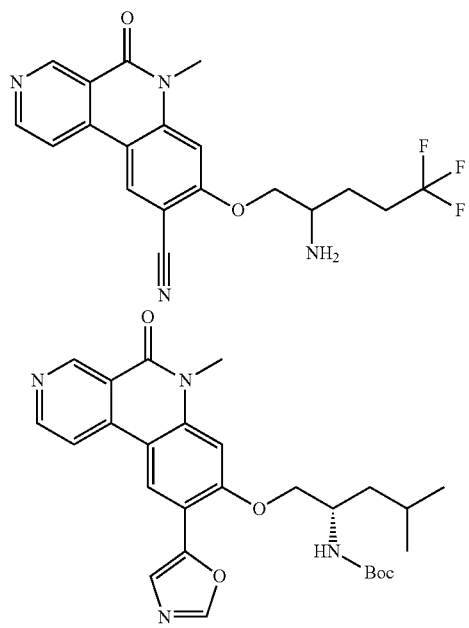

Part A: tert-butyl (1-((9-bromo-6-methyl-5-oxo-5,6-dihydrobenzo[c][2,7]naphthyridin-8-yl)oxy)-5,5,5-trifluoropentan-2-yl)carbamate Prepared as described in Example 15, Part E and Example 3, Part A to afford the title product tert-butyl (1-((9-bromo-6-methyl-5-oxo-5,6-dihydrobenzo[c][2,7]naphthyridin-8-yl)oxy)-5,5,5 trifluoropentan-2-yl)carbamate (0.720 g, 0.807 mmol, 60% yield) as a yellow solid. LC/MS (ESI) m/e 546.5, [(M+2H)$^+$, calcd for $C_{23}H_{27}BrF_3N_3O_4$, 546.1]; LC/MS retention time (method D): $t_R$=0.90 min.

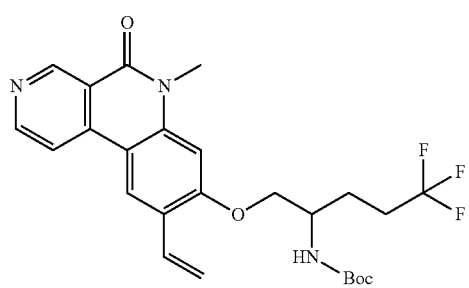 [SMILES: C=Cc1cc2c3ccncc3c(=O)n(C)c2cc1OCC(CCC(F)(F)F)NC(=O)OC(C)(C)C]

Part B: a tert-butyl (5,5,5-trifluoro-1-((6-methyl-5-oxo-9-vinyl-5,6-dihydrobenzo[c][2,7]naphthyridin-8-yl)oxy)pentan-2-yl)carbamate Prepared as described in Example 46, Part B to afford the title product tert-butyl (5,5,5-trifluoro-1-((6-methyl-5-oxo-9-vinyl-5,6-dihydrobenzo[c][2,7]naphthyridin-8 yl)oxy)pentan-2-yl)carbamate (0.6 g, 0.855 mmol, 75% yield) as a yellow solid.
LC/MS (ESI) m/e 492.6, [(M+H)$^+$, calcd for C$_{25}$H$_{29}$F$_3$N$_3$O$_4$, 492.2]; LC/MS retention time (method D): t$_R$=0.90 min.

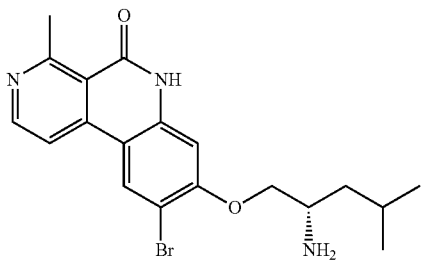 [SMILES: Cc1nccc2c1c(=O)[nH]c1cc(OC[C@@H](N)CC(C)C)c(Br)cc12]

Part C: tert-butyl (5,5,5-trifluoro-1-((9-formyl-6-methyl-5-oxo-5,6-dihydrobenzo[c][2,7]naphthyridin-8-yl)oxy)pentan-2-yl)carbamate Prepared as described in Example 55, Part B to afford the title product tert-butyl (5,5,5-trifluoro-1-((9-formyl-6-methyl-5-oxo-5,6-dihydrobenzo[c][2,7]naphthyridin-8-yl)oxy)pentan-2-yl)carbamate (0.081 g, 0.079 mmol, 62% yield) as a brown solid. LC/MS (ESI) m/e 494.5 (M+H)$^+$, calcd for C$_{24}$H$_{27}$F$_3$N$_3$O$_5$, 494.2]; LC/MS retention time (method D): t$_R$=0.85 min.

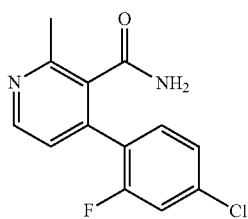 [SMILES: Cc1nccc(-c2ccc(Cl)cc2F)c1C(N)=O]

Part D: tert-butyl (1-((9-cyano-6-methyl-5-oxo-5,6-dihydrobenzo[c][2,7]naphthyridin-8 yl)oxy)-5,5,5-trifluoropentan-2-yl)carbamate Iodine (0.047 g, 0.184 mmol) was added to a stirred solution of tert-butyl (5,5,5-trifluoro-1-((9-formyl-6-methyl-5-oxo-5,6-dihydrobenzo[c][2,7]naphthyridin-8-yl)oxy)pentan-2-yl)carbamate (0.165 g, 0.167 mmol) in aqueous ammonia (4 mL, 48.1 mmol) and tetrahydrofuran (6 mL) at room temperature. The dark solution became light gray after stirring for 3 h, an indication that the reaction was complete. The reaction mixture was charged with aqueous Na2S2O3 (25 mL of 5% solution) and extracted with ethyl acetate (3×30 mL). The combined the organic layers were dried over sodium sulphate and concentrated under reduced pressure to afford tert-butyl (1-((9-cyano-6-methyl-5-oxo-5,6 dihydrobenzo[c][2,7]naphthyridin-8-yl)oxy)-5,5,5-trifluoropentan-2-yl)carbamate (0.14 g, 0.143 mmol, 85% crude yield) as a pale yellow solid. The material was carried forward without further purification. LC/MS (ESI) m/e 491.5 (M+H)$^+$, calcd for C$_{24}$H$_{26}$F$_3$N$_4$O$_4$, 491.2]; LC/MS retention time (method D): t$_R$=0.87 min.

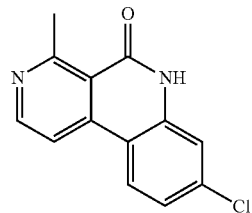 [SMILES: Cc1nccc2c1c(=O)[nH]c1cc(Cl)ccc12]

Part E: 8-((2-amino-5,5,5-trifluoropentyl)oxy)-6-methyl-5-oxo-5,6 dihydrobenzo[c][2,7]naphthyridine-9-carbonitrile Prepared as described in Example 2, Part E to afford the title product 8-((2-amino-5,5,5-trifluoropentyl)oxy)-6-methyl-5-oxo-5,6-dihydrobenzo[c][2,7]naphthyridine-9-carbonitrile (0.027 g, 0.066 mmol, 34% yield) as a white solid. LC/MS (ESI) m/e 391.2 [(M+H)$^+$, calcd for C$_{19}$H$_{18}$F$_3$N$_4$O$_2$, 391.1] LC/MS retention time (method C): t$_R$=1.61 min. HPLC retention time (method A): t$_R$=8.09 min; HPLC retention time (method B): t$_R$=10.36 min. $^1$H NMR (400 MHz, METHANOL-d$_4$) δ ppm 9.50 (s, 1H), 8.87-8.78 (m, 2H), 8.31 (d, J=5.8 Hz, 1H), 7.20 (s, 1H), 4.42-4.30 (m, 1H), 4.29-4.20 (m, 1H), 3.84 (s, 3H), 3.40-3.38 (m, 1H), 2.58-2.31 (m, 2H), 2.09-1.94 (m, 1H), 1.90-1.72 (m, 1H).

Example 57

6-methyl-8-(piperidin-2-ylmethoxy)benzo[c][2,7]naphthyridin-5(6H)-one

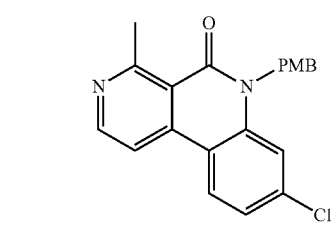

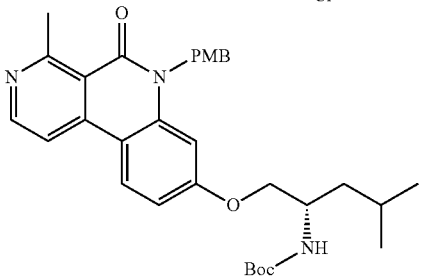

Part A: tert-butyl 2-(hydroxymethyl)piperidine-1-carboxylate

To a stirred solution of piperidin-2-ylmethanol (1.5 g, 13.02 mmol) in dichloromethane (25 mL) was added DIPEA (6.82 mL, 39.1 mmol). After stirring for 5 min Boc₂O (3.63 mL, 15.63 mmol) was added and the mixture was stirred at RT overnight. The mixture was quenched with water and diluted with DCM (50 mL). The organic layer was separated, dried over Na₂SO₄ and concentrated to give tert-butyl 2-(hydroxymethyl)piperidine-1-carboxylate (2 g, 9.29 mmol, 71% crude yield) as a colorless oil, which was taken to the next step without further purification. ¹H NMR (400 MHz, CDCl₃) ppm δ 4.27-4.28 (m, 1H), 3.80-3.82 (m, 1H), 3.75-3.77 (m, 1H), 3.56-3.58 (m, 1H), 2.63 (t, J=7.20 Hz, 1H), 1.55-1.55 (m, 5H), 1.43 (s, 9H).

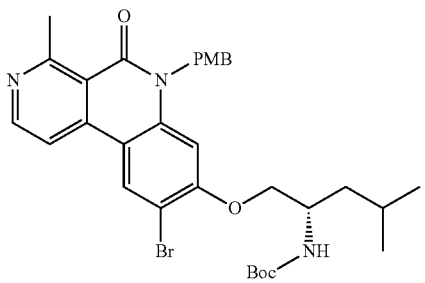

Part B: tert-butyl 2-(((6-methyl-5-oxo-5,6-dihydrobenzo[c][2,7]naphthyridin-8-yl)oxy)methyl)piperidine-1-carboxylate Prepared as described in Example 16, Part H to afford the title product (380 mg, 0.332 mmol, 41% yield), yellow oil. LC/MS (ESI) m/e 424.2, [(M+H)⁺, calcd for $C_{24}H_{30}N_3O_4$, 424.2]; LC/MS retention time (method I): $t_R$=2.29 min.

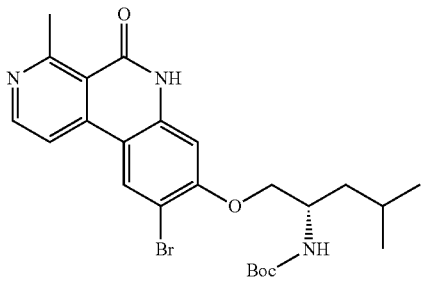 [SMILES: Cc1nccc2c1c(=O)[nH]c1cc(OC[C@H](CC(C)C)NC(=O)OC(C)(C)C)c(Br)cc12]

Part B: 6-methyl-8-(piperidin-2-ylmethoxy)benzo[c][2,7]naphthyridin-5(6H)-one

Prepared as described in Example 2, Part E to afford the title compound (30 mg, 0.092 mmol, 53% yield) as a pale yellow mono TFA salt. LC/MS (ESI) m/e 324.2 [(M+H)⁺, calcd for $C_{19}H_{22}N_3O_2$ 324.2]; LC/MS retention time (method F): $t_R$=1.23 min. HPLC retention time (method A): $t_R$=5.95 min; HPLC retention time (method B): $t_R$=6.87 min. ¹H NMR (400 MHz, METHANOL-d₄) δ ppm 9.52 (s, 1H), 8.82 (d, J=6.0 Hz, 1H), 8.51 (d, J=9.3 Hz, 1H), 8.42 (d, J=5.8 Hz, 1H), 7.25-7.15 (m, 2H), 4.49 (dd, J=10.5, 3.5 Hz, 1H), 4.30 (dd, J=10.8, 7.3 Hz, 1H), 3.83 (s, 3H), 3.70 (td, J=7.5, 3.6 Hz, 1H), 3.56-3.45 (m, 1H), 3.21-3.07 (m, 1H), 2.19-1.95 (m, 3H), 1.88-1.64 (m, 3H).

Example 58 and Example 59

(S)-tert-butyl (2,4-dimethyl-1-((6-methyl-5-oxo-5,6 dihydrobenzo[c][2,7]naphthyridin-8-yl)oxy)pentan-2-yl)carbamate and (R)-tert-butyl (2,4-dimethyl-1-((6-methyl-5-oxo-5,6 dihydrobenzo[c][2,7]naphthyridin-8-yl)oxy)pentan-2-yl)carbamate

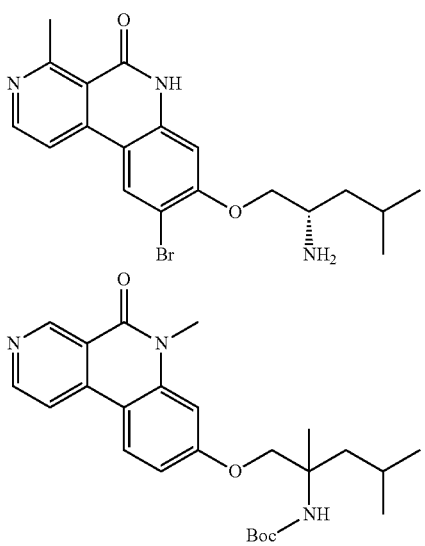

Part A: tert-butyl (2,4-dimethyl-1-((6-methyl-5-oxo-5,6-dihydrobenzo[c][2,7]naphthyridin-8-yl)oxy)pentan-2-yl)carbamate Synthesis of 8-chloro-6-methylbenzo[c][2,7]naphthyridin-5(6H)-one was described in example 2, Part C. 8-chloro-6-methylbenzo[c][2,7]naphthyridin-5(6H)-one (0.15 g, 0.613 mmol) and tert-butyl (1-hydroxy-2,4-dimethylpentan-2-yl)carbamate (0.284 g, 1.226 mmol) were subjected to ether synthesis as described in Example 16, Part H, to afford product, tert-butyl(2,4-dimethyl-1-((6-methyl-5-oxo-5,6-dihydrobenzo[c][2,7]naphthyridin-8-yl)oxy)pentan-2-yl)carbamate (0.3 g, 28% yield) as pale yellow solid. LC/MS (ESI) m/e 440.2 [(M+H)⁺, calcd for $C_{25}H_{34}N_3O_4$, 440.2]; LC/MS retention time (method C): $t_R$=2.67 min.

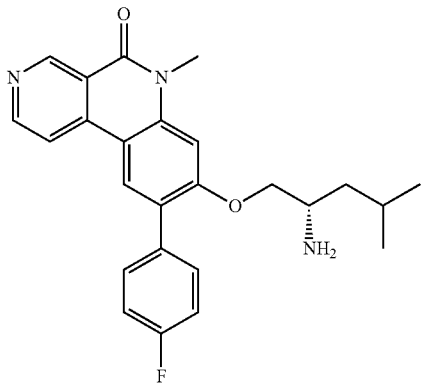

Part B: 8-((2-amino-2,4-dimethylpentyl)oxy)-6-methylbenzo[c][2,7]naphthyridin-5(6H)-one tert-Butyl (2,4-dimethyl-1-((6-methyl-5-oxo-5,6 dihydrobenzo[c][2,7]naphthyridin-8-yl)oxy)pentan-2-yl)carbamate was subjected to deprotection of the Boc group as described in Example 2, Part E to afford 8-((2-amino-2,4-dimethylpentyl)oxy)-6-methylbenzo[c][2,7]naphthyridin-5(6H)-one (30 mg, 12% yield) as an off-white solid. Resolution of 8-((2-amino-2,4-dimethylpentyl)oxy)-6-methylbenzo[c][2,7]naphthyridin-5(6H)-one by chiral HPLC (Co-solvent: 0.3% DEA in methanol, Column: Chiralpak AD H (250×21) mm 5 u) resulted into two enantiomers.

Enantiomer-1: LC/MS (ESI) m/e 340.0 [(M+H)$^+$, calcd for $C_{20}H_{26}N_3O_2$, 340.2]; LC/MS retention time (Method C): $t_R$=1.88 min. HPLC retention time (method B): $t_R$=9.29 min; HPLC retention time (method A): $t_R$=8.19 min. $^1$H NMR (400 MHz, METHANOL-$d_4$) 9.43 (s, 1H), 8.73 (d, J=6.0 Hz, 1H), 8.35 (d, J=8.5 Hz, 1H), 8.19 (d, J=6.0 Hz, 1H), 7.12-7.01 (m, 2H), 4.05-3.92 (m, 2H), 3.77 (s, 3H), 1.95-1.80 (m, 1H), 1.58 (qd, J=14.2, 5.5 Hz, 2H), 1.30 (s, 3H), 1.04 (d, J=6.5 Hz, 3H), 1.01 (d, J=6.5 Hz, 3H); HPLC retention time, $t_R$=5.44 min.

Enantiomer-2: LC/MS (ESI) m/e 340.0 [(M+H)$^+$, calcd for $C_{20}H_{26}N_3O_2$, 340.2]; LC/MS retention time (Method C): $t_R$=1.88 min. HPLC retention time (method B): $t_R$=9.29 min; HPLC retention time (method A): $t_R$=8.19 min. $^1$H NMR (400 MHz, METHANOL-$d_4$) 9.43 (s, 1H), 8.73 (d, J=6.0 Hz, 1H), 8.35 (d, J=8.5 Hz, 1H), 8.19 (d, J=6.0 Hz, 1H), 7.12-7.01 (m, 2H), 4.05-3.92 (m, 2H), 3.77 (s, 3H), 1.95-1.80 (m, 1H), 1.58 (qd, J=14.2, 5.5 Hz, 2H), 1.30 (s, 3H), 1.04 (d, J=6.5 Hz, 3H), 1.01 (d, J=6.5 Hz, 3H); HPLC retention time: $t_R$=7.77 min.

Example 60

(S)-8-(2-amino-4-methylpentyloxy)-4-(difluoromethyl)-6-methylbenzo[c][2,7]naphthyridin-5(6H)-one

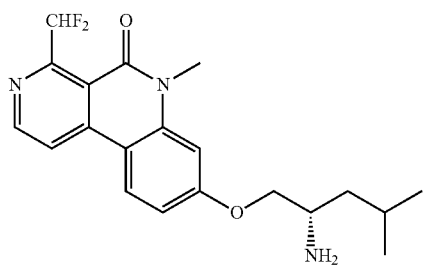

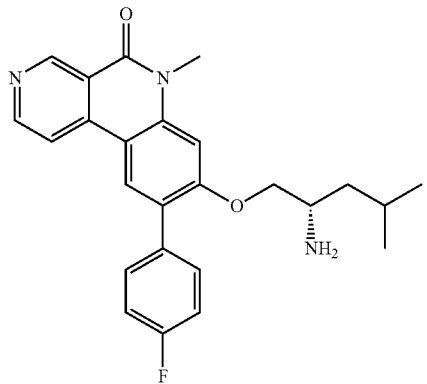 [SMILES: CC(C)C[C@H](N)COc1cc2c(cc1-c1ccc(F)cc1)c1ccncc1c(=O)n2C]

Part A: 8-chloro-6-methyl-5-oxo-5,6-dihydrobenzo[c][2,7]naphthyridine-4-carbaldehyde To a solution of 8-chloro-4,6-dimethylbenzo[c][2,7]naphthyridin-5(6H)-one (100 mg, 0.387 mmol), prepared as described in Example 16, Part G, in AcOH (4 mL) was added selenium dioxide (51.5 mg, 0.464 mmol). The reaction mixture was allowed to stir at 70° C. for 3 h. Volatiles were removed under reduced pressure and the residue so obtained was dissolved in dichloromethane (2 mL). The mixture was filtered through diatomaceous earth (Celite®) and the filtrate was concentrated under reduced pressure to afford the title product (0.1 g, 0.202 mmol, 52% crude yield) as pale yellow solid. The material was carried on without further purification. LC/MS, (ESI) m/z 273.0 [(M+H)$^+$, calcd for $C_{14}H_{10}ClN_2O_2$, 273.0]; LC/MS retention time (method H): $t_R$=1.89 min.

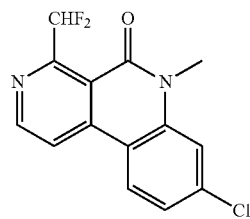 [SMILES: Cn1c(=O)c2c(C(F)F)nccc2c2ccc(Cl)cc21]

Part B: 8-chloro-4-(difluoromethyl)-6-methylbenzo[c][2,7]naphthyridin-5(6H)-one

To the solution of 8-chloro-6-methyl-5-oxo-5,6-dihydrobenzo[c][2,7]naphthyridine-4-carbaldehyde (200 mg, 0.733 mmol) in DCM (1 mL) was added bis-(2-methoxyethyl)aminosulfur trifluoride (811 mg, 3.67 mmol). The tube was sealed and the reaction mixture was allowed to stir at 50° C. overnight. The reaction mixture was basified with saturated aqueous NaHCO3 (15 mL) and extracted with ethyl acetate (3×10 mL). The combined organic layers were dried over Na$_2$SO$_4$ and concentrated under reduced pressure to afford 8-chloro-4-(difluoromethyl)-6-methylbenzo[c][2,7]naphthyridin-5(6H)-one (43 mg, 0.092 mmol, 13% crude yield) as a white solid. The material was carried on without further purification. LC/MS, (ESI) m/z 295.0 [(M+H)$^+$, calcd for $C_{14}H_{10}ClF_2N_2O$, 295.0]; LC/MS retention time (Method H): $t_R$=1.96 min.

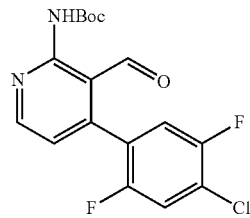 [SMILES: CC(C)(C)OC(=O)Nc1nccc(-c2cc(F)c(Cl)cc2F)c1C=O]

Part C: (S)-tert-butyl (1-((4-(difluoromethyl)-6-methyl-5-oxo-5,6-dihydrobenzo[c][2,7]naphthyridin-8-yl)oxy)-4-methylpentan-2-yl)carbamate Preparation as described in Example 16, Part H to afford the title compound (15 mg, 0.016 mmol, 19% yield). LC/MS, (ESI) m/z 476.3 [(M+H)+, calcd for C25H32F2N3O4 476.2]; LC/MS retention time (method E): t$_R$=1.14 min.

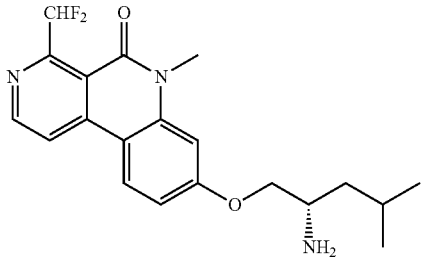 [SMILES: CC(C)C[C@H](N)COc1ccc2c3ccnc(C(F)F)c3c(=O)n(C)c2c1]

Part D: (S)-8-((2-amino-4-methylpentyl)oxy)-4-(difluoromethyl)-6-methylbenzo[c][2,7]naphthyridin-5(6H)-one Preparation as described in Example 2, Part E to afford title product (1.5 mg, 3.95 μmol, 9% yield) as an off-white solid. LC/MS, (ESI) m/z 376.2 [(M+H)+, calcd for C20H24F2N3O2, 376.2]; LC/MS retention time (method C): t$_R$=1.63 min. HPLC retention time (method A): t$_R$=5.97 min; HPLC retention time (method B): t$_R$=7.12 min. $^1$H NMR (400 MHz, METHANOL-d$_4$) δ ppm 8.81 (d, J=5.52 Hz, 1H) 8.42-8.48 (m, 2H) 7.97-8.26 (m, 1H) 7.09-7.15 (m, 2H) 4.22 (dd, J=9.54, 4.02 Hz, 1H) 4.04 (dd, J=9.29, 7.03 Hz, 1H) 3.79 (s, 3H) 3.39 (dt, J=3.33, 1.73 Hz, 1H) 1.81-1.92 (m, 1H) 1.43-1.57 (m, 2H) 1.02 (dd, J=8.78, 6.53 Hz, 6H). $^{19}$F NMR (400 MHz, METHANOL-d$_4$) δ ppm 120.45.

Example 61

(S)-8-((2-amino-4-methylpentyl)oxy)-7-chloro-4,6-dimethylbenzo[c][2,7]naphthyridin-5(6H)-one

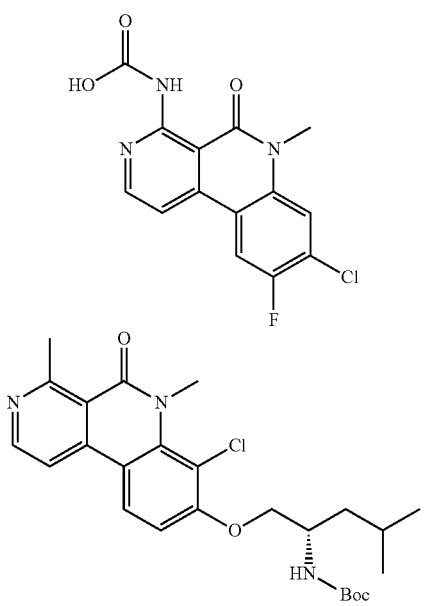

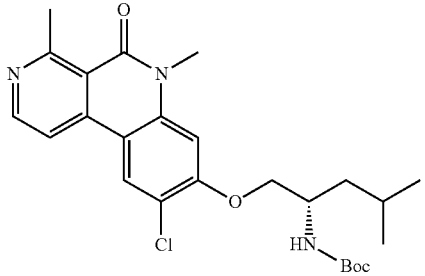

Part A: (S)-tert-butyl (1-((7 or 9-chloro-4,6-dimethyl-5-oxo-5,6-dihydrobenzo[c][2,7]naphthyridin-8-yl)oxy)-4-methylpentan-2-yl)carbamate To a solution of (S)-tert-butyl (1-((4,6-dimethyl-5-oxo-5,6-dihydrobenzo[c][2,7]naphthyridin-8-yl)oxy)-4-methylpentan-2-yl)carbamate (50 mg, 0.114 mmol), prepared as described in Example 16, Part H, in acetonitrile (2 mL) was added 1-chloropyrrolidine-2,5-dione (15.19 mg, 0.114 mmol). The reaction mixture was allowed to stir at 55° C. for 16 h overnight. The reaction mixture was basified with saturate aqueous sodium bicarbonate (2 mL) and water (10 mL). The solution was extracted with methylene dichloride (3×10 mL). The combined organic layers were washed with brine (10 mL), dried with sodium sulfate, filtered and concentrated under reduced pressure to afford a mixture of (S)-tert-butyl (1-((7-chloro-4,6-dimethyl-5-oxo-5,6-dihydrobenzo[c][2,7]naphthyridin-8-yl)oxy)-4-methylpentan-2-yl)carbamate and (S)-tert-butyl (1-((9-chloro-4,6-dimethyl-5-oxo-5,6-dihydrobenzo[c][2,7]naphthyridin-8-yl)oxy)-4-methylpentan-2-yl)carbamate (60 mg, 0.037 mmol, 32% combined crude yield) as a pale yellow solid. The material was carried on without further purification. LC/MS (ESI) m/e 474.4, [(M+H)+, calcd for C25H33ClN3O4, 474.2]; LC/MS retention time (method E): t$_R$=1.24 min.

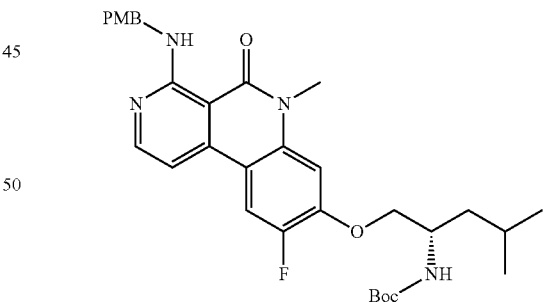

Part B: (S)-8-((2-amino-4-methylpentyl)oxy)-7-chloro-4,6-dimethylbenzo[c][2,7]naphthyridin-5(6H)-one To a mixture of (S)-tert-butyl (1-((7-chloro-4,6-dimethyl-5-oxo-5,6-dihydrobenzo[c][2,7]naphthyridin-8-yl)oxy)-4-methylpentan-2-yl)carbamate and (S)-tert-butyl (1-((9-chloro-4,6-dimethyl-5-oxo-5,6-dihydrobenzo[c][2,7]naphthyridin-8-yl)oxy)-4-methylpentan-2-yl)carbamate (30 mg, 0.063 mmol) was added HCl in 1,4-dioxane (241 μL, 0.964 mmol) at 0° C. The reaction mixture was allowed to stir for 2 h, then was concentrated under reduced pressure. The residue was purified by reverse phase HPLC (Symmetry C18 column (19×250 mm) 7.0 micron; mobile phase A: 0.1% TFA in water; mobile phase B: acetonitrile; flow rate: 14.0 mL). The HPLC fractions were concentrated, basified with NaHCO$_3$ and extracted with DCM (2×). The combined organic layers were concentrated in vacuo to afford the purified mixture of 7-Cl and 9-Cl final products as an off-white solid. This was subjected to second purification (to resolve regioisomers) by normal phase HPLC (chiralpak ODH, (4.6× 250 mm) 5.0 micron; mobile phase A: n-hexane; mobile phase B: ethanol); The HPLC fractions were concentrated in vacuo to afford the 7-chloro-regioisomer: (S)-8-((2-amino-4-methylpentyl)oxy)-7-chloro-4,6-dimethylbenzo[c][2,7]naphthyridin-5(6H)-one (3 mg, 7.2 umol, 11% yield) as a pale yellow solid. LC/MS, (ESI) m/z 373.8 [(M+H)$^+$, calcd for C$_{20}$H$_{25}$ClN$_3$O$_2$, 374.2]; LC/MS retention time (method C): t$_R$=1.64 min. HPLC retention time (method A): t$_R$=8.44 min; $^1$H NMR (400 MHz, DMSO-d$_6$) δ ppm 8.65 (d, J=5.65 Hz, 1H) 8.44 (d, J=9.22 Hz, 1H) 8.20 (d, J=5.58 Hz, 1H) 7.22 (d, J=9.04 Hz, 1H) 4.05-4.10 (m, 1H) 3.98 (dd, J=9.25, 6.43 Hz, 1H) 3.73 (s, 3H) 3.13-3.18 (m, 1H) 2.99 (s, 3H) 1.81-1.89 (m, 1H) 1.28-1.42 (m, 2H) 0.91 (dd, J=13.80, 6.59 Hz, 2H).

Example 62

(S)-8-((2-amino-4-methylpentyl)oxy)-9-chloro-4,6-dimethylbenzo[c][2,7]naphthyridin-5(6H)-one

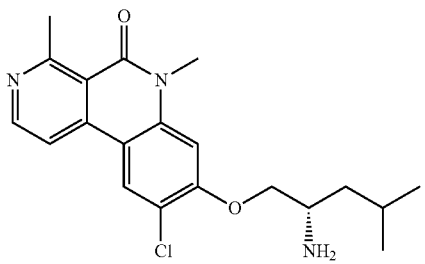

The mixture of 7-Cl and 9-Cl products prepared in Example 61, Part B was purified (to resolve regioisomers) as shown above by normal phase HPLC (chiralpak ODH, (4.6× 250 mm) 5.0 micron; mobile phase A: n-hexane; mobile phase B: ethanol); The HPLC fractions were concentrated in vacuo to afford the 9-chloro-regioisomer: (S)-8-((2-amino-4-methylpentyl)oxy)-9-chloro-4,6-dimethylbenzo[c][2,7]naphthyridin-5(6H)-one (5 mg, 0.013 mmol, 21% yield) as an off white solid. LC/MS, (ESI) m/z 373.8 [(M+H)$^+$, calcd for C$_{20}$H$_{25}$ClN$_3$O$_2$, 374.2]; LC/MS retention time (method C): t$_R$=1.61 min. HPLC retention time (method A): t$_R$=8.37 min; HPLC retention time (method B): t$_R$=9.14 min. $^1$H NMR (400 MHz, DMSO-d$_6$) δ ppm 8.63 (d, J=5.65 Hz, 1H) 8.60 (s, 1H) 8.26 (d, J=5.71 Hz, 1H) 7.12 (s, 1H) 4.11-4.16 (m, 1H) 4.00-4.06 (m, 1H) 3.70 (s, 3H) 3.13-3.16 (m, 1H) 3.00 (s, 3H) 1.82-1.90 (m, 1H) 1.34-1.42 (m, 1H) 1.23-1.32 (m, 1H) 0.90-0.95 (m, 6H).

Example 63

(S)-8-(2-amino-4-methylpentyloxy)-4,6,9-trimethyl-benzo[c][2,7]naphthyridin-5(6H)-one

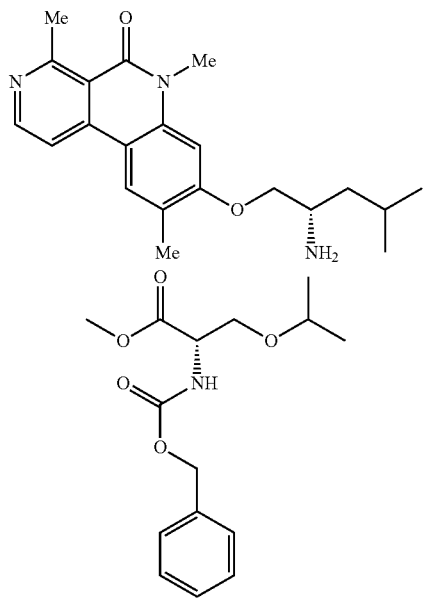

Part A: (S)-tert-butyl (4-methyl-1-((4,6,9-trimethyl-5-oxo-5,6-dihydrobenzo[c][2,7]naphthyridin-8-yl)oxy)pentan-2-yl)carbamate Prepared as described in Example 3, Part A and Example 4, Part A to afford (S)-tert-butyl (4-methyl-1-((4,6,9-trimethyl-5-oxo-5,6-dihydrobenzo[c][2,7]naphthyridin-8-yl)oxy)pentan-2-yl)carbamate (30 mg, 0.038 mmol, 40% yield) as a pale yellow solid. LC/MS, (ESI) m/z 453.9 [(M+H)$^+$, calcd for C$_{26}$H$_{36}$N$_3$O$_4$ 454.3]; LC/MS retention time (method C): t$_R$=2.16 min.

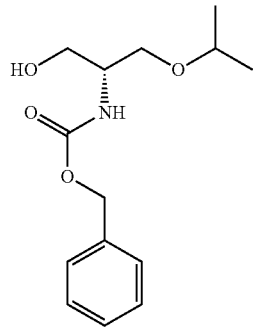 [SMILES: CC(C)OC[C@@H](CO)NC(=O)OCc1ccccc1]

Part B: (S)-8-((2-amino-4-methylpentyl)oxy)-4,6,9-trimethylbenzo[c][2,7]naphthyridin-5(6H)-one Prepared as described in Example 2, Part E to afford (S)-8-((2-amino-4-methylpentyl)oxy)-4,6,9-trimethylbenzo[c][2,7]naphthyridin-5(6H)-one (15 mg, 0.040 mmol, 62% yield) as an off-white solid. LC/MS, (ESI) m/z 353.9 [(M+

H)+, calcd for $C_{21}H_{28}N_3O_2$ 354.2]; LC/MS retention time (method C): $t_R$=1.64 min. HPLC retention time (method A): $t_R$=8.21 min. $^1$H NMR (400 MHz, DMSO-$d_6$) δ ppm 8.59 (d, J=5.77 Hz, 1H) 8.27 (s, 1H) 8.15 (d, J=5.60 Hz, 1H) 6.92 (s, 1H) 3.90-4.08 (m, 2H) 3.68 (s, 3H) 3.12-3.20 (m, 1H) 2.99 (s, 3H) 2.24 (s, 3H) 1.85 (td, J=13.68, 6.53 Hz, 3H) 1.22-1.43 (m, 3H) 0.86-0.95 (m, 6H).

Example 64

(S)-8-(2-amino-4-methylpentyloxy)-4,6-dimethyl-5-oxo-5,6-dihydrobenzo[c][2,7]naphthyridine-9-carbonitrile

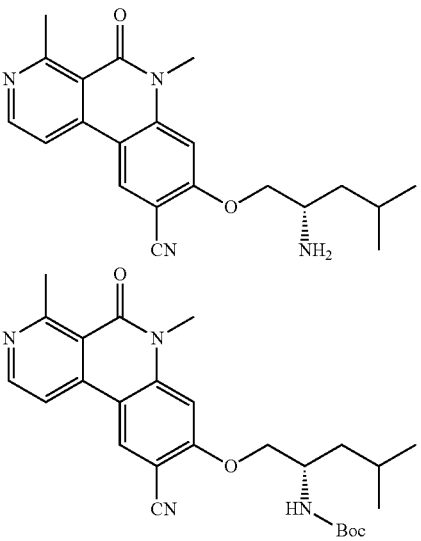

Part A. (S)-tert-butyl 1-(9-cyano-4,6-dimethyl-5-oxo-5,6-dihydrobenzo[c][2,7]naphthyridin-8-yloxy)-4-methylpentan-2-ylcarbamate A suspension of (S)-tert-butyl (1-((9-bromo-4,6-dimethyl-5-oxo-5,6-dihydrobenzo[c][2,7]naphthyridin-8-yl)oxy)-4-methylpentan-2-yl)carbamate (2.4 g, 4.63 mmol), prepared as described in Example 3, Part A, $Pd_2(dba)_3$ (0.212 g, 0.231 mmol), DPPF (0.257 g, 0.463 mmol) and zinc(II) cyanide (0.544 g, 4.63 mmol) in DMF (20 mL) and water (1 mL) was degassed with nitrogen and heated to 130° C. overnight. Ater cooling to room temperature, the volatiles were concentrated under reduced pressure. The residue was reconstituted in ethyl acetate and filtered through diatomaceous earth (Celite®). The organic layer was washed with $H_2O$, followed by brine, dried over $Na_2SO_4$ and concentrated under reduced pressure. The crude product was purified by silica gel column (petroleum ether and ethyl acetate) to afford (S)-tert-butyl 1-(9-cyano-4,6-dimethyl-5-oxo-5,6-dihydrobenzo[c][2,7]naphthyridin-8-yloxy)-4-methylpentan-2-ylcarbamate (1.9 g, 4.09 mmol, 88% yield) as a yellow solid. LC/MS (ESI) m/e 465.2 [(M+H)+, calcd for $C_{26}H_{33}N_4O_4$, 465.2]; LC/MS retention time (method C): $t_R$=2.74 min.

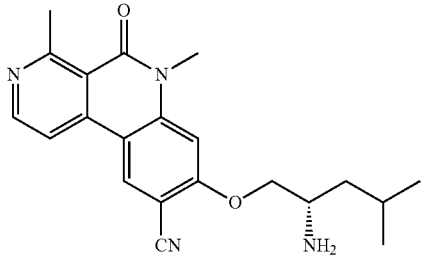 [SMILES: Cc1nccc2c1c(=O)n(C)c1cc(OC[C@@H](N)CC(C)C)c(C#N)cc21]

Part B. (S)-8-(2-amino-4-methylpentyloxy)-4,6-dimethyl-5-oxo-5,6-dihydrobenzo[c][2,7]naphthyridine-9-carbonitrile Prepared as described in Example 2, Part E to afford (S)-8-(2-amino-4-methylpentyloxy)-4,6-dimethyl-5-oxo-5,6-dihydrobenzo[c][2,7]naphthyridine-9-carbonitrile (1.6 g, 3.89 mmol, 95% yield) as a light yellow solid. LC/MS (ESI) m/e 365.2 [(M+H)+, calcd for $C_{21}H_{25}N_4O_2$, 365.2]; LC/MS retention time (method C): $t_R$=2.13 min. HPLC retention time (method A): $t_R$=8.70 min; HPLC retention time (method B): $t_R$=9.57 min. $^1$H NMR (400 MHz, MeOD) δ ppm 9.07 (s, 1H), 8.75 (s, 2H), 7.28 (s, 1H), 4.69 (m, 1H), 4.55 (m, 1H), 3.87 (m, 4H), 3.27 (s, 3H), 1.87 (m, 2H), 1.74 (m, 1H), 1.08 (m, 6H).

Example 65

(S)-4,6-dimethyl-8-(4-methyl-2-(methylamino)pentyloxy)-5-oxo-5,6-dihydrobenzo[c][2,7]naphthyridine-9-carbonitrile

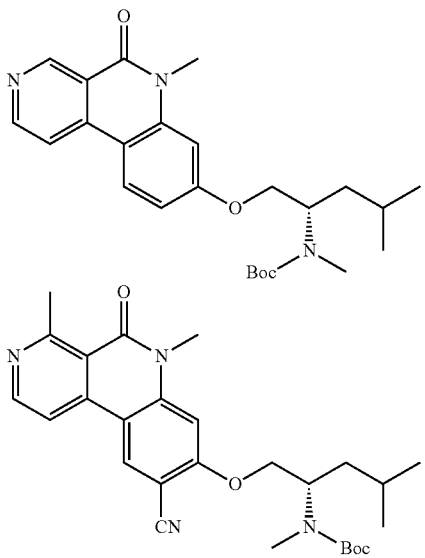

Part A. (S)-tert-butyl (1-((9-cyano-4,6-dimethyl-5-oxo-5,6-dihydrobenzo[c][2,7]naphthyridin-8-yl)oxy)-4-methylpentan-2-yl)(methyl)carbamate (S)-tert-Butyl (1-((9-cyano-4,6-dimethyl-5-oxo-5,6-dihydrobenzo[c][2,7]naphthyridin-8-yl)oxy)-4-methylpentan-2-yl)carbamate (60 mg, 0.129 mmol), prepared as described in Example 64, Part B, was taken in DMF (3 mL) and cooled to 0° C. The reaction mixture was treated with NaH (10.33 mg, 0.258 mmol) followed by MeI (0.016 mL, 0.258 mmol). After stirring at 0° C. for 10 min, the reaction mixture was warmed to room temperature and stirred overnight. The mixture was then quenched with ice-cold water and extracted with ethyl acetate (2×3 mL). The combined organic layers were dried with sodium sulfate and concentrated under reduced pressure to afford (S)-tert-butyl (1-((9-cyano-4,6-dimethyl-5-oxo-5,6-dihydrobenzo[c][2,7]naphthyridin-8-yl)oxy)-4-methylpentan-2-yl)(methyl)carbamate (70 mg, 0.127 mmol, 99% crude yield) as an off-white solid. The material was carried forward without further purification. LC/MS (ESI) m/e 479.2 [(M+H)$^+$, calcd for $C_{27}H_{35}N_4O_4$ 479.3]; LC/MS retention time (method C): $t_R$=2.16 min.

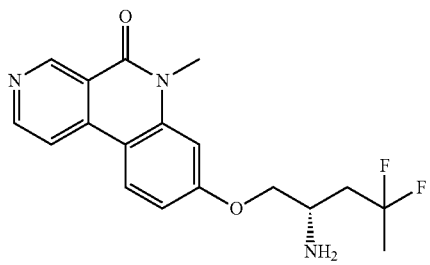 [SMILES: Cn1c(=O)c2cnccc2c2ccc(OC[C@@H](N)CC(C)(F)F)cc21]

Part B. (S)-4,6-dimethyl-8-((4-methyl-2-(methylamino)pentyl)oxy)-5-oxo-5,6-dihydrobenzo[c][2,7]naphthyridine-9-carbonitrile Prepared as described in Example 2, Part E to afford (S)-4,6-dimethyl-8-((4-methyl-2-(methylamino)pentyl)oxy)-5-oxo-5,6-dihydrobenzo[c][2,7]naphthyridine-9-carbonitrile (25 mg, 0.058 mmol, 46% yield) as an off-white solid. LC/MS (ESI) m/e 379.0, [(M+H)$^+$, calcd for $C_{22}H_{27}N_4O_2$ 379.2]; LC/MS retention time (method C): $t_R$=1.87 min. HPLC retention time (method A): $t_R$=8.59 min; HPLC retention time (method B): $t_R$=9.88 min. $^1$H-NMR (400 MHz, MeOD): δ ppm 1.03 (d, J=22.80 Hz, 6H), 1.56-1.62 (m, 1H), 1.67-1.72 (m, 1H), 1.84-1.87 (m, 1H), 2.67 (s, 3H), 3.10 (s, 3H), 3.28-3.30 (m, 1H), 3.81 (s, 3H), 4.35 (s, 1H), 4.49 (s, 1H), 7.18 (s, 1H), 8.20 (d, J=5.60 Hz, 1H), 8.82 (s, 1H).

Example 66

(S)-8-((2-amino-4-methylpentyl)oxy)-2,6-dimethylbenzo[c][2,7]naphthyridin-5(6H)-one

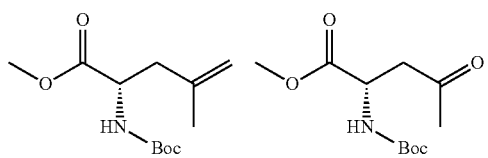

Part A: Methyl 4-chloro-6-methylnicotinate

To a solution of methyl 4,6-dichloronicotinate (3.00 g, 14.56 mmol) and trimethylboroxine (1.097 g, 8.74 mmol) in 1,4-dioxane (70 mL) and water (7 mL) was added cesium carbonate (14.23 g, 43.7 mmol). The mixture was degassed with argon over a period of 5 minutes. PdCl$_2$(dppf)-CH$_2$Cl$_2$ adduct (1.189 g, 1.456 mmol) was added and the reaction mixture was heated to 110° C. for 16 h. The reaction mixture was cooled to room temperature, diluted with water (100 mL) and extracted with ethyl acetate (200 mL). The organic phase was washed with brine (2×100 mL), dried over Na$_2$SO$_4$, and concentrated under reduced pressure. The residue obtained was purified by silica gel chromatography using ethyl acetate-petroleum ether mixture to afford methyl 4-chloro-6-methylnicotinate (700 mg, 2.87 mmol, 20% yield) as a yellow liquid. LC/MS (ESI) m/e 186.0 [(M+H)$^+$, calcd for $C_8H_9ClNO_2$ 185.6]; LC/MS retention time (Method I) $t_R$=1.79 min.

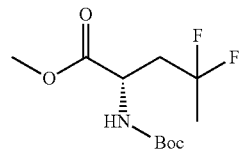 [SMILES: COC(=O)[C@H](CC(C)(F)F)NC(=O)OC(C)(C)C]

Part B: Methyl 4-(4-chloro-2-fluorophenyl)-6-methylnicotinate

To a solution of methyl 4-chloro-6-methylnicotinate (660 mg, 3.56 mmol) and (4-chloro-2-fluorophenyl)boronic acid (620 mg, 3.56 mmol) in 1,4-dioxane (20 mL) was added cesium carbonate (3.48 g, 10.67 mmol). The reaction mixture was degassed with argon over a period of 5 min. Pd(Ph$_3$P)$_4$ (205 mg, 0.178 mmol) was added to the reaction mixture and heated to 80° C. for 16 h. The mixture was cooled to room temperature, diluted with water, and extracted with ethyl acetate (100 mL). The organic phase was washed with brine (2×50 mL), dried over Na$_2$SO$_4$, and concentrated under reduced pressure. The residue obtained was purified by silica gel chromatography to afford methyl 4-(4-chloro-2-fluorophenyl)-6-methylnicotinate (500 mg, 1.53 mmol, 43% yield) as a yellow liquid. LC/MS (ESI) m/e 280.0 [(M+H)$^+$, calcd for $C_{14}H_{12}ClFNO_2$ 279.6]; LC/MS retention time (method C): $t_R$=1.87 min.

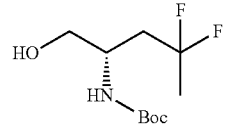

Part C: 4-(4-chloro-2-fluorophenyl)-6-methylnicotinic Acid

To a solution of methyl 4-(4-chloro-2-fluorophenyl)-6-methylnicotinate (700 mg, 2.50 mmol) in MeOH (5 mL) was added NaOH (200 mg, 7.51 mmol) in water (5 mL). The reaction mixture was stirred at room temperature for 2 h. The solvent was evaporated under reduced pressure and the residue obtained was adjusted to pH ~3 by adding 1.5N HCl. The reaction mixture was extracted with dichloromethane. The organic phase was dried over Na$_2$SO$_4$, and concentrated under reduced pressure to afford 4-(4-chloro-2-fluorophenyl)-6-methylnicotinic acid (500 mg, 1.730 mmol, 92% crude yield) as white solid. The material was carried forward without further purification. LC/MS (ESI) m/e 266.0 [(M+H)⁺, calcd for C₁₃H₁₀ClFNO₂ 266.03]; LC/MS (Method I) t_R=1.51 min.

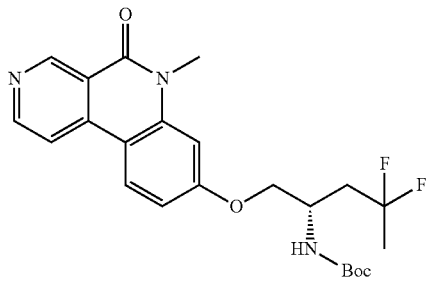 [SMILES: Cn1c(=O)c2cnccc2c2ccc(OC[C@H](CC(C)(F)F)NC(=O)OC(C)(C)C)cc21]

Part D: 4-(4-chloro-2-fluorophenyl)-N,6-dimethylnicotinamide

To a solution of 4-(4-chloro-2-fluorophenyl)-6-methylnicotinic acid (500 mg, 1.88 mmol) in dichloromethane (10 mL) at 0° C. was added oxalyl chloride (0.988 mL, 11.29 mmol) drop wise followed by DMF (0.2 mL). The reaction mixture was stirred at room temperature for 4 h. The reaction mixture was evaporated to dryness. The residue was taken in up dichloromethane (50 mL) and cooled to 0° C. Methylamine hydrochloride (1.27 g, 18.82 mmol) was added to followed by triethylamine (2.62 mL, 18.82 mmol) and the reaction mixture was stirred at room temperature for 2 h. The reaction mixture was diluted with water (50 mL) and extracted with dichloromethane (100 mL). The organic layer was separated, dried over Na₂SO₄ and concentrated under reduced pressure to afford 4-(4-chloro-2-fluorophenyl)-N,6-dimethylnicotinamide (520 mg, 1.43 mmol, 76% crude yield) as yellow solid. The material was carried forward without further purification. LC/MS (ESI) m/e 279.0 [(M+H)⁺, calcd for C₁₄H₁₃ClFN₂O 279.1]; LC/MS retention time ((Method I) t_R=1.82 min.

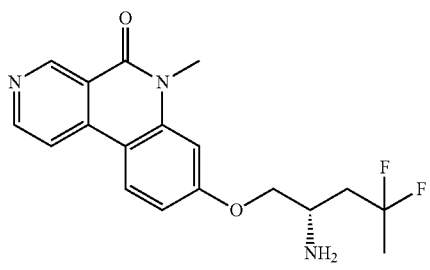

Part E: 8-chloro-2,6-dimethylbenzo[c][2,7]naphthyridin-5(6H)-one

To a solution of 4-(4-chloro-2-fluorophenyl)-N,6-dimethylnicotinamide (520 mg, 1.86 mmol) in tetrahydrofuran (20 mL) at 0° C. was added NaH (224 mg, 5.60 mmol). The reaction mixture was brought to room temperature gradually and stirred at room temperature for 15 h. The reaction mixture was diluted with water (50 mL) and extracted with ethyl acetate (100 mL). The organic layer was separated, dried over Na₂SO₄ and concentrated under reduced pressure to afford 8-chloro-2,6 dimethylbenzo[c][2,7]naphthyridin-5(6H)-one (480 mg, 1.51 mmol, 81% yield) as a brick-red solid. LC/MS (ESI) m/e 259.0 [(M+H)⁺, calcd for C₁₄H₁₂ClN₂O 259.05]; LC/MS retention time (method C): t_R=1.91 min. ¹H NMR (400 MHz, METHANOL-d₄) δ ppm 9.41 (s, 1H), 8.48 (d, J=8.59 Hz, 1H), 8.23 (s, 1H), 7.69 (d, J=1.98 Hz, 1H), 7.44 (dd, J=8.64, 1.94 Hz, 1H), 3.78 (s, 3H), 2.75 (s, 3H).

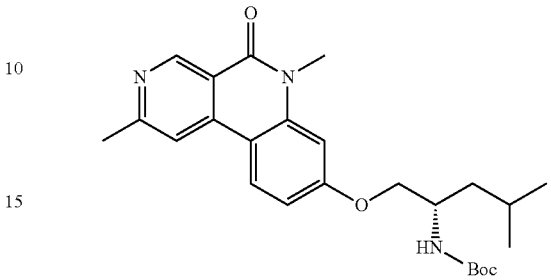

Part F: (S)-tert-butyl (1-((2,6-dimethyl-5-oxo-5,6-dihydrobenzo[c][2,7]naphthyridin-8-yl)oxy)-4-methylpentan-2-yl)carbamate To the stirred solution of 8-chloro-2,6-dimethylbenzo[c][2,7]naphthyridin-5(6H)-one (100 mg, 0.387 mmol) and tert-butyl (1-hydroxy-2,4-dimethylpentan-2-yl)carbamate (168 mg, 0.773 mmol) in toluene (5 mL) was added cesium carbonate (189 mg, 0.580 mmol) and 2-di-t-butylphosphino-2',4',6'-tri-i-propyl-1,1'-biphenyl (9.85 mg, 0.023 mmol). The reaction mixture was degassed with argon for 5 minutes and palladium(II) acetate (26 mg, 0.116 mmol) was added. The reaction mixture was heated to 100° C. for 18 h. The reaction mixture was filtered through diatomaceous earth (Celite®) and the filtrate was concentrated under reduced pressure. The residue was purified by silica gel chromatography using ethyl acetate-petroleum ether to afford (S)-tert-butyl (1-((2,6-dimethyl-5-oxo-5,6 dihydrobenzo[c][2,7]naphthyridin-8-yl)oxy)-4-methylpentan-2-yl)carbamate (100 mg, 0.171 mmol, 44% yield) as a dark yellow semi-solid. LC/MS (ESI) m/e 440.6 [(M+H+)⁺, calcd for C₂₅H₃₄N₃O₄ 440.2]; LC/MS retention time (method D): t_R=0.89 min.

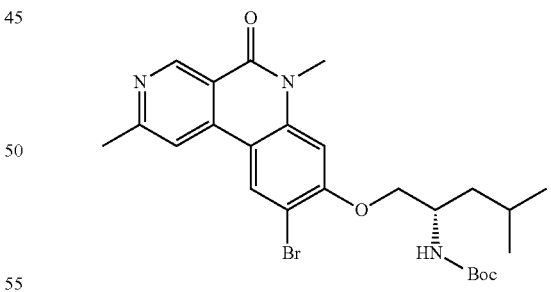

Part G: (S)-tert-butyl (1-((9-bromo-2,6-dimethyl-5-oxo-5,6-dihydrobenzo[c][2,7]naphthyridin-8-yl)oxy)-4-methylpentan-2-yl)carbamate To the stirred solution of (S)-tert-butyl (1-((2,6-dimethyl-5-oxo-5,6 dihydrobenzo[c][2,7]naphthyridin-8-yl)oxy)-4-methylpentan-2-yl)carbamate (40 mg, 0.069 mmol) in acetonitrile (3 mL) at room temperature was added NBS (12 mg, 0.069 mmol). The reaction mixture was heated to reflux for 2 h. The reaction mixture was diluted with water (50 mL) and extracted with dichloromethane (100 mL). The organic layer was separated, dried over Na$_2$SO$_4$ and concentrated under reduced pressure to afford (S)-tert-butyl (1-((9-bromo-2,6-dimethyl-5-oxo-5,6-dihydrobenzo[c][2,7]naphthyridin-8-yl)oxy)-4-methylpentan-2-yl)carbamate (30 mg, 0.027 mmol, 40% crude yield) as a yellow oil. The material was carried forward without further purification. LC/MS (ESI) m/e 518.2 [(M+H)$^+$, calcd for C$_{25}$H$_{33}$BrN$_3$O$_4$ 518.2]; LC/MS retention time (method E): $t_R$=1.25 min.

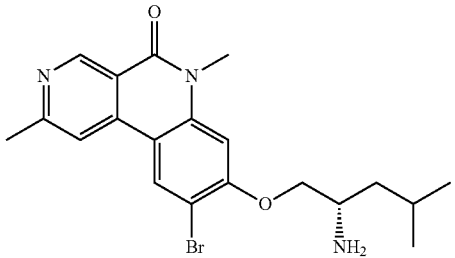

Part H: (S)-8-((2-amino-4-methylpentyl)oxy)-2,6-dimethylbenzo[c][2,7]naphthyridin-5(6H)-one To a solution of (S)-tert-butyl (1-((9-bromo-2,6-dimethyl-5-oxo-5,6-dihydrobenzo[c][2,7]naphthyridin-8-yl)oxy)-4-methylpentan-2-yl)carbamate (30 mg, 0.058 mmol) in MeOH (3 mL) at 0° C. was added 4M HCl in 1,4-dioxane (0.362 mL, 1.447 mmol). The reaction mixture was stirred at 0° C. for 2 h. The reaction mixture was concentrated under reduced pressure to afford crude product which was purified by preparative HPLC to afford (S)-8-((2-amino-4-methylpentyl)oxy)-2,6-dimethylbenzo[c][2,7]naphthyridin-5(6H)-one (6 mg, 0.014 mmol, 24% yield) as an off-white solid. LC/MS (ESI) m/e 418.0 [(M+H)$^+$, calcd for C$_{20}$H$_{25}$BrN$_3$O$_2$ 418.1]; LC/MS retention time (method H): $t_R$=1.70 min; HPLC retention time (method A): $t_R$=6.33 min; HPLC retention time (method B): $t_R$=7.19 min. $^1$H NMR (400 MHz, METHANOL-d$_4$) δ ppm 9.31 (s, 1H), 9.28-9.33 (m, 1H), 8.58 (s, 1H), 8.08 (s, 1H), 7.09 (s, 1H), 4.42 (dd, J=9.79, 3.26 Hz, 1H), 4.25 (dd, J=9.91, 6.15 Hz, 1H), 3.78 (s, 3H), 3.63 (br. s., 1H), 2.73 (s, 3H), 2.00 (br. s., 4H), 1.85-1.92 (m, 1H), 1.71-1.80 (m, 1H), 1.57-1.66 (m, 1H), 1.06 (dd, J=6.40, 4.64 Hz, 6H).

Example 67

(S)-8-((2-amino-4-methylpentyl)oxy)-2,6 dimethyl-benzo[c][2,7]naphthyridin-5(6H)-one

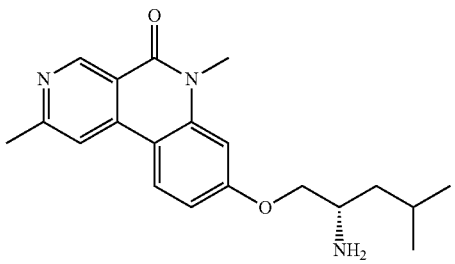

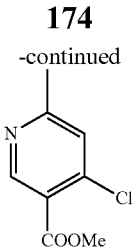

Part A: Methyl 4-chloro-6-methylnicotinate

To a solution of methyl 4,6-dichloronicotinate (3.00 g, 14.56 mmol) and trimethylboroxine (1.097 g, 8.74 mmol) in 1,4-dioxane (70 mL) and water (7 mL), was added cesium carbonate (14.23 g, 43.7 mmol). The mixture was degassed with argon over a period of 5 min. PdCl$_2$(dppf)-CH$_2$Cl$_2$ adduct (1.189 g, 1.456 mmol) was added to the reaction mixture and heated to 110° C. for 16 h. The reaction mixture was cooled to room temperature, diluted with water (100 mL) and extracted with ethyl acetate (200 mL). The organic phase was washed with brine (2×100 mL), dried over Na$_2$SO$_4$, and concentrated under reduced pressure. The residue obtained was purified by silica gel chromatography using ethyl acetate-petroleum ether mixture to afford methyl 4-chloro-6-methylnicotinate (700 mg, 2.87 mmol, 20% yield) as a yellow liquid. LC/MS (ESI) m/e 186.0 [(M+H)$^+$, calcd for C$_8$H$_9$ClNO$_2$ 186.0]; LC/MS retention time (Method I): $t_R$=1.79 min.

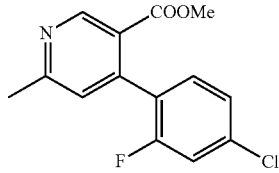 [SMILES: COC(=O)c1cnc(C)cc1-c1ccc(Cl)cc1F]

Part B: Methyl 4-(4-chloro-2-fluorophenyl)-6-methylnicotinate

To a solution of methyl 4-chloro-6-methylnicotinate (660 mg, 3.56 mmol) and (4-chloro-2-fluorophenyl)boronic acid (620 mg, 3.56 mmol) in 1,4-dioxane (20 mL) was added cesium carbonate (3.48 g, 10.67 mmol). The reaction mixture was degassed with argon over a period of 5 min. Pd(Ph$_3$P)$_4$ (205 mg, 0.178 mmol) was added to the reaction mixture and heated to 80° C. for 16 h. The mixture was cooled to room temperature, diluted with water, and extracted with ethyl acetate (100 mL). The organic phase was washed with brine (2×50 mL), dried over Na$_2$SO$_4$, and concentrated under reduced pressure. The residue obtained was purified by silica gel chromatography to afford Methyl 4-(4-chloro-2-fluorophenyl)-6-methylnicotinate (500 mg, 1.53 mmol, 43% yield) as a yellow liquid. LC/MS (ESI) m/e 280.0 [(M+H)$^+$, calcd for C$_{14}$H$_{12}$ClFNO$_2$ 280.0]; LC/MS retention time (Method C): $t_R$=1.87 min.

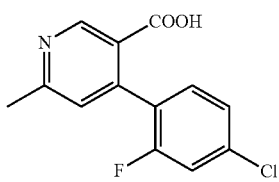 [SMILES: Cc1cc(-c2ccc(Cl)cc2F)c(C(=O)O)cn1]

Part C:
4-(4-chloro-2-fluorophenyl)-6-methylnicotinic Acid

To a solution of Methyl 4-(4-chloro-2-fluorophenyl)-6-methylnicotinate (700 mg, 2.50 mmol) in MeOH (5 mL) was added NaOH (200 mg, 7.51 mmol) in water (5 mL). The reaction mixture was stirred at room temperature for 2 h. Then it was evaporated under reduced pressure and the residue obtained was adjusted to pH ~3 by adding 1.5N HCl solution. The product was extracted with dichloromethane. The organic phase was dried over $Na_2SO_4$, and concentrated under reduced pressure to afford 4-(4-chloro-2-fluorophenyl)-6-methylnicotinic acid (500 mg, 1.730 mmol, 69% crude yield) as white solid. The material was carried forward without further purification. LC/MS (ESI) m/e 266.0 [(M+H)$^+$, calcd for $C_{13}H_{10}ClFNO_2$ 266.0]; LC/MS retention time (Method I): $t_R$=1.51 min.

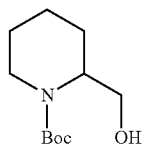 [SMILES: CC(C)(C)OC(=O)N1CCCCC1CO]

Part D: 4-(4-chloro-2-fluorophenyl)-N,6-dimethylnicotinamide

To a solution of 4-(4-chloro-2-fluorophenyl)-6-methylnicotinic acid (500 mg, 1.88 mmol) in dichloromethane (10 mL) at 0° C. was added oxalyl chloride (0.988 mL, 11.29 mmol) drop wise followed by DMF (0.2 mL). The reaction mixture was stirred at room temperature for 4 h. The reaction mixture was evaporated to dryness. The residue was taken in dichloromethane (50 mL) and cooled to 0° C. Methylamine hydrochloride (1.27 g, 18.82 mmol) and triethylamine (2.62 mL, 18.82 mmol) were added. The reaction mixture was stirred at room temperature for 2 h. The reaction mixture was diluted with water (50 mL) and extracted with dichloromethane (100 mL). The organic layer was separated, dried over $Na_2SO_4$ and concentrated under reduced pressure to afford 4-(4-chloro-2-fluorophenyl)-N,6-dimethylnicotinamide (520 mg, 1.43 mmol, 76% crude yield) as yellow solid. The material was carried forward without further purification. LC/MS (ESI) m/e 279.0 [(M+H)$^+$, calcd for $C_{14}H_{13}ClFN_2O$ 279.1]; LC/MS retention time (Method I): $t_R$=1.82 min.

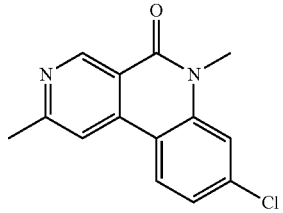 [SMILES: Cc1cc2c(cn1)c(=O)n(C)c1cc(Cl)ccc21]

Part E: 8-chloro-2,6-dimethylbenzo[c][2,7]naphthyridin-5(6H)-one

To a solution of 4-(4-chloro-2-fluorophenyl)-N,6-dimethylnicotinamide (520 mg, 1.86 mmol) in tetrahydrofuran (20 mL) at 0° C. was added NaH (224 mg, 5.60 mmol). The reaction mixture was brought to room temperature gradually and stirred at room temperature for 15 h. The reaction mixture was diluted with water (50 mL) and extracted with ethyl acetate (100 mL). The organic layer was separated, dried over $Na_2SO_4$ and concentrated under reduced pressure to afford product, 8-chloro-2,6 dimethylbenzo[c][2,7]naphthyridin-5 (6H)-one (480 mg, 1.51 mmol, 81% crude yield) as a red solid. The material was carried forward without further purification. LC/MS (ESI) m/e 259.0 [(M+H)$^+$, calcd for $C_{14}H_{12}ClN_2O$ 259.0]; LC/MS retention time (Method C): $t_R$=1.74 min. $^1$H NMR (300 MHz, METHANOL-$d_4$) δ ppm 9.41 (s, 1H), 8.48 (d, J=8.59 Hz, 1H), 8.23 (s, 1H), 7.69 (d, J=1.98 Hz, 1H), 7.44 (dd, J=8.64, 1.94 Hz, 1H), 3.78 (s, 3H), 2.75 (s, 3H).

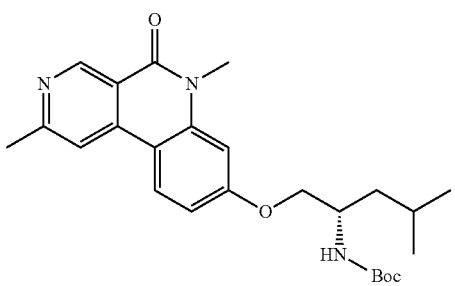 [SMILES: Cc1cc2c(cn1)c(=O)n(C)c1cc(OC[C@H](CC(C)C)NC(=O)OC(C)(C)C)ccc21]

Part F: (S)-tert-butyl (1-((2,6-dimethyl-5-oxo-5,6-dihydrobenzo[c][2,7]naphthyridin-8-yl)oxy)-4-methylpentan-2-yl)carbamate To the stirred solution of 8-chloro-2,6-dimethylbenzo[c][2,7]naphthyridin-5(6H)-one (100 mg, 0.387 mmol) and tert-butyl (1-hydroxy-2,4-dimethylpentan-2-yl)carbamate (168 mg, 0.773 mmol) in toluene (5 mL) was added cesium carbonate (189 mg, 0.580 mmol) and 2-di-t-butylphosphino-2',4',6'-tri-i-propyl-1,1'-biphenyl (9.85 mg, 0.023 mmol). The reaction mixture was degassed with argon for 5 min and palladium(II) acetate (26 mg, 0.116 mmol) was added to it. The reaction mixture was heated to 100° C. for 18 h. The reaction mixture was filtered through diatomaceous earth (Celite®) and the filtrate was evaporated. The residue obtained was purified by silica gel chromatography using ethyl acetate-petroleum ether to afford product, (S)-tert-butyl (1-((2,6-dimethyl-5-oxo-5,6 dihydrobenzo[c][2,7]naphthyridin-8-yl)oxy)-4-methylpentan-2-yl)carbamate (100 mg, 0.171 mmol, 44% yield) as dark yellow semi-solid. LC/MS (ESI) m/e 440.7 [(M+H)⁺, calcd for $C_{25}H_{34}N_3O_4$ 440.2]; LC/MS retention time (method D): $t_R$=0.89 min.

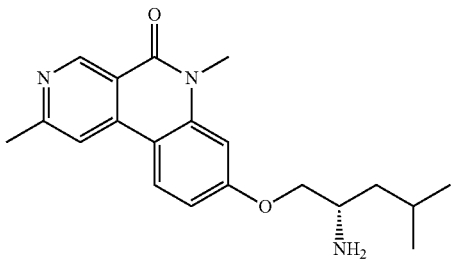 [SMILES: Cc1cc2c(cn1)c(=O)n(C)c1cc(OC[C@@H](N)CC(C)C)ccc21]

Part G. (S)-8-((2-amino-4-methylpentyl)oxy)-2,6 dimethylbenzo[c][2,7]naphthyridin-5(6H)-one (S)-tert-Butyl (1-((2,6-dimethyl-5-oxo-5,6-dihydrobenzo[c][2,7]naphthyridin-8-yl)oxy)-4-methylpentan-2-yl)carbamate (0.05 g, 0.114 mmol) was subjected to deprotection of the Boc group as described in Example 2, Part E, to give (S)-8-((2-amino-4-methylpentyl)oxy)-2,6 dimethylbenzo[c][2,7]naphthyridin-5(6H)-one (13 mg, 0.037 mmol, 33%) as colorless semi-solid. LC/MS (ESI) m/e 340.2 [(M+H)⁺, calcd for $C_{20}H_{26}N_3O_2$ 340.2]; LC/MS retention time (Method I): $t_R$=1.62 min. HPLC retention time (method A): $t_R$=8.17 min; HPLC retention time (method B): $t_R$=7.50 min. ¹H NMR (400 MHz, METHANOL-$d_4$) ppm 9.33 (s, 1H), 8.38 (d, J=8.78 Hz, 1H), 8.34-8.41 (m, 1H), 8.10 (s, 1H), 8.06-8.12 (m, 1H), 7.04-7.13 (m, 2H), 4.17 (dd, J=9.29, 4.02 Hz, 1H), 3.99 (dd, J=9.29, 7.28 Hz, 1H), 3.77 (s, 3H), 3.66 (d, J=2.76 Hz, 1H), 2.72 (s, 3H), 1.80-1.92 (m, 1H), 1.39-1.54 (m, 2H), 1.01 (dd, J=9.29, 6.53 Hz, 7H).

Example 68

(S)-8-((2-amino-4-methylpentyl)oxy)-9-chloro-2,6-dimethylbenzo[c][2,7]naphthyridin-5(6H)-one

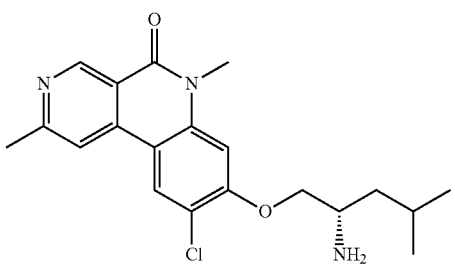

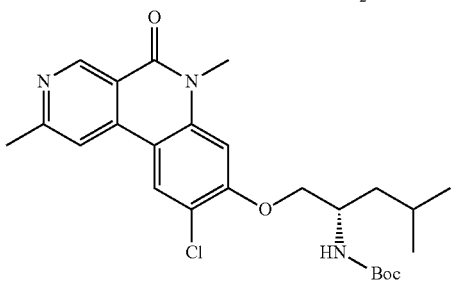

Part A. (S)-tert-butyl (1-((9-chloro-2,6-dimethyl-5-oxo-5,6-dihydrobenzo[c][2,7]naphthyridin-8-yl)oxy)-4-methylpentan-2-yl)carbamate (S)-tert-butyl (1-((2,6-dimethyl-5-oxo-5,6-dihydrobenzo[c][2,7]naphthyridin-8-yl)oxy)-4-methylpentan-2-yl)carbamate (0.05 g, 0.114 mmol), prepared as described in Example 67, Part F, was subjected to chlorination using NCS (0.018 g, 0.137 mmol), using the procedure described in Example 20, Part A, to give (S)-tert-butyl (1-((9-chloro-2,6-dimethyl-5-oxo-5,6-dihydrobenzo[c][2,7]naphthyridin-8-yl)oxy)-4-methylpentan-2-yl)carbamate (50 mg, 0.052 mmol, 45% yield) as colorless oil. LC/MS (ESI) m/e 474.7 [(M+H)⁺, calcd for $C_{25}H_{32}ClN_3O_4$ 474.2]; LC/MS retention time (method H): $t_R$=0.94 min.

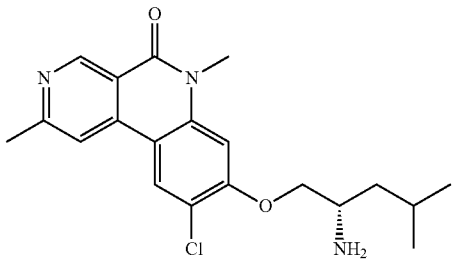

Part B. (S)-8-((2-amino-4-methylpentyl)oxy)-9-chloro-2,6-dimethylbenzo[c][2,7]naphthyridin-5(6H)-one (S)-tert-Butyl (1-((9-chloro-2,6-dimethyl-5-oxo-5,6 dihydrobenzo[c][2,7]naphthyridin-8-yl)oxy)-4-methylpentan-2-yl)carbamate (0.04 g, 0.041 mmol) was subjected to deprotection of the Boc group using the procedure described in Example 2, Part E, to afford (S)-8-((2-amino-4-methylpentyl)oxy)-9-chloro-2,6-dimethylbenzo[c][2,7]naphthyridin-5(6H)-one (0.006 g, 0.015 mmol, 37% yield) as an off-white solid. LC/MS (ESI) m/e 373.8 [(M+H)⁺, calcd for $C_{20}H_{25}ClN_3O_2$ 374.2]; LC/MS retention time (Method C): $t_R$=1.55 min; HPLC retention time (Method A): $t_R$=10.18 min; HPLC retention time (Method B): $t_R$=15.48 min. ¹H NMR (400 MHz, METHANOL-$d_4$) ppm 9.37 (s, 1H), 8.46-8.53 (m, 1H), 8.14 (s, 1H), 7.19 (s, 1H), 4.23-4.31 (m, 1H), 4.03-4.11 (m, 1H), 3.78-3.88 (m, 3H) 2.73 (s, 1H), 2.70-2.77 (m, 3H), 1.81-1.90 (m, 1H), 1.44-1.58 (m, 2H), 0.96-1.06 (m, 6H).

Example 69

(S)-8-(2-amino-3-methoxypropoxy)-6-methylbenzo[c][2,7]naphthyridin-5(6H)-one

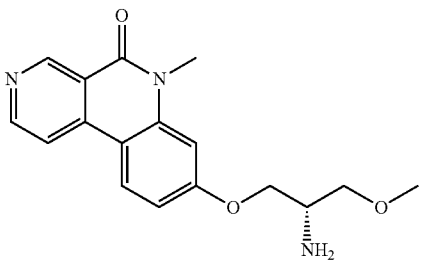

-continued

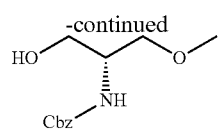

Part A: (R)-2-amino-3-methoxypropan-1-ol

Preparation as described in the literature Kim, H. J. et al. *Bioorg Med. Chem. Lett.*, 2011, 21, 3809-3812

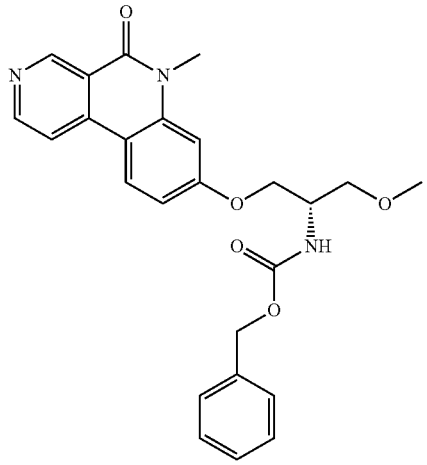 [SMILES: COC[C@@H](COc1ccc2c3ccncc3c(=O)n(C)c2c1)NC(=O)OCc1ccccc1]

Part B: (S)-benzyl (1-methoxy-3-((6-methyl-5-oxo-5,6-dihydrobenzo[c][2,7]naphthyridin-8-yl)oxy)propan-2-yl)carbamate Preparation as described in Example 16, Part H to afford the title product (0.12 g, 0.145 mmol, 24% yield) yellow gum. LC/MS, (ESI) m/z 448.6 [(M+H)$^+$, calcd for $C_{25}H_{26}N_3O_5$, 448.5]; LC/MS retention time (method D): $t_R$=0.74 min.

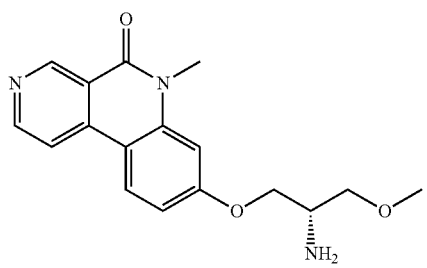

Part C: (S)-8-(2-amino-3-methoxypropoxy)-6-methylbenzo[c][2,7]naphthyridin-5(6H)-one Prepared as described in Example 2, Part E to afford the title product (14 mg, 0.042 mmol, 70% yield) as a brown gum. LC/MS, (ESI) m/z 314.2 [(M+H)$^+$, calcd for $C_{17}H_{20}N_3O_3$, 314.1]; LC/MS retention time (method C): $t_R$=1.38 min. HPLC retention time (method A): $t_R$=5.29 min; HPLC retention time (method B): $t_R$=5.31 min. $^1$H NMR (400 MHz, METHANOL-d4) δ ppm 9.47 (s, 1H) 8.77 (d, J=5.77 Hz, 1H) 8.42 (d, J=8.78 Hz, 1H) 8.25 (d, J=5.77 Hz, 1H) 7.04-7.17 (m, 2H) 4.26 (dd, J=9.29, 4.77 Hz, 1H) 4.10-4.19 (m, 1H) 3.81 (s, 3H) 3.52-3.65 (m, 2H) 3.44 (s, 3H) 3.38 (dt, J=3.33, 1.73 Hz, 1H).

Example 70

(S)-8-(2-amino-4-methylpentyloxy)-9-fluoro-4,6-dimethylbenzo[c][2,7]naphthyridin-5(6H)-one

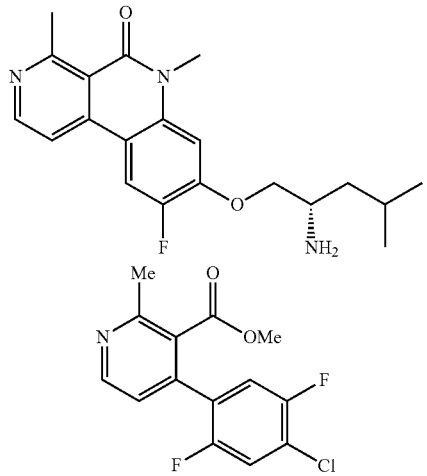

Part A. Methyl 4-(4-chloro-2,5-difluorophenyl)-2-methylnicotinate

Prepared as described in Example 16, Part D by carrying out a Suzuki coupling between methyl 4-chloro-2-methylnicotinate (prepared as described in Example 14, Part A) and 2-(4-chloro-2,5-difluorophenyl)-4,4,5,5-tetramethyl-1,3,2-dioxaborolane (prepared as described in Example 16, Part A-Part C) to afford methyl 4-(4-chloro-2,5-difluorophenyl)-2-methylnicotinate (3 g, 4.13 mmol, 24% yield) as a brown oil. $^1$H NMR (400 MHz, CDCl$_3$) δ ppm 8.60 (d, J=5.2 Hz, 1H), 7.36 (m, 1H), 7.20 (m, 2H), 3.74 (s, 3H), 2.49 (s, 3H).

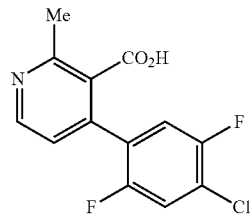 [SMILES: Cc1nccc(-c2cc(F)c(Cl)cc2F)c1C(=O)O]

Part B. 4-(4-chloro-2,5-difluorophenyl)-2-methylnicotinic Acid

Prepared as described in Example 16, Part E by carrying out hydrolysis of Methyl 4-(4-chloro-2,5-difluorophenyl)-2-methylnicotinate to afford 4-(4-chloro-2,5-difluorophenyl)-2-methylnicotinic acid (1.7 g, 4.02 mmol, 97% yield) as a white solid. $^1$H NMR (400 MHz, DMSO-d$_6$) δ ppm 13.38 (br. s., 1H), 8.58 (d, J=5.2 Hz, 1H), 7.74 (m, 1H), 7.53 (m, 1H), 7.41 (d, J=4.8 Hz, 1H), 2.43 (s, 3H).

181

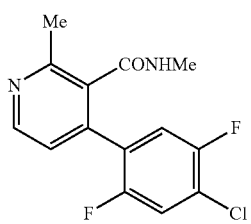

Part C. 4-(4-chloro-2,5-difluorophenyl)-N,2-dimethylnicotinamide

To the stirred solution of 4-(4-chloro-2,5-difluorophenyl)-2-methylnicotinic acid (1.7 g, 4.02 mmol) in DMF (0.5 mL) was added DIEA (2.81 mL, 16.06 mmol), HOBT (1.230 g, 8.03 mmol), EDC (1.155 g, 6.02 mmol) at 0° C. followed by addition of methylamine hydrochloride (0.488 g, 7.23 mmol). After stirring for 10 min, the ice bath was removed and the reaction mixture was allowed to stir overnight. The reaction mixture was concentrated under reduced pressure. The residue was diluted with ethyl acetate (10 mL) and washed with water (10 mL) followed by brine (10 mL). The organic layer was separated and dried over sodium sulphate, filtered, and concentrated under reduced pressure to afford 4-(4-chloro-2,5-difluorophenyl)-N,2-dimethylnicotinamide (1 g, 2.123 mmol, 53% crude yield) as a brown solid which was taken to the next step without purification. LC/MS (ESI) m/e 297.3 [(M+H)⁺, calcd for $C_{14}H_{12}ClF_2N_2O$ 297.1]; LC/MS retention time (method B): $t_R$=0.76 min.

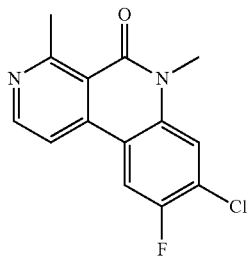 [SMILES: Cc1nccc2c1c(=O)n(C)c1cc(Cl)c(F)cc21]

Part D. 8-chloro-9-fluoro-4,6-dimethylbenzo[c][2,7]naphthyridin-5(6H)-one

Prepared as described in Example 16, Part G from 4-(4-chloro-2,5-difluorophenyl)-2-methylnicotinic acid to afford 8-chloro-9-fluoro-4,6 dimethylbenzo[c][2,7]naphthyridin-5(6H)-one (530 mg, 1.532 mmol, 72% yield) as a white solid. LC/MS (ESI) m/e 277.2 [(M+H)⁺, calcd for $C_{14}H_{11}ClFN_2O$ 277.04]; LC/MS retention time (method C): $t_R$=1.83 min.

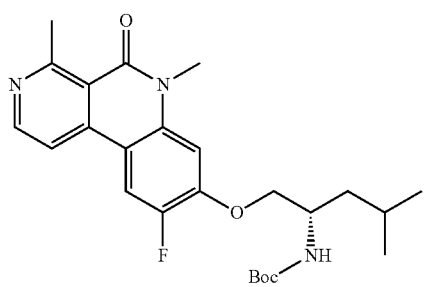 [SMILES: Cc1nccc2c1c(=O)n(C)c1cc(OC[C@H](CC(C)C)NC(=O)OC(C)(C)C)c(F)cc21]

182

Part E. (S)-tert-butyl 1-(9-fluoro-4,6-dimethyl-5-oxo-5,6-dihydrobenzo[c][2,7]naphthyridin-8-yloxy)-4-methylpentan-2-ylcarbamate Prepared as described in Example 16, Part H from 8-chloro-9-fluoro-4,6-dimethylbenzo[c][2,7]naphthyridin-5(6H)-one to afford (S)-tert-butyl 1-(9-fluoro-4,6-dimethyl-5-oxo-5,6-dihydrobenzo[c][2,7]naphthyridin-8-yloxy)-4-methylpentan-2-ylcarbamate (350 mg, 0.367 mmol, 24%) as an oil. LC/MS (ESI) m/e 458.6 [(M+H)⁺, calcd for $C_{25}H_{33}FN_3O_4$ 458.23]; LC/MS retention time (method B): $t_R$=1.24 min.

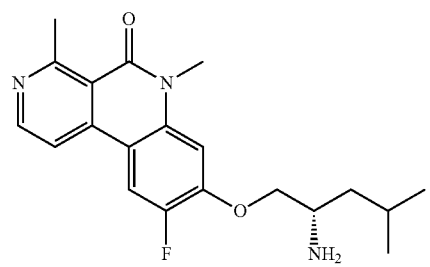

Part F. (S)-8-(2-amino-4-methylpentyloxy)-9-fluoro-4,6-dimethylbenzo[c][2,7]naphthyridin-5(6H)-one Prepared as described in Example 16, Part I from (S)-tert-butyl 1-(9-fluoro-4,6-dimethyl-5-oxo-5,6-dihydrobenzo[c][2,7]naphthyridin-8-yloxy)-4-methylpentan-2-ylcarbamate to afford (S)-8-(2-amino-4-methylpentyloxy)-9-fluoro-4,6-dimethylbenzo[c][2,7]naphthyridin-5(6H)-one (57.6 mg, 0.095 mmol, 91%) as an yellow oil. LC/MS (ESI) m/e 358.2 [(M+H)⁺, calcd for $C_{20}H_{25}FN_3O_2$ 358.2]; LC/MS retention time (method C): $t_R$=1.53 min; HPLC retention time (method B): $t_R$=8.16 min. ¹H NMR (400 MHz, METHANOL-$d_4$) δ ppm 8.58 (d, J=5.8 Hz, 1H), 8.23 (d, J=12.0 Hz, 1H), 8.09 (d, J=5.0 Hz, 1H), 7.19 (d, J=6.8 Hz, 1H), 4.26 (dd, J=9.5, 4.0 Hz, 1H), 4.08 (t, J=8.2 Hz, 1H), 3.79 (s, 3H), 3.41-3.38 (m, 1H), 3.10 (s, 3H), 1.94-1.82 (m, 1H), 1.58-1.39 (m, 2H), 1.04 (d, J=6.5 Hz, 3H), 1.01 (d, J=6.5 Hz, 3H).

Example 71

(S)-8-(2-amino-4-methylpentyloxy)-9-(hydroxymethyl)-4,6-dimethylbenzo[c][2,7]naphthyridin-5(6H)-one

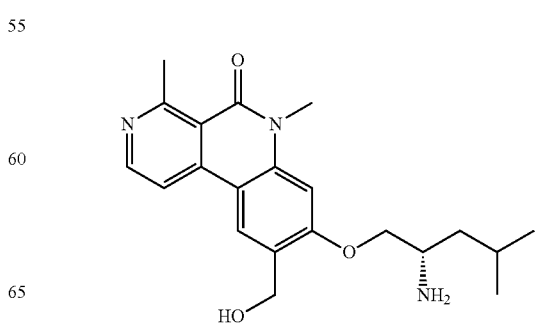

-continued

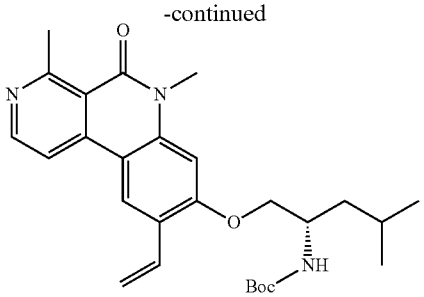

Part A. (S)-tert-butyl 1-(4,6-dimethyl-5-oxo-9-vinyl-5,6-dihydrobenzo[c][2,7]naphthyridin-8-yloxy)-4-methylpentan-2-ylcarbamate Prepared as described in Example 64, Part A and Example 46, Part B from (S)-tert-butyl 1-(9-bromo-4,6-dimethyl-5-oxo-5,6-dihydrobenzo[c][2,7]naphthyridin-8-yloxy)-4-methylpentan-2-ylcarbamate to afford the title product (1.2 g, 1.985 mmol, 64% yield). LC/MS (ESI) m/e 466.2 [(M+H)$^+$, calcd for $C_{27}H_{36}N_3O_4$ 466.3]; LC/MS retention time (method B): $t_R$=1.79 min.

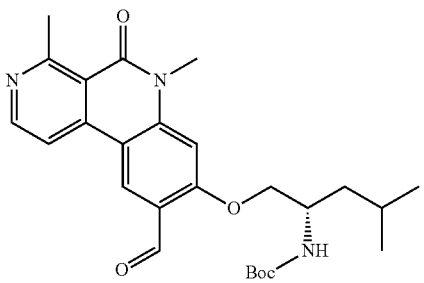 [SMILES: Cc1nccc2c1c(=O)n(C)c1cc(OC[C@H](CC(C)C)NC(=O)OC(C)(C)C)c(C=O)cc21]

Part B. (S)-tert-butyl 1-(9-formyl-4,6-dimethyl-5-oxo-5,6-dihydrobenzo[c][2,7]naphthyridin-8-yloxy)-4-methylpentan-2-ylcarbamate Prepared as described in Example 55, Part B from (S)-tert-butyl 1-(4,6-dimethyl-5-oxo-9-vinyl-5,6-dihydrobenzo[c][2,7]naphthyridin-8-yloxy)-4-methylpentan-2-ylcarbamate to afford the title product (1.2 g, 0.980 mmol, 49% yield) as a yellow gum. LC/MS (ESI) m/e 468.2 [(M+H)$^+$, calcd for $C_{26}H_{34}N_3O_5$ 468.2]; LC/MS retention time (method B): $t_R$=1.66 min.

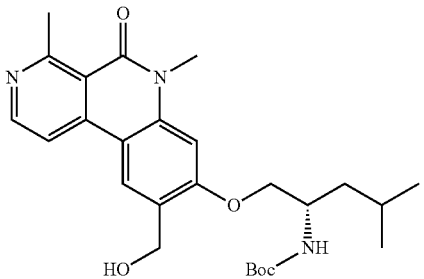 [SMILES: Cc1nccc2c1c(=O)n(C)c1cc(OC[C@H](CC(C)C)NC(=O)OC(C)(C)C)c(CO)cc21]

Part C. (S)-tert-butyl 1-(9-(hydroxymethyl)-4,6-dimethyl-5-oxo-5,6-dihydrobenzo[c][2,7]naphthyridin-8-yloxy)-4-methylpentan-2-ylcarbamate Prepared as described in Example 31, Part E to afford the title product (0.100 g, 0.160 mmol, 87% yield) as a brown gum. LC/MS (ESI) m/e 470.2 [(M+H)$^+$, calcd for $C_{26}H_{36}N_3O_5$ 470.2]; LC/MS retention time (method B): $t_R$=1.48 min.

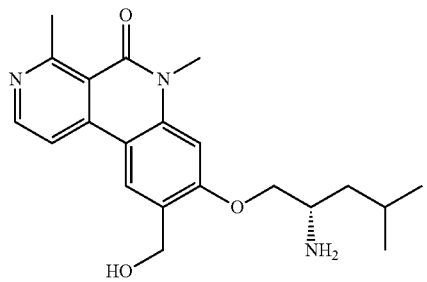 [SMILES: Cc1nccc2c1c(=O)n(C)c1cc(OC[C@@H](N)CC(C)C)c(CO)cc21]

Part D. (S)-8-(2-amino-4-methylpentyloxy)-9-(hydroxymethyl)-4,6-dimethylbenzo[c][2,7]naphthyridin-5(6H)-one Prepared as described in Example 2, Part E to afford the title product (28 mg, 0.073 mmol, 34% yield) as an off-white solid. LC/MS (ESI) m/e 370.2 [(M+H)$^+$, calcd for $C_{21}H_{28}N_3O_3$ 370.2]; LC/MS retention time (method B): $t_R$=1.03 min. HPLC retention time (method A): $t_R$=7.46 min; HPLC retention time (method B): $t_R$=8.13 min; $^1$H NMR (400 MHz, METHANOL-d$_4$) δ ppm 8.55 (d, J=5.8 Hz, 1H), 8.37 (s, 1H), 8.12 (d, J=5.8 Hz, 1H), 7.01 (s, 1H), 4.80 (s, 2H), 4.28 (dd, J=9.5, 3.5 Hz, 1H), 4.08 (dd, J=9.5, 7.0 Hz, 1H), 3.78 (s, 3H), 3.48-3.40 (m, 1H), 3.08 (s, 3H), 1.92-1.80 (m, 1H), 1.64-1.41 (m, 2H), 1.05 (d, J=6.5 Hz, 3H), 1.03 (d, J=6.8 Hz, 3H).

Example 72

(S)-8-(2-amino-4-methylpentyloxy)-4,6-dimethyl-9-(oxazol-5-yl)benzo[c][2,7]naphthyridin-5(6H)-one

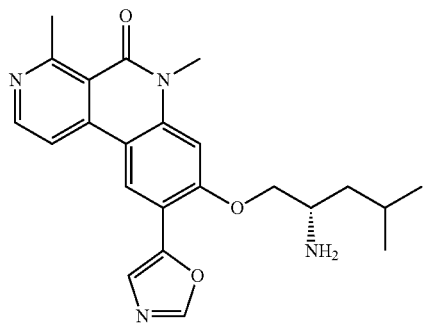

-continued

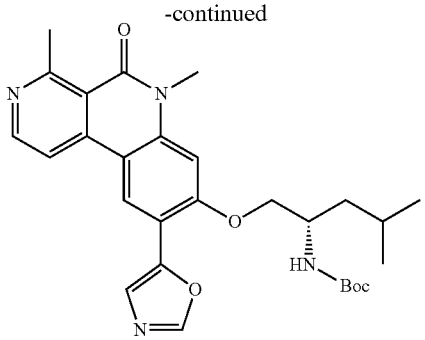

Part A. (S)-tert-butyl 1-(4,6-dimethyl-9-(oxazol-5-yl)-5-oxo-5,6-dihydrobenzo[c][2,7]naphthyridin-8-yloxy)-4-methylpentan-2-ylcarbamate Prepared as described in an Example 71, Part D and Example 48, Part B from (S)-tert-butyl 1-(9-formyl-4,6-dimethyl-5-oxo-5,6-dihydrobenzo[c][2,7]naphthyridin-8-yloxy)-4-methylpentan-2-ylcarbamate to afford the title product (150 mg, 0.068 mmol, 56% yield) as a yellow gum. LC/MS (ESI) m/e 507.2 [(M+H)$^+$, calcd for $C_{28}H_{35}N_4O_5$ 507.2] LC/MS retention time (method B): $t_R$=1.64 min.

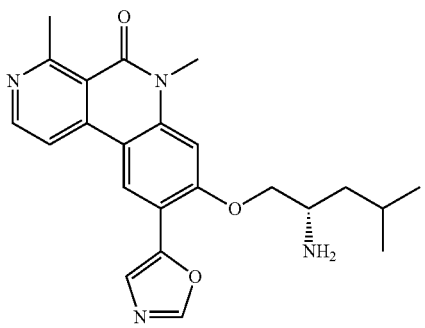

Part B. (S)-8-(2-amino-4-methylpentyloxy)-4,6-dimethyl-9-(oxazol-5-yl)benzo[c][2,7]naphthyridin-5(6H)-one Prepared as described in Example 2, Part E from (S)-tert-butyl 1-(9-formyl-4,6-dimethyl-5-oxo-5,6-dihydrobenzo[c][2,7]naphthyridin-8-yloxy)-4-methylpentan-2-ylcarbamate to afford the title product (20 mg, 0.045 mmol, 67% yield) as a yellow solid. LC/MS (ESI) m/e 407.2 [(M+H)$^+$, calcd for $C_{23}H_{27}N_4O_3$ 407.2] LC/MS retention time (method B): $t_R$=1.64 min. HPLC retention time (method A): $t_R$=7.46 min; HPLC retention time (method A): $t_R$=8.89 min HPLC retention time (method B): $t_R$=8.80 min $^1$H NMR (400 MHz, METHANOL-$d_4$) δ ppm 8.66 (s, 1H), 8.57 (d, J=5.8 Hz, 1H), 8.34 (s, 1H), 8.15 (d, J=5.8 Hz, 1H), 7.60 (s, 1H), 7.08 (s, 1H), 4.38-4.26 (m, 1H), 4.24-4.17 (m, 1H), 3.76 (s, 3H), 3.48 (dd, J=3.3, 1.8 Hz, 1H), 3.05 (s, 3H), 1.93-1.82 (m, 1H), 1.65-1.44 (m, 2H), 1.04 (d, J=2.5 Hz, 3H), 1.02 (d, J=2.5 Hz, 3H).

Example 73

8-(2-amino-5,5,5-trifluoropentyloxy)-4,6-dimethyl-5-oxo-5,6-dihydrobenzo[c][2,7]naphthyridine-9-carbonitrile

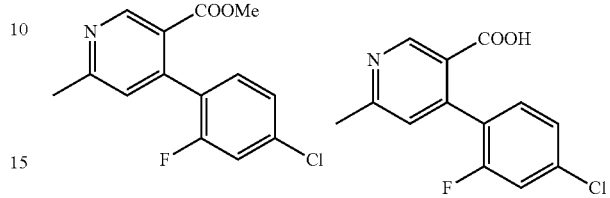

8-chloro-4,6-dimethylbenzo[c][2,7]naphthyridin-5(6H)-one

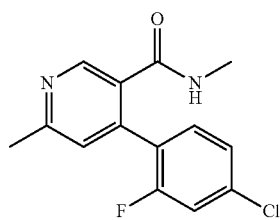 [SMILES: CNC(=O)c1cnc(C)cc1-c1ccc(Cl)cc1F]

Part A. tert-butyl 1-(4,6-dimethyl-5-oxo-5,6-dihydrobenzo[c][2,7]naphthyridin-8-yloxy)-5,5,5-trifluoropentan-2-ylcarbamate Prepared as described in Example 16, Part H to afford tert-butyl 1-(4,6-dimethyl-5-oxo-5,6-dihydrobenzo[c][2,7]naphthyridin-8-yloxy)-5,5,5-trifluoropentan-2-ylcarbamate (300 mg, 0.416 mmol, 54% yield) as a white solid. $^1$H LC/MS (ESI) m/e 480.2 [(M+H)$^+$, calcd for $C_{24}H_{29}F_3N_3O_4$ 480.2] LC/MS retention time (method H): $t_R$=2.22 min.

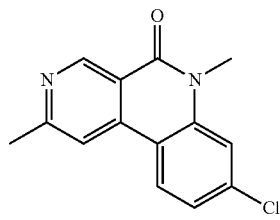 [SMILES: Cc1cc2c(cn1)c(=O)n(C)c1cc(Cl)ccc21]

Part B. tert-butyl 1-(9-bromo-4,6-dimethyl-5-oxo-5,6-dihydrobenzo[c][2,7]naphthyridin-8-yloxy)-5,5,5-trifluoropentan-2-ylcarbamate Prepared as described in Example 3, Part A to afford the title product (50 mg, 0.06 mmol, 58% yield) as a pale yellow solid. $^1$H LC/MS (ESI) m/e 559.0 [(M+2H)$^+$, calcd for $C_{24}H_{29}BrF_3N_3O_4$ 559.1] LC/MS retention time (method C): $t_R$=2.24 min.

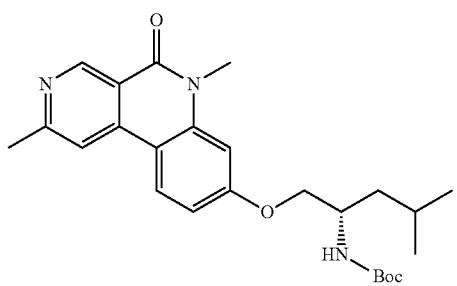 [SMILES: Cc1cc2c(cn1)c(=O)n(C)c1cc(OC[C@H](CC(C)C)NC(=O)OC(C)(C)C)ccc21]

Part C. tert-butyl 1-(9-cyano-4,6-dimethyl-5-oxo-5,6-dihydrobenzo[c][2,7]naphthyridin-8-yloxy)-5,5,5-trifluoropentan-2-ylcarbamate Prepared as described in Example 64, Part B to afford the title product (40 mg, 0.079 mmol, 11% yield) as a pale yellow solid. LC/MS (ESI) m/e 505.4 [(M+H)$^+$, calcd for $C_{25}H_{28}F_3N_4O_4$ 505.2] LC/MS retention time (method E): $t_R$=1.1 min.

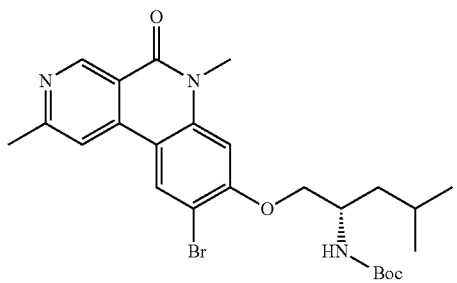 [SMILES: Cc1cc2c(cn1)c(=O)n(C)c1cc(OC[C@H](CC(C)C)NC(=O)OC(C)(C)C)c(Br)cc21]

Part D. 8-(2-amino-5,5,5-trifluoropentyloxy)-4,6-dimethyl-5-oxo-5,6-dihydrobenzo[c][2,7]naphthyridine-9-carbonitrile Prepared as described in Example 2, Part E to afford the title product (50 mg, 0.036 mmol, 45% yield) as an off white solid. LC/MS (ESI) m/e 405.4 [(M+H)$^+$, calcd for $C_{20}H_{20}F_3N_4O_2$ 405.1]; LC/MS retention time (method E): $t_R$=0.71 min. HPLC retention time (method A): $t_R$=8.35 min; HPLC retention time (method B): $t_R$=9.38 min. $^1$H NMR (400 MHz, DMSO-$d_6$) δ ppm 8.98 (s, 1H), 8.67 (d, J=5.6 Hz, 1H), 8.30 (d, J=5.6 Hz, 1H), 7.12 (s, 1H), 4.19 (d, J=6.0 Hz, 2H), 3.71 (s, 3H), 3.16-3.14 (m, 1H), 3.00 (s, 3H), 2.45-2.30 (m, 2H), 1.89-1.80 (m, 1H), 1.58-1.55 (m, 1H).

Example 74

(S)-8-(2-amino-4-methylpentyloxy)-4,6-dimethyl-9-(trifluoromethyl)benzo[c][2,7]naphthyridin-5(6H)-one

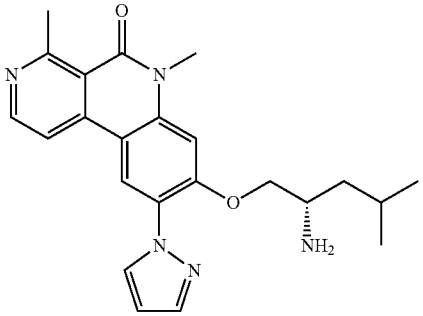

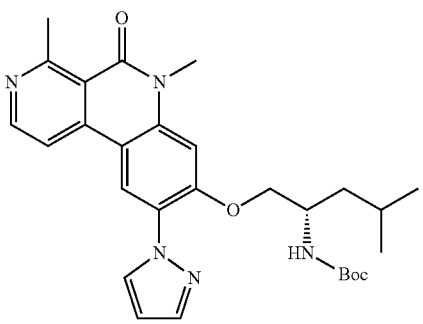

Part A. (S)-tert-butyl 1-(4,6-dimethyl-5-oxo-9-(1H-pyrazol-1-yl)-5,6-dihydrobenzo[c][2,7]naphthyridin-8-yloxy)-4-methylpentan-2-ylcarbamate To the solution of (S)-tert-butyl (1-((9-bromo-4,6-dimethyl-5-oxo-5,6-dihydrobenzo[c][2,7]naphthyridin-8-yl)oxy)-4-methylpentan-2-yl)carbamate (50 mg, 0.096 mmol) and 1H-pyrazole (7.88 mg, 0.116 mmol) in 1,4-dioxane (2 mL) and DMF (0.5 mL), was added copper(I) iodide (18.37 mg, 0.096 mmol), N1,N2-dimethylethane-1,2-diamine (17.00 mg, 0.193 mmol) and potassium phosphate (61.4 mg, 0.289 mmol). The reaction mixture was degassed with nitrogen for 5 min and heated to 170° C. for 1 h in a microwave. The reaction mixture was cooled to room temperature, filtered through diatomaceous earth (Celite®) and the filtrate concentrated under reduced pressure. The residue was purified by preparative TLC (eluent 2% MeOH:DCM) to afford (S)-tert-butyl 1-(4,6-dimethyl-5-oxo-9-(1H-pyrazol-1-yl)-5,6-dihydrobenzo[c][2,7]naphthyridin-8-yloxy)-4-methylpentan-2-ylcarbamate (40 mg, 0.028 mmol, 29% yield) as a brown solid. LC/MS (ESI) m/e 406.5 [(M+H)$^+$, calcd for $C_{23}H_{28}N_5O_2$ 406.2] LC/MS retention time (method E): $t_R$=0.71 min.

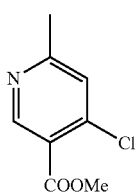

Part B. (S)-8-(2-amino-4-methylpentyloxy)-4,6-dimethyl-9-(trifluoromethyl)benzo[c][2,7]naphthyridin-5(6H)-one Prepared as described in Example 2, Part E from (S)-tert-butyl 1-(4,6-dimethyl-5-oxo-9-(1H-pyrazol-1-yl)-5,6-dihydrobenzo[c][2,7]naphthyridin-8-yloxy)-4-methylpentan-2-ylcarbamate to afford (S)-8-(2-amino-4-methylpentyloxy)-4,6-dimethyl-9-(trifluoromethyl)benzo[c][2,7]naphthyridin-5(6H)-one (2 mg, 0.005 mmol, 24% yield) as a green yellow semisolid. LC/MS (ESI) m/e 406.2 [(M+H)+, calcd for $C_{23}H_{28}N_5O_2$ 406.2]; HPLC retention time (method A): $t_R$=8.37 min HPLC retention time (method B): $t_R$=9.54 min; $^1$H NMR of racemic compound (400 MHz, DMSO-$d_6$) δ ppm 8.98 (s, 1H), 8.67 (d, J=5.6 Hz, 1H), 8.30 (d, J=5.6 Hz, 1H), 7.12 (s, 1H), 4.19 (d, J=6.0 Hz, 2H), 3.71 (s, 3H), 3.16-3.14 (m, 1H), 3.00 (s, 3H), 2.45-2.30 (m, 2H), 1.89-1.80 (m, 1H), 1.58-1.55 (m, 1H).

Example 75

(S)-8-(2-amino-4-methylpentyloxy)-4,6-dimethyl-9-(trifluoromethyl)benzo[c][2,7]naphthyridin-5(6H)-one

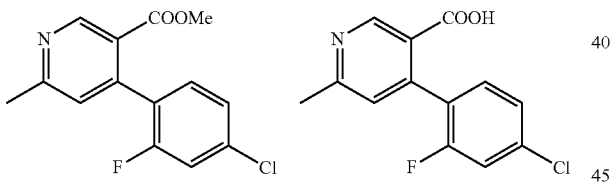

Part A. (S)-2-(1-(4,6-dimethyl-5-oxo-5,6-dihydrobenzo[c][2,7]naphthyridin-8-yloxy)-4-methylpentan-2-yl)isoindoline-1,3-dione (S)-tert-butyl (1-((4,6-dimethyl-5-oxo-5,6-dihydrobenzo[c][2,7]naphthyridin-8-yl)oxy)-4-methylpentan-2-yl)carbamate (300 mg, 0.683 mmol) was taken up in AcOH (15 mL) and treated with periodic acid (156 mg, 0.683 mmol) and $H_2SO_4$ (0.018 mL, 0.341 mmol). The reaction mixture was heated to 80° C. for 20 min after which time iodine (104 mg, 0.410 mmol) was added and heating was continued for an additional 3 h. After cooling, the volatiles were evaporated. The residue was taken up in ethyl acetate (25 mL) and organic layer was washed with saturated aqueous $NaHCO_3$ (10 mL), then brine (10 mL), dried with $Na_2SO_4$, filtered and concentrated under reduced pressure to afford (S)-2-(1-(4,6-dimethyl-5-oxo-5,6-dihydrobenzo[c][2,7]naphthyridin-8-yloxy)-4-methylpentan-2-yl)isoindoline-1,3-dione (300 mg, 0.61 mmol, 90% crude yield) as a brown solid. This was taken to the next step without further purification. LC/MS (ESI) m/e 466.1 [(M+H)+, calcd for $C_{20}H_{25}IN_3O_2$ 466.1]; LC/MS retention time (method F): $t_R$=0.58 min.

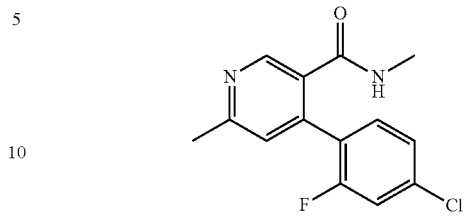

Part B. (S)-2-(1-(9-iodo-4,6-dimethyl-5-oxo-5,6-dihydrobenzo[c][2,7]naphthyridin-8-yloxy)-4-methylpentan-2-yl)isoindoline-1,3-dione To a solution of (S)-8-((2-amino-4-methylpentyl)oxy)-9-iodo-4,6-dimethylbenzo[c][2,7]naphthyridin-5(6H)-one (130 mg, 0.140 mmol) in 1,4-dioxane (3 mL) was added N-ethyl-N-isopropylpropan-2-amine (54.2 mg, 0.419 mmol) and isobenzofuran-1,3-dione (24.83 mg, 0.168 mmol). The reaction mixture was refluxed for 16 h. After cooling, the reaction mixture was diluted with EtOAc (10 mL). The organics were washed with water, saturated aqueous $NaHCO_3$. The combined aqueous layers were extracted with ethyl acetate (3×10 mL). The combined organic layers were dried over sodium sulfate and concentrated under reduced pressure. The residue was purified by preparative TLC plate using 2% Methanol: DCM as a eluent system to afford (S)-2-(1-((9-iodo-4,6-dimethyl-5-oxo-5,6-dihydrobenzo[c][2,7]naphthyridin-8-yl)oxy)-4-methylpentan-2-yl)isoindoline-1,3-dione (85 mg, 0.084 mmol, 60% yield) as a pale yellow solid. LC/MS (ESI) m/e 596.5 [(M+H)+, calcd for $C_{28}H_{27}IN_3O_4$ 596.1] LC/MS retention time (method E): $t_R$=1.3 min.

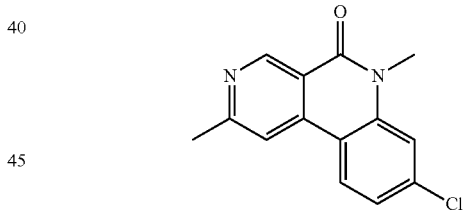

Part C. (S)-2-(1-(4,6-dimethyl-5-oxo-9-(trifluoromethyl)-5,6-dihydrobenzo[c][2,7]naphthyridin-8-yloxy)-4-methylpentan-2-yl)isoindoline-1,3-dione Dried potassium fluoride (19.51 mg, 0.336 mmol) and copper(I) iodide (64.0 mg, 0.336 mmol) were mixed and heated to 200° C. under gentle shaking at reduced pressure (1 Torr) until a light yellow-greenish color appeared. After cooling, anhydrous N-methyl-2-pyrrolidinone (1 mL) was added, followed by (S)-2-(1-((9-iodo-4,6-dimethyl-5-oxo-5,6-dihydrobenzo[c][2,7]naphthyridin-8-yl)oxy)-4-methylpentan-2-yl)isoindoline-1,3-dione (100 mg, 0.168 mmol) and trimethyl(trifluoromethyl)silane (0.075 mL, 0.504 mmol). The brown solution thus obtained was heated at 90° C. for 16 h. After cooling, aqueous ammonia (10 mL) was added to the reaction mixture. The reaction mixture was and extracted with ethyl acetate (3×10 mL). The combined organic layers were washed with brine (1×10 mL), dried over sodium sulfate and concentrated under reduced pressure. The residue was purified by preparative TLC (50% ethyl acetate: petroleum ether as eluent system) to afford (S)-2-(1-(4,6-dimethyl-5-oxo-9-(trifluoromethyl)-5,6-dihydrobenzo[c][2,7]naphthyridin-8-yloxy)-4-methylpentan-2-yl)isoindoline-1,3-dione (80 mg, 0.033 mmol, 20% yield, 22% purity) as a pale yellow solid. LC/MS (ESI) m/e 538.6 [(M+H)$^+$, calcd for $C_{29}H_{27}F_3N_3O_4$ 538.2] LC/MS retention time (method E): $t_R$=1.27 min.

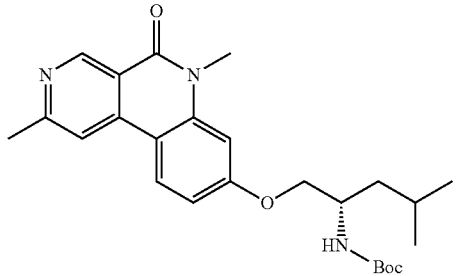 [SMILES: Cc1cc2c(cn1)c(=O)n(C)c1cc(OC[C@H](CC(C)C)NC(=O)OC(C)(C)C)ccc21]

Part D. (S)-8-(2-amino-4-methylpentyloxy)-4,6-dimethyl-9-(trifluoromethyl)benzo[c][2,7]naphthyridin-5(6H)-one To a solution of (S)-2-(1-((4,6-dimethyl-5-oxo-9-(trifluoromethyl)-5,6-dihydrobenzo[c][2,7]naphthyridin-8-yl)oxy)-4-methylpentan-2-yl)isoindoline-1,3-dione (50 mg, 0.019 mmol) in EtOH (4 mL) was added hydrazine hydrate (6.52 mg, 0.130 mmol). The reaction mixture was allowed to stir at 45° C. for 2 h. After cooling, the reaction mixture was concentrated under reduced pressure. The residue was purified by reverse phase HPLC (Symmetry C-18 column (19.0×250 mm) 7.0 micron; mobile phase A: Ammonium acetate in water; mobile phase B: acetonitrile; flow rate: 16.0 mL) to afford the (S)-8-((2-amino-4-methylpentyl)oxy)-4,6-dimethyl-9 (trifluoromethyl)benzo[c][2,7]naphthyridin-5(6H)-one (5 mg, 0.012 mmol, 64% yield) as an off-white solid. LC/MS (ESI) m/e 408.2 [(M+H)$^+$, calcd for $C_{21}H_{25}F_3N_3O_2$ 408.2] LC/MS retention time (method B): $t_R$=1.25 min. HPLC retention time (method A): $t_R$=10.10 min HPLC retention time (method B): $t_R$=10.69 min; $^1$H NMR (400 MHz, METHANOL-d$_4$) δ ppm 8.66 (s, 1H), 8.63 (d, J=5.6 Hz, 1H), 8.22 (d, J=5.6 Hz, 1H), 7.19 (s, 1H), 4.42-4.38 (m, 1H), 4.28-4.20 (m, 1H), 3.83 (s, 3H), 3.58-3.49 (m, 1H), 3.11 (s, 3H), 1.90-1.82 (m, 1H), 1.68-1.62 (m, 1H), 1.58-1.53 (m, 1H), 1.10-1.00 (m, 6H).

Example 76

(S)-8-(2-amino-4-methylpentyloxy)-4,6-dimethyl-9-(methylsulfonyl)benzo[c][2,7]naphthyridin-5(6H)-one

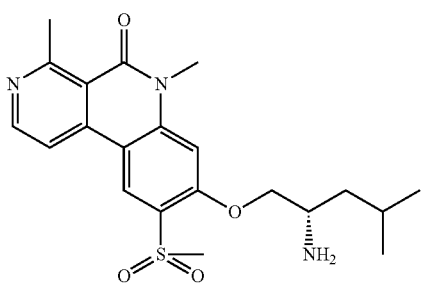

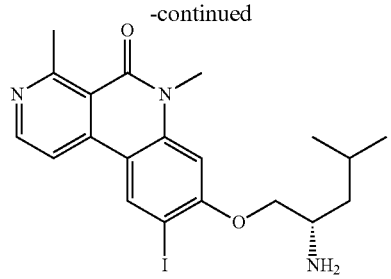

Part A. (S)-2-(1-(4,6-dimethyl-5-oxo-5,6-dihydrobenzo[c][2,7]naphthyridin-8-yloxy)-4-methylpentan-2-yl)isoindoline-1,3-dione (S)-tert-Butyl (1-((4,6-dimethyl-5-oxo-5,6-dihydrobenzo[c][2,7]naphthyridin-8-yl)oxy)-4-methylpentan-2-yl)carbamate (300 mg, 0.683 mmol) was taken up in AcOH (15 mL) and treated with periodic acid (156 mg, 0.683 mmol), and H$_2$SO$_4$ (0.018 mL, 0.341 mmol). The reaction mixture was heated to 80° C. and maintained for 20 min after which iodine (104 mg, 0.410 mmol) was added and heating was continued at 80° C. for an additional 3 h. After cooling, the volatiles were evaporated and the residue was taken up in with ethyl acetate (25 mL). The organic layer was washed with saturated aqueous NaHCO$_3$ (10 mL), then brine (10 mL), dried over Na$_2$SO$_4$, filtered and concentrated under reduced pressure to afford (S)-2-(1-(4,6-dimethyl-5-oxo-5,6-dihydrobenzo[c][2,7]naphthyridin-8-yloxy)-4-methylpentan-2-yl)isoindoline-1,3-dione (300 mg, 0.61 mmol, 90% crude yield) as a brown solid. The material was taken to the next step without further purification. LC/MS (ESI) m/e 466.1 [(M+H)$^+$, calcd for $C_{20}H_{25}IN_3O_2$ 466.1] LC/MS retention time (method D): $t_R$=0.58 min.

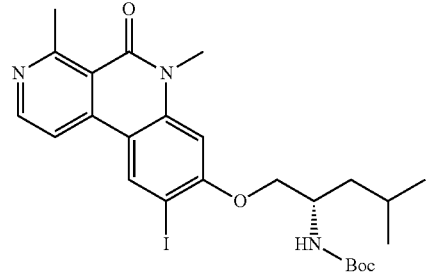 [SMILES: Cc1nccc2c1c(=O)n(C)c1cc(OC[C@H](CC(C)C)NC(=O)OC(C)(C)C)c(I)cc21]

Part B. (S)-tert-butyl 1-(9-iodo-4,6-dimethyl-5-oxo-5,6-dihydrobenzo[c][2,7]naphthyridin-8-yloxy)-4-methylpentan-2-ylcarbamate Prepared as described in Example 15, Part C to afford (S)-tert-butyl 1-(9-iodo-4,6-dimethyl-5-oxo-5,6-dihydrobenzo[c][2,7]naphthyridin-8-yloxy)-4-methylpentan-2-ylcarbamate (300 mg, 0.531 mmol, 82% yield) as a red-orange solid. LC/MS (ESI) m/e 566.5 [(M+H)$^+$, calcd for $C_{25}H_{33}IN_3O_4$ 566.2]; LC/MS retention time (method E): $t_R$=1.27 min.

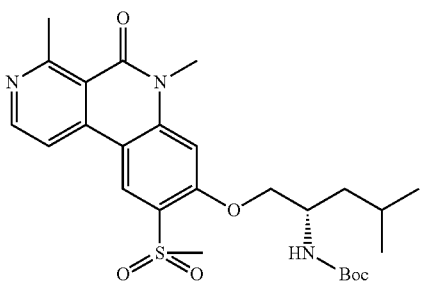 [SMILES: Cc1nccc2c1c(=O)n(C)c1cc(OC[C@H](CC(C)C)NC(=O)OC(C)(C)C)c(S(C)(=O)=O)cc21]

Part C. (S)-tert-butyl 1-(4,6-dimethyl-9-(methylsulfonyl)-5-oxo-5,6-dihydrobenzo[c][2,7]naphthyridin-8-yloxy)-4-methylpentan-2-ylcarbamate (S)-tert-butyl (1-((9-iodo-4,6-dimethyl-5-oxo-5,6-dihydrobenzo[c][2,7]naphthyridin-8-yl)oxy)-4-methylpentan-2-yl)carbamate (100 mg, 0.177 mmol), L-proline (20.36 mg, 0.177 mmol), methanesulfinic acid, sodium salt (181 mg, 1.769 mmol), NaOH (11.32 mg, 0.283 mmol) and copper(I) iodide (33.7 mg, 0.177 mmol) were taken up in DMSO (5 mL) and purged with nitrogen gas for 5 min. The resultant mixture was sealed in a microwave tube and heated at 100° C. in a microwave for 2.5 h. The reaction mixture was cooled to room temperature, treated with ice-cold water (5 mL) and extracted with ethyl acetate (3×5 mL). The combined organic layers were dried over sodium sulfate, filtered and concentrated under reduced pressure to afford (S)-tert-butyl 1-(4,6-dimethyl-9-(methylsulfonyl)-5-oxo-5,6-dihydrobenzo[c][2,7]naphthyridin-8-yloxy)-4-methylpentan-2-ylcarbamate (150 mg, 0.07 mmol, 39% crude yield, 24% purity) as a black gummy solid. The material was taken to the next step with out purification. LC/MS (ESI) m/e 518.2 [(M+H)$^+$, calcd for $C_{26}H_{36}N_3O_6S$ 518.2] LC/MS retention time (method B): $t_R$=1.51 min.

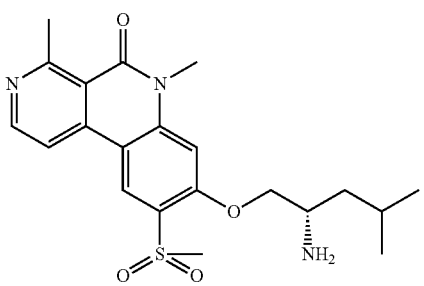 [SMILES: Cc1nccc2c1c(=O)n(C)c1cc(OC[C@@H](N)CC(C)C)c(S(C)(=O)=O)cc21]

Part D. (S)-8-(2-amino-4-methylpentyloxy)-4,6-dimethyl-9-(methylsulfonyl)benzo[c][2,7]naphthyridin-5(6H)-one Prepared as in Example 2, Part E to afford (S)-8-(2-amino-4-methylpentyloxy)-4,6-dimethyl-9-(methylsulfonyl)benzo[c][2,7]naphthyridin-5(6H)-one (4 mg, 0.009 mmol, 13% yield) as an off-white solid. LC/MS (ESI) m/e 466.1 [(M+H)$^+$, calcd for $C_{20}H_{25}IN_3O_2$ 466.1]; LC/MS retention time (method D): $t_R$=0.58 min. HPLC retention time (method): $t_R$=min and HPLC retention time (method): $t_R$=min. $^1$H NMR (400 MHz, CD$_3$OD) δ ppm −8.85 (s 1H), 8.65 (d, J=6 Hz, 1H), 8.25 (d, J=6 Hz, 1H), 7.25 (s, 1H), 4.65 (m, 1H), 4.32 (m, 1H), 3.85 (s, 4H), 3.1 (s, 3H), 1.93 (s, 3H), 1.92 (m, 1H), 1.65 (m, 2H), 1.01 (m, 6H).

Example 77

(S)-8-(2-amino-4-methylpentyloxy)-4-methylbenzo[c][2,7]naphthyridin-5(6H)-one

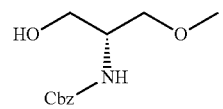

To a solution of (S)-tert-butyl (1-((6-(4-methoxybenzyl)-4-methyl-5-oxo-5,6-dihydrobenzo[c][2,7]naphthyridin-8-yl)oxy)-4-methylpentan-2-yl)carbamate (500 mg, 0.192 mmol) (prepared as described in Example 49), in acetonitrile (5 mL) and water (5 mL) was added ceric ammonium nitrate (527 mg, 0.962 mmol). The reaction mixture was stirred for 5 h at room temperature. The reaction mixture was diluted with ethyl acetate (5 mL) and water (5 mL). The organic layer was separated, dried with sodium sulfate and concentrated under reduced pressure. The residue was purified by silica gel chromatography (1:1 ethyl acetate:hexane) to afford (S)-8-(2-amino-4-methylpentyloxy)-4-methylbenzo[c][2,7]naphthyridin-5(6H)-one (100 mg, 0.154 mmol, 80% yield) as an off-white solid. LC/MS (ESI) m/e 326.2 [(M+H)$^+$, calcd for $C_{19}H_{24}N_3O_2$ 326.2] LC/MS retention time (method C): $t_R$=1.56 min. HPLC retention time (method A): $t_R$=6.98 min; HPLC retention time (method B): $t_R$=6.96 min. $^1$H NMR (400 MHz, CD$_3$OD) δ ppm 6.32 (m, 1H), 8.44 (m, 2H), 7.13 (m, 1H), 6.94 (d, J=2.4 Hz, 1H), 4.4 (m, 1H), 4.3 (m, 1H), 3.75 (m, 1H), 3.2 (s, 3H), 1.75 (m, 3H), 1.10 (m, 6H).

Example 78

(R)-8-(2-amino-4-methylpentyloxy)-4,6-dimethyl-5-oxo-5,6-dihydrobenzo[c][2,7]naphthyridine-9-carbonitrile

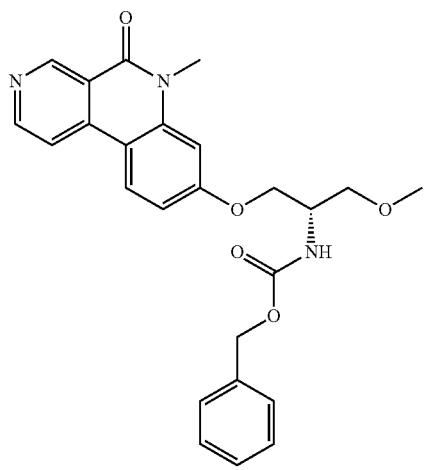

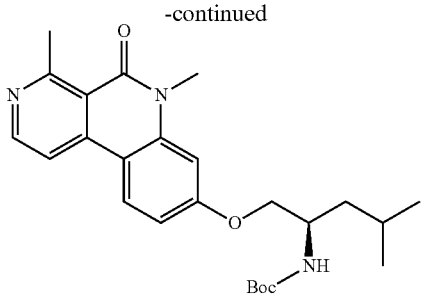

Part A. (R)-tert-butyl 1-(4,6-dimethyl-5-oxo-5,6-dihydrobenzo[c][2,7]naphthyridin-8-yloxy)-4-methylpentan-2-ylcarbamate Buchwald coupling performed as described in Example 16, Part H to afford title compound (900 mg, 1.58 mmol, 54% yield, 77% purity) as an off-white solid. LC/MS (ESI) m/e 440.3 [(M+H)$^+$, calcd for $C_{25}H_{34}N_3O_4$ 440.2] LC/MS retention time (method D): $t_R$=0.89 min.

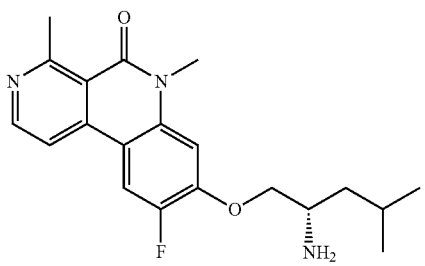 [SMILES: Cc1nccc2c1c(=O)n(C)c1cc(OC[C@@H](N)CC(C)C)c(F)cc21]

Part B. (R)-tert-butyl 1-(9-bromo-4,6-dimethyl-5-oxo-5,6-dihydrobenzo[c][2,7]naphthyridin-8-yloxy)-4-methylpentan-2-ylcarbamate Prepared as described in Example 3, Part A to afford title compound (750 mg, 0.94 mmol, 79% yield, 65% purity) as an orange red solid. LC/MS (ESI) m/e 518.2 [(M+H)$^+$, calcd for $C_{25}H_{33}BrN_3O_4$ 518.2] LC/MS retention time (method D): $t_R$=0.92 min.

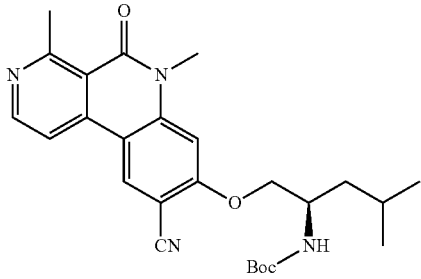 [SMILES: Cc1nccc2c1c(=O)n(C)c1cc(OC[C@@H](CC(C)C)NC(=O)OC(C)(C)C)c(C#N)cc21]

Part C. (R)-tert-butyl 1-(9-cyano-4,6-dimethyl-5-oxo-5,6-dihydrobenzo[c][2,7]naphthyridin-8-yloxy)-4-methylpentan-2-ylcarbamate Prepared as described in Example 64, Part B to afford title compound (300 mg, 0.18 mmol, 47% yield, 28% purity) as a black gum. LC/MS (ESI) m/e 465.2 [(M+H)$^+$, calcd for $C_{26}H_{33}N_4O_4$ 465.2] LC/MS retention time (method C): $t_R$=2.74 min.

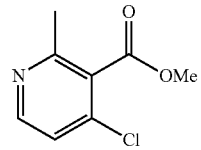

Part D. (R)-8-(2-amino-4-methylpentyloxy)-4,6-dimethyl-5-oxo-5,6-dihydrobenzo[c][2,7]naphthyridine-9-carbonitrile Prepared as described in Example 2, Part E to afford title compound (20 mg, 0.051 mmol, 59% yield, 93% purity) as a yellow solid. LC/MS (ESI) m/e 365.2 [(M+H)$^+$, calcd for $C_{21}H_{25}N_4O_2$ 365.2] LC/MS retention time (method C): $t_R$=2.10 min. HPLC retention time (method A): $t_R$=8.35 min and HPLC retention time (method B): $t_R$=9.17 min. $^1$H NMR (400 MHz, METHANOL-$d_4$) δ ppm 8.98 (s, 1H), 8.71 (d, J=6.3 Hz, 1H), 8.53 (d, J=6.5 Hz, 1H), 7.23 (s, 1H), 4.65 (dd, J=10.7, 3.1 Hz, 1H), 4.50 (dd, J=10.8, 6.0 Hz, 1H), 3.85 (br. s., 1H), 3.84 (s, 3H), 3.20 (s, 3H), 1.92-1.80 (m, 2H), 1.78-1.66 (m, 1H), 1.09 (d, J=1.8 Hz, 3H), 1.07 (d, J=1.5 Hz, 3H).

Example 79

(S)-8-((2-amino-4-methylpentyl)oxy)-9-chloro-6-(2-methoxyethyl)-4-methylbenzo[c][2,7]naphthyridin-5(6H)-one

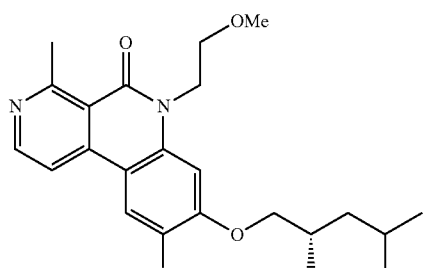

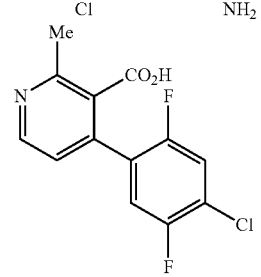

Part A: 4-(4-chloro-2-fluorophenyl)-N-(2-methoxyethyl)-2-methylnicotinamide

A solution of 4-(4-chloro-2-fluorophenyl)-2-methylnicotinic acid (2 g, 5.19 mmol), prepared as described in Example 16, Part E, in thionyl chloride (5 mL, 68.5 mmol) was heated at 70° C. for 2 h. After cooling, the volatiles were removed under reduced pressure. The residue was dissolved in 4 mL of anhydrous DCM and added to a pre-cooled solution of 2-methoxyethanamine (0.390 g, 5.19 mmol) and triethyl amine (3.62 mL, 26.0 mmol) in DCM (8 mL) at 0° C. The resulting reaction mixture was stirred at rt for 4 h. Water (30 mL) was then added and the solution was extracted with DCM (2×20 mL). The combined organic layers were washed with brine (20 mL), dried over sodium sulphate, and concentrated under reduced pressure. The residue was purified by silica gel chromatography using a gradient of EtOAc and hexane as eluant to yield 4-(4-chloro-2-fluorophenyl)-N-(2-methoxyethyl)-2-methylnicotinamide (1.3 g, 2.88 mmol, 56% yield) as a yellow oil. LC/MS (ESI) m/e 323.1 [(M+H)$^+$, calcd for $C_{16}H_{17}ClFN_2O_2$ 323.1]; LC/MS retention time (method D): $t_R$=0.61 min.

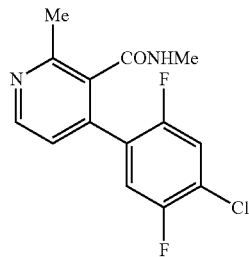

Part B: 8-chloro-6-(2-methoxyethyl)-4-methylbenzo[c][2,7]naphthyridin-5(6H)-one 4-(4-Chloro-2-fluorophenyl)-N-(2-methoxyethyl)-2-methylnicotinamide was subjected to a cyclization reaction as described in Example 2, Part C to yield 8-chloro-6-(2-methoxyethyl)-4-methylbenzo[c][2,7]naphthyridin-5(6H)-one (1.12 g, 2.55 mmol, 89% yield) as a white solid. LC/MS (ESI) m/e 303.2 [(M+H)$^+$, calcd for $C_{16}H_{16}ClN_2O_2$ 303.1]; LC/MS retention time (method B): $t_R$=1.38 min.

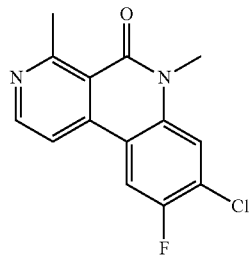 [SMILES: Cc1nccc2c1c(=O)n(C)c1cc(Cl)c(F)cc21]

Part C: (S)-tert-butyl (1-((6-(2-methoxyethyl)-4-methyl-5-oxo-5,6-dihydrobenzo[c][2,7]naphthyridin-8-yl)oxy)-4-methylpentan-2-yl)carbamate 8-Chloro-6-(2-methoxyethyl)-4-methylbenzo[c][2,7]naphthyridin-5(6H)-one was subjected to ether synthesis as described Example 16, Part H to afford (S)-tert-butyl (1-((6-(2-methoxyethyl)-4-methyl-5-oxo-5,6-dihydrobenzo[c][2,7]naphthyridin-8-yl)oxy)-4-methylpentan-2-yl)carbamate (511 mg, 0.723 mmol, 53% yield) as a white solid. LC/MS (ESI) m/e 484.6 [(M+H)$^+$, calcd for $C_{27}H_{38}N_3O_5$ 484.3]; LC/MS retention time (method E): $t_R$=1.17 min.

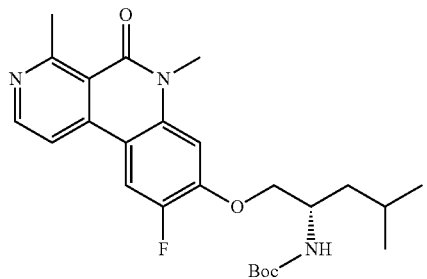

Part D: (S)-tert-butyl (1-((9-chloro-6-(2-methoxyethyl)-4-methyl-5-oxo-5,6-dihydrobenzo[c][2,7]naphthyridin-8-yl)oxy)-4-methylpentan-2-yl)carbamate (S)-tert-Butyl (1-((6-(2-methoxyethyl)-4-methyl-5-oxo-5,6-dihydrobenzo[c][2,7]naphthyridin-8-yl)oxy)-4-methylpentan-2-yl)carbamate was subjected to chlorination as described in Example 41, Part A to afford (S)-tert-butyl (1-((9-chloro-6-(2-methoxyethyl)-4-methyl-5-oxo-5,6 dihydrobenzo[c][2,7]naphthyridin-8-yl)oxy)-4-methylpentan-2-yl)carbamate (260 mg, 0.227 mmol, 80% crude yield) as a brown solid. LC/MS (ESI) m/e 518.2 [(M+H)$^+$, calcd for $C_{27}H_{37}ClN_3O_5$ 518.2]; LC/MS retention time (method D): $t_R$=0.91 min; HPLC retention time (method B): $t_R$=1.84 min.

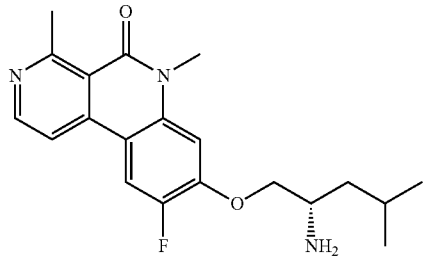

Part E: (S)-8-((2-amino-4-methylpentyl)oxy)-9-chloro-6-(2-methoxyethyl)-4-methylbenzo[c][2,7]naphthyridin-5(6H)-one (S)-tert-Butyl (1-((9-chloro-6-(2-methoxyethyl)-4-methyl-5-oxo-5,6-dihydrobenzo[c][2,7]naphthyridin-8-yl)oxy)-4-methylpentan-2-yl)carbamate was subjected Boc-deprotection as described in Example 2, Part E to afford (S)-8-((2-amino-4-methylpentyl)oxy)-9-chloro-6-(2-methoxyethyl)-4-methylbenzo[c][2,7]naphthyridin-5(6H)-one, 2HCl (11.23 mg, 0.021 mmol, 48% yield) as a yellow solid. LC/MS (ESI) m/e 418.2 [(M+H)$^+$, calcd for $C_{22}H_{29}ClN_3O_3$ 418.2]; HPLC retention time (method A): $t_R$=7.91 min; HPLC retention time (Method B): $t_R$=9.29 min; $^1$H NMR (400 MHz, METHANOL-$d_4$) δ ppm 8.79-8.66 (m, 3H), 7.51 (s, 1H), 4.70 (t, J=4.9 Hz, 2H), 4.63-4.54 (m, 1H), 4.45 (dd, J=10.4, 5.1 Hz, 1H), 3.89-3.86 (m, 3H), 3.38 (s, 3H), 3.28 (s, 3H), 1.91-1.81 (m, 2H), 1.80-1.69 (m, 1H), 1.11-1.08 (m, 3H), 1.07 (br. s., 3H).

Example 80

(S)-8-((2-amino-4-methylpentyl)oxy)-6-(2-methoxy-ethyl)-4-methylbenzo[c][2,7]naphthyridin-5(6H)-one

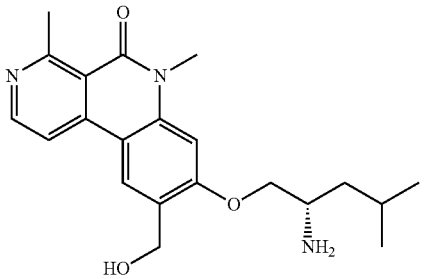 [SMILES: Cc1nccc2c1c(=O)n(C)c1cc(OC[C@@H](N)CC(C)C)c(CO)cc21]

Boc-deprotection of (S)-tert-butyl (1-((6-(2-methoxyethyl)-4-methyl-5-oxo-5,6-dihydrobenzo[c][2,7]naphthyridin-8-yl)oxy)-4-methylpentan-2-yl)carbamate, (prepared as described in Example 79, Part C) was carried out as described in Example 2, Part E to afford (S)-8-((2-amino-4-methylpentyl)oxy)-6-(2-methoxyethyl)-4 methylbenzo[c][2,7]naphthyridin-5(6H)-one (31.3 mg, 0.081 mmol, 77% yield) as a white solid. LC/MS (ESI) m/e 384.2 [(M+H)$^+$, calcd for $C_{22}H_{30}N_3O_3$ 384.2]; LC/MS retention time (method B): $t_R$=1.06 min; HPLC retention time (method A): $t_R$=8.11 min; HPLC retention time (method B): $t_R$=9.29 min; $^1$H NMR (400 MHz, METHANOL-$d_4$) δ ppm 8.55 (d, J=5.8 Hz, 1H), 8.36 (d, J=9.0 Hz, 1H), 8.12 (d, J=5.8 Hz, 1H), 7.22 (d, J=2.3 Hz, 1H), 7.04 (dd, J=9.0, 2.5 Hz, 1H), 4.58 (t, J=5.8 Hz, 2H), 4.18 (dd, J=9.4, 3.9 Hz, 1H), 4.00 (dd, J=9.3, 7.0 Hz, 1H), 3.81 (t, J=5.8 Hz, 2H), 3.39 (s, 3H), 3.38-3.36 (m, 1H), 3.08 (s, 3H), 1.91-1.79 (m, 1H), 1.57-1.40 (m, 2H), 1.04 (d, J=6.5 Hz, 3H), 1.01 (d, J=6.8 Hz, 3H).

Example 81

(S)-8-(2-amino-4-methylpentyloxy)-7-fluoro-4,6-dimethylbenzo[c][2,7]naphthyridin-5(6H)-one

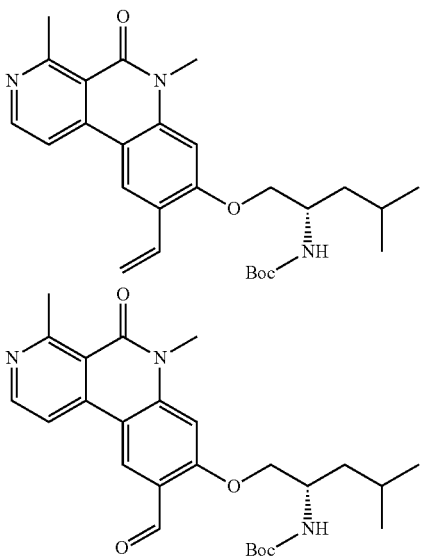

Part A: (S)-tert-butyl 1-(7-fluoro-4,6-dimethyl-5-oxo-5,6-dihydrobenzo[c][2,7]naphthyridin-8-yloxy)-4-methylpentan-2-ylcarbamate Prepared as described in Example 16, Part H from 8-bromo-7-fluoro-4,6-dimethylbenzo[c][2,7]naphthyridin-5(6H)-one, (prepared as described in Example 29, Part F). to afford (S)-tert-butyl 1-(7-fluoro-4,6-dimethyl-5-oxo-5,6-dihydrobenzo[c][2,7]naphthyridin-8-yloxy)-4-methylpentan-2-ylcarbamate (0.013 g, 0.028 mmol, 37% yield) as a white solid. NMR (400 MHz, DMSO-$d_6$) δ ppm 8.64 (d, J=7.2 Hz, 1H), 8.36 (m, 1H), 8.21 (m, 1H), 7.23 (m, 1H), 6.84 (d, J=11.2 Hz, 1H), 6.28 (s, 1H), 4.06 (m, 2H), 3.92 (m, 1H), 3.78 (m, 3H), 2.99 (s, 1H), 1.65 (m, 1H), 1.38 (m, 11H), 0.89 (m, 6H).

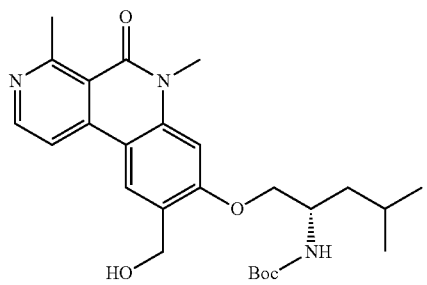 [SMILES: Cc1nccc2c1c(=O)n(C)c1cc(OC[C@H](CC(C)C)NC(=O)OC(C)(C)C)c(CO)cc21]

Part B: (S)-8-(2-amino-4-methylpentyloxy)-7-fluoro-4,6-dimethylbenzo[c][2,7]naphthyridin-5(6H)-one Prepared as described in Example 2, Part E to afford the title product (8.5 mg, 0.024 mmol, 98% yield as a brown solid. LC/MS (ESI) m/e 358.2 [(M+H)$^+$, calcd for $C_{20}H_{25}FN_3O_2$ 358.2] LC/MS retention time (method B): $t_R$=3.58 min. HPLC retention time (method A): $t_R$=7.68 min and HPLC retention time (method B): $t_R$=8.02 min. $^1$H NMR (400 MHz, DMSO-$d_6$) δ ppm 8.69 (d, J=5.8 Hz, 1H), 8.36 (d, J=7.5 Hz, 1H), 8.27 (d, J=5.8 Hz, 1H), 8.07 (br. s., 2H), 7.35-7.24 (m, 1H), 4.38 (dd, J=10.7, 3.4 Hz, 1H), 4.26 (dd, J=10.8, 6.0 Hz, 1H), 3.81 (d, J=9.3 Hz, 3H), 3.67-3.60 (m, 1H), 3.02 (s, 3H), 1.87-1.72 (m, 1H), 1.59 (td, J=7.1, 3.9 Hz, 2H), 0.96 (d, J=2.8 Hz, 3H), 0.94 (d, J=2.8 Hz, 3H).

Example 82

(S)-8-(2-amino-4-methylpentyloxy)-7-fluoro-4-methylbenzo[c][2,7]naphthyridin-5(6H)-one

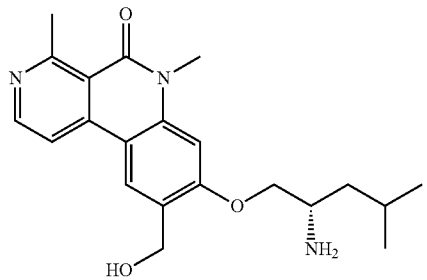

-continued

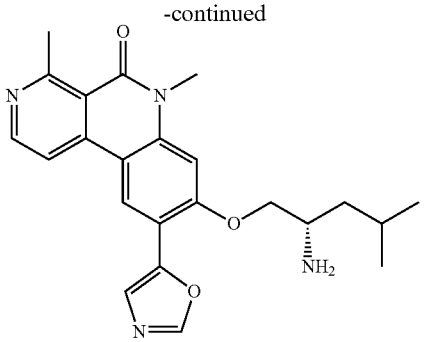

Part A. 4-(4-bromo-2,3-difluorophenyl)-N-(4-methoxybenzyl)-2-methylnicotinamide Prepared as described in Example 29, Part E by reaction of biaryl acid (described in Example 29, Part D) with PMB-amine to afford 4-(4-bromo-2,3-difluorophenyl)-N-(4-methoxybenzyl)-2-methylnicotinamide (0.16 g, 0.314 mmol, 92%) as an off-white solid. LC/MS (ESI) m/e 447.0 [(M+H)$^+$, calcd for $C_{21}H_{18}BrF_2N_2O_2$ 447.1]; LC/MS retention time (method E): $t_R$=0.94 min.

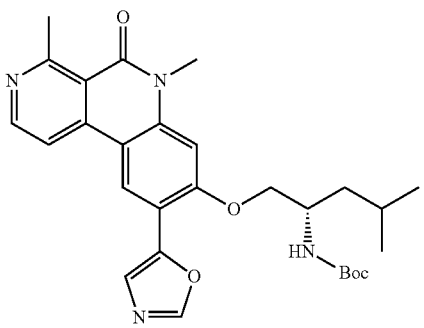 [SMILES: Cc1nccc2c1c(=O)n(C)c1cc(OC[C@H](CC(C)C)NC(=O)OC(C)(C)C)c(-c3cnco3)cc21]

Part B: 8-bromo-7-fluoro-6-(4-methoxybenzyl)-4-methylbenzo[c][2,7]naphthyridin-5(6H)-one Prepared as described in Example 29, Part F to afford 8-bromo-7-fluoro-6-(4-methoxybenzyl)-4-methylbenzo[c][2,7]naphthyridin-5(6H)-one (0.12 g, 0.269 mmol, 90%) as a off-white solid. LC/MS (ESI) m/e 429.1 [(M+2H)$^+$, calcd for $C_{21}H_{18}BrFN_2O_2$ 429.0]; LC/MS retention time (method E): $t_R$=1.15 min.

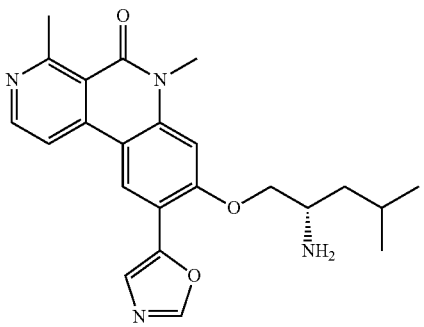

Part C. tert-butyl 1-(7-fluoro-6-(4-methoxybenzyl)-4-methyl-5-oxo-5,6-dihydrobenzo[c][2,7]naphthyridin-8-yloxy)-2,4-dimethylpentan-2-ylcarbamate Prepared as described in Example 16, Part H to afford tert-butyl 1-(7-fluoro-6-(4-methoxybenzyl)-4-methyl-5-oxo-5,6-dihydrobenzo[c][2,7]naphthyridin-8-yloxy)-2,4-dimethylpentan-2-ylcarbamate (46 mg, 0.081 mmol, 13% yield) as an off-white solid. LC/MS (ESI) m/e 564.3 [(M+H)$^+$, calcd for $C_{32}H_{39}FN_3O_5$ 564.3]; LC/MS retention time (Method H): $t_R$=2.35 min.

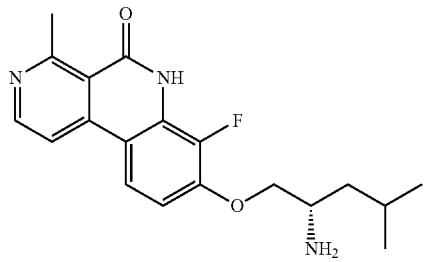

Part D. (S)-8-(2-amino-4-methylpentyloxy)-7-fluoro-4-methylbenzo[c][2,7]naphthyridin-5(6H)-one Prepared as described in Example 17, Part I to afford (S)-8-(2-amino-4-methylpentyloxy)-7-fluoro-4-methylbenzo[c][2,7]naphthyridin-5(6H)-one (8 mg, 0.023 mmol, 72% yield) as an off-white solid. LC/MS (ESI) m/e 342.2 [(M)$^-$, calcd for $C_{19}H_{21}FN_3O_2$ 342.2]; LC/MS retention time (method C): $t_R$=1.99 min; HPLC retention time (method B): $t_R$=6.91 min; $^1$H NMR (400 MHz, METHANOL-$d_4$) δ ppm 8.69 (d, J=6.3 Hz, 1H), 8.44 (d, J=6.3 Hz, 1H), 8.28 (dd, J=9.3, 2.0 Hz, 1H), 7.26 (dd, J=9.0, 7.8 Hz, 1H), 4.51 (dd, J=10.7, 3.1 Hz, 1H), 4.36 (dd, J=10.7, 6.1 Hz, 1H), 3.85-3.72 (m, 1H), 3.19 (s, 3H), 1.92-1.63 (m, 3H), 1.07 (d, J=3.8 Hz, 3H), 1.06 (d, J=3.8 Hz, 3H).

Example 83

(S)-8-(2-amino-4-methylpentyloxy)-4,6-dimethyl-9-(thiazol-5-yl)benzo[c][2,7]naphthyridin-5(6H)-one

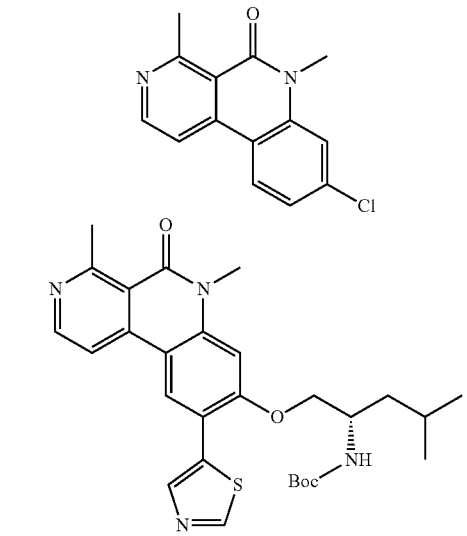

203

Part A. (S)-tert-butyl 1-(4,6-dimethyl-5-oxo-9-(thiazol-5-yl)-5,6-dihydrobenzo[c][2,7]naphthyridin-8-yloxy)-4-methylpentan-2-ylcarbamate 5-Bromothiazole (0.050 g, 0.305 mmol) and hexamethyltin (0.158 mL, 0.762 mmol) were taken up in 1,4-dioxane (1 mL) and purged with nitrogen for 10 min. Tetrakis (triphenylphosphine)palladium (0.035 g, 0.030 mmol) was added and the reaction mixture was stirred for 2 h at rt. (S)-tert-butyl (1-((9-bromo-4,6-dimethyl-5-oxo-5,6 dihydrobenzo[c][2,7]naphthyridin-8-yl)oxy)-4-methylpentan-2-yl)carbamate (0.158 g, 0.305 mmol) and lithium chloride (0.013 g, 0.305 mmol) were added and the mixture was purged with $N_2$ for 10 min. The reaction mixture was then heated for 16 h at 90° C. After cooling, the reaction mixture was filtered through diatomaceous earth (Celite®) and concentrated under reduced pressure. The residue was purified by preparative HPLC to afford (S)-tert-butyl 1-(4,6-dimethyl-5-oxo-9-(thiazol-5-yl)-5,6-dihydrobenzo[c][2,7]naphthyridin-8-yloxy)-4-methylpentan-2-ylcarbamate (40 mg, 0.053 mmol, 18% yield) as a yellow solid. LC/MS (ESI) m/e 23.6 [(M+H)$^+$, calcd for $C_{28}H_{35}N_4O_4S$ 523.2]; LC/MS retention time (method E): $t_R$=1.09 min.

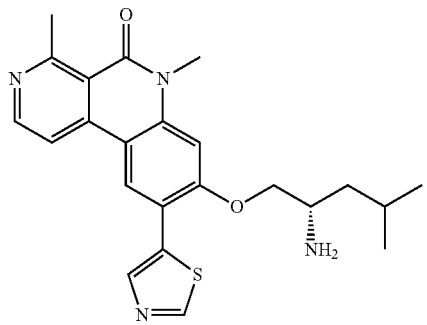 [SMILES: Cc1nccc2c1c(=O)n(C)c1cc(OC[C@@H](N)CC(C)C)c(-c3cncs3)cc21]

Part B. (S)-8-(2-amino-4-methylpentyloxy)-4,6-dimethyl-9-(thiazol-5-yl)benzo[c][2,7]naphthyridin-5(6H)-one Prepared as described in Example 2, Part E to afford (S)-8-(2-amino-4-methylpentyloxy)-4,6-dimethyl-9-(thiazol-5-yl)benzo[c][2,7]naphthyridin-5(6H)-one (16 mg, 0.037 mmol, 80% yield) as an off-white solid. LC/MS (ESI) m/e 423.2 [(M+H)$^+$, calcd for $C_{23}H_{27}N_4O_2S$ 423.2]; LC/MS retention time (method C): $t_R$=2.04 min; HPLC retention time (method A): $t_R$=9.1 min; retention time (method B): $t_R$=9.72 min; $^1$H NMR (400 MHz, METHANOL-$d_4$) δ ppm 9.10 (s, 1H), 8.73 (s, 1H), 8.61 (d, J=5.8 Hz, 1H), 8.49 (s, 1H), 8.30 (d, J=5.8 Hz, 1H), 7.16 (s, 1H), 4.38 (dd, J=9.5, 4.0 Hz, 1H), 4.25 (dd, J=9.5, 6.5 Hz, 1H), 3.82 (s, 3H), 3.59-3.51 (m, 1H), 3.10 (s, 3H), 1.91-1.82 (m, 1H), 1.69-1.46 (m, 2H), 1.04 (d, J=5.5 Hz, 3H), 1.03 (d, J=5.8 Hz, 3H).

204

Example 84

(S)-methyl 8-((2-amino-4-methylpentyl)oxy)-4,6-dimethyl-5-oxo-5,6-dihydrobenzo[c][2,7]naphthyridine-9-carboxylate

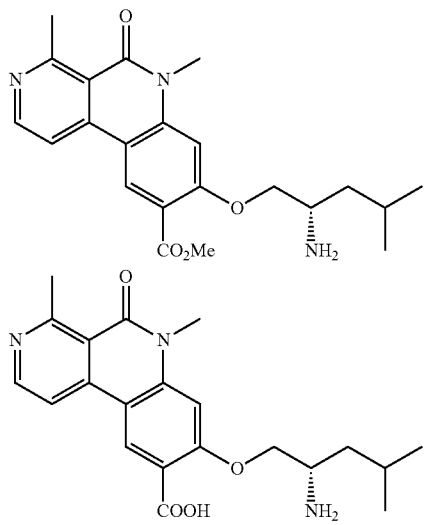

Part A: (S)-8-((2-amino-4-methylpentyl)oxy)-4,6-dimethyl-5-oxo-5,6-dihydrobenzo[c][2,7]naphthyridine-9-carboxylic Acid To a flask containing (S)-8-((2-amino-4-methylpentyl)oxy)-4,6-dimethyl-5-oxo-5,6-dihydrobenzo[c][2,7]naphthyridine-9-carbonitrile (60 mg, 0.165 mmol), (prepared as described in Example 64) was added concentrated HCl (5 mL). The resultant mixture was heated to 80° C. for 12 h. After cooling, the volatiles were removed under reduced pressure to afford (S)-8-((2-amino-4-methylpentyl)oxy)-4,6-dimethyl-5-oxo-5,6-dihydrobenzo[c][2,7]naphthyridine-9-carboxylic acid (40 mg, 0.104 mmol, 63% crude yield) as a yellow solid. The material was carried on without further purification. LC/MS (ESI) m/e 384.1 [(M+H)$^+$, calcd for $C_{21}H_{26}N_3O_4$ 384.2]; LC/MS retention time (method D): $t_R$=0.71 min.

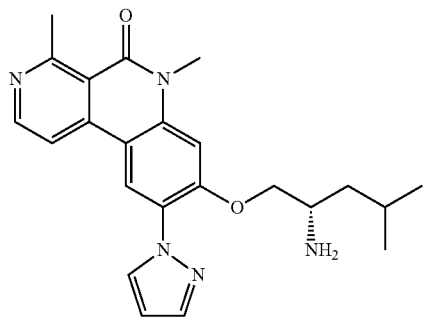 [SMILES: Cc1nccc2c1c(=O)n(C)c1cc(OC[C@@H](N)CC(C)C)c(-n3cccn3)cc21]

Part B: (S)-methyl 8-((2-amino-4-methylpentyl)oxy)-4,6-dimethyl-5-oxo-5,6-dihydrobenzo[c][2,7]naphthyridine-9-carboxylate To a flask containing (S)-8-((2-amino-4-methylpentyl)oxy)-4,6-dimethyl-5-oxo-5,6-dihydrobenzo[c][2,7]naphthyridine-9-carboxylic acid (40 mg, 0.104 mmol) in MeOH (3 mL) at 0° C. was added SOCl$_2$ (0.076 mL, 1.043 mmol) dropwise. The resultant solution was heated to 70° C. for 12 h. After cooling, the volatiles were removed under reduced pressure. The residue was purified by prep HPLC (using 0.1% TFA ACN:water) to afford (S)-methyl 8-((2-amino-4-methylpentyl)oxy)-4,6-dimethyl-5-oxo-5,6-dihydrobenzo[c][2,7]naphthyridine-9-carboxylate, 2 TFA (1.65 mg, 2.427 µmol, 2% yield) as pale brown solid. LC/MS (ESI) m/e 398.2 [(M+H)$^+$, calcd for C$_{22}$H$_{28}$N$_3$O$_4$ 398.2]; LC/MS retention time (method C): t$_R$=1.58 min; HPLC retention time (method A): t$_R$=9.14 min; HPLC retention time (method B): t$_R$=9.58 min; $^1$H NMR (400 MHz, METHANOL-d$_4$) δ ppm 9.01 (s, 1H), 8.68 (d, J=6.0 Hz, 1H), 8.40 (d, J=6.0 Hz, 1H), 7.23 (s, 1H), 4.69 (dd, J=10.0, 3.0 Hz, 1H), 4.36 (dd, J=10.5, 7.0 Hz, 1H), 4.02 (s, 3H), 3.88-3.81 (m, 4H), 3.16 (s, 3H), 1.93-1.65 (m, 3H), 1.09 (d, J=4.0 Hz, 3H), 1.07 (d, J=4.0 Hz, 3H).

Example 85

(S)-8-((2-amino-4-methylpentyl)oxy)-1-fluoro-6-methylbenzo[c][2,7]naphthyridin-5(6H)-one

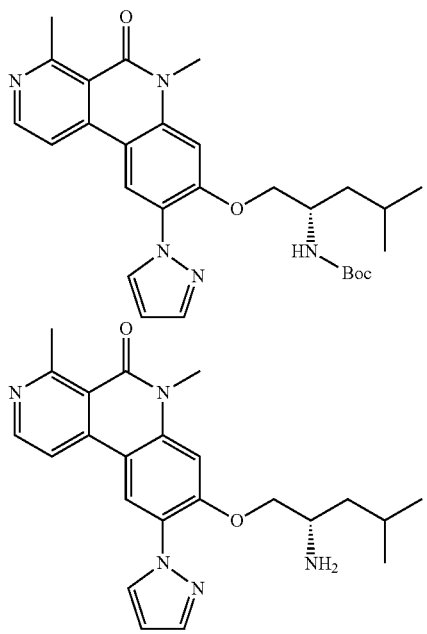

Part A: Methyl 4-chloro-5-fluoronicotinate

To a solution of 4-chloro-5-fluoronicotinic acid (1.7 g, 9.68 mmol) in acetonitrile (18 mL) cooled to 0° C. was added DBU (3.65 mL, 24.21 mmol) dropwise. The reaction mixture was stirred for 30 min. To this mixture iodomethane (3.03 mL, 48.4 mmol) was added dropwise and stirred at rt for 12 h. The volatiles were removed under reduced pressure. The residue was purified via silica gel column chromatography (hexane and ethyl acetate) to afford methyl 4-chloro-5-fluoronicotinate (1.2 g, 6.33 mmol, 65% yield) as a yellow solid. LC/MS (ESI) m/e 190.0 [(M+H)$^+$, calcd for C$_7$H$_6$ClFNO$_2$ 189.9]; LC/MS retention time (method D): t$_R$=0.77 min.

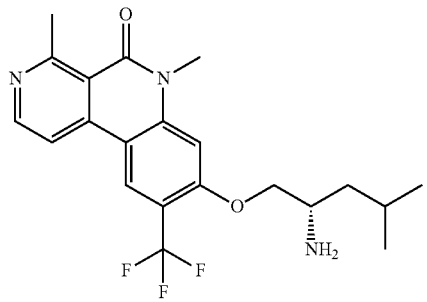 [SMILES: Cc1nccc2c1c(=O)n(C)c1cc(OC[C@@H](N)CC(C)C)c(C(F)(F)F)cc21]

Part B: Methyl 4-(4-chloro-2-fluorophenyl)-5-fluoronicotinate

To a solution of methyl 4-chloro-5-fluoronicotinate (1.2 g, 6.33 mmol) in 1,4-dioxane (12 mL) and water (0.5 mL) was added (4-chloro-2-fluorophenyl)boronic acid (1.214 g, 6.96 mmol). The mixture was then purged with nitrogen gas for 5 min. Potassium phosphate, dibasic (2.205 g, 12.66 mmol) and PdCl$_2$(dppf) (0.371 g, 0.506 mmol) were added and again the mixture was purged with N$_2$ for 5 min. The reaction mixture was heated to 80° C. for 12 h. After cooling, water was added to and the mixture was extracted with ethyl acetate (3×25 mL). The combined organic layers were washed with brine, dried over sodium sulfate and concentrated under reduced pressure. The residue was purified by silica gel chromatography using hexane and ethyl acetate to afford methyl 4-(4-chloro-2-fluorophenyl)-5-fluoronicotinate (900 mg, 3.17 mmol, 50% yield) as a yellow solid. LC/MS (ESI) m/e 284.0 [(M+H)$^+$, calcd for C$_{13}$H$_9$ClF$_2$NO$_2$ 284.02]; LC/MS retention time (method D): t$_R$=1.01 min.

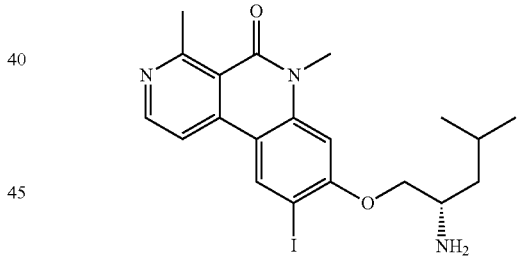

Part C: 4-(4-chloro-2-fluorophenyl)-5-fluoronicotinic Acid

To the solution of methyl 4-(4-chloro-2-fluorophenyl)-5-fluoronicotinate (600 mg, 2.115 mmol) in tetrahydrofuran (2.5 mL), MeOH (2.5 mL) and water (2.5 mL) was added LiOH (50.7 mg, 2.115 mmol) and the mixture was stirred at rt for 12 h. The volatiles were removed and the residue was diluted with water. The pH was adjusted to 4 with 1.5N HCl. The product was extracted with ethyl acetate (2×5 mL). The combined organic layers were dried over sodium sulfate and concentrated under reduced pressure to afford 4-(4-chloro-2-fluorophenyl)-5-fluoronicotinic acid (530 mg, 1.966 mmol, 93% crude yield) the pale brown solid. The material was carried on without further purification. LC/MS (ESI) m/e 269.9 [(M+H)$^+$, calcd for C$_{12}$H$_7$ClF$_2$NO$_2$ 270.0]; LC/MS retention time (method D): t$_R$=0.88 min.

207

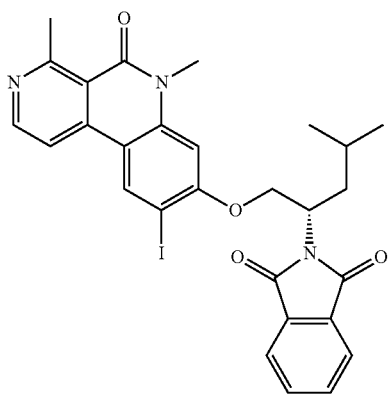 [SMILES: Cc1nccc2c1c(=O)n(C)c1cc(OC[C@H](CC(C)C)N3C(=O)c4ccccc4C3=O)c(I)cc21]

Part D: 4-(4-chloro-2-fluorophenyl)-5-fluoro-N-methylnicotinamide

To the solution of 4-(4-chloro-2-fluoronicotinic acid (530 mg, 1.966 mmol) in DMF (5 mL) cooled at 0° C., was added HOBT (602 mg, 3.93 mmol) and EDC (565 mg, 2.95 mmol), then the mixture was stirred for 5 min. Methylamine hydrochloride (531 mg, 7.86 mmol) and DIEA (1.030 mL, 5.90 mmol) were added and the resultant mixture was stirred at RT for 12 h. Ice-cold water was added to the reaction and the solid obtained was collected by vacuum filtration. The solid so obtained was washed with water (50 mL) and air dried to afford 4-(4-chloro-2-fluorophenyl)-5-fluoro-N-methylnicotinamide (350 mg, 1.238 mmol, 63% yield) as an orange oil. LC/MS (ESI) m/e 282.9 [(M+H)$^+$, calcd for $C_{13}H_{10}ClF_2N_2O$ 283.0]; LC/MS retention time (method D): $t_R$=0.83 min.

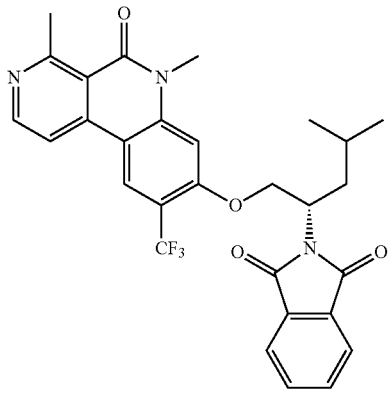 [SMILES: Cc1nccc2c1c(=O)n(C)c1cc(OC[C@H](CC(C)C)N3C(=O)c4ccccc4C3=O)c(C(F)(F)F)cc21]

Part E: 8-chloro-1-fluoro-6-methylbenzo[c][2,7]naphthyridin-5(6H)-one 4-(4-Chloro-2-fluorophenyl)-5-fluoro-N-methylnicotinamide was subjected to cyclization as described in Example 2 and Part C to afford 8-chloro-1-fluoro-6-methylbenzo[c][2,7]naphthyridin-5(6H)-one (85 mg, 0.320 mmol, 60% yield) as a white solid. LC/MS (ESI) m/e 263.0 [(M+H)$^+$, calcd for $C_{13}H_9ClFN_2O$ 263.0]; LC/MS retention time (method C): $t_R$=1.77 min.

208

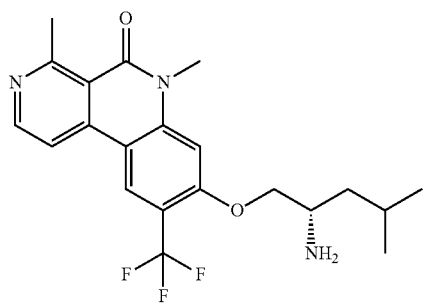 [SMILES: Cc1nccc2c1c(=O)n(C)c1cc(OC[C@@H](N)CC(C)C)c(C(F)(F)F)cc21]

Part F: (S)-tert-butyl (1-((1-fluoro-6-methyl-5-oxo-5,6-dihydrobenzo[c][2,7]naphthyridin-8-yl)oxy)-4-methylpentan-2-yl)carbamate 8-Chloro-1-fluoro-6-methylbenzo[c][2,7]naphthyridin-5(6H)-one was subjected to ether synthesis as described in Example 16, Part H to afford (S)-tert-butyl (1-((1-fluoro-6-methyl-5-oxo-5,6-dihydrobenzo[c][2,7]naphthyridin-8-yl) oxy)-4-methylpentan-2-yl)carbamate (60 mg, 0.135 mmol, 71% yield) as an off white solid. LC/MS (ESI) m/e 444.2 [(M+H)$^+$, calcd for $C_{24}H_{31}FN_3O_4$ 445.2]; LC/MS retention time (method D): $t_R$=1.11 min.

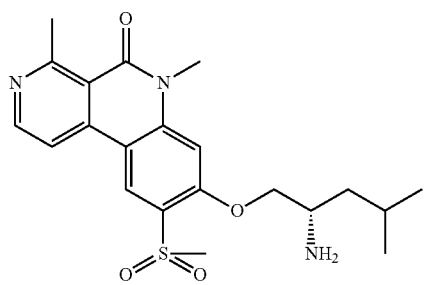 [SMILES: Cc1nccc2c1c(=O)n(C)c1cc(OC[C@@H](N)CC(C)C)c(S(C)(=O)=O)cc21]

Part G: (S)-8-((2-amino-4-methylpentyl)oxy)-1-fluoro-6-methylbenzo[c][2,7]naphthyridin-5(6H)-one (S)-tert-Butyl (1-((1-fluoro-6-methyl-5-oxo-5,6-dihydrobenzo[c][2,7]naphthyridin-8-yl)oxy)-4-methylpentan-2-yl)carbamate was subjected to Boc-deprotection as described in Example 2, Part E. The crude product was purified by preparative HPLC using 0.1% TFA ACN:water to afford (S)-8-((2-amino-4-methylpentyl)oxy)-1-fluoro-6-methylbenzo [c][2,7]naphthyridin-5(6H)-one, TFA (42.68 mg, 0.091 mmol, 95% yield) as a yellow solid. LC/MS (ESI) m/e 344.2 [(M+H)$^+$, calcd for $C_{19}H_{23}FN_3O_2$ 344.2]; LC/MS retention time (method C): $t_R$=2.07 min; HPLC retention time (method A): $t_R$=5.52 min; HPLC retention time (method B): $t_R$=6.63 min; $^1$H NMR (400 MHz, METHANOL-$d_4$) δ ppm 9.38 (s, 1H), 8.77 (d, J=5.0 Hz, 1H), 8.67 (dd, J=9.0, 3.0 Hz, 1H), 7.21 (d, J=2.0 Hz, 1H), 7.16 (dq, J=9.1, 1.3 Hz, 1H), 4.48 (dd, J=10.5, 3.0 Hz, 1H), 4.29 (dd, J=10.5, 6.0 Hz, 1H), 3.82 (s, 3H), 3.80-3.73 (m, 1H), 1.94-1.82 (m, 1H), 1.82-1.63 (m, 2H), 1.08 (d, J=4.0 Hz, 3H), 1.07 (d, J=4.0 Hz, 3H).

Example 86

(S)-8-((2-amino-4-methylpentyl)oxy)-4,6-dimethyl-9-(pyridin-2-yl)benzo[c][2,7]naphthyridin-5(6H)-one

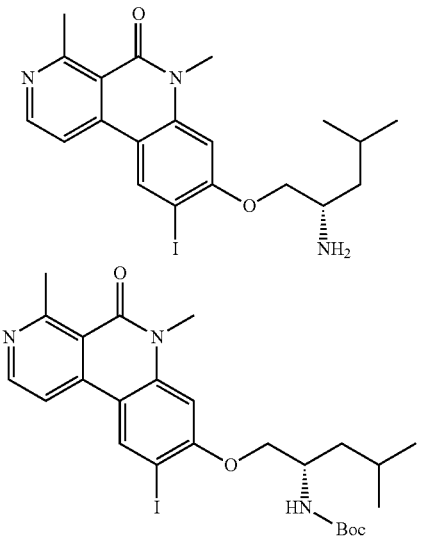

Part A. (S)-tert-butyl (1-((4,6-dimethyl-5-oxo-9-(pyridin-2-yl)-5,6-dihydrobenzo[c][2,7]naphthyridin-8-yl)oxy)-4-methylpentan-2-yl)carbamate To a solution of (S)-tert-butyl (1-((9-bromo-4,6-dimethyl-5-oxo-5,6-dihydrobenzo[c][2,7]naphthyridin-8-yl)oxy)-4-methylpentan-2-yl)carbamate (100 mg, 0.193 mmol) in 1,4-dioxane (2 mL) was added 2-(tributylstannyl)pyridine (85 mg, 0.231 mmol) and Pd(PPh$_3$)$_4$ (11.14 mg, 9.64 µmol). The reaction mixture was degassed for 30 min and heated to 120° C. for 1 h in a microwave. The reaction mixture was cooled and diluted with water (10 mL) and extracted with ethyl acetate (3×10 mL). The combined organic layers were dried over sodium sulfate and concentrated under reduced pressure. The crude product was purified by silica gel chromatography (3% methanol in chloroform) to afford (S)-tert-butyl (1-((4,6-dimethyl-5-oxo-9-(pyridin-2-yl)-5,6-dihydrobenzo[c][2,7]naphthyridin-8-yl)oxy)-4-methylpentan-2-yl)carbamate (50 mg, 0.120 mmol, 62% yield) as a pale yellow solid which was carried on without further purification LC/MS (ESI) m/e 517.7 [(M+H)$^+$, calcd for C$_{30}$H$_{37}$N$_4$O$_4$ 517.3]; LC/MS retention time (method E): t$_R$=1.19 min.

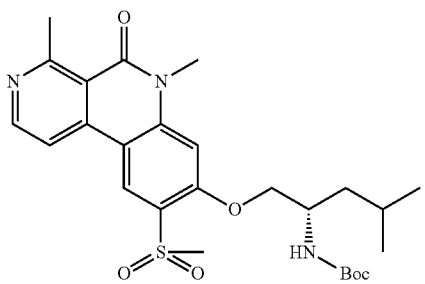 [SMILES: Cc1nccc2c1c(=O)n(C)c1cc(OC[C@H](CC(C)C)NC(=O)OC(C)(C)C)c(S(C)(=O)=O)cc21]

Part B. (S)-8-((2-amino-4-methylpentyl)oxy)-4,6-dimethyl-9-(pyridin-2-yl)benzo[c][2,7]naphthyridin-5(6H)-one To a solution of (S)-tert-butyl (1-((4,6-dimethyl-5-oxo-9-(pyridin-2-yl)-5,6-dihydrobenzo[c][2,7]naphthyridin-8-yl)oxy)-4-methylpentan-2-yl)carbamate (35 mg, 0.068 mmol) in Methanol (4 mL) was added HCl in 1,4-dioxane (0.169 mL, 0.677 mmol) at 0° C. Then the reaction mixture was stirred at RT for 2 h. The volatiles were concentrated under reduced pressure. The residue so obtained was basified with saturated aqueous NaHCO$_3$, diluted with water and extracted with DCM (3×5 mL). The combined organic layers were dried over Na$_2$SO$_4$ and concentrated in vacuo. The crude product was purified by reverse phase prep HPLC (Sunfire C18 column (19.0×150 mm) 10.0 micron; mobile phase A: 10 mM ammonium acetate in water; mobile phase B: acetonitrile; flow rate: 16.0 mL) to afford (S)-8-((2-amino-4-methylpentyl)oxy)-4,6-dimethyl-9-(pyridin-2-yl)benzo[c][2,7]naphthyridin-5(6H)-one (10 mg, 0.024 mmol, 35% yield) as an off-white solid. LC/MS (ESI) m/e 417.6 [(M+H)$^+$, calcd for C$_{25}$H$_{29}$N$_4$O$_2$ 417.2]; LC/MS retention time (method E): t$_R$=0.84 min; HPLC retention time (method A): t$_R$=7.61 min; HPLC retention time (method B): t$_R$=8.29 min; $^1$H NMR (400 MHz, METHANOL-d$_4$). $^1$H NMR (400 MHz, METHANOL-d$_4$) δ ppm 8.70 (d, J=4.3 Hz, 1H), 8.64 (s, 1H), 8.58 (d, J=5.5 Hz, 1H), 8.21 (d, J=5.8 Hz, 1H), 8.04-7.94 (m, 1H), 7.93-7.86 (m, 1H), 7.46 (ddd, J=7.3, 5.0, 1.3 Hz, 1H), 7.18 (s, 1H), 4.32 (dd, J=9.5, 4.3 Hz, 1H), 4.13 (dd, J=9.4, 6.7 Hz, 1H), 3.84 (s, 3H), 3.36-3.34 (m, 1H), 3.11 (s, 3H), 1.86-1.70 (m, 1H), 1.53-1.32 (m, 2H), 0.97 (d, J=6.8 Hz, 3H), 0.93 (d, J=6.5 Hz, 3H).

Example 87 and Example 88

(S)-8-((2-amino-5,5,5-trifluoro-4-methylpentyl)oxy)-4,6-dimethylbenzo[c][2,7]naphthyridin-5(6H)-one; Diastereomers 1 and 2

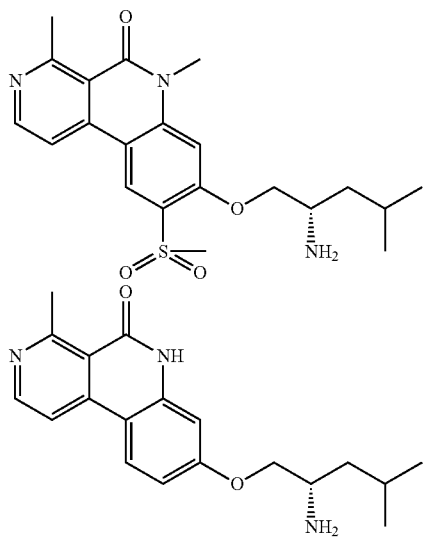

Part A. Ethyl 2-amino-5,5,5-trifluoro-4-methylpentanoate Hydrochloride

To 2-amino-5,5,5-trifluoro-4-methylpentanoic acid (50 mg, 0.270 mmol) in a flask was added hydrochloric acid 2N in ethanol (1350 μl, 5.40 mmol). The solution was refluxed at 80° C. for 5 h. After cooling, the ethanol was removed under reduced pressure. The residue was triturated with diethyl ether (2×). The solid so obtained (60 mg, 0.240 mmol) was taken up in dichloromethane (5 mL). To this suspension cooled to 0° C. was added triethylamine (0.167 mL, 1.202 mmol) and di-tert-butyl carbonate (0.054 mL, 0.312 mmol). The reaction mixture was allowed to warm to room temperature and stirred for 12 h. The reaction mixture was diluted with water (10 mL) and extracted with ethyl acetate (3×10 mL). The combined organic layers were dried over sodium sulfate and concentrated under reduced pressure to afford ethyl 2-((tert-butoxycarbonyl)amino)-5,5,5-trifluoro-4-methylpentanoate (55 mg, 0.176 mmol, 73% crude yield) as a white solid. The material was carried on without further purification. GCMS (ESI) m/e 212 [(M)⁻, calcd for $C_8H_{13}F_3NO_2$ 212] GC/MS (Method: Agilent GCMS Module-7890 (GC) 5975 C (MSD) HP-5MS, 30 m×0.25 mm ID×0.25 u Film thickness 0.9 mL/min at constant flow of Helium) retention time $t_R$=6.38 min.

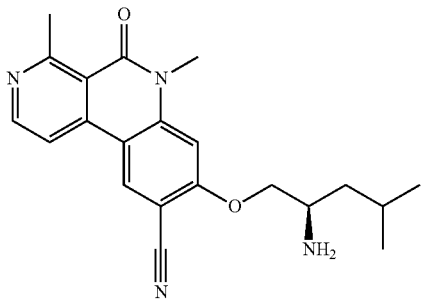 [SMILES: Cc1nccc2c1c(=O)n(C)c1cc(OC[C@H](N)CC(C)C)c(C#N)cc21]

Part B. Tert-butyl (5,5,5-trifluoro-1-hydroxy-4-methylpentan-2-yl)carbamate

To the solution of ethyl 2-((tert-butoxycarbonyl)amino)-5,5,5-trifluoro-4-methylpentanoate (500 mg, 1.596 mmol) in ethanol (2 mL) at 0° C. was added NaBH₄ (604 mg, 15.96 mmol). The reaction mixture was allowed to stir at RT for 16 h. The reaction mixture was quenched with aqueous ammonia. The solution was filter through a glass funnel and the resulting filtrate was concentrated to afford the tert-butyl (5,5,5-trifluoro-1-hydroxy-4-methylpentan-2-yl)carbamate (400 mg, 1.475 mmol, 92% crude yield) as a colorless gummy semisolid material. The material was carried on without further purification. LC/MS (ESI) m/e 172.1 [(M+H)⁺, calcd for $C_6H_{13}F_3NO$ 172.1] LC/MS retention time (Method A): $t_R$=2.1 min.

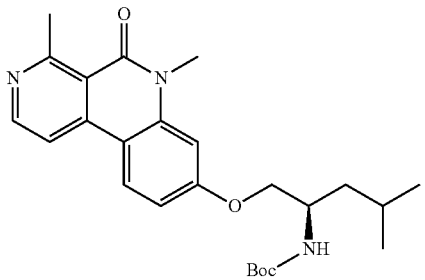 [SMILES: Cc1nccc2c1c(=O)n(C)c1cc(OC[C@@H](CC(C)C)NC(=O)OC(C)(C)C)ccc21]

Part C: Tert-butyl (1-((4,6-dimethyl-5-oxo-5,6-dihydrobenzo[c][2,7]naphthyridin-8-yl)oxy)-5,5,5-trifluoro-4-methylpentan-2-yl)carbamate 8-Chloro-4,6-dimethylbenzo[c][2,7]naphthyridin-5(6H)-one and tert-butyl (5,5,5-trifluoro-1-hydroxy-4-methylpentan-2-yl)carbamate was subjected to ether synthesis as described in Example 16, Part H. The compound was purified by reverse phase HPLC (Sunfire C18 (250×30 mm, 10 μm) column; mobile phase A: 10 mM ammonium acetate in water; mobile phase B: acetonitrile; flow rate: 25 mL) to afford the product as a off-white solid. The diasteromeric mixture so obtained was subjected to diastereomeric separation by normal phase chiral prep HPLC column. IC (250×30 mm, 5 μm); mobile phase A: 0.2% DEA: hexane; mobile phase B: Ethanol; flow rate: 16 mL/min) to afford tert-butyl (1-((4,6-dimethyl-5-oxo-5,6-dihydrobenzo[c][2,7]naphthyridin-8-yl)oxy)-5,5,5-trifluoro-4-methylpentan-2-yl)carbamate as two diastereomeric mixtures (1 and 2). The absolute stereochemistry of the diasteromers was not determined.

Diastereomeric Mixture 1:
(30 mg, 0.061 mmol, 10% yield) as an off-white solid. LC/MS of Diastereomeric mixture (ESI) m/e 494.3 [(M+H)⁺, calcd for $C_{25}H_{31}F_3N_3O_4$ 494.2]; LC/MS retention time (Method C) $t_R$=2.17 min.

Diastereomeric Mixture 2:
(80 mg, 0.162 mmol, 26% yield) as an off-white solid. LC/MS of Diastereomeric mixture (ESI) m/e 494.2 [(M+H)⁺, calcd for $C_{25}H_{31}F_3N_3O_4$ 494.2]; LC/MS retention time (Method C) $t_R$=2.16 min.

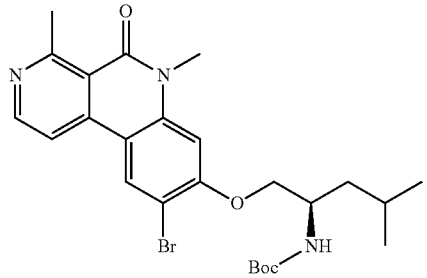 [SMILES: Cc1nccc2c1c(=O)n(C)c1cc(OC[C@@H](CC(C)C)NC(=O)OC(C)(C)C)c(Br)cc21]

Part D: 8-((2-amino-5,5,5-trifluoro-4-methylpentyl)oxy)-4,6-dimethylbenzo[c][2,7]naphthyridin-5(6H)-one: (Diastereomer 2)

Diastereomeric mixture 1 (30 mg, 0.061 mmol) was subjected to Boc deprotection as described in Example 2, Part E to afford 8-((2-amino-5,5,5-trifluoro-4-methylpentyl)oxy)-4,6-dimethylbenzo[c][2,7]naphthyridin-5(6H)-one (72.3 mg, 0.172 mmol, 99% yield) as an off white solid. LC/MS (ESI) m/e 394.6 [(M+H)⁺, calcd for $C_{20}H_{23}F_3N_3O_2$ 394.2]; HPLC retention time (method A): $t_R$=8.62 min; HPLC retention time (method B): $t_R$=8.77 min; ¹H NMR (400 MHz, DMSO-d₆) δ ppm 8.62 (d, J=5.5 Hz, 1H), 8.44 (d, J=8.8 Hz, 1H), 8.19 (d, J=5.8 Hz, 1H), 7.08-6.92 (m, 2H), 4.11-3.90 (m, 2H), 3.67 (s, 3H), 3.01 (s, 3H), 3.17-3.10 (m, 1H), 1.96-1.82 (m, 1H), 1.66-1.48 (m, 2H), 1.10 (d, J=6.8 Hz, 3H).

Boc-protected Diastereomeric mixture 2 (80 mg, 0.162 mmol) was subjected to Boc deprotection as described in Example 2, Part E to afford 8-((2-amino-5,5,5-trifluoro-4-methylpentyl)oxy)-4,6-dimethylbenzo[c][2,7]naphthyridin-5(6H)-one (10 mg, 0.025 mmol, 50% yield) as an off white solid. LC/MS (ESI) m/e 394.6 [(M+H)⁺, calcd for $C_{20}H_{23}F_3N_3O_2$ 394.2]; HPLC retention time (method A): $t_R$=8.75 min; HPLC retention time (method B): $t_R$=8.8 min; $^1$H NMR (400 MHz, CHLOROFORM-d) δ ppm 8.64 (d, J=5.5 Hz, 1H), 8.16 (d, J=8.8 Hz, 1H), 7.83 (d, J=5.8 Hz, 1H), 6.89 (dd, J=8.8, 2.3 Hz, 1H), 6.85 (d, J=2.3 Hz, 1H), 4.05 (dd, J=9.0, 4.0 Hz, 1H), 3.89 (dd, J=8.8, 6.5 Hz, 1H), 3.73 (s, 3H), 3.40-3.34 (m, 1H), 3.16 (s, 3H), 2.60-2.42 (m, 1H), 1.98 (dt, J=14.3, 6.1 Hz, 1H), 1.50-1.40 (m, 1H), 1.23 (d, J=7.0 Hz, 3H).

Example 89

(S)-8-((2-amino-4-methylpentyl)oxy)-9-methoxy-4,6-dimethylbenzo[c][2,7]naphthyridin-5(6H)-one

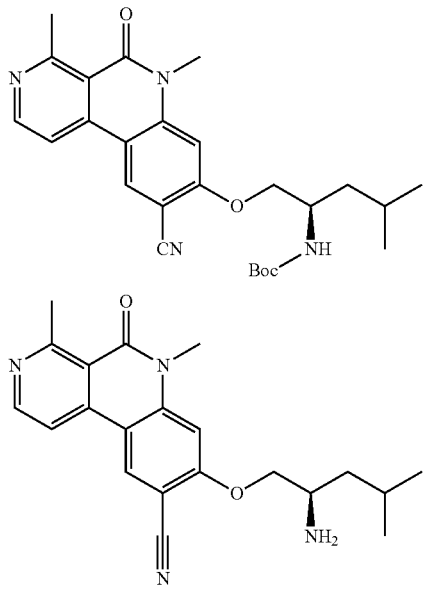

Part A. 8-chloro-9-iodo-4,6-dimethylbenzo[c][2,7]naphthyridin-5(6H)-one

To a stirred solution of 8-chloro-4,6-dimethylbenzo[c][2,7]naphthyridin-5(6H)-one (1.0 g, 3.87 mmol) in acetic Acid (25 mL) was added $H_2SO_4$ (0.206 mL, 3.87 mmol) followed by periodic acid (0.881 g, 3.87 mmol). The mixture was then heated to 80° C. for 20 min. $I_2$ (0.294 g, 1.160 mmol) was then added at 80° C. and stirred for 120 min. After cooling to ambient temperature, the acetic acid was removed under reduced pressure. The residue was neutralized with 70 mL of saturated aqueous sodium bicarbonate solution. The solid so obtained was collected by vacuum filtration and air dried to afford 8-chloro-9-iodo-4,6-dimethylbenzo[c][2,7]naphthyridin-5(6H)-one (1.3 g, 3.21 mmol, 83% yield) as a brown solid. LC/MS (ESI) m/e 385.1 [(M+H)$^+$, calcd for $C_{14}H_{11}ClIN_2O$ 384.9]; LC/MS retention time (method E): $t_R$=1.09 min; $^1$H NMR (400 MHz, DMSO-d$_6$) δ ppm 8.96 (s, 1H) 8.69 (d, J=5.58 Hz, 1H) 8.36 (d, J=5.52 Hz, 1H) 7.76 (s, 1H) 3.63 (s, 3H) 3.00 (s, 3H).

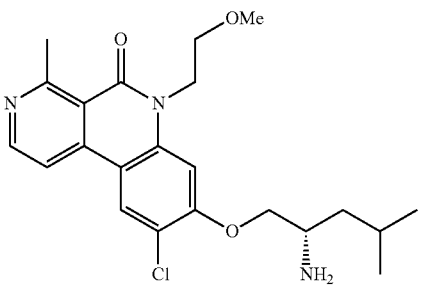 [SMILES: COCCn1c(=O)c2c(C)nccc2c2cc(Cl)c(OC[C@@H](N)CC(C)C)cc21]

Part B. 8-chloro-9-hydroxy-4,6-dimethylbenzo[c][2,7]naphthyridin-5(6H)-one

To the stirred solution of 8-chloro-9-iodo-4,6-dimethylbenzo[c][2,7]naphthyridin-5(6H)-one (1.0 g, 2.60 mmol) in DMSO (5 mL) and Water (5 mL) in an inert atmosphere were added copper(I) iodide (0.050 g, 0.260 mmol) followed by 1,10-phenanthroline (0.047 g, 0.260 mmol) and KOH (2.188 g, 39.0 mmol). The reaction mixture was heated to 100° C. for 16 h and monitored by LC/MS. Upon completion, the reaction mixture was cooled and pH adjusted to between 3 to 4 with 1 N HCl. The reaction mixture was diluted with 50 mL of water and extracted with 80 mL of dichloromethane. The organic layer was separated, washed with brine, dried over $Na_2SO_4$ and concentrated under reduced pressure to afford 8-chloro-9-hydroxy-4,6-dimethylbenzo[c][2,7]naphthyridin-5(6H)-one (0.6 g, 2.053 mmol, 79% crude yield) as a green solid. The material was carried on without further purification. LC/MS (ESI) m/e 273.0 [(M)$^-$, calcd for $C_{14}H_{10}ClN_2O_2$ 273.05]; LC/MS retention time (method C): $t_R$=2.06 min.

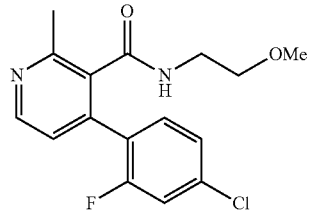 [SMILES: COCCNC(=O)c1c(-c2ccc(Cl)cc2F)ccnc1C]

Part C. 8-chloro-9-methoxy-4,6-dimethylbenzo[c][2,7]naphthyridin-5(6H)-one

To the stirred solution of 8-chloro-9-hydroxy-4,6-dimethylbenzo[c][2,7]naphthyridin-5(6H)-one (0.3 g, 1.092 mmol) in DMF (10 mL) cooled to 0° C., was added NaH (0.052 g, 2.184 mmol) followed by methyl iodide (0.205 mL, 3.28 mmol). The resultant mixture was allowed to stir at ambient temperature for 10 h. The reaction mixture was then diluted with water (50 mL) and extracted with ethyl acetate (2×80 mL). The combined organic layers were separated, washed with brine, dried over $Na_2SO_4$ and concentrated under reduced pressure. The crude product was purified by silica gel column chromatography using 70% ethyl acetate in petroleum ether to afford 8-chloro-9-methoxy-4,6-dimethylbenzo[c][2,7]naphthyridin-5(6H)-one (0.12 g, 0.416 mmol, 38% yield) as a semi-solid. LC/MS (ESI) m/e 288.4 [(M)$^+$, calcd for $C_{15}H_{13}ClN_2O_2$ 288.1]; LC/MS retention time (Method A): $t_R$=1.9 min.

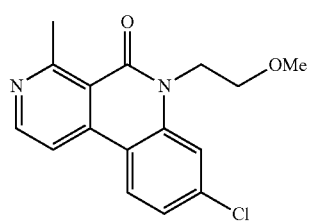 [SMILES: COCCn1c(=O)c2c(C)nccc2c2ccc(Cl)cc21]

Part D. (S)-tert-butyl (1-((9-methoxy-4,6-dimethyl-5-oxo-5,6-dihydrobenzo[c][2,7]naphthyridin-8-yl)oxy)-4-methylpentan-2-yl)carbamate 8-Chloro-9-methoxy-4,6-dimethylbenzo[c][2,7]naphthyridin-5(6H)-one was subjected to ether synthesis as described in Example 16, Part H to afford (S)-tert-butyl (1-((9-methoxy-4,6-dimethyl-5-oxo-5,6-dihydrobenzo[c][2,7]naphthyridin-8-yl)oxy)-4-methylpentan-2-yl)carbamate (90 mg, 0.073 mmol, 18% yield) as a semi solid. LC/MS (ESI) m/e 470.3 [(M+H)$^+$, calcd for $C_{26}H_{36}N_3O_5$ 470.5]; LC/MS retention time (method D) $t_R$=0.87 min.

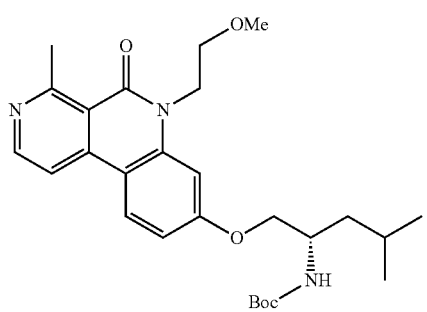 [SMILES: COCCn1c(=O)c2c(C)nccc2c2ccc(OC[C@H](CC(C)C)NC(=O)OC(C)(C)C)cc21]

Part E. (S)-8-((2-amino-4-methylpentyl)oxy)-9-methoxy-4,6-dimethylbenzo[c][2,7]naphthyridin-5(6H)-one (S)-tert-Butyl (1-((9-methoxy-4,6-dimethyl-5-oxo-5,6-dihydrobenzo[c][2,7]naphthyridin-8-yl)oxy)-4-methylpentan-2-yl)carbamate was subjected to Boc-deprotection as described in Example 2, Part E to afford (S)-8-((2-amino-4-methylpentyl)oxy)-9-methoxy-4,6-dimethylbenzo[c][2,7]naphthyridin-5(6H)-one (6 mg, 0.015 mmol, 8% yield) as a yellow solid. LC/MS (ESI) m/e 370.2 [(M+H)$^+$, calcd for $C_{21}H_{28}N_3O_3$ 370.2]; LC/MS retention time (method C): $t_R$=2.03 min. HPLC retention time (method A): $t_R$=7.31 min and HPLC retention time (method B): $t_R$=8.32 min; $^1$H NMR (400 MHz, METHANOL-$d_4$) δ ppm 8.63 (d, J=6.3 Hz, 1H), 8.50 (d, J=6.3 Hz, 1H), 8.01 (s, 1H), 7.22 (s, 1H), 4.49 (dd, J=10.7, 3.1 Hz, 1H), 4.35 (dd, J=10.9, 6.4 Hz, 1H), 4.09 (s, 3H), 3.83 (s, 3H), 3.81-3.75 (m, 1H), 3.19 (s, 3H), 1.92-1.74 (m, 2H), 1.73-1.61 (m, 1H), 1.07 (d, J=4.0 Hz, 3H), 1.06 (d, J=4.0 Hz, 3H).

Example 90

(S)-8-((2-amino-4-methylpentyl)oxy)-9-(difluoromethoxy)-4,6-dimethylbenzo[c][2,7]naphthyridin-5(6H)-one

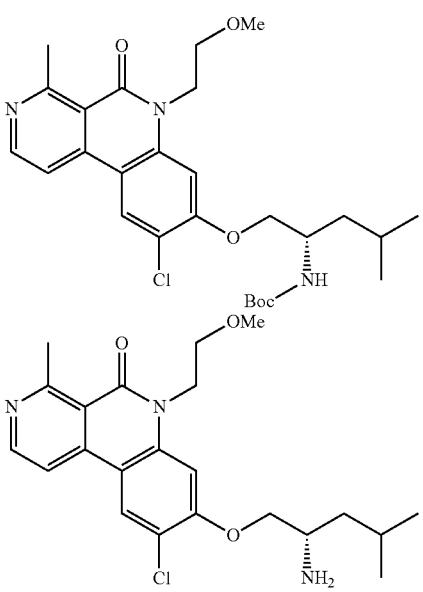

Part A: 8-chloro-9-(difluoromethoxy)-4,6-dimethylbenzo[c][2,7]naphthyridin-5(6H)-one To the stirred solution of 8-chloro-9-hydroxy-4,6-dimethylbenzo[c][2,7]naphthyridin-5(6H)-one (0.5 g, 1.456 mmol), prepared as described in Example 89, Part B in acetonitrile (5 mL) was added $K_2CO_3$ (0.604 g, 4.37 mmol) followed by sodium 2-chloro-2,2-difluoroacetate (0.444 g, 2.91 mmol). The mixture was heated to 80° C. for 18 h. After cooling, the reaction mixture was diluted with water (50 mL) and extracted with ethyl acetate (2×80 mL). The organic layer was washed with brine solution, dried over $Na_2SO_4$, filtered and concentrated under reduced pressure to afford 8-chloro-9-(difluoromethoxy)-4,6-dimethylbenzo[c][2,7]naphthyridin-5(6H)-one (50 mg, 0.154 mmol, 11% crude yield) as a semi solid. The material was carried on without further purification. LC/MS (ESI) m/e 325.0 [(M+H)$^+$, calcd for $C_{15}H_{12}ClF_2N_2O_2$ 325.04]; LC/MS retention time (method C): $t_R$=2.39 min.

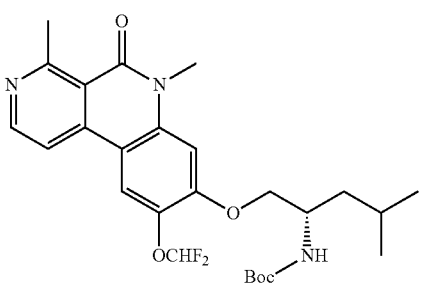 [SMILES: Cc1nccc2c1c(=O)n(C)c1cc(OC[C@H](CC(C)C)NC(=O)OC(C)(C)C)c(OC(F)F)cc21]

Part B: (S)-tert-butyl (1-((9-(difluoromethoxy)-4,6-dimethyl-5-oxo-5,6-dihydrobenzo[c][2,7]naphthyridin-8-yl)oxy)-4-methylpentan-2-yl)carbamate 8-Chloro-9-(difluoromethoxy)-4,6-dimethylbenzo[c][2,7]naphthyridin-5(6H)-one was subjected to ether synthesis as described in Example 16, Part H to afford (S)-tert-butyl (1-((9-(difluoromethoxy)-4,6-dimethyl-5-oxo-5,6-dihydrobenzo[c][2,7]naphthyridin-8-yl)oxy)-4-methylpentan-2-yl)carbamate (0.2 g, 0.033 mmol, 27% yield) as a colorless oil. LC/MS (ESI) m/e 506.3 [(M+H)$^+$, calcd for $C_{26}H_{34}F_2N_3O_5$ 506.2]; LC/MS retention time (method E): $t_R$=1.21 min.

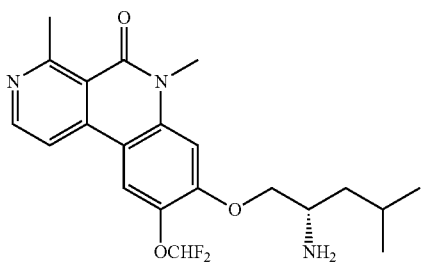

Part C: (S)-8-((2-amino-4-methylpentyl)oxy)-9-(difluoromethoxy)-4,6-dimethylbenzo[c][2,7]naphthyridin-5(6H)-one (S)-tert-Butyl (1-((9-(difluoromethoxy)-4,6-dimethyl-5-oxo-5,6-dihydrobenzo[c][2,7]naphthyridin-8-yl)oxy)-4-methylpentan-2-yl)carbamate was subjected to Boc deprotection as described in Example 2, Part E to afford (S)-8-((2-amino-4-methylpentyl)oxy)-9-(difluoromethoxy)-4,6-dimethylbenzo[c][2,7]naphthyridin-5(6H)-one (2 mg, 4.24 umol, 13% yield) as a green gum. LC/MS (ESI) m/e 406.2 [(M+H)$^+$, calcd for $C_{21}H_{26}F_2N_3O_3$ 406.2]; LC/MS retention time (method C): $t_R$=1.75 min. HPLC retention time (method B): $t_R$=10.11 min; $^1$H NMR (400 MHz, METHANOL-$d_4$) δ ppm 8.3 (s, 1H), 8.2 (m, 1 H), 7.25 (s, 1H), 6.9 (t, 1H), 4.55 (m, 1H), 4.45 (m, 1H), 3.8 (m, 4H), 3.05-3.2 (m, 3H), 1.8-1.95 (m, 3H), 1.05-1.1 (m, 6H).

Example 91 and Example 92

(S)-8-(2-amino-4,4,4-trifluorobutoxy)-4,6-dimethylbenzo[c][2,7]naphthyridin-5(6H)-one and (R)-8-(2-amino-4,4,4-trifluorobutoxy)-4,6-dimethylbenzo[c][2,7]naphthyridin-5(6H)-one

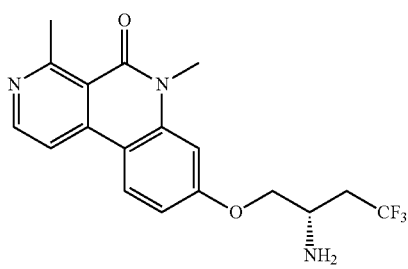

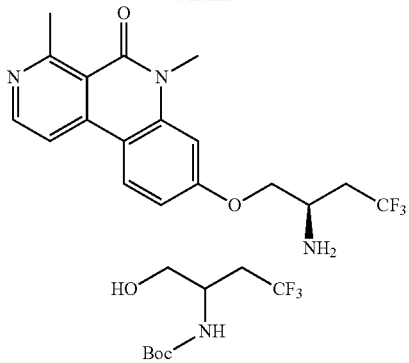

Part A. Prepared as Per Literature Reference: Ling, et. al., *J. Org. Chem.*, 2003, 68, 7544-7547

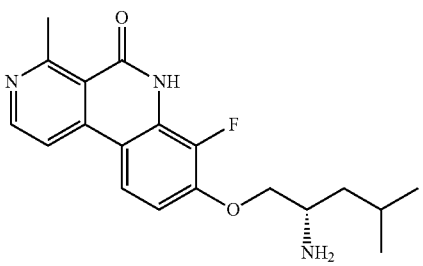 [SMILES: Cc1nccc2c1c(=O)[nH]c1c(F)c(OC[C@@H](N)CC(C)C)ccc12]

Part B. tert-butyl (1-((4,6-dimethyl-5-oxo-5,6-dihydrobenzo[c][2,7]naphthyridin-8-yl)oxy)-4,4,4-trifluorobutan-2-yl)carbamate 8-Chloro-4,6-dimethylbenzo[c][2,7]naphthyridin-5(6H)-one and tert-butyl (4,4,4-trifluoro-1-hydroxybutan-2-yl)carbamate were used for ether synthesis as described in Example 16, Part H to afford tert-butyl (1-((4,6-dimethyl-5-oxo-5,6-dihydrobenzo[c][2,7]naphthyridin-8-yl)oxy)-4,4,4-trifluorobutan-2-yl)carbamate (0.22 g, 0.473 mmol, 49% yield) as a semi-solid. LC/MS (ESI) m/e 466.2 [(M+H)$^+$, calcd for $C_{23}H_{27}F_3N_3O_4$ 466.2]; LC/MS retention time (method D): $t_R$=0.82 min.

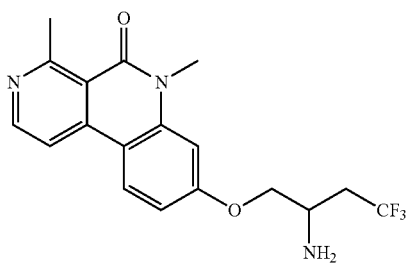 [SMILES: Cc1nccc2c1c(=O)n(C)c1cc(OCC(N)CC(F)(F)F)ccc21]

Part C. 8-(2-amino-4,4,4-trifluorobutoxy)-4,6-dimethylbenzo[c][2,7]naphthyridin-5(6H)-one Prepared as described in Example 2, Part E to afford racemic 8-(2-amino-4,4,4-trifluorobutoxy)-4,6-dimethylbenzo[c][2,7]naphthyridin-5(6H)-one (40 mg, 0.066 mmol, 26% yield, 98% purity) as an off-white solid. The racemic product was resolved by Chiral preparative SFC purification Conditions: (CHIRALPAK IA (250×21 mm) 5 micron Mob. Phase: 60% $CO_2$, Co-solvent: 40% (0.5% DEA in Methanol), Flow rate: 60 g per min, Back pressure: 100 bar) to afford two enantiomers. The absolute stereochemistry of the enantiomers was not determined Enantiomer 1:

(7 mg, 0.014 mmol, 6% yield, 98% purity) as an off-white solid. LC/MS (ESI) m/e 366.1 [(M+H)$^+$, calcd for $C_{18}H_{19}F_3N_3O_2$ 366.1]; LC/MS retention time (Method A): $t_R$=1.81 min; $^1$H NMR (400 MHz, METHANOL-$d_4$) δ ppm 8.57 (d, J=5.5 Hz, 1H), 8.41 (d, J=9.0 Hz, 1H), 8.16 (d, J=6.0 Hz, 1H), 7.12-7.05 (m, 2H), 4.30-4.08 (m, 2H), 3.77 (s, 3H), 3.62-3.58 (m, 1H), 3.10 (s, 3H), 2.74-2.58 (m, 1H), 2.44 (m, 1H). Chiral HPLC retention time (method B): $t_R$=8.08 min; Chiral SFC Method (CHIRALPAK IA (250×4.6 mm) 5 micron Mob. Phase: 65% $CO_2$, Flow rate: 2.6 g per min, Co-solvent: 35% (0.3% DEA in Methanol), Flow rate: 1.4 g per min, Back pressure: 100 bar) $t_R$=3.53 min.

Enantiomer 2:

(7 mg, 0.014 mmol, 6% yield, 98% purity) as an off-white solid. LC/MS (ESI) m/e 366.1 [(M+H)$^+$, calcd for $C_{18}H_{19}F_3N_3O_2$ 366.1]; LC/MS retention time (Method A): $t_R$=1.81 min; $^1$H NMR (400 MHz, METHANOL-$d_4$) δ ppm 8.57 (d, J=5.5 Hz, 1H), 8.41 (d, J=9.0 Hz, 1H), 8.16 (d, J=6.0 Hz, 1H), 7.12-7.05 (m, 2H), 4.30-4.08 (m, 2H), 3.77 (s, 3H), 3.62-3.58 (m, 1H), 3.10 (s, 3H), 2.74-2.58 (m, 1H), 2.44 (m, 1H). Chiral HPLC retention time (method B): $t_R$=7.93 min. Chiral SFC Method (CHIRALPAK IA (250×4.6 mm) 5 micron Mob. Phase: 65% $CO_2$, Flow rate: 2.6 g per min, Co-solvent: 35% (0.3% DEA in Methanol), Flow rate: 1.4 g per min, Back pressure: 100 bar) $t_R$=4.62 min.

Example 93

8-(2-amino-4,4,4-trifluorobutoxy)-6-methylbenzo[c][2,7]naphthyridin-5(6H)-one

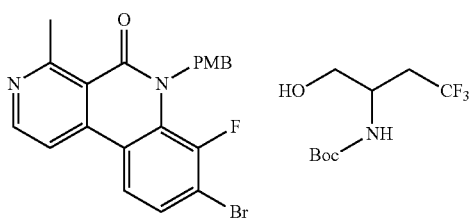

Part A. Prepared as Per Literature Reference: Ling, F. et. al., *J. Org. Chem.*, 2003, 68, 7544-7547

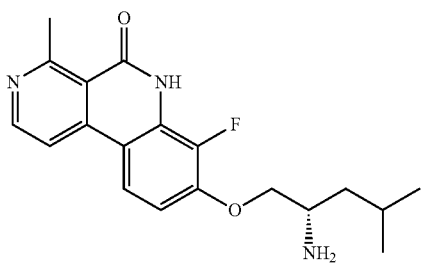

Part B. tert-butyl 4,4,4-trifluoro-1-(6-methyl-5-oxo-5,6-dihydrobenzo[c][2,7]naphthyridin-8-yloxy)butan-2-ylcarbamate Prepared as described in Example 16, Part H to afford tert-butyl 4,4,4-trifluoro-1-(6-methyl-5-oxo-5,6-dihydrobenzo[c][2,7]naphthyridin-8-yloxy)butan-2-ylcarbamate (200 mg, 0.221 mmol, 45% yield) as an off white solid. LC/MS (ESI) m/e 452.2 [(M+H)$^+$, calcd for $C_{22}H_{25}F_3N_3O_4$ 452.2]; LC/MS retention time (Method C): $t_R$=2.01 min.

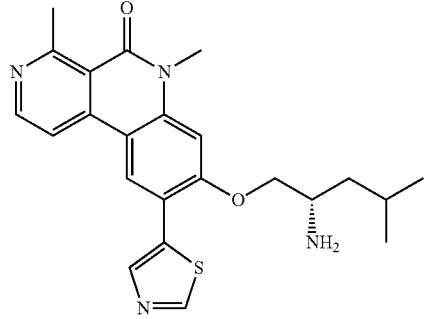 [SMILES: Cc1nccc2c1c(=O)n(C)c1cc(OC[C@@H](N)CC(C)C)c(-c3cncs3)cc21]

Part C. 8-(2-amino-4,4,4-trifluorobutoxy)-6-methylbenzo[c][2,7]naphthyridin-5(6H)-one Prepared as described in Example 2, Part E to afford 8-(2-amino-4,4,4-trifluorobutoxy)-6-methylbenzo[c][2,7]naphthyridin-5(6H)-one (35 mg, 0.098 mmol, 44% yield) as an off white solid. LC/MS (ESI) m/e 352.0 [(M+H)$^+$, calcd for $C_{12}H_{17}F_3N_3O_2$ 352.1]; LC/MS retention time (Method C): $t_R$=1.92 min; HPLC retention time (method A): $t_R$=7.07 min; HPLC retention time (method B): $t_R$=7.44 min; $^1$H NMR (400 MHz, METHANOL-$d_4$) δ 9.46 (s, 1H), 8.76 (d, J=6.0 Hz, 1H), 8.40 (d, J=8.8 Hz, 1H), 8.23 (d, J=5.6 Hz, 1H), 7.14 (d, J=2.4 Hz, 1H), 7.10 (dd, J=8.8, 2.4 Hz, 1H), 4.22-4.13 (m, 2H), 3.79 (s, 3H), 3.67-3.57 (m, 1H), 2.71-2.63 (m, 1H), 2.49-2.40 (m, 1H).

Example 94

(S)-8-((2-amino-4-methylpentyl)oxy)-4,6-dimethyl-5-oxo-5,6-dihydrobenzo[c][2,7]naphthyridine-9-carboxamide

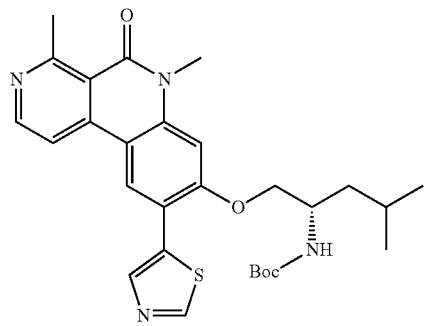 [SMILES: Cc1nccc2c1c(=O)n(C)c1cc(OC[C@H](CC(C)C)NC(=O)OC(C)(C)C)c(-c3cncs3)cc21]

In a 25 mL round-bottomed flask, (S)-8-((2-amino-4-methylpentyl)oxy)-4,6-dimethyl-5-oxo-5,6-dihydrobenzo[c][2,7]naphthyridine-9-carbonitrile (0.1 g, 0.274 mmol), (prepared as described in Example 64) and Cs₂CO₃ (0.358 g, 1.098 mmol) were taken up in DMF (2 mL) and water (0.6 mL). The mixture was irradiated in a microwave at 120° C. for 2 h. The reaction mixture was concentrated under reduced pressure, and diluted with ethyl acetate and water. The combined organics were concentrated under reduced pressure. The residue was purified by Prep. HPLC (Column: Xbridge Phenyl (150×4.6 mm) 3.5 micron SC/749 using buffer: 0.05% TFA in water) to afford (S)-8-((2-amino-4-methylpentyl)oxy)-4,6-dimethyl-5-oxo-5,6-dihydrobenzo[c][2,7]naphthyridine-9-carboxamide (5 mg, 0.012 mmol, 5% yield) as an off-white solid. LC/MS (ESI) m/e 383.2 [(M+H)⁺, calcd for C₂₁H₂₂N₄O₃ 383.2]; LC/MS retention time (method C): $t_R$=1.74 min; HPLC retention time (method A): $t_R$=10.51 min; HPLC retention time (method B): $t_R$=10.58 min; ¹H NMR (400 MHz, methanol-d₄): δ ppm 8.64 (s, 1H), 8.46 (d, 1H), 8.12 (d, 1H), 6.67 (s, 1H), 3.72-3.79 (m, 1H), 3.69 (s, 3H), 3.65-3.69 (m, 2H), 3.04 (s, 3H), 1.84-1.88 (m, 1H), 1.62-1.68 (m, 1H), 1.49-1.57 (m, 1H), 1.31 (d, 3H), 1.29 (d, 3H).

Example 95

(S)-4,6-dimethyl-8-(4-methyl-2-(methylamino)pentyloxy)benzo[c][2,7]naphthyridin-5(6H)-one

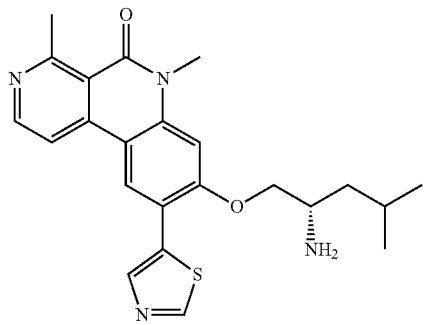

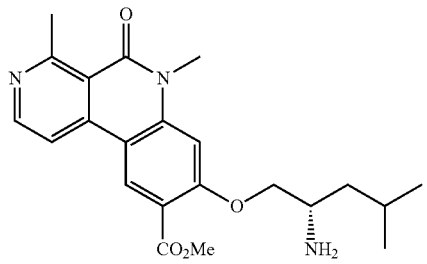 [SMILES: Cc1nccc2c1c(=O)n(C)c1cc(OC[C@@H](N)CC(C)C)c(C(=O)O)cc21]

Part A: (S)-tert-butyl 1-(4,6-dimethyl-5-oxo-5,6-dihydrobenzo[c][2,7]naphthyridin-8-yloxy)-4-methylpentan-2-yl(methyl)carbamate (S)-tert-Butyl (1-((4,6-dimethyl-5-oxo-5,6-dihydrobenzo [c][2,7]naphthyridin-8-yl)oxy)-4-methylpentan-2-yl)carbamate (0.150 g, 0.341 mmol), prepared as described in Example 16, Part H, was taken up in DMF (1 mL) and cooled to 0° C. NaH (0.027 g, 0.683 mmol) was added and the reaction mixture was stirred for 45 min at 0° C. Iodomethane (0.107 mL, 1.706 mmol) was then added and reaction mixture was warmed to room temperature and stirred for 15 min. The mixture was quenched with ice and partitioned between ethyl acetate (4 mL) and water (2 mL). The organic layer was separated, washed with brine (2 mL), dried over sodium sulfate, filtered and concentrated under reduced pressure to afford crude which was purified by preparative HPLC to afford (S)-tert-butyl (1-((4,6-dimethyl-5-oxo-5,6-dihydrobenzo[c][2,7]naphthyridin-8-yl)oxy)-4-methylpentan-2-yl)(methyl)carbamate (60 mg, 0.125 mmol, 37% yield) as a light yellow solid. LC/MS (ESI) m/e 454.4 [(M+H)⁺, calcd for C₂₆H₃₆N₃O₂ 454.3]; LC/MS retention time (method E): $t_R$=1.21 min.

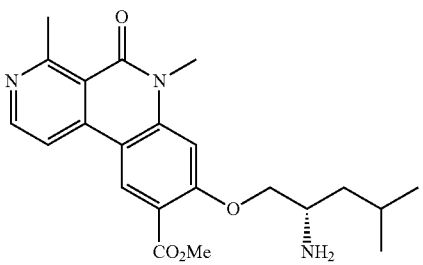

Part B: (S)-4,6-dimethyl-8-(4-methyl-2-(methylamino)pentyloxy)benzo[c][2,7]naphthyridin-5(6H)-one Prepared as described in Example 2, Part E to afford title compound (30 mg, 0.070 mmol, 64% yield) as a pale yellow solid. LC/MS (ESI) m/e 354.0 [(M+H)⁺, calcd for C₂₁H₂₈N₃O₂ 354.2] LC/MS retention time (method C): $t_R$=1.81 min. HPLC retention time (method A): $t_R$=8.22 min and HPLC retention time (method B): $t_R$=9.21 min. ¹H NMR (400 MHz, METHANOL-d₄) δ ppm 8.74 (d, J=7.0 Hz, 1H), 8.69-8.65 (m, 1H), 8.62 (d, J=9.0 Hz, 1H), 7.30-7.22 (m, 2H), 4.62 (dd, J=11.0, 3.0 Hz, 1H), 4.49 (dd, J=11.5, 5.0 Hz, 1H), 3.85 (s, 3H), 3.74 (dd, J=8.3, 3.8 Hz, 1H), 3.28 (s, 3H), 2.84 (s, 3H), 1.99-1.78 (m, 2H), 1.76-1.63 (m, 1H), 1.07 (d, J=6.0 Hz, 6H).

Example 96

(S)-8-((2-amino-4-methylpentyl)oxy)-N,N,4,6-tetramethyl-5-oxo-5,6-dihydrobenzo[c][2,7]naphthyridine-9-carboxamide

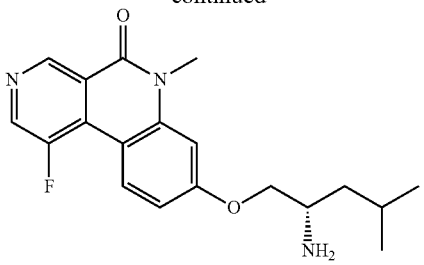

Part A: (S)-8-((2-amino-4-methylpentyl)oxy)-4,6-dimethyl-5-oxo-5,6-dihydrobenzo[c][2,7]naphthyridine-9-carboxylic Acid To a solution of (S)-8-((2-amino-4-methylpentyl)oxy)-4,6-dimethyl-5-oxo-5,6-dihydrobenzo[c][2,7]naphthyridine-9-carbonitrile (450 mg, 1.235 mmol), prepared as described in Example 64, in ethanol (5 mL) and water (5 mL) was added NaOH (494 mg, 12.35 mmol). The mixture was heated to 80° C. for 12 h. The volatiles were evaporated and the residue was diluted with water The pH was adjusted to 3 using 1.5N HCl. The solution was extracted with ethyl acetate (2×5 mL). The combined organic layers were dried over sodium sulfate, filtered and concentrated under reduced pressure to afford (S)-8-((2-amino-4-methylpentyl)oxy)-4,6-dimethyl-5-oxo-5,6-dihydrobenzo[c][2,7]naphthyridine-9-carboxylic acid (90 mg, 0.235 mmol, 19% crude yield) as a yellow solid. The material was carried forward without further purification. LC/MS (ESI) m/e 384.1 [(M+H)$^+$, calcd for $C_{21}H_{26}N_3O_4$ 384.2]; LC/MS retention time (method D): $t_R$=0.72 min.

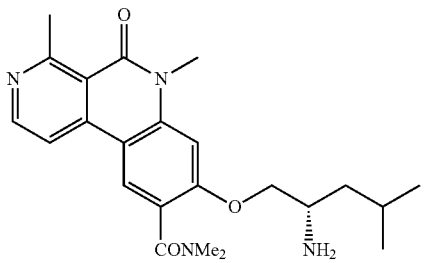

Part B: (S)-8-((2-amino-4-methylpentyl)oxy)-N,N,4,6-tetramethyl-5-oxo-5,6-dihydrobenzo[c][2,7]naphthyridine-9-carboxamide The solution of (S)-8-((2-amino-4-methylpentyl)oxy)-4,6-dimethyl-5-oxo-5,6-dihydrobenzo[c][2,7]naphthyridine-9-carboxylic acid (90 mg, 0.070 mmol) in DMF (0.9 mL) was cooled to 0° C. HOBT (21.57 mg, 0.141 mmol) and EDC (20.25 mg, 0.106 mmol) were added and stirred for 5 min. To this dimethylamine (0.282 mL, 0.563 mmol) was added followed by DIPEA (0.037 mL, 0.211 mmol) and stirred for 30 min. The reaction was then warmed to rt and stirred for 12 h. The reaction was quenched by addition of ice, the solid crashed out was filtered. The solid was washed with excess of water and dried completely to afford the orange oil upon warming to rt. The crude product was purified by prep HPLC (0.1% TFA in ACN:Water) to afford (S)-8-((2-amino-4-methylpentyl)oxy)-N,N,4,6-tetramethyl-5-oxo-5,6-dihydrobenzo[c][2,7]naphthyridine-9-carboxamide, 2 TFA (3.36 mg, 4.95 μmol, 7% yield) as a light green solid. LC/MS (ESI) m/e 411.2 [(M+H)$^+$, calcd for $C_{23}H_{31}N_4O_3$ 411.2] LC/MS retention time (method C): $t_R$=2.22 min. HPLC retention time (method A): $t_R$=10.98 min and HPLC retention time (method B): $t_R$=11.63

$^1$H NMR (400 MHz, METHANOL-$d_4$) δ ppm 8.44 (d, J=6.0 Hz, 1H), 8.31 (d, J=6.0 Hz, 1H), 8.25 (s, 1H), 6.76 (s, 1H), 3.76 (s, 3H), 3.69 (dd, J=4.8, 3.3 Hz, 2H), 3.34 (s, 3H), 3.20-3.08 (m, 7H), 1.84-1.78 (m, 1H), 1.66-1.51 (m, 2H), 1.05 (d, J=7.0 Hz, 3H), 0.99 (d, J=6.5 Hz, 3H).

Example 97

8-(2-amino-2,4-dimethylpentyloxy)-1-fluoro-6-methylbenzo[c][2,7]naphthyridin-5(6H)-one

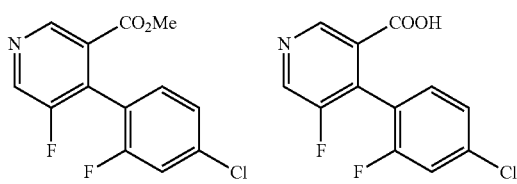 [SMILES: COC(=O)c1cncc(F)c1-c1ccc(Cl)cc1F ; O=C(O)c1cncc(F)c1-c1ccc(Cl)cc1F]

Part A: tert-butyl 1-(1-fluoro-6-methyl-5-oxo-5,6-dihydrobenzo[c][2,7]naphthyridin-8-yloxy)-2,4-dimethylpentan-2-ylcarbamate Prepared as described in Example 16, Part H from 8-chloro-1-fluoro-6-methylbenzo[c][2,7]naphthyridin-5(6H)-one, prepared as described in Example 85, Part E, to afford (S)-8-((2-amino-4-methylpentyl)oxy)-7-fluoro-4,6-dimethylbenzo[c][2,7]naphthyridin-5(6H)-one (35 mg, 0.076 mmol, 50% yield). LC/MS (ESI) m/e 458.2 [(M+H)$^+$, calcd for $C_{25}H_{33}FN_3O_4$ 458.2]; LC/MS retention time (method C): $t_R$=2.15 min.

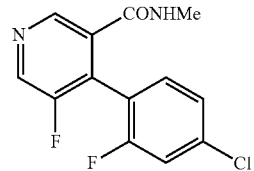

Part B: 8-(2-amino-2,4-dimethylpentyloxy)-1-fluoro-6-methylbenzo[c][2,7]naphthyridin-5(6H)-one Prepared as described in Example 2, Part E to afford 8-(2-amino-2,4-dimethylpentyloxy)-1-fluoro-6-methylbenzo[c][2,7]naphthyridin-5(6H)-one (16.5 mg, 0.035 mmol, 45% yield as a white solid. LC/MS (ESI) m/e 358.2 [(M+H)$^+$, calcd for $C_{20}H_{25}FN_3O_2$ 358.2]; LC/MS retention time (method C): $t_R$=2.06 min; HPLC retention time (method A): $t_R$=11.79 min; HPLC retention time (method B): $t_R$=6.66 min; $^1$H NMR (400 MHz, METHANOL-$d_4$) δ ppm 9.41 (s, 1H), 8.79 (d, J=4.8 Hz, 1H), 8.71 (dd, J=9.2, 2.9 Hz, 1H), 7.24 (d, J=2.3 Hz, 1H), 7.22-7.15 (m, 1H), 4.36 (d, J=10.3 Hz, 1H), 4.24 (d, J=10.3 Hz, 1H), 3.84 (s, 3H), 2.02-1.83 (m, 2H), 1.80-1.70 (m, 1H), 1.55 (s, 3H), 1.11 (d, J=6.5 Hz, 3H), 1.06 (d, J=6.3 Hz, 3H).

Example 98

(S)-8-((2-amino-4-methylpentyl)oxy)-1-methoxy-6-methylbenzo[c][2,7]naphthyridin-5(6H)-one

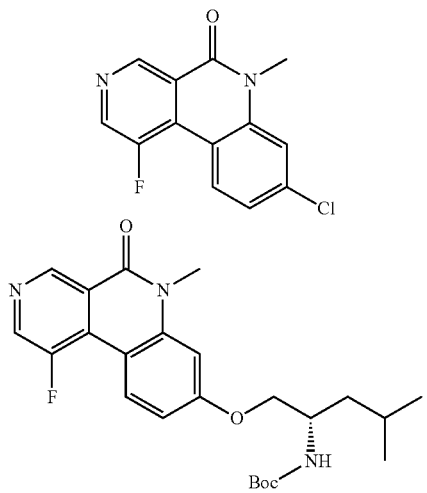

Part A: 8-chloro-1-methoxy-6-methylbenzo[c][2,7]naphthyridin-5(6H)-one

To the solution of 8-chloro-1-fluoro-6-methylbenzo[c][2,7]naphthyridin-5(6H)-one (40 mg, 0.152 mmol), prepared as described in Example 85, Part E, in MeOH (0.2 mL) in a microwave vial, 18-crown-6 (4.03 mg, 0.015 mmol) and sodium methoxide (32.9 mg, 0.152 mmol) in methanol were added and heated in a microwave oven at 100° C. for 30 min. Upon completion, the reaction mixture was diluted with water and extracted with ethyl acetate (2×5 mL). The combined organic layers were washed with brine solution, dried over sodium sulfate, filtered and concentrated under reduced pressure to afford 8-chloro-1-methoxy-6-methylbenzo[c][2,7]naphthyridin-5(6H)-one (40 mg, 0.146 mmol, 96% crude yield) as a white solid. The material was carried forward without further purification. LC/MS (ESI) m/e 275.0 [(M+H)$^+$, calcd for C$_{14}$H$_{12}$ClN$_2$O$_2$ 275.05]; LC/MS retention time (method D): t$_R$=0.72 min.

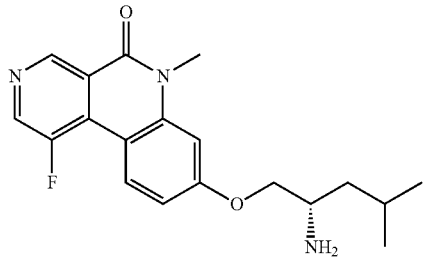

Part B: (S)-tert-butyl (1-((1-methoxy-6-methyl-5-oxo-5,6-dihydrobenzo[c][2,7]naphthyridin-8-yl)oxy)-4-methylpentan-2-yl)carbamate To the solution of 8-chloro-1-methoxy-6-methylbenzo[c][2,7]naphthyridin-5(6H)-one (40 mg, 0.146 mmol) in toluene (0.5 mL) was added cesium carbonate (71.2 mg, 0.218 mmol) and di-tert-butyl(2',4',6'-triisopropyl-[1',1'-biphenyl]-2-yl) phosphine (6.18 mg, 0.015 mmol). The solution was purged with N2 for 5 min. To this palladium (II) acetate (1.635 mg, 7.28 µmol) was added and the solution purged with N2 for 10 min. The resultant mixture was heated at 90° C. for 21 h. After cooling, the reaction mixture was filtered through diatomaceous earth (Celite®), eluting with EtOAc. The filtrate was concentrated under reduced pressure. The crude product was purified by silica gel chromatography using hexanes and ethyl acetate to afford (S)-tert-butyl (1-((1-methoxy-6-methyl-5-oxo-5,6-dihydrobenzo[c][2,7]naphthyridin-8-yl)oxy)-4-methylpentan-2-yl)carbamate (40 mg, 0.041 mmol, 28% yield). LC/MS (ESI) m/e 456.2 [(M+H)$^+$, calcd for C$_{25}$H$_{34}$N$_3$O$_5$ 456.2]; LC/MS retention time (method D): t$_R$=0.9 min.

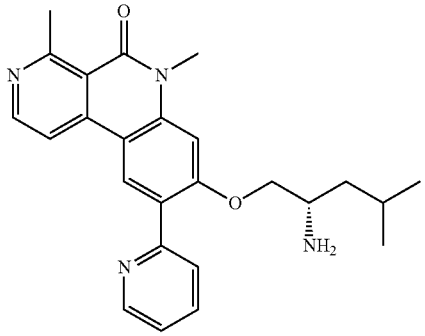 [SMILES: Cc1nccc2c1c(=O)n(C)c1cc(OC[C@@H](N)CC(C)C)c(-c3ccccn3)cc21]

Part C: (S)-8-((2-amino-4-methylpentyl)oxy)-1-methoxy-6-methylbenzo[c][2,7]naphthyridin-5(6H)-one To the solution of (S)-tert-butyl (1-((1-methoxy-6-methyl-5-oxo-5,6-dihydrobenzo[c][2,7]naphthyridin-8-yl)oxy)-4-methylpentan-2-yl)carbamate (40 mg, 0.041 mmol) in DCM (0.9 mL) cooled to 0° C., TFA (0.2 mL, 2.60 mmol) was added dropwise and stirred for 5 min. The reaction mixture was warmed to rt and stirred for 3 h. The volatiles were removed under reduced pressure. The crude product was purified by prep HPLC using (0.1% TFA in ACN:water) to afford (S)-8-((2-amino-4-methylpentyl)oxy)-1-methoxy-6-methylbenzo[c][2,7]naphthyridin-5(6H)-one, 2 TFA (17.11 mg, 0.028 mmol, 69% yield) as white solid. LC/MS (ESI) m/e 356.0 [(M+H)$^+$, calcd for C$_{20}$H$_{26}$N$_3$O$_3$ 356.2]; LC/MS retention time (method C): t$_R$=1.82 min; HPLC retention time (method A): t$_R$=9.44 min; HPLC retention time (method B): t$_R$=9.78 min; $^1$H NMR (400 MHz, METHANOL-d$_4$) δ ppm 9.17 (s, 1H), 9.14 (d, J=9.0 Hz, 1H), 8.54 (s, 1H), 7.09 (d, J=2.5 Hz, 1H), 7.02 (dd, J=9.0, 2.5 Hz, 1H), 4.21 (s, 3H), 4.19-4.15 (m, 1H), 4.04-3.95 (m, 2H), 3.78 (s, 3H), 1.97-1.80 (m, 1H), 1.51-1.42 (m, 2H), 1.04 (d, J=6.5 Hz, 3H), 1.02 (d, J=6.5 Hz, 3H).

Example 99

(S)-8-(2-amino-4-methylpentyloxy)-7-methoxy-4-methylbenzo[c][2,7]naphthyridin-5(6H)-one

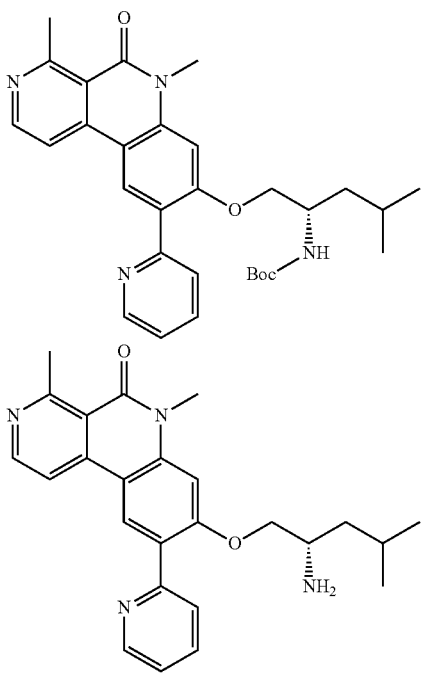

Part A. 3-bromo-6-chloro-2-fluorophenol

To a stirred solution of 1-bromo-4-chloro-2-fluorobenzene (5 g, 23.87 mmol) in tetrahydrofuran (40 mL) cooled to −78° C. was added LDA (14.92 mL, 29.8 mmol) dropwise. The reaction mixture was stirred at this temperature for 30 min. then allowed to warm to −20° C. and stirred for 30 min. The reaction was then cooled to −78° C. and trimethyl borate (3.47 mL, 31.0 mmol) dissolved in THF (5 mL) was added dropwise. The reaction mixture was warmed to −20° C. and stirred for 1 h. The reaction mixture was then cooled to −78° C. and peracetic acid (16 mL, 84 mmol) as slowly added dropwise. The mixture was allowed to warm to rt and stirred for 12 h. The reaction mixture was again cooled to 0° C. and quenched with 5% ammonium chloride The solution was extracted with ethyl acetate (2×50 mL). The combined organic layers were washed with brine (50 mL), dried over sodium sulfate, filtered and concentrated under reduced pressure to afford 3-bromo-6-chloro-2-fluorophenol (4.99 g, 18.25 mmol, 76% crude yield) as a yellow oil. The material was carried forward without further purification. LC/MS (ESI) m/e 225.1 [(M+H)$^+$, calcd for $C_6H_4BrClFO$ 224.9]; LC/MS retention time (method E): $t_R$=0.87 min.

Part B. 1-bromo-4-chloro-2-fluoro-3-methoxybenzene

To a stirred solution of 3-bromo-6-chloro-2-fluorophenol (4.2 g, 18.63 mmol) in acetonitrile (35 mL) was added potassium carbonate (5.15 g, 37.3 mmol) followed by methyl iodide (2.330 mL, 37.3 mmol) dropwise at rt. The reaction mixture was heated to 85° C. for 3 h. After cooling, the volatiles were concentrated under reduced pressure and the residue was diluted with water (50 mL) and extracted with ethyl acetate (2×80 mL). The combined organic layers were washed with brine (100 mL), dried over sodium sulfate, filtered and concentrated under reduced pressure to afford 1-bromo-4-chloro-2-fluoro-3-methoxybenzene (4 g, 16.7 mmol, 90% crude yield) as a brown solid. The material was carried forward without further purification. $^1$H NMR (400 MHz, CDCl$_3$) δ ppm 7.2 (m, 1H), 7.04 (m, 1H), 3.98 (s, 3H).

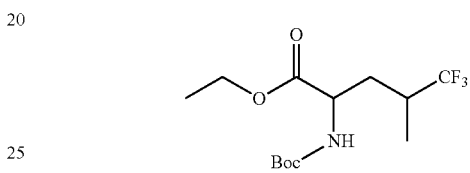

Part C. 2-(4-chloro-2-fluoro-3-methoxyphenyl)-4,4,5,5-tetramethyl-1,3,2-dioxaborolane To a stirred solution of 1-bromo-4-chloro-2-fluoro-3-methoxybenzene (3 g, 12.53 mmol) in tetrahydrofuran (20 mL) cooled to −10° C. was added isopropylmagnesium bromide (5.18 mL, 15.03 mmol) dropwise and the reaction mixture was stirred at −10° C. for 1 h. The reaction mixture was then warmed to 0° C. and stirred for 1 h. The reaction was then cooled to −10° C. and 2-isopropoxy-4,4,5,5-tetramethyl-1,3,2-dioxaborolane (2.56 mL, 12.53 mmol) was slowly added dropwise. The reaction mixture was allowed to warm to room temperature and stirred for 16 h. The reaction mixture was quenched with 5% aqueous sodium hydroxide and extracted with ethyl acetate (2×25 mL). The combined organic layers were washed with brine solution, dried over sodium sulfate, filtered and concentrated under reduced pressure to afford 2-(4-chloro-2-fluoro-3-methoxyphenyl)-4,4,5,5-tetramethyl-1,3,2-dioxaborolane (2.3 g, 8.03 mmol, 64% crude yield) as a brown oil. The material was carried forward without further purification. $^1$H NMR (400 MHz, CDCl$_3$) δ ppm 7.35 (m, 1H), 7.15 (m, 1H), 3.95 (s, 3H), 1.33 (s, 6H), 1.23 (s, 6H).

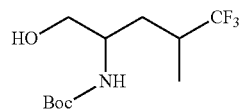

Part D. Methyl 4-(4-chloro-2-fluoro-3-methoxyphenyl)-2-methylnicotinate

A mixture of methyl 4-chloro-2-methylnicotinate (1.5 g, 8.08 mmol), 2-(4-chloro-2-fluoro-3-methoxyphenyl)-4,4,5,5-tetramethyl-1,3,2-dioxaborolane (2.316 g, 8.08 mmol), phosphoric acid, potassium salt (3.43 g, 16.16 mmol) and PdCl$_2$(dppf)-CH$_2$Cl$_2$ adduct (0.660 g, 0.808 mmol) in 1,4- dioxane (25 mL) and water (5 mL) was purged with nitrogen for 5 min. The reaction was then heated to 100° C. for 18 h. After cooling, the reaction was diluted with water (50 mL) and extracted with ethyl acetate (2×75 mL). The combined organic layers were washed with brine solution, dried over sodium sulfate, filtered and concentrated. The residue was purified by silica gel chromatography using 50% ethyl acetate in hexanes to yield methyl 4-(4-chloro-2-fluoro-3-methoxyphenyl)-2-methylnicotinate (1.2 g, 2.52 mmol, 31% yield) as pale brown oil. LC/MS (ESI) m/e 309.9 [(M+H)$^+$, calcd for C$_{15}$H$_{14}$ClFNO$_3$ 310.1]; LC/MS retention time (method D): t$_R$=0.84 min.

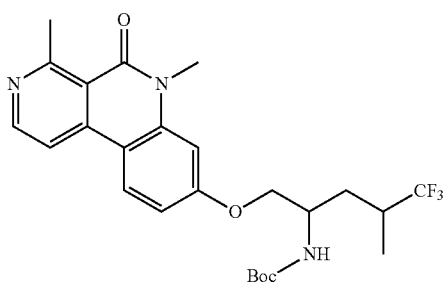 [SMILES: Cc1nccc2c1c(=O)n(C)c1cc(OCC(CC(C)C(F)(F)F)NC(=O)OC(C)(C)C)ccc21]

Part E. 4-(4-chloro-2-fluoro-3-methoxyphenyl)-2-methylnicotinic Acid

Prepared as described in Example 16, Part E by hydrolysis of the methyl 4-(4-chloro-2-fluoro-3-methoxyphenyl)-2-methylnicotinate to afford 4-(4-chloro-2-fluoro-3-methoxyphenyl)-2-methylnicotinic acid (780 mg, 2.137 mmol, 93% yield) as a brown oil. LC/MS (ESI) m/e 295.9 [(M+H)$^+$, calcd for C$_{14}$H$_{12}$ClFNO$_3$ 296.04]; LC/MS retention time (method D): t$_R$=0.61 min.

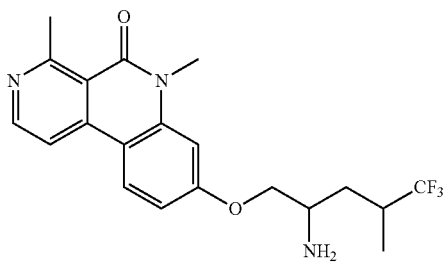 [SMILES: Cc1nccc2c1c(=O)n(C)c1cc(OCC(N)CC(C)C(F)(F)F)ccc21]

Part F. 4-(4-chloro-2-fluoro-3-methoxyphenyl)-N-(4-methoxybenzyl)-2-methylnicotinamide To a stirred solution of (4-methoxyphenyl)methanamine (0.437 g, 3.18 mmol) in CH$_2$Cl$_2$ (25 mL) was added DIEA (0.556 mL, 3.18 mmol) and the reaction mixture was stirred at 0° C. for 15 min. 4-(4-chloro-2-fluoro-3-methoxyphenyl)-2-methylnicotinoyl chloride (1 g, 3.18 mmol) (prepared by treatment of carboxylic acid with thionyl chloride) dissolved in 10 mL of DCM was then added to the reaction mixture and the reaction was stirred at rt for 10 h. The reaction was quenched by addition of water (50 mL) and the solution was extracted with DCM (2×50 mL). The combined organic layers were washed with brine solution 50 mL, dried over sodium sulfate, filtered and concentrated under reduced pressure. The residue was purified by silica gel chromatography using ethyl acetate in hexanes as eluant to yield 4-(4-chloro-2-fluoro-3-methoxyphenyl)-N-(4-methoxybenzyl)-2-methylnicotinamide (800 mg, 1.109 mmol, 35% yield) as a brown oil. LC/MS (ESI) m/e 415.1 [(M+H)$^+$, calcd for C$_{22}$H$_{21}$ClFN$_2$O$_3$ 415.1]; LC/MS retention time (method D): t$_R$=0.78 min.

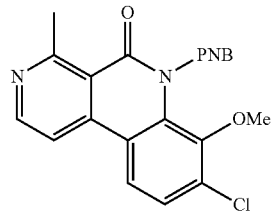

Part G. 8-chloro-7-methoxy-6-(4-methoxybenzyl)-4-methylbenzo[c][2,7]naphthyridin-5(6H)-one Prepared as described in Example 2, Part C from 4-(4-chloro-2-fluoro-3-methoxyphenyl)-N-(4-methoxybenzyl)-2-methylnicotinamide to afford 8-chloro-7-methoxy-6-(4-methoxybenzyl)-4-methylbenzo[c][2,7]naphthyridin-5 (6H)-one (110 mg, 0.245 mmol, 34% yield) as yellow solid. LC/MS (ESI) m/e 395.1 [(M+H)$^+$, calcd for C$_{22}$H$_{20}$ClN$_2$O$_3$ 395.1] LC/MS retention time (method D): t$_R$=0.81 min.

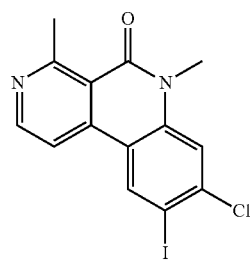

Part H. (S)-tert-butyl 1-(7-methoxy-6-(4-methoxybenzyl)-4-methyl-5-oxo-5,6-dihydrobenzo[c][2,7]naphthyridin-8-yloxy)-4-methylpentan-2-ylcarbamate Prepared as described in Example 16, Part H to afford the title compound (325 mg, 0.119 mmol, 49% crude yield) as a white solid. The material was carried forward without purification. LC/MS (ESI) m/e 576.3 [(M+H)$^+$, calcd for C$_{33}$H$_{42}$N$_3$O$_6$ 576.3]; LC/MS retention time (method D): t$_R$=0.99 min.

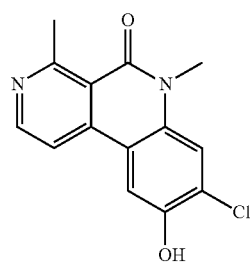 [SMILES: Cc1nccc2c1c(=O)n(C)c1cc(Cl)c(O)cc21]

Part I. (S)-8-(2-amino-4-methylpentyloxy)-7-methoxy-4-methylbenzo[c][2,7]naphthyridin-5(6H)-one Prepared as described in Example 2, Part E to afford (S)-8-(2-amino-4-methylpentyloxy)-7-methoxy-4-methylbenzo[c][2,7]naphthyridin-5(6H)-one (12.3 mg, 0.033 mmol, 28% yield) as a white solid. LC/MS (ESI) m/e 356.2 [(M+H)$^+$, calcd for $C_{20}H_{26}N_3O_3$ 356.2]; LC/MS retention time (method C): $t_R$=1.49 min; HPLC retention time (method A): $t_R$=7.36 min; HPLC retention time (method B): $t_R$=8.52 min; $^1$H NMR (400 MHz, METHANOL-d$_4$) δ ppm 8.59 (d, J=5.5 Hz, 1H), 8.14 (d, J=5.5 Hz, 1H), 8.10 (d, J=9.0 Hz, 1H), 7.11 (d, J=9.0 Hz, 1H), 4.18 (dd, J=9.3, 4.3 Hz, 1H), 4.08-4.03 (m, 1H), 4.02 (s, 3H), 4.01-3.96 (m, 1H), 3.10 (s, 3H), 1.91-1.80 (m, 1H), 1.57-1.40 (m, 2H), 1.03 (d, J=6.5 Hz, 3H), 1.01 (d, J=7.0 Hz, 3H).

Example 100

(S)-8-(2-amino-4-methylpentyloxy)-9-bromo-7-fluoro-4-methylbenzo[c][2,7]naphthyridin-5(6H)-one

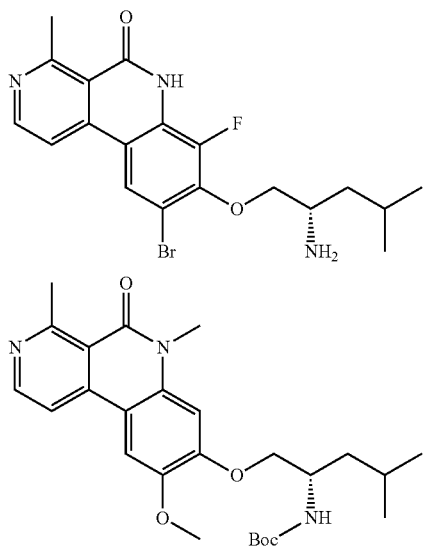

Part A: (S)-tert-butyl 1-(9-bromo-7-fluoro-6-(4-methoxybenzyl)-4-methyl-5-oxo-5,6-dihydrobenzo[c][2,7]naphthyridin-8-yloxy)-4-methylpentan-2-ylcarbamate Prepared from (S)-tert-butyl 1-(7-fluoro-6-(4-methoxybenzyl)-4-methyl-5-oxo-5,6-dihydrobenzo[c][2,7]naphthyridin-8-yloxy)-4-methylpentan-2-ylcarbamate prepared as described in Example 82, Part C, using the method described in Example 3, Part A to afford title compound (120 mg, 0.065 mmol, 44% yield). LC/MS (ESI) m/e 642.4 [(M+H)$^+$, calcd for $C_{32}H_{38}BrFN_3O_5$ 642.2]; LC/MS retention time (method E): $t_R$=1.26 min.

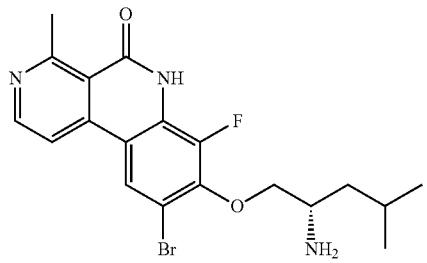

Part B: (S)-8-(2-amino-4-methylpentyloxy)-9-bromo-7-fluoro-4-methylbenzo[c][2,7]naphthyridin-5(6H)-one Prepared as described in Example 2, Part E to afford (S)-8-(2-amino-4-methylpentyloxy)-9-bromo-7-fluoro-4-methylbenzo[c][2,7]naphthyridin-5(6H)-one (3.5 mg, 8.22 μmol, 13% yield) as an off-white solid. LC/MS (ESI) m/e 423.0 [(M+H)$^+$, calcd for $C_{19}H_{22}BrFN_3O_2$ 423.3]; LC/MS retention time (method C): $t_R$=2.10 min; HPLC retention time (method A): $t_R$=8.58 min; HPLC retention time (method B): $t_R$=9.08 min; $^1$H NMR (400 MHz, METHANOL-d$_4$) δ ppm 8.73 (d, J=6.0 Hz, 1H), 8.57 (d, J=2.0 Hz, 1H), 8.40 (d, J=6.0 Hz, 1H), 4.51 (dd, J=10.3, 2.5 Hz, 1H), 4.38 (dd, J=10.4, 5.6 Hz, 1H), 3.78-3.73 (m, 1H), 3.17 (s, 3H), 1.94-1.82 (m, 2H), 1.73-1.60 (m, 1H), 1.08 (d, J=2.5 Hz, 3H), 1.06 (d, J=2.8 Hz, 3H).

Example 101

(S)-8-(2-amino-4-methylpentyloxy)-9-fluoro-4-methylbenzo[c][2,7]naphthyridin-5(6H)-one

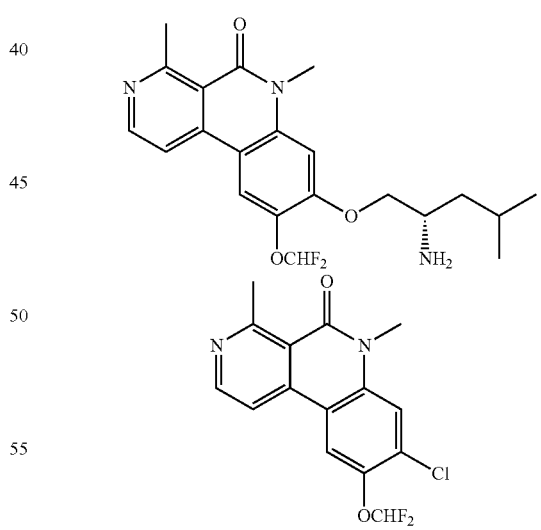

Part A: 4-(4-chloro-2,5-difluorophenyl)-N-(4-methoxybenzyl)-2-methylnicotinamide Prepared as described in Example 82, Part A from 4-(4-chloro-2,5-difluorophenyl)-2-methylnicotinic acid (prepared as described in Example 70, Part D) to afford title compound (440 mg, 1.015 mmol, 87% yield) as an off-white solid.

LC/MS (ESI) m/e 403.1 [(M+H)$^+$, calcd for C$_{21}$H$_{18}$ClF$_2$N$_2$O$_2$ 403.1]; LC/MS retention time (method E): t$_R$=0.93 min.

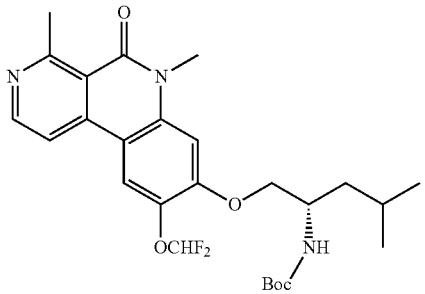 [SMILES: Cc1nccc2c1c(=O)n(C)c1cc(OC[C@H](CC(C)C)NC(=O)OC(C)(C)C)c(OC(F)F)cc21]

Part B: 8-chloro-9-fluoro-6-(4-methoxybenzyl)-4-methylbenzo[c][2,7]naphthyridin-5(6H)-one Prepared as described in Example 73, Part B to afford 8-chloro-9-fluoro-6-(4-methoxybenzyl)-4-methylbenzo[c][2,7]naphthyridin-5(6H)-one (260 mg, 0.669 mmol, 61% yield) as a white solid. LC/MS (ESI) m/e 383.0 [(M+H)$^+$, calcd for C$_{21}$H$_{17}$ClFN$_2$O$_2$ 383.1]; LC/MS retention time (method C): t$_R$=2.04 min.

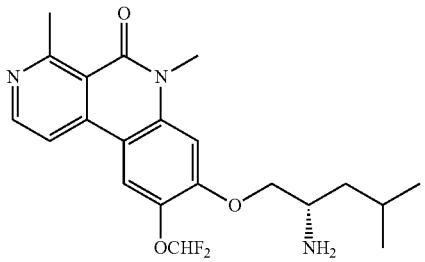

Part C: (S)-tert-butyl 1-(9-fluoro-6-(4-methoxybenzyl)-4-methyl-5-oxo-5,6-dihydrobenzo[c][2,7]naphthyridin-8-yloxy)-4-methylpentan-2-ylcarbamate Prepared as described in Example 16, Part H to afford (S)-tert-butyl 1-(9-fluoro-6-(4-methoxybenzyl)-4-methyl-5-oxo-5,6-dihydrobenzo[c][2,7]naphthyridin-8-yloxy)-4-methylpentan-2-ylcarbamate (0.2 g, 0.244 mmol, 62% yield). LC/MS (ESI) m/e 564.4 [(M+H)$^+$, calcd for C$_{32}$H$_{39}$FN$_3$O$_5$ 564.3]; LC/MS retention time (method E): t$_R$=1.25 min.

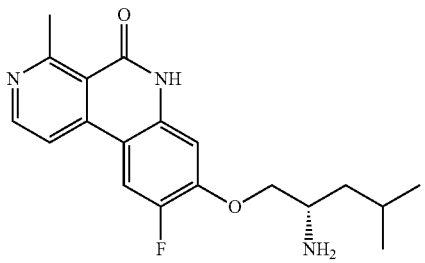

Part D: (S)-8-(2-amino-4-methylpentyloxy)-9-fluoro-4-methylbenzo[c][2,7]naphthyridin-5(6H)-one Prepared as described in Example 2, Part E to afford title compound (55 mg, 0.158 mmol, 87% yield) as a white solid. LC/MS (ESI) m/e 344.0 [(M+H)$^+$, calcd for C$_{19}$H$_{23}$FN$_3$O$_2$ 344.2]; LC/MS retention time (method C): t$_R$=1.76 min; HPLC retention time (method A): t$_R$=7.88 min; HPLC retention time (method B): t$_R$=7.92 min; $^1$H NMR (400 MHz, METHANOL-d$_4$) δ ppm 8.60 (d, J=5.8 Hz, 1H), 8.15 (d, J=12.0 Hz, 1H), 8.08 (d, J=5.8 Hz, 1H), 6.99 (d, J=7.5 Hz, 1H), 4.22-4.12 (m, 1H), 4.06-3.92 (m, 1H), 3.40 (br. s., 1H), 3.10 (s, 3H), 1.92-1.80 (m, 1H), 1.59-1.41 (m, 2H), 1.03 (d, J=6.5 Hz, 3H), 1.01 (d, J=6.5 Hz, 3H).

Example 102

8-(2-amino-2,4-dimethylpentyloxy)-9-fluoro-4-methylbenzo[c][2,7]naphthyridin-5(6H)-one

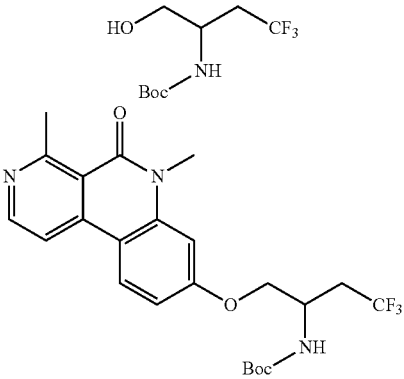

Part A. tert-butyl 1-(9-fluoro-6-(4-methoxybenzyl)-4-methyl-5-oxo-5,6-dihydrobenzo[c][2,7]naphthyridin-8-yloxy)-2,4-dimethylpentan-2-ylcarbamate Prepared from coupling of 8-chloro-9-fluoro-6-(4-methoxybenzyl)-4-methylbenzo[c][2,7]naphthyridin-5(6H)-one (synthesis described in Example 101, Part C) following the procedure described in Example 16, Part H to afford title compound (0.130 g, 0.123 mmol, 47% yield) as a brown oil. LC/MS (ESI) m/e 578.5 [(M+H)$^+$, calcd for C$_{33}$H$_{41}$FN$_3$O$_5$ 578.3]; LC/MS retention time (method E): t$_R$=1.28 min.

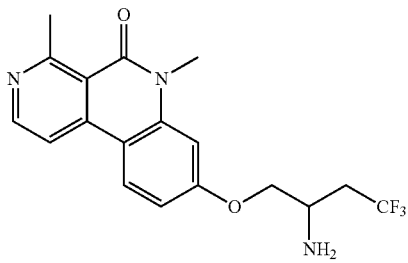 [SMILES: Cc1nccc2c1c(=O)n(C)c1cc(OCC(N)CC(F)(F)F)ccc21]

Part B. 8-(2-amino-2,4-dimethylpentyloxy)-9-fluoro-4-methylbenzo[c][2,7]naphthyridin-5(6H)-one Prepared as described in Example 2, Part E to afford title compound (10 mg, 0.017 mmol, 22% yield) as a pale yellow solid. LC/MS (ESI) m/e 358.0 [(M+H)+, calcd for $C_{20}H_{25}FN_3O_2$ 358.2]; LC/MS retention time (method C): $t_R$=1.69 min; HPLC retention time (method A): $t_R$=7.87 min; HPLC retention time (method B): $t_R$=8.59 min; $^1$H NMR (400 MHz, METHANOL-$d_4$) δ ppm 8.67 (d, J=6.3 Hz, 1H), 8.39 (d, J=6.3 Hz, 1H), 8.32 (d, J=12.0 Hz, 1H), 7.08 (d, J=7.3 Hz, 1H), 4.44-4.15 (m, 2H), 3.37-3.35 (m, 1H), 3.19 (s, 3H), 1.97-1.83 (m, 2H), 1.81-1.70 (m, 1H), 1.56 (s, 2H), 1.10 (d, J=6.3 Hz, 3H), 1.06 (d, J=6.3 Hz, 3H).

Example 103

(S)-8-(2-amino-4-methylpentyloxy)-9-chloro-7-fluoro-4-methylbenzo[c][2,7]naphthyridin-5(6H)-one

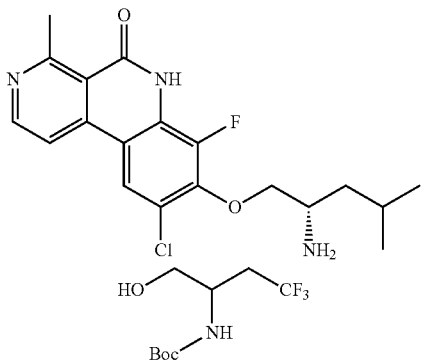

Part A: (S)-tert-butyl 1-(9-chloro-7-fluoro-6-(4-methoxybenzyl)-4-methyl-5-oxo-5,6-dihydrobenzo[c][2,7]naphthyridin-8-yloxy)-4-methylpentan-2-ylcarbamate Prepared as described in Example 41, Part A from (S)-tert-butyl (1-((7-fluoro-6-(4-methoxybenzyl)-4-methyl-5-oxo-5,6-dihydrobenzo[c][2,7]naphthyridin-8-yl)oxy)-4-methylpentan-2-yl)carbamate (synthesis described in Example 82, Part C) to afford title compound (2135 mg, 0.063 mmol, 60% crude yield) as a yellow solid. The material was carried forward without purification. LC/MS (ESI) m/e 598.3 [(M+H)+, calcd for $C_{32}H_{38}ClFN_3O_5$ 598.2]; LC/MS retention time (method E): $t_R$=1.32 min.

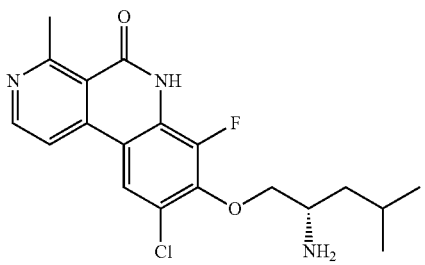 [SMILES: Cc1nccc2c1c(=O)[nH]c1c(F)c(OC[C@@H](N)CC(C)C)c(Cl)cc12]

Part B. (S)-8-(2-amino-4-methylpentyloxy)-9-chloro-7-fluoro-4-methylbenzo[c][2,7]naphthyridin-5(6H)-one To a solution of (S)-tert-butyl (1-((9-chloro-7-fluoro-6-(4-methoxybenzyl)-4-methyl-5-oxo-5,6-dihydrobenzo[c][2,7]naphthyridin-8-yl)oxy)-4-methylpentan-2-yl)carbamate (0.08 g, 0.037 mmol) in TFA (8 mL) cooled to 0° C. was added methanesulfonic acid (0.243 µl, 3.75 µmol). The reaction mixture was then heated at 70° C. for 2 h. The volatiles were evaporated. The residue was taken up in water and neutralized with 10% aqueous NaHCO3. The solution was extracted with EtOAc (3×15 mL). The combined organic layers were washed with brine (1×15 mL), dried over Na2SO4, filtered and concentrated under reduced pressure. The residue was purified by preparative HPLC (Column: X-Bridge (19×150 mm) 5 µm, Flow rate: 15 ml/min; Solvent A: 0.01% TFA, Solvent B: ACN) to afford (S)-8-((2-amino-4-methylpentyl)oxy)-9-chloro-7-fluoro-4-methylbenzo[c][2,7]naphthyridin-5(6H)-one, 3 TFA (9.5 mg, 0.013 mmol, 34.4% yield) as an off-white solid. LC/MS (ESI) m/e 378.0 [(M+H)+, calcd for $C_{19}H_{22}ClFN_3O_2$ 378.1]; LC/MS retention time (method C): $t_R$=2.02 min; HPLC retention time (method A): $t_R$=7.47 min; HPLC retention time (method B): $t_R$=8.41 min; $^1$H NMR (400 MHz, METHANOL-$d_4$) δ ppm 8.70 (d, J=6.0 Hz, 1H), 8.40 (d, J=2.0 Hz, 1H), 8.35 (d, J=6.3 Hz, 1H), 4.49 (dd, J=10.7, 2.6 Hz, 1H), 4.35 (dd, J=10.5, 5.8 Hz, 1H), 3.75-3.69 (m, 1H), 3.14 (s, 3H), 1.90-1.74 (m, 2H), 1.70-1.56 (m, 1H), 1.04 (d, J=2.3 Hz, 3H), 1.03 (d, J=2.5 Hz, 3H).

Example 104

(S)-8-(2-amino-4-methylpentyloxy)-9-(methoxymethyl)-4,6-dimethylbenzo[c][2,7]naphthyridin-5(6H)-one

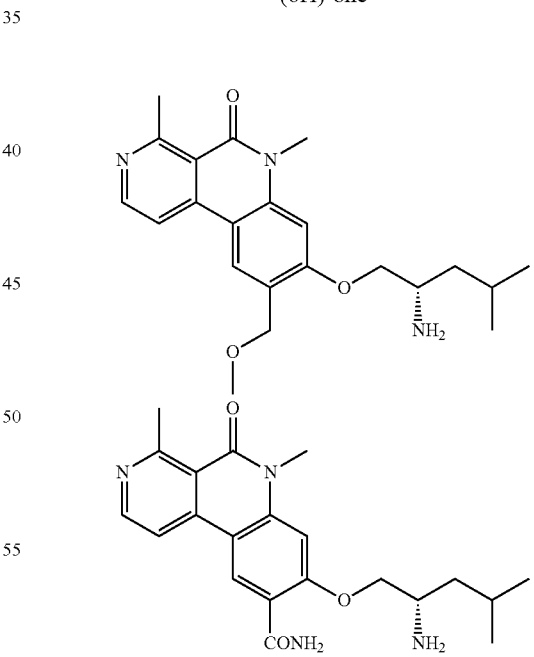

Part A. (S)-tert-butyl 1-(9-(methoxymethyl)-4,6-dimethyl-5-oxo-5,6-dihydrobenzo[c][2,7]naphthyridin-8-yloxy)-4-methylpentan-2-ylcarbamate Prepared as described in Example 16, Part H to afford title compound (S)-tert-butyl (1-((9-(methoxymethyl)-4,6-dimethyl-5-oxo-5,6-dihydrobenzo[c][2,7]naphthyridin-8-yl)oxy)-4-methylpentan-2-yl)carbamate (100 mg, 0.066 mmol, 84% yield). LC/MS (ESI) m/e 484.4 [(M+H)$^+$, calcd for $C_{27}H_{38}N_3O_5$ 484.3]; LC/MS retention time (method B): $t_R$=1.65 min.

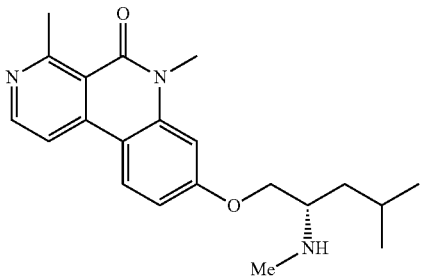 [SMILES: CN[C@H](COc1ccc2c3ccnc(C)c3c(=O)n(C)c2c1)CC(C)C]

Part B. (S)-8-(2-amino-4-methylpentyloxy)-9-(methoxymethyl)-4,6-dimethylbenzo[c][2,7]naphthyridin-5(6H)-one Prepared as described in Example 2, Part E to afford title compound (9 mg, 0.022 mmol, 33% yield) as a yellow solid. LC/MS (ESI) m/e 384.2 [(M+H)$^+$, calcd for $C_{22}H_{30}N_3O_3$ 384.2]; LC/MS retention time (method C): $t_R$=1.66 min; HPLC retention time (method A): $t_R$=7.96 min; HPLC retention time (method B): $t_R$=9.01 min; $^1$H NMR (400 MHz, METHANOL-d$_4$) δ ppm 8.54 (d, J=5.9 Hz, 1H), 8.33 (s, 1H), 8.11 (d, J=5.8 Hz, 1H), 7.00 (s, 1H), 4.73-4.55 (m, 2H), 4.33 (dd, J=10.0, 3.5 Hz, 1H), 4.13 (dd, J=9.9, 6.8 Hz, 1H), 3.75 (s, 3H), 3.59-3.50 (m, 1H), 3.47 (s, 3H), 3.06 (s, 3H), 1.97-1.77 (m, 1H), 1.69-1.45 (m, 2H), 1.04 (d, J=4.7 Hz, 3H), 1.02 (d, J=4.7 Hz, 3H).

Example 105

8-(2-amino-2,4-dimethylpentyloxy)-7-fluoro-4-methylbenzo[c][2,7]naphthyridin-5(6H)-one

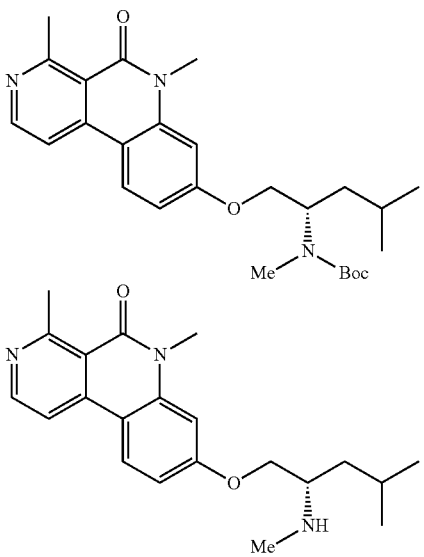

Part A. 4-(4-bromo-2,3-difluorophenyl)-N-(4-methoxybenzyl)-2-methylnicotinamide

Prepared as described in Example 82, Part A to afford 4-(4-bromo-2,3-difluorophenyl)-N-(4-methoxybenzyl)-2-methylnicotinamide (0.320 g, 0.693 mmol, 97% yield) as an off-white solid. LC/MS (ESI) m/e 447.0 [(M+H)$^+$, calcd for $C_{21}H_{18}BrF_2N_2O_2$ 447.0]; LC/MS retention time (method E): $t_R$=0.95 min.

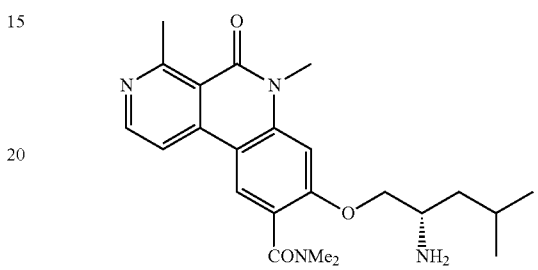

Part B. 8-bromo-7-fluoro-6-(4-methoxybenzyl)-4-methylbenzo[c][2,7]naphthyridin-5(6H)-one Prepared as described in Example 2, Part C to afford 8-bromo-7-fluoro-6-(4-methoxybenzyl)-4-methylbenzo[c][2,7]naphthyridin-5(6H)-one (0.12 g, 0.269 mmol, 90% yield) as an off-white solid. LC/MS (ESI) m/e 427.1 [(M+H)$^+$, calcd for $C_{21}H_{17}BrFN_2O_2$ 427.0]; LC/MS retention time (method E): $t_R$=1.15 min.

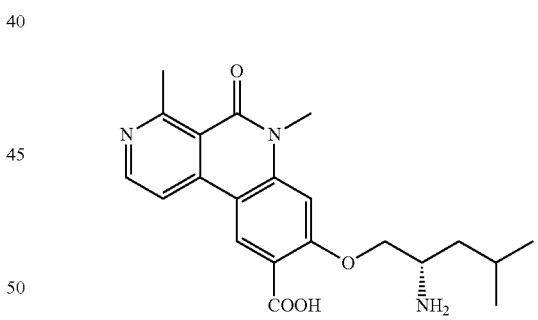

Part C. tert-butyl 1-(7-fluoro-6-(4-methoxybenzyl)-4-methyl-5-oxo-5,6-dihydrobenzo[c][2,7]naphthyridin-8-yloxy)-2,4-dimethylpentan-2-ylcarbamate Prepared as described in Example 16, Part H to afford (R)-tert-butyl (1-((7-fluoro-6-(4-methoxybenzyl)-4-methyl-5-oxo-5,6-dihydrobenzo[c][2,7]naphthyridin-8-yl)oxy)-2,4-dimethylpentan-2-yl)carbamate (0.025 g, 0.042 mmol, 13% yield). LC/MS (ESI) m/e 578.5 [(M+H)$^+$, calcd for $C_{33}H_{41}FN_3O_5$ 578.3]; LC/MS retention time (method E): $t_R$=1.28 min.

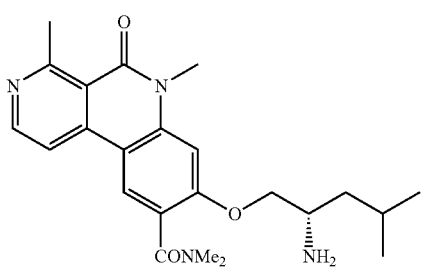

Part D. 8-(2-amino-2,4-dimethylpentyloxy)-7-fluoro-4-methylbenzo[c][2,7]naphthyridin-5(6H)-one Prepared as described in Example 17, Part I to afford 8-(2-amino-2,4-dimethylpentyloxy)-7-fluoro-4-methylbenzo[c][2,7]naphthyridin-5(6H)-one (0.013 g, 0.030 mmol, 69% yield) as an off-white solid. LC/MS (ESI) m/e 358.0 [(M+H)+, calcd for $C_{20}H_{25}FN_3O_2$ 358.2]; HPLC retention time (method A): $t_R$=7.71 min; HPLC retention time (method B): $t_R$=8.57 min; $^1$H NMR (400 MHz, METHANOL-$d_4$) δ ppm 8.75-8.70 (m, 1H), 8.70-8.63 (m, 1H), 8.36 (dd, J=9.3, 1.8 Hz, 1H), 7.34 (dd, J=9.3, 7.8 Hz, 1H), 4.47-4.39 (m, 1H), 4.38-4.30 (m, 1H), 3.26 (s, 3H), 1.96-1.85 (m, 2H), 1.81-1.70 (m, 1H), 1.55 (s, 3H), 1.10 (d, J=6.5 Hz, 3H), 1.06 (d, J=6.0 Hz, 3H).

Example 106

(S)-8-((2-amino-5,5-difluoropent-4-en-1-yl)oxy)-4,6-dimethyl-5-oxo-5,6-dihydrobenzo[c][2,7]naphthyridine-9-carbonitrile

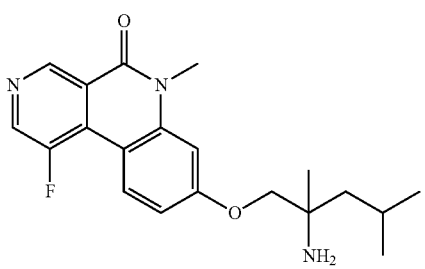

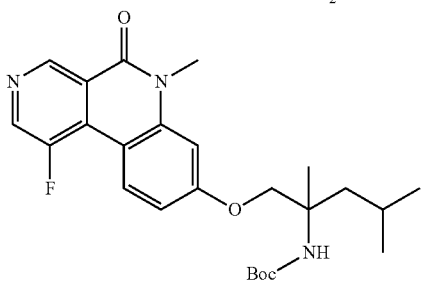

Part A: (S)-dimethyl 2-((tert-butoxycarbonyl)amino)succinate

A 0° C. suspension of L-aspartic acid (10.1 g, 76.0 mmol) in anhydrous methanol (100 mL) was treated with trimethylsilyl chloride (24.7 g, 228 mmol) via rapid dropwise addition. The cooling bath was removed and the resulting solution stirred at ambient temperature overnight (16 h) and then concentrated under reduced pressure. The resulting oil was taken up in dichloromethane (100 mL), treated with di-t-butyl dicarbonate (17.4 g, 80.1 mmol) and diisopropylethylamine (26.5 mL, 152 mmol) and stirred at ambient temperature overnight (16 h). The resulting solution was washed with 0.25 N aqueous hydrochloric acid (3×50 mL), 0.25 N aqueous sodium hydroxide (3×50 mL), and brine (1×50 mL); dried over MgSO$_4$ and concentrated under reduced pressure to afford (S)-dimethyl 2-((tert-butoxycarbonyl)amino)succinate (15.9 g, 60.9 mmol, 80% crude yield) as a near colorless oil. The crude product was used in the next step without further purification. $^1$H NMR (400 MHz, CDCl$_3$) δ ppm 5.50 (br. s., 1H), 4.60 (br. s., 1H), 3.78 (s, 3H), 3.71 (s, 3H), 3.02 (dd, J=16.9, 4.4 Hz, 1H), 2.84 (dd, J=16.8, 4.8 Hz, 1H), 1.47 (s, 9H).

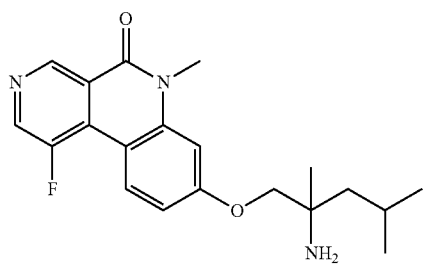

Part B: (S)-dimethyl 2-[bis(tert-butoxycarbonyl)amino]butane-1,4-dioate

A 0° C. solution of (S)-dimethyl 2-((tert-butoxycarbonyl)amino)succinate (15.8 g, 60.5 mmol) in acetonitrile (200 mL) was treated with di-t-butyl dicarbonate (13.9 g, 63.5 mmol) and 4-dimethylaminopyridine (1.48 g, 12.1 mmol). The cooling bath was removed and the reaction solution stirred at ambient temperature overnight (18 h). The resulting solution was concentrated under reduced pressure. The residue was dissolved in ethyl acetate (200 mL), washed with 0.25 N aqueous hydrochloric acid (2×50 mL), 0.25N aqueous sodium hydroxide (2×50 mL), and brine (1×50 mL); dried over magnesium sulfate and concentrated under reduced pressure to afford (S)-dimethyl 2-[bis(tert-butoxycarbonyl)amino]butane-1,4-dioate (18.8 g, 52.0 mmol, 86% crude yield) as a pale yellow oil. The crude product was used without further purification. $^1$H NMR (400 MHz, CDCl$_3$) δ ppm 5.46 (t, J=6.8 Hz, 1H), 3.72 (s, 3H), 3.74 (s, 3H), 3.26 (dd, J=16.4, 7.2 Hz, 1H), 2.75 (dd, J=16.3, 6.5 Hz, 1H), 1.52 (s, 18H).

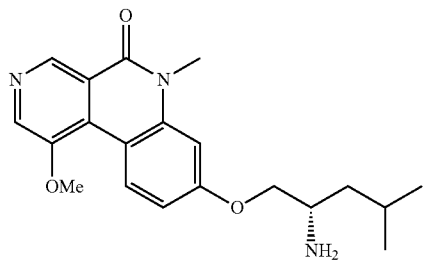 [SMILES: COc1cncc2c(=O)n(C)c3cc(OC[C@@H](N)CC(C)C)ccc3c12]

Part C: (S)-methyl-2-{(tert-butoxy)-N-[(tert-butyl)oxycarbonyl]carbonylamino}-4-oxobutanoate A −78° C. solution of (S)-dimethyl 2-[bis(tert-butoxycarbonyl)amino]butane-1,4-dioate (9.07 g, 25.1 mmol) in diethyl ether (100 mL) was treated dropwise with 1 M diisobutyl aluminum hydride in dichloromethane (37.6 mL, 37.6 mmol). The resulting solution was stirred for 15 min and then quenched sequentially in 15 minutes intervals with water (3.3 mL), 1N aqueous sodium hydroxide (10 mL), and again with water (3.3 mL). The resulting suspension was filtered through diatomaceous earth (Celite®) and concentrated under reduced pressure to afford (S)-methyl-2-{(tert-butoxy)-N-[(tert-butyl)oxycarbonyl]carbonylamino}-4-oxobutanoate (8.26 g, 24.9 mmol, 99% crude yield) as a colorless oil. The crude product was used without further purification. ¹H NMR (400 MHz, CDCl₃) δ ppm 9.81 (s, 1H), 5.55 (t, J=6.4 Hz, 1H), 3.75, (s, 3H), 3.43 (ddd, J=18.0, 5.9, 1.0 Hz, 1H), 2.85 (ddd, J=17.9, 6.0, 1.0 Hz, 1H), 1.52 (s, 18H).

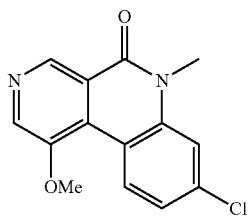 [SMILES: COc1cncc2c(=O)n(C)c3cc(Cl)ccc3c12]

Part D: (S)-methyl 2-((tert-butoxycarbonyl)amino)-4-oxobutanoate

A solution of (S)-methyl-2-{(tert-butoxy)-N-[(tert-butyl)oxycarbonyl]carbonylamino}-4-oxobutanoate (29.2 g, 88.0 mmol) in acetonitrile (300 mL) was treated with lithium bromide (11.5 g, 132 mmol), heated to reflux for 2 h, and then concentrated under reduced pressure. The residue was dissolved in ethyl acetate (300 mL), washed with water (1×50 mL) and brine (1×50 mL); dried over magnesium sulfate, and concentrated under reduced pressure to a dark amber oil. The crude material was purified over SiO₂ (20-100% ethyl acetate/hexanes gradient elution) to afford (S)-methyl 2-((tert-butoxycarbonyl)amino)-4-oxobutanoate (12.5 g, 54.1 mmol, 62% crude yield) as a pale amber oil. ¹H NMR (400 MHz, CDCl₃) δ ppm 9.76 (s, 1H), 5.41 (br. s., 1H), 4.62 (dt, J=8.1, 4.4 Hz, 1H), 3.77 (s, 3H), 3.19-2.94 (m, 2H), 1.46 (s, 9H).

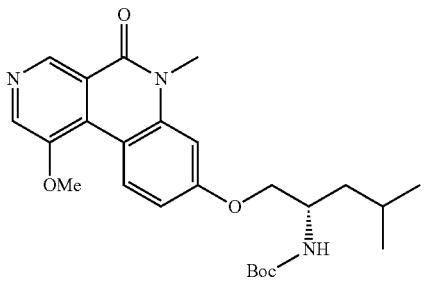 [SMILES: COc1cncc2c(=O)n(C)c3cc(OC[C@H](CC(C)C)NC(=O)OC(C)(C)C)ccc3c12]

Part E: (S)-methyl 2-((tert-butoxycarbonyl)amino)-5,5-difluoropent-4-enoate

A solution of (S)-methyl 2-((tert-butoxycarbonyl)amino)-4-oxobutanoate (5.97 g, 25.8 mmol), sodium 2-chloro-2,2-difluoroacetate (11.8 g, 77.0 mmol), triphenylphosphine (20.3 g, 77.0 mmol), and N,N-dimethylformamide (50 mL) was charged to a 500 mL 3-necked flask and heated to 115° C. for 15 min. The resulting mixture was filtered through diatomaceous earth (Celite®) and concentrated under reduced pressure. The crude material was purified over SiO₂ (5-40% ethyl acetate/hexanes gradient elution) to afford (S)-methyl 2-((tert-butoxycarbonyl)amino)-5,5-difluoropent-4-enoate (0.91 g, 3.43 mmol, 13% yield) as a colorless oil. ¹H NMR (400 MHz, CDCl₃) δ ppm 5.25-5.06 (br. s., 1H), 4.42 (br. s., 1H), 4.24-4.10 (m, 1H), 3.78 (s, 3H), 2.59 (dd, J=14.4, 6.7 Hz, 1H), 2.51-2.31 (m, 1H), 1.47 (s, 9H).

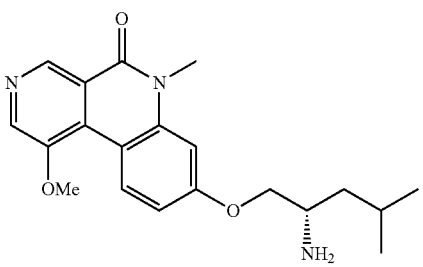 [SMILES: COc1cncc2c(=O)n(C)c3cc(OC[C@@H](N)CC(C)C)ccc3c12]

Part F: (S)-tert-butyl (5,5-difluoro-1-hydroxypent-4-en-2-yl)carbamate

An ambient temperature solution of (S)-methyl 2-((tert-butoxycarbonyl)amino)-5,5-difluoropent-4-enoate (1.91 g, 7.20 mmol) in tetrahydrofuran (25 mL) was treated with lithium borohydride (0.31 g, 14 mmol) and stirred for 1 h. The resulting solution was cooled to 5° C., quenched with 0.1 N aqueous hydrochloric acid (50 mL), and extracted with ethyl acetate (3×25 mL). The pooled organic extracts were washed with brine (1×20 mL), dried over MgSO₄, and concentrated under reduced pressure. The crude material was purified over SiO₂ (20-100% ethyl acetate/hexanes gradient elution) to afford (S)-tert-butyl (5,5-difluoro-1-hydroxypent-4-en-2-yl)carbamate (1.4 g, 5.90 mmol, 82% yield) as a colorless oil. ¹H NMR (400 MHz, CHLOROFORM-d) δ ppm 4.75 (d, J=6.0 Hz, 1H), 4.35-4.05 (m, 1H), 3.82-3.51 (m, 3H), 2.46-2.16 (m, 3H), 1.47 (s, 9H).

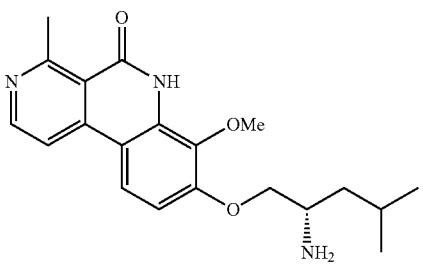 [SMILES: COc1c(OC[C@@H](N)CC(C)C)ccc2c1[nH]c(=O)c1c(C)nccc12]

Part G: (S)-tert-butyl (1-((4,6-dimethyl-5-oxo-5,6-dihydrobenzo[c][2,7]naphthyridin-8-yl)oxy)-5,5-difluoropent-4-en-2-yl)carbamate A suspension of 8-chloro-4,6-dimethylbenzo[c][2,7]naphthyridin-5(6H)-one (1.26 g, 4.88 mmol), prepared as in Example 16, Part G, (S)-tert-butyl (5,5-difluoro-1-hydroxypent-4-en-2-yl)carbamate (1.39 g, 5.86 mmol), 2-di-t-butylphosphino-2',4',6'-triisopropylbiphenyl (0.42 g, 0.98 mmol), Pd(OAc)$_2$ (0.11 g, 0.49 mmol), Cs$_2$CO$_3$ (3.18 g, 9.76 mmol), and anhydrous toluene (15 mL) was purged with nitrogen for 10 minutes and heated to 90° C. overnight (15 h). After cooling, the reaction mixture was filtered through diatomaceous earth (Celite®), concentrated under reduced pressure and dissolved in ethyl acetate (50 mL). The organic layer was washed with brine (1×100 mL) and water (1×100 mL); dried over Na$_2$SO$_4$ and concentrated under reduced pressure to afford an amber oil. The crude material was purified over SiO$_2$ (1-5% 2M ammonia in methanol/dichloromethane gradient elution) to afford (S)-tert-butyl (1-((4,6-dimethyl-5-oxo-5,6-dihydrobenzo[c][2,7]naphthyridin-8-yl)oxy)-5,5-difluoropent-4-en-2-yl)carbamate (1.04 g, 2.26 mmol, 46% yield) as a tan solid. LC/MS, (ESI) m/z 460.0 [(M+H)$^+$, calcd for C$_{24}$H$_{28}$F$_2$N$_3$O$_4$, 460.2]; $^1$H NMR (400 MHz, CDCl$_3$) δ ppm 8.59 (d, J=5.5 Hz, 1H), 8.05 (d, J=8.8 Hz, 1H), 7.73 (d, J=5.8 Hz, 1H), 6.83 (dd, J=8.8, 1.8 Hz, 1H), 6.79 (br. s., 1H), 5.13-4.89 (m, 1H), 4.39-4.21 (m, 1H), 4.20-3.96 (m, 3H), 3.66 (s, 3H), 3.12 (s, 3H), 2.61-2.31 (m, 2H), 1.48 (s, 9H).

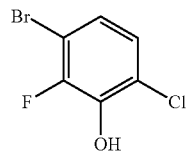

Part H: (S)-tert-butyl (1-((9-bromo-4,6-dimethyl-5-oxo-5,6-dihydrobenzo[c][2,7]naphthyridin-8-yl)oxy)-5,5-difluoropent-4-en-2-yl)carbamate A solution of (S)-tert-butyl (1-((4,6-dimethyl-5-oxo-5,6-dihydrobenzo[c][2,7]naphthyridin-8-yl)oxy)-5,5-difluoropent-4-en-2-yl)carbamate (1.03 g, 2.24 mmol) in acetonitrile (22 mL) was treated with N-bromosuccinimide (0.44 g, 2.5 mmol), heated to 80° C. for 45 min, and then concentrated under reduced pressure. The crude material was purified over SiO$_2$ (1-4% 2M ammonia in methanol/dichloromethane gradient elution) to afford (S)-tert-butyl (1-((9-bromo-4,6-dimethyl-5-oxo-5,6-dihydrobenzo[c][2,7]naphthyridin-8-yl)oxy)-5,5-difluoropent-4-en-2-yl)carbamate (0.81 g, 1.51 mmol, 67% yield) as a white solid. LC/MS, (ESI) m/z 537.9 [(M+H)$^+$, calcd for C$_{24}$H$_{27}$BrF$_2$N$_3$O$_4$, 538.1]; $^1$H NMR (400 MHz, CDCl$_3$) δ ppm 8.62 (d, J=5.8 Hz, 1H), 8.22 (s, 1H), 7.65 (d, J=5.5 Hz, 1H), 6.75 (s, 1H), 5.01 (d, J=8.3 Hz, 1H), 4.41-4.26 (m, 1H), 4.24-4.04 (m, 3H), 3.67 (s, 3H), 3.12 (s, 3H), 2.64-2.34 (m, 2H), 1.48 (s, 9H).

Part I: (S)-tert-butyl (1-((9-cyano-4,6-dimethyl-5-oxo-5,6-dihydrobenzo[c][2,7]naphthyridin-8-yl)oxy)-5,5-difluoropent-4-en-2-yl)carbamate A suspension of (S)-tert-butyl (1-((9-bromo-4,6-dimethyl-5-oxo-5,6-dihydrobenzo[c][2,7]naphthyridin-8-yl)oxy)-5,5-difluoropent-4-en-2-yl)carbamate (0.48 g, 0.892 mmol), zinc cyanide (0.115 g, 0.981 mmol), 1,1'-bis(diphenylphosphino)ferrocene (0.074 g, 0.134 mmol), Pd2(dba)3 (0.041 g, 0.045 mmol), N,N-dimethylformamide (3 mL), and water (0.3 mL) was charged to a 20 mL pressure rated vial and bubbled with a stream of nitrogen for 10 minutes. The vial was sealed, purged of oxygen, and stirred under nitrogen in a pre-heated reaction block at 115° C. overnight. After cooling, the reaction mixture was diluted with ethyl acetate (35 mL) and filtered through diatomaceous earth (Celite®). The filtrate was washed with brine (3×50 mL), dried over sodium sulfate, and concentrated under reduced pressure. The crude material was purified over SiO$_2$ (0-4% 2M ammonia in methanol/dichloromethane gradient elution) to afford (S)-tert-butyl (1-((9-cyano-4,6-dimethyl-5-oxo-5,6-dihydrobenzo[c][2,7]naphthyridin-8-yl)oxy)-5,5-difluoropent-4-en-2-yl)carbamate (0.15 g, 0.280 mmol, 32% yield) as a tan solid. LC/MS, (ESI) m/z 485.1 [(M+H)$^+$, calcd for C$_{25}$H$_{27}$F$_2$N$_4$O$_4$, 485.2]; $^1$H NMR (400 MHz, CDCl$_3$) δ ppm 8.75 (d, J=5.5 Hz, 1H), 8.45 (s, 1H), 7.81 (d, J=5.8 Hz, 1H), 7.00 (s, 1H), 4.85 (d, J=10.0 Hz, 1H), 4.40-4.21 (m, 3H), 4.07 (br. s., 1H), 3.80 (s, 3H), 3.17 (s, 3H), 2.62-2.52 (m, 1H), 2.49-2.38 (m, 1H), 1.49 (s, 9H).

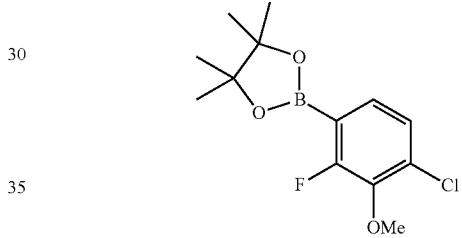

Part J: (S)-8-((2-amino-5,5-difluoropent-4-en-1-yl)oxy)-4,6-dimethyl-5-oxo-5,6-dihydrobenzo[c][2,7]naphthyridine-9-carbonitrile An ambient temperature solution of (S)-tert-butyl (1-((9-cyano-4,6-dimethyl-5-oxo-5,6-dihydrobenzo[c][2,7]naphthyridin-8-yl)oxy)-5,5-difluoropent-4-en-2-yl)carbamate (60 mg, 0.124 mmol) in methanol (1 mL) was treated with 4M HCl in 1,4-dioxane (1.3 mL, 5.20 mmol) and held overnight. The resulting solution was concentrated under reduced pressure. The crude material was purified via preparative LC/MS with the following conditions: Column: XBridge C18, 19×200 mm, 5-μm particles;

Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired were combined and concentrated via centrifugal evaporation to afford (S)-8-((2-amino-5,5-difluoropent-4-en-1-yl)oxy)-4,6-dimethyl-5-oxo-5,6-dihydrobenzo[c][2,7]naphthyridine-9-carbonitrile (7.6 mg, 0.020 mmol, 16% yield) as a white solid. LC/MS, (ESI) m/z 385.3 [(M+H)$^+$, calcd for C$_{20}$H$_{19}$F$_2$N$_4$O$_2$, 385.1]; $^1$H NMR (500 MHz, DMSO) δ ppm 8.82 (s, 1H), 8.60 (d, J=5.5 Hz, 1H), 8.18 (d, J=5.8 Hz, 1H), 6.97 (s, 1H), 4.74-4.59 (m, 1H), 4.22-4.05 (m, 2H), 3.62 (s, 3H), 3.19-3.10 (m, 1H), 2.93 (s, 3H), 2.36-2.25 (m, 1H), 2.19-2.08 (m, 1H).

Example 107

(S)-8-((2-amino-4-methylpentyl)oxy)-9-chloro-7-fluoro-4,6-dimethylbenzo[c][2,7]naphthyridin-5(6H)-one

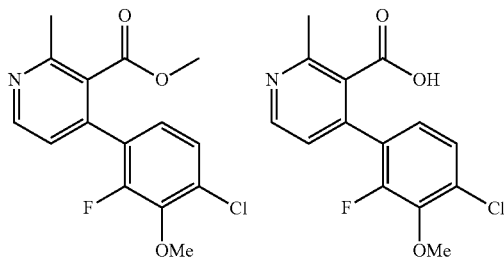 [SMILES: COC(=O)c1c(-c2ccc(Cl)c(OC)c2F)ccnc1C ; COc1c(Cl)ccc(-c2ccnc(C)c2C(=O)O)c1F]

Part A: (S)-tert-butyl (1-((9-chloro-7-fluoro-4,6-dimethyl-5-oxo-5,6-dihydrobenzo[c][2,7]naphthyridin-8-yl)oxy)-4-methylpentan-2-yl)carbamate (S)-tert-butyl (1-((7-fluoro-4,6-dimethyl-5-oxo-5,6-dihydrobenzo[c][2,7]naphthyridin-8-yl)oxy)-4-methylpentan-2-yl)carbamate (0.08 g, 0.175 mmol), prepared as described in Example 29, Part G, was subjected to chlorination using NCS to afford (S)-tert-butyl (1-((9-chloro-7-fluoro-4,6-dimethyl-5-oxo-5,6-dihydrobenzo[c][2,7]naphthyridin-8-yl)oxy)-4-methylpentan-2 yl)carbamate (80 mg, 0.104 mmol, 60% crude yield) as semi-solid. The material was carried forward without further purification. LC/MS (ESI) m/e 492.2 [(M+H)$^+$, calcd for $C_{25}H_{32}ClFN_3O_4$ 492.2].

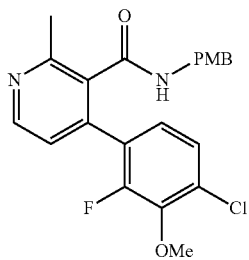

Part B: (S)-8-((2-amino-4-methylpentyl)oxy)-9-chloro-7-fluoro-4,6-dimethylbenzo[c][2,7]naphthyridin-5(6H)-one (S)-tert-Butyl (1-((9-chloro-7-fluoro-4,6-dimethyl-5-oxo-5,6-dihydrobenzo[c][2,7]naphthyridin-8-yl)oxy)-4-methylpentan-2-yl)carbamate (0.08 g, 0.104 mmol)) was subjected to deprotection of the Boc group as described in Example 2, Part E. The crude material was purified via reverse phase HPLC (10MM ammonium acetate in water/AcCN) to provide (S)-8-((2-amino-4-methylpentyl)oxy)-9-chloro-7-fluoro-4,6-dimethylbenzo[c][2,7]naphthyridin-5(6H)-one (0.006 g, 0.015 mmol, 14% yield) as off-white solid. LC/MS (ESI) m/e 392.2 [(M+H)$^+$, calcd for $C_{20}H_{24}ClFN_3O_2$ 392.1]; LC/MS retention time (LC/MS Method C) $t_R$=2.11 min. HPLC retention time (method A): $t_R$=8.96 min; HPLC retention time (method B): $t_R$=5.15 min. $^1$H NMR (400 MHz, METHANOL-d$_4$) 8.62 (d, J=5.8 Hz, 1H), 8.32 (d, J=2.0 Hz, 1H), 8.12 (d, J=5.8 Hz, 1H), 4.26 (ddd, J=9.3, 3.8, 1.0 Hz, 1H), 4.06 (dd, J=8.7, 7.2 Hz, 1H), 3.87 (d, J=9.3 Hz, 3H), 3.67-3.64 (m, 1H), 3.08 (s, 3H), 1.92-1.78 (m, 1H), 1.56-1.37 (m, 2H), 1.02 (d, J=5.3 Hz, 3H), 1.01 (d, J=5.3 Hz, 3H).

Methods

AAK1 Kinase Assay

The assays were performed in U-bottom 384-well plates. The final assay volume was 30 µl prepared from 15 µl additions of enzyme and substrates (fluoresceinated peptide (5-FAM)-Aha-KEEQSQITSQVTGQIGWR-NH2 and ATP) and test compounds in assay buffer (10 mM Tris-HCL pH 7.4, 10 mM MgCl$_2$, 0.01% Tween-20 and 1.0 mM DTT). The reactions were initiated by the combination of bacterially expressed, GST-Xa-hAAK1 with substrates and test compounds. The reactions were incubated at room temperature for 3 hours and terminated by adding 60 µl of 35 mM EDTA buffer to each sample. The reactions were analyzed on the Caliper LabChip 3000 (Caliper, Hopkinton, Mass.) by electrophoretic separation of the fluorescent substrate and phosphorylated product. Inhibition data were calculated by comparison to EDTA quenched control reactions for 100% inhibition and vehicle-only reactions for 0% inhibition. The final concentration of reagents in the assays are ATP, 22 µM; (5-FAM)-Aha-KEEQSQITSQVTGQIGWR-NH2, 1.5 µM; GST-Xa-hAAK1, 3.5 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis.

HEK281 Cell-Based Assay

HEK293F cells were cultured in media containing DMEM (Gibco, cat. #11965), 10% FBS (SAFC Biosciences, cat. #12103C), 1×GPS (glutamine, penicillin and streptomycin). On day one, cells were plated on a 10 cm dish so that they are ~80% confluent at time of transfection. Roughly 12 million cells were in a 10 cm dish at time of transfection. On day two, each dish was transfected with 48 ug DNA and 144 ul Lipofectamine 2000 (Invitrogen, cat. #11668-019). The DNA was comprised of a mixture (per 10 cm dish) containing 3 ug AAK1/HA/pIRES (full length human, NCBI accession no. NP_055726.2), 45 µg Flag/AP2MI/pcDNA (full length human), and 1.5 ml OPTI-MEM. The Lipofectamine 2000 is made up of a mixture (per 10 cm dish) containing 144 µl Lipofectamine 2000 and 1.5 ml OPTI-MEM. Each mixture was transferred to individual 15 ml tubes and incubated at RT for 5 minutes, and then the two mixes were combined and incubated at RT for 20 minutes. Growth media was then aspirated from each 10 cm plate and replaced with 10 ml of DMEM+10% FBS (no GPS). Finally, 3 ml DNA/Lipofectamine mix was added to each 10 cm dish and mix gently followed by incubate of plate overnight at 37° C. and 5% CO$_2$.

On day three, compounds were diluted in 100% DMSO at 1000× final concentration, followed by 3-fold serial dilutions for a total of 5 concentrations tested. Four compounds were tested per 10 cm dish. One ul of each compound dilution was then pipetted into a deep-well, 96-well plate, followed by addition of 500 µl DMEM+0.5% FBS into each well for a 2× final concentration of each compound. Cells were resuspended in a 10 cm dish by simple pipetting (HEK293 cells come off the plate that easy at this point) and then transferred to a 50 ml conical tube and pelleted by centrifugation at 1000 rpm for 5 min. Cell pellets were then resuspended in 2.75 ml DMEM+0.5% FBS per 10 cm dish and 100 µl of cell suspension transferred into each well of 96-well TC plate. Finally, 100 µl of 2× compound diluted in DMEM+0.5% FBS was then added into wells containing cell suspension for a 1× final concentration. Plates were then incubated at 37° C. and 5%

$CO_2$ for 3 hours followed by transferring of cell suspensions from each well into 12-tube PCR strips. The PCR strips were spun in a tip rack at 1000 rpm for 5 minutes to pellet cells and media was then removed by pipetting without disturbing the cell pellet.

To prepare for Western Blot analysis, cell pellets were resuspend in 40 ul 1×LDS-PAGE sample buffer (Invitrogen, cat. # NP0008)+2× Halt phosphatase and protease inhibitor cocktail (Thermo Scientific, cat. #1861284), followed by sonicating each with microtip sonicator set at 5 for 8-10 seconds. Five ul of 10× NuPage Sample Reducing Agent (with 50 mM DTT) was to each sample followed by heat denaturing at 70 C for 10 min on PCR machine. A total of 10 µl per sample was loaded into each lane of a 4-20% Tris-Glycine Criterion 26-well gel (Biorad, cat. #345-0034) for the phospho-mu2 blot and 10 µl per lane in a 4-12% Bis-Tris (+MES buffer) NuPAGE 26-well gel (Invitrogen, cat. # WG1403BX10) for the mu2 blot. For controls, 2 ng of phospho-mu2 or 20 ng mu2/Flag proteins were loaded in the last well of each gel. After SDS-PAGE, samples on each gel were transferred to PVDF membrane using an iBlot and membranes were blocked for one hour in TBST+5% milk, followed by wash 3× for 5-10 min with TBST. Criterion gels were probed with rabbit anti-phospho-mu2 (1:5000; a rabbit polyclonal antibody produced by New England Peptide and affinity purified at Lexicon) in TBST+5% BSA, whereas, NuPAGE gels were probed with mouse anti-Flag (1:500; Sigma, cat. # F1804) in TBST+5% milk, and these primary antibodies were incubated overnight at 4° C. on a rocker.

On day four, Western blots were washed 3× for 5-10 minutes with TBST, probe with anti-rabbit-HRP (1:2000; Bio-Rad, cat. #170-6515) or anti-mouse-HRP (1:2000; Biorad, cat. #170-6516) in TBST+5% milk for 1 hour at RT, washed 3× for 10 minutes with TBST, and developed with ECL reagent (GE Healthcare, cat. # RPN2132) on a Versadoc. Finally, the camera was set up to take a picture every 30 seconds for 10 minutes and the best image saved for each blot with no saturated signal (when the signal is saturated, the bands will be highlighted red). A volume analysis on each band was performed to obtain density values. Percent inhibition was calculated for each sample by first normalizing to total Mu2 expression levels and then comparing to 0% and 100% controls. $IC_{50}$ values were then calculated using Excel fitting software.

AAK1 Knockout Mice

Mice homozygous (−/−) for the disruption of the AAK1 gene were prepared by two methods; gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789,215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day postpartum (lactating), 3 day post-weaning (early involution), and 7 day post-weaning (late involution)).

AAK1 homozygous (−/−) and their wild-type (+/+) littermates were tested using the formalin paw test in order to assess their acute and tonic nociceptive responses. For these tests, Automatic Nociception Analyzers (purchased from the Ozaki lab at University of California, San Diego) were used. A metal band was placed around the left hind paw of each mouse 30 minutes prior to testing. After the 30-minute acclimation period, 20 µl of 5% formalin is subcutaneously injected in the dorsal surface of the left hind paw. Mice were individually housed in cylindrical chambers for 45 minutes. Fresh 5% formalin solution was prepared by diluting formaldehyde (Formalde-fresh 20%, Fisher Scientific, Fair Lawn, N.J.) with distilled water. Investigatory compounds were administered 30 minutes prior to formalin injection.

A computer recorded flinches per minute, total flinches for phase I (acute phase=first 8 minutes), and total flinches for phase II (tonic phase=time between minutes 20-40) through an electromagnetic field. See Yaksh T L, Ozaki G, McCumber D, Rathbun M, Svensson C, Malkmus S, Yaksh M C. *An automated flinch detecting system for use in the formalin nociceptive bioassay. J Appl Physiol.*, 2001; 90:2386-402. As shown in FIG. 1, phase 1 and phase 2 data were obtained using homozygous (−/−) mice females (n=16), wild-type females (n=15), homozygous (−/−) mice males (n=9), and wild-type males (n=18). In all groups and in both phases, the AAK1 homozygous (−/−) mice exhibited significantly less recorded paw flinching than their wild-type (+/+) littermates.

Studies of AAK1 knockout mice showed that disruption of the AAK1 gene affects pain response as measured using the formalin paw test described above. The same test was used to confirm that the administration of an AAK1 inhibitor can also affect pain response.

A compound of the disclosure was tested in this assay at different doses. Gabapentin and pregabalin were used as positive controls. Results are shown below in Table 2, wherein the effect of gabapentin at 200 mg/kg is considered a 100% response, the % response for the other compounds is relative to the 200 mg/kg dose of gabapentin, "sc" means subcutaneous administration; "po" means oral administration.

TABLE 2

| Compound | Dose (mg/kg) | Response |
|---|---|---|
| Gabapentin | 50 sc | 60% |
| Gabapentin | 200 sc | 100% |
| Pregabalin | 50 sc | 90% |
| Example 14: (S)-8-((2-amino-4-methylpentyl)oxy)-9-fluoro-6-methylbenzo[c][2,7]naphthyridin-5(6H)-one | 30 po | 62% |

The invention claimed is:

1. A compound of formula (I)

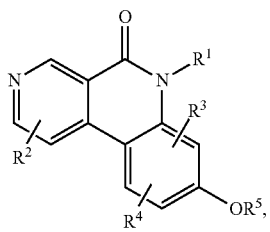

(I)

or a pharmaceutically acceptable salt thereof, wherein:
$R^1$ is selected from hydrogen, $C_2$-$C_4$alkenyl, $C_1$-$C_3$alkoxy, $C_1$-$C_3$alkoxy$C_1$-$C_3$alkyl, $C_1$-$C_3$alkyl, $C_1$-$C_3$alkylamino, aryl$C_1$-$C_3$alkyl, $C_3$-$C_6$cycloalkyl, $C_3$-$C_6$cycloalkyl$C_1$-$C_3$alkyl, $C_1$-$C_3$haloalkyl, and $C_1$-$C_3$hydroxyalkyl;

$R^2$ is selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, $C_1$-$C_3$haloalkyl, $C_2$-$C_3$haloalkylamino, $C_2$-$C_3$haloalkylcarbonylamino, hydroxy, and phenyl$C_1$-$C_3$alkylamino, wherein the phenyl is optionally substituted with a $C_1$-$C_3$alkoxy group;

$R^3$ and $R^4$ are independently selected from hydrogen, $C_1$-$C_4$alkoxy, $C_1$-$C_3$alkoxy$C_1$-$C_3$alkyl, $C_1$-$C_3$alkoxycarbonyl, $C_1$-$C_4$alkyl, $C_1$-$C_3$alkylsulfonyl, aminocarbonyl, cyano, $C_3$-$C_6$cycloalkyl, di($C_1$-$C_3$alkyl)aminocarbonyl, halo, $C_1$-$C_3$haloalkoxy, $C_1$-$C_3$haloalkyl, heteroaryl, hydroxy, $C_1$-$C_3$hydroxyalkyl, and phenyl optionally substituted with a halo group;

$R^5$ is $C_1$-$C_3$alkyl-Y or $C_2$-$C_8$alkyl, wherein the $C_2$-$C_8$alkyl is optionally substituted with one, two, three, or four groups independently selected from $C_1$-$C_3$alkoxy, $C_1$-$C_3$alkylamino, $C_1$-$C_3$alkoxy$C_2$-$C_3$alkylamino, amino, aryl, di($C_1$-$C_3$alkyl)amino, halo, $C_1$-$C_3$haloalkylamino, $C_1$-$C_3$haloalkylcarbonylamino, hydroxy, —NR$^x$R$^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;

R$^x$ and R$^y$, together with the nitrogen atom to which they are attached, form a three- to six-membered ring; and Y is selected from

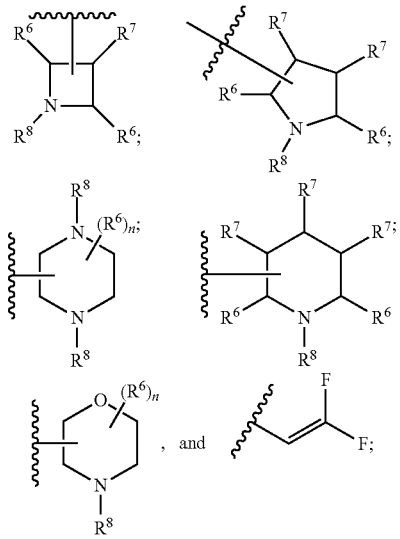

, and wherein n is 0, 1, 2, or 3;

each $R^6$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl;

each $R^7$ is independently selected from hydrogen, $C_1$-$C_3$alkoxy and hydroxy; and $R^8$ is selected from hydrogen, $C_1$-$C_6$alkyl, $C_3$-$C_6$cycloalkyl, and $C_1$-$C_6$alkylcarbonyl.

2. A compound of claim 1 wherein $R^5$ is $C_2$-$C_8$alkyl, wherein the $C_2$-$C_8$alkyl is optionally substituted with one, two, three, or four groups independently selected from $C_1$-$C_3$alkoxy, amino, $C_1$-$C_3$ alkylamino, di($C_1$-$C_3$alkyl)amino, halo, and $C_3$-$C_8$ cycloalkyl; or $R^5$ is $C_1$-$C_3$alkyl-Y wherein Y is

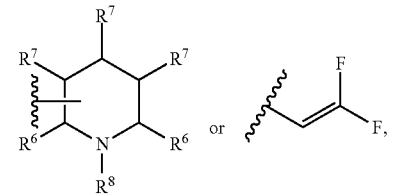

wherein $R^6$, $R^7$, and $R^8$ are hydrogen.

3. A compound of claim 2, or a pharmaceutically acceptable salt thereof, wherein $R^5$ is $C_2$-$C_8$alkyl optionally substituted with one, two, three, or four groups independently selected from amino and halo.

4. A compound of claim 1, or a pharmaceutically acceptable salt thereof, wherein:
$R^1$ is selected from hydrogen, $C_2$-$C_4$alkenyl, $C_1$-$C_3$alkoxy $C_1$-$C_3$ alkyl, $C_1$-$C_3$ alkyl, aryl$C_1$-$C_3$ alkyl, $C_3$-$C_6$ cycloalkyl$C_1$-$C_3$ alkyl, $C_1$-$C_3$haloalkyl, and $C_1$-$C_3$ hydroxyalkyl;

$R^2$ is selected from hydrogen, $C_1$-$C_3$alkoxy, $C_1$-$C_3$alkyl, $C_1$-$C_3$alkylcarbonylamino, amino, halo, $C_1$-$C_3$haloalkyl, and phenyl$C_1$-$C_3$alkylamino, wherein the phenyl is optionally substituted with a $C_1$-$C_3$alkoxy group;

$R^3$ and $R^4$ are independently selected from hydrogen, $C_1$-$C_4$alkoxy, $C_1$-$C_3$alkoxy$C_1$-$C_3$alkyl, $C_1$-$C_3$alkoxycarbonyl, $C_1$-$C_4$alkyl, $C_1$-$C_3$alkylsulfonyl, aminocarbonyl, cyano, $C_3$-$C_6$cycloalkyl, di($C_1$-$C_3$alkyl)aminocarbonyl, halo, $C_1$-$C_3$haloalkoxy, $C_1$-$C_3$haloalkyl, heteroaryl, hydroxy, $C_1$-$C_3$hydroxyalkyl, and phenyl optionally substituted with a halo group;

$R^5$ is $C_1$-$C_3$alkyl-Y or $C_2$-$C_8$alkyl, wherein the $C_2$-$C_8$alkyl is optionally substituted with one, two, three, or four groups independently selected from $C_1$-$C_3$alkoxy, $C_1$-$C_3$alkylamino, amino, di($C_1$-$C_3$alkyl)amino, halo, and $C_3$-$C_8$cycloalkyl; and wherein Y is selected from

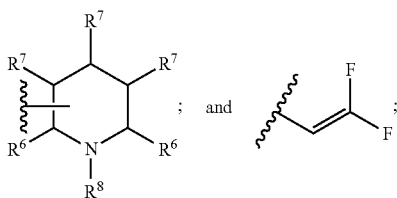

wherein $R^6$, $R^7$, and $R^8$ are hydrogen.

5. A compound of formula (II)

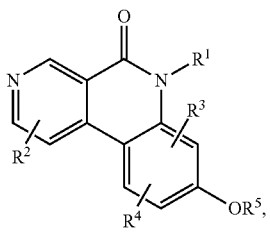

(II)

or a pharmaceutically acceptable salt thereof, wherein:
$R^1$ is selected from hydrogen, $C_2$-$C_4$alkenyl, $C_1$-$C_3$alkoxy, $C_1$-$C_3$alkoxy $C_1$-$C_3$alkyl, $C_1$-$C_3$alkyl, $C_1$-$C_3$alkylamino, aryl$C_1$-$C_3$alkyl, $C_3$-$C_6$cycloalkyl, $C_3$-$C_6$cycloalkyl$C_1$-$C_3$alkyl, and $C_1$-$C_3$haloalkyl;

$R^2$ is selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, $C_1$-$C_3$haloalkyl, $C_2$-$C_3$haloalkylamino, $C_2$-$C_3$haloalkylcarbonylamino, and hydroxy;

$R^3$ and $R^4$ are independently selected from hydrogen, $C_1$-$C_4$alkyl, cyano, $C_3$-$C_6$cycloalkyl, halo, $C_1$-$C_3$haloalkyl, and hydroxy;

$R^5$ is $C_1$-$C_3$alkyl-Y or $C_2$-$C_8$alkyl, wherein the $C_2$-$C_8$alkyl is optionally substituted with one, two, or three groups independently selected from $C_1$-$C_3$alkoxy, $C_1$-$C_3$alkylamino, $C_1$-$C_3$alkoxy$C_2$-$C_3$alkylamino, amino, aryl, halo, $C_1$-$C_3$haloalkylamino, $C_1$-$C_3$haloalkylcarbonylamino, hydroxy, —NR$^x$R$^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;

$R^x$ and $R^y$, together with the nitrogen atom to which they are attached, form a three- to six-membered ring; and Y is selected from

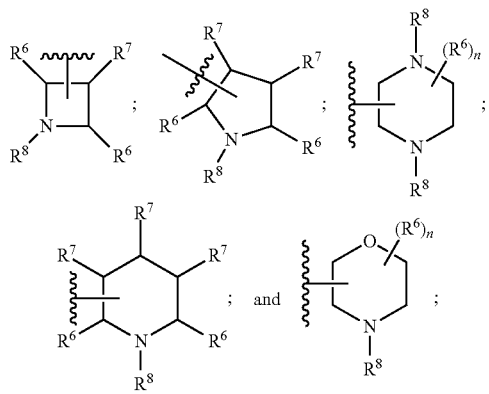

wherein n is 0, 1, 2, or 3;
each $R^6$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl;
each $R^7$ is independently selected from hydrogen, $C_1$-$C_3$alkoxy and hydroxy; and
$R^8$ is selected from hydrogen, $C_1$-$C_6$alkyl, $C_3$-$C_6$cycloalkyl, and $C_1$-$C_6$alkylcarbonyl.

6. A compound selected from
(S)-8-(2-amino-4-methylpentyloxy)benzo[c][2,7]naphthyridin-5(6H)-one;
(S)-8-((2-amino-4-methylpentyl)oxy)-6-methylbenzo[c][2,7]naphthyridin-5(6H)-one;
(S)-8-(2-amino-4-methylpentyloxy)-9-bromo-6-methylbenzo[c][2,7]naphthyridin-5(6H)-one;
(S)-8-((2-amino-4-methylpentyl)oxy)-6,9-dimethylbenzo[c][2,7]naphthyridin-5(6H)-one;
(S)-8-((2-amino-4-methylpentyl)oxy)-6-methyl-5-oxo-5,6 dihydrobenzo[c][2,7]naphthyridine-9-carbonitrile;
(S)-8-((2-amino-4-methylpentyl)oxy)-9-cyclopropyl-6-methylbenzo[c][2,7]naphthyridin-5(6H)-one;
(S)-8-(2-amino-4-methylpentyloxy)-9-hydroxy-6-methylbenzo[c][2,7]naphthyridin-5(6H)-one;
(S)-8-((2-amino-4-methylpentyl)oxy)-6-isopropylbenzo[c][2,7]naphthyridin-5(6H)-one;
(S)-6-allyl-8-((2-amino-4-methylpentyl)oxy)benzo[c][2,7]naphthyridin-5(6H)-one;
(S)-8-((2-amino-4-methylpentyl)oxy)-7,9-dichloro-6-methylbenzo[c][2,7]naphthyridin-5(6H) one;
(S)-8-((2-amino-4-methylpentyl)oxy)-6-benzylbenzo[c][2,7]naphthyridin-5(6H)-one;
(S)-8-((2-amino-4-methylpentyl)oxy)-6-(2-methoxyethyl)benzo[c][2,7]naphthyridin-5(6H)-one;
(S)-8-((2-amino-4-methylpentyl)oxy)-6-(cyclopropylmethyl)benzo[c][2,7]naphthyridin-5(6H)-one;
(S)-8-((2-amino-4-methylpentyl)oxy)-9-fluoro-6-methylbenzo[c][2,7]naphthyridin-5(6H)-one;
8-(2-amino-5,5,5-trifluoropentyloxy)-6-methylbenzo[c][2,7]naphthyridin-5(6H)-one;
(S)-8-((2-amino-4-methylpentyl)oxy)-4,6-dimethylbenzo[c][2,7]naphthyridin-5(6H)-one;

(S)-4-amino-8-(2-amino-4-methylpentyloxy)-6-methyl-benzo[c][2,7]naphthyridin-5(6H)-one;
(S)—N-(8-(2-amino-4-methylpentyloxy)-6-methyl-5-oxo-5,6 dihydrobenzo[c][2,7]naphthyridin-2-yl)acetamide;
(R)-8-((2-amino-4-methylpentyl)oxy)-4,6-dimethylbenzo[c][2,7]naphthyridin-5(6H)-one;
(R)-8-((2-amino-4-methylpentyl)oxy)-9-chloro-4,6-dimethylbenzo[c][2,7]naphthyridin-5(6H)-one;
(S)-8-(2-amino-3-cyclopropylpropoxy)-4,6-dimethyl-benzo[c][2,7]naphthyridin-5(6H)-one;
(S)-8-(2-amino-3-cyclobutylpropoxy)-4,6-dimethylbenzo[c][2,7]naphthyridin-5(6H)-one;
(S)-8-(2-amino-3-cyclopropylpropoxy)-9-chloro-4,6-dimethylbenzo[c][2,7]naphthyridin-5(6H)-one;
(S)-8-(2-amino-3-cyclobutylpropoxy)-9-chloro-4,6-dimethylbenzo[c][2,7]naphthyridin-5(6H)-one;
(S)-8-(2-amino-3-cyclopropylpropoxy)-4,6,9-trimethyl-benzo[c][2,7]naphthyridin-5(6H)-one;
(S)-8-(2-amino-3-cyclobutylpropoxy)-4,6,9-trimethyl-benzo[c][2,7]naphthyridin-5(6H)-one;
(S)-8-((2-amino-4-methylpentyl)oxy)-9-(difluoromethyl)-4,6-dimethylbenzo[c][2,7]naphthyridin-5(6H)-one;
tert-butyl (2,4-dimethyl-1-((6-methyl-5-oxo-5,6 dihydrobenzo[c][2,7]naphthyridin-8-yl)oxy)pentan-2-yl) carbamate;
8-((2-amino-2,4-dimethylpentyl)oxy)-7-fluoro-4,6-dimethylbenzo[c][2,7]naphthyridin-5(6H)-one;
8-(((S)-2-amino-4-methylpentyl)oxy)-9-(1-hydroxyethyl)-4,6 dimethylbenzo[c][2,7]naphthyridin-5(6H)-one;
8-((2-amino-2,4-dimethylpentyl)oxy)-4,6-dimethylbenzo[c][2,7]naphthyridin-5(6H)-one;
8-(((2S,3S)-3-amino-5-methylhexan-2-yl)oxy)-4,6 dim-ethylbenzo[c][2,7]naphthyridin-5(6H)-one;
8-((2-amino-2,4-dimethylpentyl)oxy)-9-methoxy-4,6-dimethylbenzo[c][2,7]naphthyridin-5(6H)-one;
(S)-8-((2-amino-4-methylpentyl)oxy)-9-(2-hydroxypropan-2-yl)-4,6-dimethylbenzo[c][2,7]naphthyridin-5 (6H)-one;
(S)-8-((2-amino-4-methylpentyl)oxy)-9-ethyl-4,6-dimethylbenzo[c][2,7]naphthyridin-5(6H)-one;
(R)-8-((2-amino-2,4-dimethylpentyl)oxy)-4,6-dimethylbenzo[c][2,7]naphthyridin-5(6H)-one;
(S)-8-((2-amino-2,4-dimethylpentyl)oxy)-4,6-dimethylbenzo[c][2,7]naphthyridin-5(6H)-one;
(S)-8-((2-(dimethylamino)-4-methylpentyl)oxy)-6-methylbenzo[c][2,7]naphthyridin-5(6H)-one;
(S)-8-((2-(dimethylamino)-4-methylpentyl)oxy)-4,6-dimethylbenzo[c][2,7]naphthyridin-5(6H)-one;
8-((2-amino-2,4-dimethylpentyl)oxy)-9-chloro-4,6-dimethylbenzo[c][2,7]naphthyridin-5(6H)-one;
(S)-8-(2-amino-4-methylpentyloxy)-4-methoxy-6-methylbenzo[c][2,7]naphthyridin-5(6H)-one;
(S)-8-((2-amino-4-methylpentyl)oxy)-9-chloro-6-methylbenzo[c][2,7]naphthyridin-5(6H)-one;
(S)-8-(2-amino-4-methylpentyloxy)-6-(2-hydroxyethyl)benzo[c][2,7]naphthyridin-5(6H)-one;
(S)-8-(2-amino-4-methylpentyloxy)-6-(2,2,2-trifluoroethyl)benzo[c][2,7]naphthyridin-5(6H)-one;
S)-8-(2-amino-4-methylpentyloxy)-9-ethyl-6-methylbenzo[c][2,7]naphthyridin-5(6H)-one;
(S)-8-(2-amino-4-methylpentyloxy)-9-isopropyl-6-methylbenzo[c][2,7]naphthyridin-5(6H)-one;
(S)-8-(2-amino-4-methylpentyloxy)-6-methyl-9-(oxazol-5-yl)benzo[c][2,7]naphthyridin-5(6H)-one;
(S)-8-(2-amino-4-methylpentyloxy)-9-bromo-4-methylbenzo[c][2,7]naphthyridin-5(6H)-one;
(S)-8-((2-amino-4-methylpentyl)oxy)-4-((4-methoxybenzyl)amino)-6-methylbenzo[c][2,7]naphthyridin-5(6H)-one;
(S)-8-((2-amino-4-methylpentyl)oxy)-9-(4-fluorophenyl)-6 methylbenzo[c][2,7]naphthyridin-5(6H)-one;
(S)-4-amino-8-(2-amino-4-methylpentyloxy)-9-fluoro-6-methylbenzo[c][2,7]naphthyridin-5(6H)-one;
(S)-8-(2-amino-3-isopropoxypropoxy)-6-methylbenzo[c][2,7]naphthyridin-5(6H)-one;
(S)-6-methyl-8-((4-methyl-2-(methylamino)pentyl)oxy)benzo[c][2,7]naphthyridin-5(6H)-one;
(S)-8-((2-amino-4,4-difluoropentyl)oxy)-6-methylbenzo[c][2,7]naphthyridin-5(6H)-one;
8-((2-amino-5,5,5-trifluoropentyl)oxy)-6-methyl-5-oxo-5,6 dihydrobenzo[c][2,7]naphthyridine-9-carbonitrile;
6-methyl-8-(piperidin-2-ylmethoxy)benzo[c][2,7]naphthyridin-5(6H)-one;
(S)-tert-butyl (2,4-dimethyl-1-((6-methyl-5-oxo-5,6 dihydrobenzo[c][2,7]naphthyridin-8-yl)oxy)pentan-2-yl) carbamate;
(R)-tert-butyl (2,4-dimethyl-1-((6-methyl-5-oxo-5,6 dihydrobenzo[c][2,7]naphthyridin-8-yl)oxy)pentan-2-yl) carbamate;
(S)-8-(2-amino-4-methylpentyloxy)-4-(difluoromethyl)-6-methylbenzo[c][2,7]naphthyridin-5(6H)-one;
(S)-8-((2-amino-4-methylpentyl)oxy)-7-chloro-4,6-dimethylbenzo[c][2,7]naphthyridin-5(61)-one;
(S)-8-((2-amino-4-methylpentyl)oxy)-9-chloro-4,6-dimethylbenzo[c][2,7]naphthyridin-5(6H)-one;
(S)-8-(2-amino-4-methylpentyloxy)-4,6,9-trimethyl-benzo[c][2,7]naphthyridin-5(6H)-one;
(S)-8-(2-amino-4-methylpentyloxy)-4,6-dimethyl-5-oxo-5,6-dihydrobenzo[c][2,7]naphthyridine-9-carbonitrile;
(S)-4,6-dimethyl-8-(4-methyl-2-(methylamino)pentyloxy)-5-oxo-5,6-dihydrobenzo[c][2,7]naphthyridine-9-carbonitrile;
(S)-8-((2-amino-4-methylpentyl)oxy)-2,6-dimethylbenzo[c][2,7]naphthyridin-5(6H)-one;
(S)-8-((2-amino-4-methylpentyl)oxy)-2,6 dimethylbenzo[c][2,7]naphthyridin-5(6H)-one;
(S)-8-((2-amino-4-methylpentyl)oxy)-9-chloro-2,6-dimethylbenzo[c][2,7]naphthyridin-5(6H)-one;
(S)-8-(2-amino-3-methoxypropoxy)-6-methylbenzo[c][2,7]naphthyridin-5(6H)-one;
(S)-8-(2-amino-4-methylpentyloxy)-9-fluoro-4,6-dimethylbenzo[c][2,7]naphthyridin-5(6H)-one;
(S)-8-(2-amino-4-methylpentyloxy)-9-(hydroxymethyl)-4,6-dimethylbenzo[c][2,7]naphthyridin-5(6H)-one;
(S)-8-(2-amino-4-methylpentyloxy)-4,6-dimethyl-9-(oxazol-5-yl)benzo[c][2,7]naphthyridin-5(6H)-one;
8-(2-amino-5,5,5-trifluoropentyloxy)-4,6-dimethyl-5-oxo-5,6-dihydrobenzo[c][2,7]naphthyridine-9-carbonitrile;
(S)-8-(2-amino-4-methylpentyloxy)-4,6-dimethyl-9-(trifluoromethyl)benzo[c][2,7]naphthyridin-5(6H)-one;
(S)-8-(2-amino-4-methylpentyloxy)-4,6-dimethyl-9-(trifluoromethyl)benzo[c][2,7]naphthyridin-5(6H)-one;
(S)-8-(2-amino-4-methylpentyloxy)-4,6-dimethyl-9-(methylsulfonyl)benzo[c][2,7]naphthyridin-5(6H)-one;
(S)-8-(2-amino-4-methylpentyloxy)-4-methylbenzo[c][2,7]naphthyridin-5(6H)-one;
(R)-8-(2-amino-4-methylpentyloxy)-4,6-dimethyl-5-oxo-5,6-dihydrobenzo[c][2,7]naphthyridine-9-carbonitrile;

(S)-8-((2-amino-4-methylpentyl)oxy)-9-chloro-6-(2-methoxyethyl)-4-methylbenzo[c][2,7]naphthyridin-5(6H)-one;
(S)-8-((2-amino-4-methylpentyl)oxy)-6-(2-methoxyethyl)-4-methylbenzo[c][2,7]naphthyridin-5(6H)-one;
(S)-8-(2-amino-4-methylpentyloxy)-7-fluoro-4,6-dimethylbenzo[c][2,7]naphthyridin-5(6H)-one;
(S)-8-(2-amino-4-methylpentyloxy)-7-fluoro-4-methylbenzo[c][2,7]naphthyridin-5(6H)-one;
(S)-8-(2-amino-4-methylpentyloxy)-4,6-dimethyl-9-(thiazol-5-yl)benzo[c][2,7]naphthyridin-5(6H)-one;
(S)-methyl 8-((2-amino-4-methylpentyl)oxy)-4,6-dimethyl-5-oxo-5,6-dihydrobenzo[c][2,7]naphthyridine-9-carboxylate;
(S)-8-((2-amino-4-methylpentyl)oxy)-1-fluoro-6-methylbenzo[c][2,7]naphthyridin-5(6H)-one;
(S)-8-((2-amino-4-methylpentyl)oxy)-4,6-dimethyl-9-(pyridin-2-yl)benzo[c][2,7]naphthyridin-5(6H)-one;
(S)-8-((2-amino-5,5,5-trifluoro-4-methylpentyl)oxy)-4,6-dimethylbenzo[c][2,7]naphthyridin-5(6H)-one;
(S)-8-((2-amino-4-methylpentyl)oxy)-9-methoxy-4,6-dimethylbenzo[c][2,7]naphthyridin-5(6H)-one;
(S)-8-((2-amino-4-methylpentyl)oxy)-9-(difluoromethoxy)-4,6-dimethylbenzo[c][2,7]naphthyridin-5(6H)-one;
(S)-8-(2-amino-4,4,4-trifluorobutoxy)-4,6-dimethylbenzo[c][2,7]naphthyridin-5(6H)-one;
(R)-8-(2-amino-4,4,4-trifluorobutoxy)-4,6-dimethylbenzo[c][2,7]naphthyridin-5(6H)-one;
8-(2-amino-4,4,4-trifluorobutoxy)-6-methylbenzo[c][2,7]naphthyridin-5(6H)-one;
(S)-8-((2-amino-4-methylpentyl)oxy)-4,6-dimethyl-5-oxo-5,6-dihydrobenzo[c][2,7]naphthyridine-9-carboxamide;
(S)-4,6-dimethyl-8-(4-methyl-2-(methylamino)pentyloxy)benzo[c][2,7]naphthyridin-5(6H)-one;
(S)-8-((2-amino-4-methylpentyl)oxy)-N,N,4,6-tetramethyl-5-oxo-5,6-dihydrobenzo[c][2,7]naphthyridine-9-carboxamide;
8-(2-amino-2,4-dimethylpentyloxy)-1-fluoro-6-methylbenzo[c][2,7]naphthyridin-5(6H)-one;
(S)-8-((2-amino-4-methylpentyl)oxy)-1-methoxy-6-methylbenzo[c][2,7]naphthyridin-5(6H)-one;
(S)-8-(2-amino-4-methylpentyloxy)-7-methoxy-4-methylbenzo[c][2,7]naphthyridin-5(6H)-one;
(S)-8-(2-amino-4-methylpentyloxy)-9-bromo-7-fluoro-4-methylbenzo[c][2,7]naphthyridin-5(6H)-one;
(S)-8-(2-amino-4-methylpentyloxy)-9-fluoro-4-methylbenzo[c][2,7]naphthyridin-5(6H)-one;
8-(2-amino-2,4-dimethylpentyloxy)-9-fluoro-4-methylbenzo[c][2,7]naphthyridin-5(6H)-one;
(S)-8-(2-amino-4-methylpentyloxy)-9-chloro-7-fluoro-4-methylbenzo[c][2,7]naphthyridin-5(6H)-one;
(S)-8-(2-amino-4-methylpentyloxy)-9-(methoxymethyl)-4,6-dimethylbenzo[c][2,7]naphthyridin-5(6H)-one;
8-(2-amino-2,4-dimethylpentyloxy)-7-fluoro-4-methylbenzo[c][2,7]naphthyridin-5(6H)-one; and
(S)-8-((2-amino-5,5-difluoropent-4-en-1-yl)oxy)-4,6-dimethyl-5-oxo-5,6-dihydrobenzo[c][2,7]naphthyridine-9-carbonitrile;
(S)-8-((2-amino-4-methylpentyl)oxy)-9-chloro-7-fluoro-4,6-dimethylbenzo[c][2,7]naphthyridin-5(6H)-one;
or a pharmaceutically acceptable salt thereof.

7. A composition comprising a pharmaceutically acceptable amount of a compound of claim 1, or a pharmaceutically acceptable salt thereof, and a pharmaceutically acceptable carrier.

8. A method of inhibiting adaptor associated kinase 1 (AAK1) activity, comprising contacting AAK1 with a compound of claim 1, or a pharmaceutically acceptable salt thereof.

9. A method for inhibiting, relieving, or managing pain, the method comprising administering to a patient in need thereof a therapeutically effective amount of a compound of claim 1, or a pharmaceutically acceptable salt thereof.

10. The method of claim 9 wherein the pain is neuropathic pain.

11. The method of claim 10 wherein the neuropathic pain is fibromyalgia or peripheral neuropathy.

\* \* \* \* \*